United States Patent
Burger et al.

(10) Patent No.: US 9,173,883 B2
(45) Date of Patent: *Nov. 3, 2015

(54) RING-SUBSTITUTED N-PYRIDINYL AMIDES AS KINASE INHIBITORS

(71) Applicant: Novartis AG, Basel (CH)

(72) Inventors: Matthew Burger, Cambridge, MA (US); Joseph E. Drumm, III, Walnut Creek, CA (US); Gisele Nishiguchi, Arlington, MA (US); Alice Rico, Castro Valley, CA (US); Robert Lowell Simmons, San Francisco, CA (US); Benjamin Taft, Oakland, CA (US); Huw Tanner, San Francisco, CA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/402,541

(22) PCT Filed: May 20, 2013

(86) PCT No.: PCT/IB2013/054145
§ 371 (c)(1),
(2) Date: Nov. 20, 2014

(87) PCT Pub. No.: WO2013/175388
PCT Pub. Date: Nov. 28, 2013

(65) Prior Publication Data
US 2015/0133473 A1    May 14, 2015

Related U.S. Application Data

(60) Provisional application No. 61/695,533, filed on Aug. 31, 2012, provisional application No. 61/649,645, filed on May 21, 2012.

(51) Int. Cl.

| | | |
|---|---|---|
| *C07D 403/12* | (2006.01) |
| *C07D 401/14* | (2006.01) |
| *C07D 401/12* | (2006.01) |
| *C07D 403/14* | (2006.01) |
| *C07D 407/14* | (2006.01) |
| *C07D 409/14* | (2006.01) |
| *C07D 417/12* | (2006.01) |
| *C07D 417/14* | (2006.01) |
| *C07D 213/81* | (2006.01) |
| *C07D 405/14* | (2006.01) |
| *A61K 31/506* | (2006.01) |
| *A61K 31/4439* | (2006.01) |
| *A61K 31/444* | (2006.01) |
| *A61K 31/4545* | (2006.01) |
| *A61K 31/675* | (2006.01) |

(Continued)

(52) U.S. Cl.
CPC ............. *A61K 31/506* (2013.01); *A61K 31/444* (2013.01); *A61K 31/4439* (2013.01); *A61K 31/4545* (2013.01); *A61K 31/675* (2013.01); *A61K 45/06* (2013.01); *C07D 213/81* (2013.01); *C07D 401/12* (2013.01); *C07D 401/14* (2013.01); *C07D 403/12* (2013.01); *C07D 403/14* (2013.01); *C07D 405/14* (2013.01); *C07D 407/14* (2013.01); *C07D 409/14* (2013.01); *C07D 417/12* (2013.01); *C07D 417/14* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 8,168,794 B2 | 5/2012 | Burger et al. | |
| 8,329,732 B2 | 12/2012 | Burger et al. | |
| 8,822,497 B2 * | 9/2014 | Burger et al. | 514/318 |

(Continued)

FOREIGN PATENT DOCUMENTS

| | | |
|---|---|---|
| CA | 2649043 | 11/2007 |
| WO | 01/55155 | 8/2001 |

(Continued)

OTHER PUBLICATIONS

Johnson et al., "Relationships Between Drug Activity in NCI Preclinical in vitro and in vivo Models and Early Clinical Trials," British Journal of Cancer 84:1424-1431, 2001.

(Continued)

*Primary Examiner* — Timothy R Rozof
(74) *Attorney, Agent, or Firm* — Rona Nardone

(57) ABSTRACT

The present invention provides a compound of formula (A):

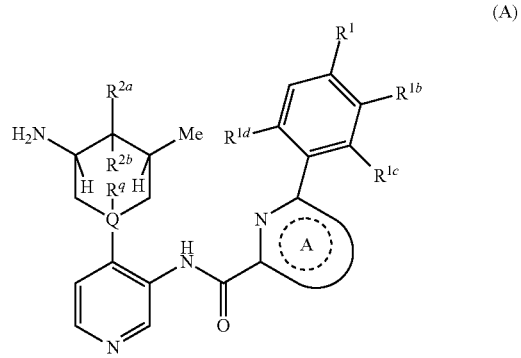

as described herein, and pharmaceutically acceptable salts, enantiomers, rotamers, tautomers, or racemates thereof. Also provided are methods of treating a disease or condition mediated by PIM kinase using the compounds of Formula I, and pharmaceutical compositions comprising such compounds.

20 Claims, No Drawings

(51) Int. Cl.
*A61K 45/06* (2006.01)
*C07F 9/6558* (2006.01)

(56) References Cited

U.S. PATENT DOCUMENTS

| | | | |
|---|---|---|---|
| 8,987,457 B2 * | 3/2015 | Burger et al. | 546/193 |
| 2005/0245530 A1 | 11/2005 | Borzilleri | |
| 2006/0004197 A1 | 1/2006 | Thrash | |
| 2009/0286766 A1 | 11/2009 | Sugasawa et al. | |
| 2010/0056576 A1 | 3/2010 | Burger et al. | |
| 2010/0216839 A1 | 8/2010 | Burger et al. | |
| 2010/0311980 A1 | 12/2010 | Rao | |
| 2012/0208815 A1 | 8/2012 | Burger et al. | |
| 2013/0336965 A1 | 12/2013 | Burger et al. | |

FOREIGN PATENT DOCUMENTS

| | | |
|---|---|---|
| WO | 02/057261 | 7/2002 |
| WO | 02/76986 | 10/2002 |
| WO | 03/008365 | 1/2003 |
| WO | 2005/033097 | 4/2005 |
| WO | 2005/042488 | 5/2005 |
| WO | 2005/056547 | 6/2005 |
| WO | 2006/015081 | 10/2006 |
| WO | 2007/019344 | 2/2007 |
| WO | 2007/044724 | 4/2007 |
| WO | 2007/058942 | 5/2007 |
| WO | 2007/123269 | 11/2007 |
| WO | 2008/022164 | 2/2008 |
| WO | 2008/054701 | 5/2008 |
| WO | 2008/054702 | 5/2008 |
| WO | 2008/054749 | 5/2008 |
| WO | 2008/106692 | 9/2008 |
| WO | 2009/014637 | 1/2009 |
| WO | 2009/103739 | 8/2009 |
| WO | 2009/109541 | 9/2009 |
| WO | 2009/109576 | 9/2009 |
| WO | 2009/110844 | 9/2009 |
| WO | 2009/111309 | 9/2009 |
| WO | 2009/111337 | 9/2009 |
| WO | 2009/118475 | 10/2009 |
| WO | 2010/026124 | 3/2010 |
| WO | 2011/016234 | 8/2010 |
| WO | 2012/004217 | 1/2012 |
| WO | 2012/100135 | 7/2012 |
| WO | 2012/120415 | 9/2012 |

OTHER PUBLICATIONS

Merkel, "PIM 1 Kinase as a Target for Cancer Therapy" Expert Opin. Investig. Drug [Early Online], 1-12, 2012.
Trisha Gura "Cancer Models: Systems for Identifying New Drugs are Often Faculty" Science 278(5340):1041-1042, Nov. 1, 1997.
Simone, Oncology: Introduction, Cecil Textbook of Medicine, 20$^{th}$ Edition, 1996, 1:1004-1010.
Dorwald, Side Reactions in Organic Synthesis, 2005 Wiley; VCH Weinheim Preface, pp. 1-15 & Chapter 8, pp. 279-308.
Graham Atwell et al, "Potential Antitumor Agents. 55. 6-Phenylphenanthridine-4-Carboxamides: A New Class of DNA—Intercalating Antitumor Agents" J. Med. Chem. 31:774-779, 1988.
Second Annual Anti-Inflammatories: Small Molecule Approaches, "Newer Kinase Inflammation Targets (BTK and Beyond)" Apr. 12-13, 2011, San Diego, CA.

* cited by examiner

RING-SUBSTITUTED N-PYRIDINYL AMIDES AS KINASE INHIBITORS

FIELD OF THE INVENTION

This application is the national stage filing of PCT/IB2013/054145, filed May 20, 2013, which claims benefit of US Provisional Application No. 61/649645, filed May 21, 2012, and US Provisional Application No. 61/695533, filed Aug. 31, 2013, the content of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 20, 2014, is named PAT055129-US-PCT_Sequence Listing.txt and is 590 bytes in size.

The present invention relates to new compounds and their tautomers and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer and other cellular proliferation disorders.

BACKGROUND

Infection with the Moloney retrovirus and genome integration in the host cell genome results in development of lymphomas in mice. Provirus Integration of Moloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," *Cell* 37(1): 141-50 (1984); Selten G, et al., "Proviral activation of the putative oncogene Pim-1 in MuLV induced T-cell lymphomas" *EMBO J* 4(7):1793-8 (1985)), thus establishing a correlation between over-expression of this kinase and its oncogenic potential. Sequence homology analysis demonstrated that there are three highly homologous Pim-Kinases (Pim1, 2 & 3), Pim1 being the proto-oncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" *Nature* 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" *Mol Cell Biol* 11(2): 1176-9 (1991)). Thus, these animal models establish a strong correlation between Pim over-expression and oncogenesis in hematopoietic malignancies.

In addition to these animal models, Pim over-expression has been reported in many human malignancies. Pim1, 2 & 3 over-expression is frequently observed in hematopoietic malignancies (Amson R et al., "The human protooncogene product p33pim is expressed during fetal hematopoiesis and in diverse leukemias," *PNAS USA* 86(22):8857-61 (1989); Cohen A M et al., "Increased expression of the hPim-2 gene in human chronic lymphocytic leukemia and non-Hodgkin lymphoma," *Leuk Lymph* 45(5):951-5 (2004), Huttmann A et al., "Gene expression signatures separate B-cell chronic lymphocytic leukaemia prognostic subgroups defined by ZAP-70 and CD38 expression status," *Leukemia* 20:1774-1782 (2006)) and in prostate cancer (Dhanasekaran S M, et al., "Delineation of prognostic biomarkers in prostate cancer," *Nature* 412(6849):822-6 (2001); Cibull T L, et al., "Overexpression of Pim-1 during progression of prostatic adenocarcinoma," *J Clin Pathol* 59(3):285-8 (2006)), while over-expression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," *Int J Cancer* 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," *Cancer Res* 66(13):6741-7 (2006)).

Pim1, 2 & 3 are Serine/Threonine kinases that normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling downstream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Ser112 gatekeeper site: *FEBS Letters* 571: 43-49 (2004)), cell cycle regulators such as $p21^{WF41/CIP1}$ (Wang Z, et al., "Phosphorylation of the cell cycle inhibitor p21Cip1/WAF1 by Pim-1 kinase," *Biochem Biophys Acta* 1593:4555 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," *J Biol Chem* 179:48319-48328 (2004)) and NuMA (Bhattacharya N, et al., "Pim-1 associates with protein complexes necessary for mitosis," *Chromosoma* 111(2): 80-95 (2002)) and the protein synthesis regulator 4EBP1 (Hammerman P S et al., "Pim and Akt oncogenes are independent regulators of hematopoietic cell growth and survival," *Blood* 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers in which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," *Acta Pharmacol Sin* 26(3):364-8 (2005); Fujii et al. 2005; Li et al. 2006).

Furthermore, mutational activation of several well known oncogenes in hematopoietic malignancies is thought to exert its effects at least in part through Pim(s). For example, targeted down-regulation of Pim expression impairs survival of hematopoietic cells transformed by Flt3 and BCR/ABL (Adam et al. 2006). Thus, inhibitors to Pim1, 2 and 3 would be useful in the treatment of these malignancies.

In addition to a potential role in cancer treatment and myeloproliferative diseases, such inhibitor could be useful to control expansion of immune cells in other pathologic condition such as autoimmune diseases, allergic reactions and in organ transplantation rejection syndromes. This notion is supported by the findings that differentiation of Th1 Helper T-cells by IL-12 and IFN-α results in induction of expression of both Pim1 and Pim2 (Aho T et al., "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al. 2005). These results suggest that Pim kinases are involved in the early differentiation process of Helper T-cells, which coordinate the immunological responses in autoimmune diseases, allergic reaction and tissue transplant rejection. Recent reports demonstrate that Pim kinase inhibitors show activity in animal models of inflammation and autoimmune diseases. See JE Robinson "Targeting the Pim Kinase Pathway for Treatment of Autoimmune and Inflammatory Diseases," for the Second Annual Conference on Anti-Inflammatories: Small Molecule Approaches," San Diego, Calif. (Conf. April 2011; Abstract published earlier on-line).

A continuing need exists for compounds that inhibit the proliferation of capillaries, inhibit the growth of tumors, treat cancer, modulate cell cycle arrest, and/or inhibit molecules such as Pim1, Pim2 and Pim3, and pharmaceutical formulations and medicaments that contain such compounds. A need also exists for methods of administering such compounds, pharmaceutical formulations, and medicaments to patients or subjects in need thereof. The present invention addresses such needs.

Earlier patent applications have described compounds that inhibit Pims and function as anticancer therapeutics, see, e.g., WO2012/004217, WO2010/026124, WO 2008/106692 and WO2011/124580, and as treatment for inflammatory conditions such as Crohn's disease, inflammatory bowel disease, rheumatoid arthritis, and chronic inflammatory diseases, see e.g., WO 2008/022164. The present invention provides compounds that inhibit activity of one or more Pims, preferably two or more Pims, more preferably Pim1, Pim2 and Pim3, at nanomolar levels (e.g., IC-50 under 100 nM or under 50 nM) and exhibit distinctive characteristics that may provide improved therapeutic effects and pharmacokinetic properties, such as reduced drug-drug interactions associated with inhibition of cytochrome oxidases, relative to compounds previously disclosed. Compounds of the invention contain novel substitution combinations on one or more rings that provide these distinctive properties and are suitable for treating Pim-related conditions such as those described herein.

SUMMARY OF THE INVENTION

The invention provides compounds of Formula A, having three substituents on a cyclohexyl or piperidinyl ring that is attached to an N-pyridinyl amide moiety of Formula (A):

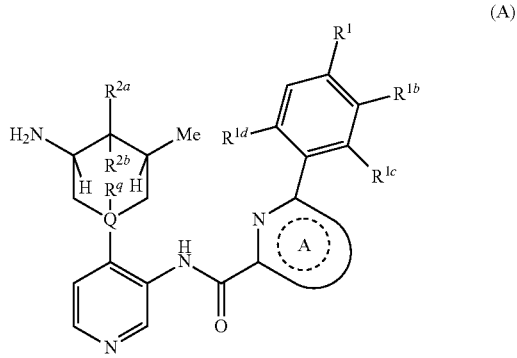

(A)

wherein:
groups attached to the ring containing Q that are depicted inside the ring are all syn to each other, and all groups attached to that ring that are depicted outside the ring are syn to one another;
Q is C or N;
$R^q$ is H when Q is C, and $R^q$ is absent when Q is N;
$R^1$ is selected from H, $C_{1-4}$ alkyl, $C_{3-6}$ cycloalkyl, $C_{4-6}$ heterocyclyl, $-(CR'_2)_{1-3}-OR'$ and $-OR'$,
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;
$R^{1b}$, $R^{1c}$, and $R^{1d}$ are each independently selected from H, halo, OR', R', $-(CH_2)_{1-2}OR'$, and $CONR'_2$;
one of $R^{2a}$ and $R^{2b}$ is H,
and the other of $R^{2a}$ and $R^{2b}$ is selected from CN, halo, azido, amino, $-OR$, $-O(CH_2)_{1-3}OR$, $-NRC(O)R$, $-NRC(O)OR$, $-NHSO_2R$, $-SO_2R$, $-OSO_2R$, $-SR$, $-S(O)R$, $-OP(O)R_2$, and 1-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;
where each R is independently $C_{5-6}$ heteroaryl or $C_{1-4}$ alkyl optionally substituted with up to three groups selected from cyano, halo, hydroxy, carboxy, $C_{1-4}$ alkylsulfonyl, and $C_{1-4}$ alkoxy;
or $R^{2a}$ and $R^{2b}$ taken together may form a dialkyl ketal or 5-6 membered cyclic ketal, =O or =N-OR", where R" is H or $C_{1-4}$ alkyl;
ring A is selected from pyridinyl, pyrimidinyl, pyrazinyl, and thiazolyl, each having N positioned as shown in Formula (I); and
Ring A is optionally substituted with 1 or 2 groups selected from halo, CN, $NH_2$, hydroxy, $C_{1-4}$ alkyl, $C_{1-4}$haloalkyl, $C_{1-4}$ alkoxy, and $C_{1-4}$haloalkoxy;
or a pharmaceutically acceptable salt thereof.
In some embodiments of the compounds of Formula A, $R^{1b}$ is H and $R^1$ is selected from H, $C_{1-4}$ alkyl, $C_{3-6}$ cycloalkyl, $C_{4-6}$heterocyclyl, $-(CR'_2)_{1-3}-OR'$ and $-OR'$,
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;
one of $R^{2a}$ and $R^{2b}$ is H,
and the other of $R^{2a}$ and $R^{2b}$ is selected from CN, halo, azido, amino, $-OR$, $-O(CH_2)_{1-3}OR$, $-NRC(O)R$, $-NRC(O)OR$, $-NHSO_2R$, $-SO_2R$, $-OSO_2R$, $-SR$, $-S(O)R$, $-OP(O)R_2$, and triazolyl optionally substituted with up to two groups selected from halo, $C_{1-4}$ alkyl, hydroxy-substituted $C_{1-4}$ alkyl, $C_{1-4}$ alkoxy, and $C_{5-6}$ heteroaryl;
where each R is independently $C_{1-4}$ alkyl optionally substituted with up to three groups selected from cyano, halo, hydroxy, carboxy, $C_{1-4}$ alkylsulfonyl, and $C_{1-4}$ alkoxy;
or $R^{2a}$ and $R^{2b}$ taken together form a dialkyl ketal or 5-6 membered cyclic ketal, =O or =N-OR", where R" is H or $C_{1-4}$ alkyl;
Ring A is selected from pyridinyl, pyrimidinyl, pyrazinyl, and thiazolyl, each having N positioned as shown in Formula (I); and Ring A is optionally substituted with 1 or 2 groups selected from halo, CN, $NH_2$, hydroxy, $C_{1-4}$ alkyl, $C_{1-4}$ haloalkyl, $C_{1-4}$ alkoxy, and $C_{1-4}$ haloalkoxy;

or a pharmaceutically acceptable salt thereof.

Additional embodiments of these compounds and pharmaceutical compositions and uses for these compounds and compositions are described below.

These compounds are inhibitors of Pim kinases as further discussed herein. These compounds and their pharmaceutically acceptable salts, and pharmaceutical compositions containing these compounds and salts are useful for therapeutic methods such as treatment of cancers and autoimmune disorders that are caused by or exacerbated by excessive levels of Pim kinase activity.

DETAILED DESCRIPTION OF EMBODIMENTS OF THE INVENTION

"PIM inhibitor" is used herein to refer to a compound that exhibits an $IC_{50}$ with respect to PIM Kinase activity of no more than about 100 μM and more typically not more than about 50 μM, as measured in the PIM depletion assays described herein below for at least one of Pim1, Pim2 and Pim3. Preferred compounds have on $IC_{50}$ below about 1 micromolar on at least one Pim, and generally have an $IC_{50}$ below 100 nM on each of Pim1, Pim2 and Pim3.

The phrase "alkyl" refers to hydrocarbon groups that do not contain heteroatoms, i.e., they consist of carbon atoms and hydrogen atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH_3)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)—CH(CH_3)(CH_2CH_3)$, $—CH_2CH_2CH(CH_3)_2$, $—CH_2CH_2CH(CH_3)(CH_2CH_3)$, $—CH_2CH_2CH(CH_2CH_3)_2$, $—CH_2CH_2C(CH_3)_3$, $—CH_2CH_2C(CH_2CH_3)_3$, $—CH(CH_3)CH_2—CH(CH_3)_2$, $—CH(CH_3)CH(CH_3)CH(CH_3)_2$, $—CH(CH_2CH_3)CH(CH_3)CH(CH_3)(CH_2CH_3)$, and others. Thus the term 'alkyl' includes primary alkyl groups, secondary alkyl groups, and tertiary alkyl groups. Typical alkyl groups include straight and branched chain alkyl groups having 1 to 12 carbon atoms, preferably 1-6 carbon atoms. The term 'lower alkyl' or "loweralkyl" and similar terms refer to alkyl groups containing up to 6 carbon atoms.

The term "alkenyl" refers to alkyl groups as defined above, wherein there is at least one carbon-carbon double bond, i.e., wherein two adjacent carbon atoms are attached by a double bond. The term "alkynyl" refers to alkyl groups wherein two adjacent carbon atoms are attached by a triple bond. Typical alkenyl and alkynyl groups contain 2-12 carbon atoms, preferably 2-6 carbon atoms. Lower alkenyl or lower alkynyl refers to groups having up to 6 carbon atoms. An alkenyl or alkynyl group may contain more than one unsaturated bond, and may include both double and triple bonds, but of course their bonding is consistent with well-known valence limitations.

The term 'alkoxy" refers to —OR, wherein R is alkyl.

As used herein, the term "halogen" or "halo" refers to chloro, bromo, fluoro and iodo groups. Typical halo substituents are F and/or Cl. "Haloalkyl" refers to an alkyl radical substituted with one or more halogen atoms. The term "haloalkyl" thus includes monohalo alkyl, dihalo alkyl, trihalo alkyl, perhaloalkyl, and the like.

"Amino" refers herein to the group $—NH_2$. The term "alkylamino" refers herein to the group —NRR' where R and R' are each independently selected from hydrogen or a lower alkyl, provided —NRR' is not $—NH_2$. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl. The term cyano refers to the group —CN. The term nitro refers to the group $—NO_2$.

The term "alkoxyalkyl" refers to the group -alk$_1$-O-alk$_2$ where alk$_1$ is an alkyl or alkenyl linking group, and alk$_2$ is alkyl or alkenyl. The term "loweralkoxyalkyl" refers to an alkoxyalkyl where alk$_1$ is loweralkyl or loweralkenyl, and alk$_2$ is loweralkyl or loweralkenyl. The term "aryloxyalkyl" refers to the group -alkyl-O-aryl, where -alkyl- is a $C_{1-12}$ straight or branched chain alkyl linking group, preferably $C_{1-6}$. The term "aralkoxyalkyl" refers to the group -alkylenyl-O-aralkyl, where aralkyl is preferably a loweraralkyl.

The term "aminocarbonyl" refers herein to the group $—C(O)—NH_2$. "Substituted aminocarbonyl" refers herein to the group —C(O)—NRR' where R is loweralkyl and R' is hydrogen or a loweralkyl. In some embodiments, R and R', together with the N atom attached to them may be taken together to form a "heterocycloalkylcarbonyl" group. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group $—S(O)_2—NH_2$. "Substituted aminosulfonyl" refers herein to the group $—S(O)_2$—NRR' where R is loweralkyl and R' is hydrogen or a loweralkyl. The term "aralkylaminosulfonlyaryl" refers herein to the group -aryl-$S(O)_2$—NH-aralkyl, where the aralkyl is loweraralkyl.

"Carbonyl" refers to the divalent group —C(O)—. "Carboxy" refers to —C(=O)—OH. "Alkoxycarbonyl" refers to ester —C(=O)—OR wherein R is optionally substituted lower alkyl. "Loweralkoxycarbonyl" refers to ester —C(=O)—OR wherein R is optionally substituted lower loweralkyl. "Cycloalkyloxycarbonyl" refers to —C(=O)—OR wherein R is optionally substituted C3-C8 cycloalkyl.

"Cycloalkyl" refers to a mono- or polycyclic, carbocyclic alkyl substituent. Carbocycloalkyl groups are cycloalkyl groups in which all ring atoms are carbon. Typical cycloalkyl substituents have from 3 to 8 backbone (i.e., ring) atoms. When used in connection with cycloalkyl substituents, the term "polycyclic" refers herein to fused and non-fused alkyl cyclic structures. The term "partially unsaturated cycloalkyl", "partially saturated cycloalkyl", and "cycloalkenyl" all refer to a cycloalkyl group wherein there is at least one point of unsaturation, i.e., wherein to adjacent ring atoms are connected by a double bond or a triple bond. Such rings typically contain 1-2 double bonds for 5-6 membered rings, and 1-2 double bonds or one triple bond for 7-8 membered rings. Illustrative examples include cyclohexenyl, cyclooctynyl, cyclopropenyl, cyclobutenyl, cyclohexadienyl, and the like.

The term "heterocycloalkyl" refers herein to cycloalkyl substituents that have from 1 to 5, and more typically from 1 to 4 heteroatoms as ring members in place of carbon atoms. Preferably, heterocycloalkyl or "heterocyclyl" groups contain one or two heteroatoms as ring members, typically only one heteroatom for 3-5 membered rings and 1-2 heteroatoms for 6-8 membered rings. Suitable heteroatoms employed in heterocyclic groups of the present invention are nitrogen, oxygen, and sulfur. Representative heterocycloalkyl moieties include, for example, pyrrolidinyl, tetrahydrofuranyl, oxirane, oxetane, oxepane, thiirane, thietane, azetidine, morpholino, piperazinyl, piperidinyl and the like.

The terms "substituted heterocycle", "heterocyclic group" or "heterocycle" as used herein refers to any 3- or 4-membered ring containing a heteroatom selected from nitrogen, oxygen, and sulfur or a 5- or 6-membered ring containing from one to three heteroatoms, preferably 1-2 heteroatoms, selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring as described herein. Preferred heterocycles include, for example: diazapinyl, pyrrolinyl, pyrrolidinyl, pyrazolinyl, pyrazolidinyl, imidazolinyl, imidazolidinyl, piperidinyl, piperazinyl, N-methyl piperazinyl, azetidinyl, N-methylazetidinyl, oxazolidinyl, isoazolidinyl, morpholinyl, thiazolidinyl, isothiazolidinyl, and oxiranyl. The heterocyclic groups may be attached at various positions as will be apparent to those having skill in the organic and medicinal chemistry arts in conjunction with the disclosure herein.

The term 'syn to one another' as used herein means the groups being described are all on the same face of the ring they are attached to, e.g., the groups are either all above the plane of the ring, or they are all below the plane of the ring. Compounds of Formula I can thus be depicted as (Ia) or (Ib) when Q is C:

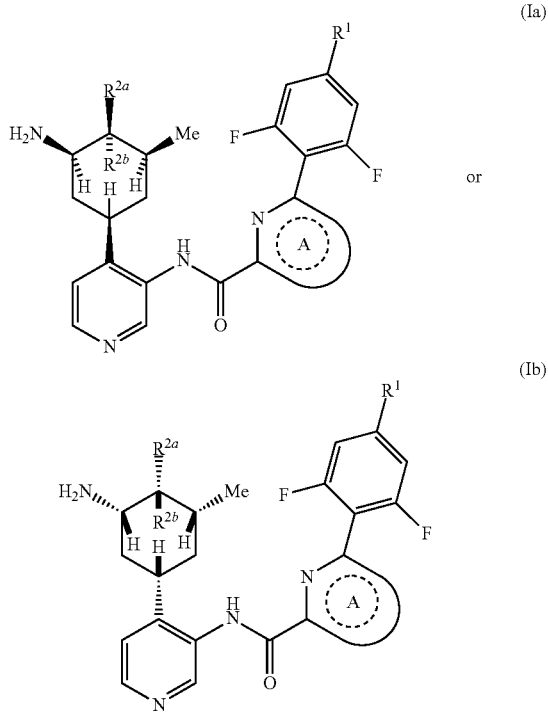

Heterocyclic moieties can be unsubstituted or they can be substituted with one or more substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, lower alkoxyalkoxy, loweralkyl, cycloalkyl or haloalkyl. Typically, substituted heterocyclic groups will have up to four substituent groups. The term "cyclic ether" as used herein refers to a 3-7 membered ring containing one oxygen atom (O) as a ring member. Where the cyclic ether is "optionally substituted" it can be substituted at any carbon atom with a group suitable as a substituent for a heterocyclic group, typically up to three substituents selected from lower alkyl, lower alkoxy, halo, hydroxy, —C(O)-lower alkyl, and —C(O)-lower alkoxy. In preferred embodiments, halo, hydroxy and lower alkoxy are not attached to the carbon atoms of the ring that are bonded directly to the oxygen atom in the cyclic ether ring. Specific examples include oxirane, oxetane (e.g., 3-oxetane), tetrahydrofuran (including 2-tetrahydrofuranyl and 3-tetrahydrofuranyl), tetrahydropyran (e.g., 4-tetrahydropyranyl), and oxepane.

"Aryl" refers to monocyclic and polycyclic aromatic groups having from 5 to 14 backbone carbon or hetero atoms, and includes both carbocyclic aryl groups and heteroaromatic aryl groups. Carbocyclic aryl groups are aryl groups in which all ring atoms in the aromatic ring are carbon, typically including phenyl and naphthyl. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, naphthyl, and the like. Where "aryl" is used, the group is preferably a carbocyclic group; the term "heteroaryl" is used for aryl groups when ones containing one or more heteroatoms are preferred.

The term "heteroaryl" refers herein to aryl groups having from 1 to 4 heteroatoms as ring atoms in an aromatic ring with the remainder of the ring atoms being carbon atoms, in a 5-14 atom aromatic ring system that can be monocyclic or polycyclic. Monocyclic heteroaryl rings are typically 5-6 atoms in size. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Aralkyl" or "arylalkyl" refers to an aryl group connected to a structure through an alkylene linking group, e.g., a structure such as —(CH$_2$)$_{1-4}$—Ar, where Ar represents an aryl group. "Lower aralkyl" or similar terms indicate that the alkyl linking group has up to 6 carbon atoms.

"Optionally substituted" or "substituted" refers to the replacement of one or more hydrogen atoms with a monovalent or divalent radical. Alkyl, alkenyl, alkynyl, cycloalkyl, heterocycloalkyl, aryl, and heteroaryl groups described herein may be substituted or unsubstituted. Suitable substitution groups include, for example, hydroxy, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkylamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, amino alkyl, cyanoalkyl, aryl and the like, provided that oxo, imidino or other divalent substitution groups are not placed on aryl or heteroaryl rings due to the well known valence limitations of such rings.

The substitution group can itself be substituted where valence permits, i.e., where the substitution group contains at least one CH, NH or OH having a hydrogen atom that can be replaced. The group substituted onto the substitution group can be carboxyl, halo (on carbon only); nitro, amino, cyano, hydroxy, loweralkyl, loweralkoxy, C(O)R, —OC(O)R, —OC(O)OR, —NRCOR, —CONR$_2$, —NRCOOR, —C(S)NR$_2$, —NRC(S)R, —OC(O)NR$_2$—SR, —SO$_3$H, —SO$_2$R or C3-8 cycloalkyl or 3-8 membered heterocycloalkyl, where each R is independently selected from hydrogen, lower haloalkyl, lower alkoxyalkyl, and loweralkyl, and where two R on the same atom or on directly connected atoms can be linked together to form a 5-6 membered heterocyclic ring.

When a substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

"Syn" as used herein has its ordinary meaning, and is used in connection with Formula I to indicate that the specified groups are attached to sp$^3$ hybridized (tetrahedral) carbon centers and extend out from one face of the cyclohexyl or piperidinyl ring, i.e., those groups all project toward the 'alpha' face of the ring, or they all project toward the 'beta' face of the ring. This is thus used as a convenient way to define the relative orientations of two or more groups, without limiting the compounds to a specific chiral configuration. This reflects the fact that the compounds of the invention have such groups in a specific relative orientation, but are not limited to either enantiomer of that specific relative orientation. Accordingly, unless described as optically active, such compounds may be racemic, but also include each of the two enantiomers having the specified relative stereochemistry. In some embodiments, the compounds of the invention are optically active form as further described herein, and in preferred embodiments of the invention, the compounds are obtained and used in optically active form. Preferably, the enantiomer having greater potency as an inhibitor of at least two of Pim1, Pim2 and Pim3 is selected.

It will also be apparent to those skilled in the art that the compounds of the invention, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that all tautomeric forms, insofar as they may exist, are included within the invention.

The compounds of the invention comprise one or more asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. The compounds of the invention are sometimes depicted herein as single enantiomers, and are intended to encompass the specific configuration depicted and the enantiomer of that specific configuration (the mirror image isomer of the depicted configuration), unless otherwise specified. The depicted structures herein describe the relative stereochemistry of the compounds where two or more chiral centers, but the invention is not limited to the depicted enantiomer's absolute stereochemistry unless otherwise stated. The invention includes both enantiomers, each of which will exhibit Pim inhibition, even though one enantiomer will be more potent than the other. In some instances, compounds of the invention have been synthesized in racemic form and separated into individual isomers by chiral chromatography or similar conventional methods, and the analytical data about the two enantiomers do not provide definitive information about absolute stereochemical configuration. In such cases, the absolute stereochemistry of the most active enantiomer has been identified based on correlation with similar compounds of known absolute stereochemistry, rather than by a definitive physical method such as X-ray crystallography. Therefore, in certain embodiments, the preferred enantiomer of a compound described herein is the specific isomer depicted or its opposite enantiomer, whichever has the lower IC-50 for Pim kinase inhibition using the assay methods described herein, i.e., the enantiomer that is more potent as a Pim inhibitor for at least two of Pim1, Pim2, and Pim3.

The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or base addition salts of the compounds of Formula I or II, wherein the compound acquires a positive or negative charge as a result of adding or removing a proton; the salt then includes a counterion of opposite charge from the compound itself, and the counterion is preferably one suitable for pharmaceutical administration under the conditions where the compound would be used. These salts can be prepared in situ during the final isolation and purification of the compounds of Formula I or II, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate.

Also, a basic nitrogen-containing group in compounds of the invention can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained. These quaternized ammonium salts when paired with a pharmaceutically acceptable anion can also serve as pharmaceutically acceptable salts.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Counterions for pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular pharmaceutically acceptable esters include formates, acetates, propionates, maleates, lactates, hydroxyacetates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, PRO-DRUGS AS NOVEL DELIVERY SYSTEMS, Vol. 14 of the A.C.S. Symposium Series, and in Edward B. Roche, ed., BIOREVERSIBLE CARRIERS IN DRUG DESIGN, American Pharmaceutical Association and Pergamon Press, 1987, both of which are incorporated herein by reference.

It will be apparent to those skilled in the art that the compounds of the invention, or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formula (I) or their tautomers, prodrugs and stereoisomers, as well as the pharmaceutically acceptable salts, esters and prodrugs of any of them, are included within the invention.

In one aspect, the invention provides compounds of Formula A:

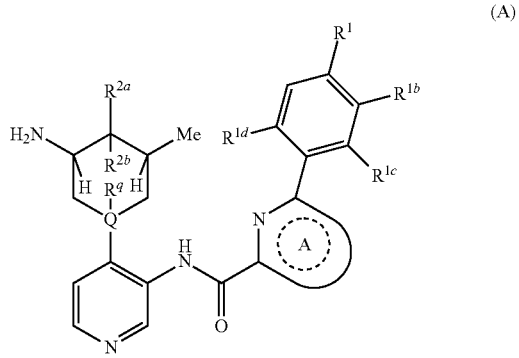

(A)

wherein:
groups attached to the ring containing Q that are depicted inside the ring are all syn to each other, and all groups attached to that ring that are depicted outside the ring are syn to one another;
Q is C or N;
$R^q$ is H when Q is C, and $R^q$ is absent when Q is N;
$R^1$ is selected from H, $C_{1-4}$ alkyl, $C_{3-6}$ cycloalkyl, $C_{4-6}$ heterocyclyl, —$(CR'_2)_{1-3}$—OR' and —OR',
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;
$R^{1b}$, $R^{1c}$, and $R^{1d}$ are each independently selected from H, halo, OR', R', —$(CH_2)_{1-2}$OR', and $CONR'_2$;
one of $R^{2a}$ and $R^{2b}$ is H,
and the other of $R^{2a}$ and $R^{2b}$ is selected from CN, halo, azido, amino, —OR, —O($CH_2$)$_{1-3}$OR, —NRC(O)R, —NRC(O)OR, —$NHSO_2R$, —$SO_2R$, —$OSO_2R$, —SR, —S(O)R, —OP(O)$R_2$, and 1-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;
where each R is independently $C_{5-6}$ heteroaryl or $C_{1-4}$ alkyl optionally substituted with up to three groups selected from cyano, halo, hydroxy, carboxy, $C_{1-4}$ alkylsulfonyl, and $C_{14}$ alkoxy;

or $R^{2a}$ and $R^{2b}$ taken together may form a dialkyl ketal or 5-6 membered cyclic ketal, =O or =N—OR", where R" is H or $C_{1-4}$ alkyl;

Ring A is selected from pyridinyl, pyrimidinyl, pyrazinyl, and thiazolyl, each having N positioned as shown in Formula (I); and Ring A is optionally substituted with 1 or 2 groups selected from halo, CN, $NH_2$, hydroxy, $C_{1-4}$ alkyl, $C_{1-4}$ haloalkyl, $C_{1-4}$ alkoxy, and $C_{1-4}$ haloalkoxy;

or a pharmaceutically acceptable salt thereof.

In some embodiments of the compounds of Formula (A), $R^{1c}$ or $R^{1d}$ or both $R^{1c}$ and $R^{1d}$ represent halo, preferably F. Typically, one of $R^1$ and $R^{1b}$, but not both, represents H. In some embodiments, $R^1$ is H and $R^{1b}$ is halo or $CONR'_2$, such as —CONHR' where R' is $C_{1-4}$ alkyl. In other embodiments, $R^{1b}$ is H, in which case $R^1$ is preferably selected from $C_{1-4}$ alkyl, $C_{3-6}$ cycloalkyl, $C_{4-6}$ heterocyclyl, —$(CR'_2)_{1-3}$—OR' and —OR', where each R' is independently H or $C_{1-4}$ alkyl, and each alkyl, cycloalkyl and heterocyclyl is optionally substituted with up to two groups selected from halo, CN, $NH_2$, hydroxy, and $C_{1-4}$ alkoxy.

In preferred embodiments of the compounds of Formula (A), Q is CH. In many embodiments of these compounds, Ring A is a pyridine or a thiazole ring. Typically, these compounds are of this formula:

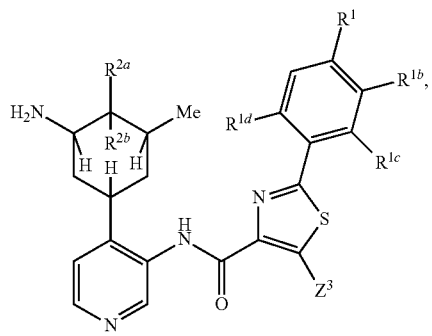

(A1)

where $Z^3$ is H or $NH_2$,
or of this formula

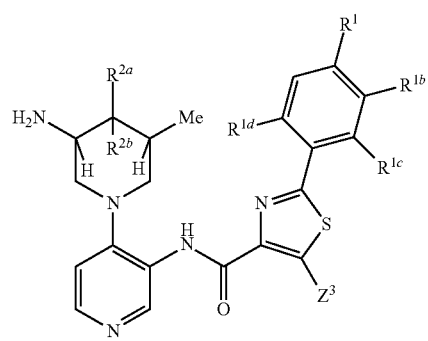

(A2)

wherein $Z^3$ is H or $NH_2$,
and $R^1$, $R^{1b}$, $R^{1c}$, $R^{1d}$, $R^{2a}$ and $R^{2b}$ are as defined above for any of the embodiments of compounds of Formula (A).

Specific embodiments of these compounds include Formula A2 and A3:

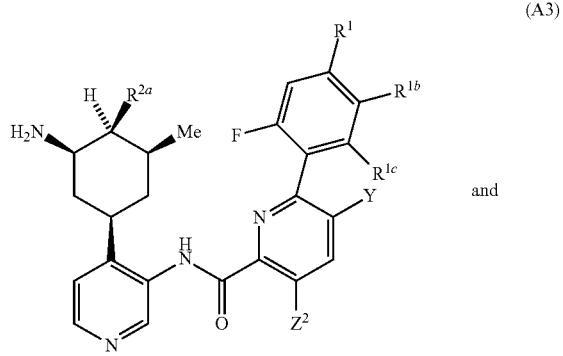

(A3)

and

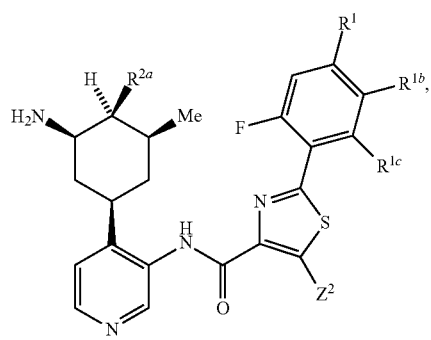

(A4)

where each $Z^2$ is H or amino, Y is halo or H, and $R^1$, $R^{1b}$, $R^{1c}$ and $R^{2a}$ are as defined above for any of the embodiments of compounds of Formula (A). In some embodiments, for example, $R^{1c}$ is F, and $R^{1b}$ is H.

In some of these embodiments, $R^{2a}$ is preferably methoxy. In other embodiments wherein $R^{2b}$ is H, $R^{2a}$ is —OMe or —O(CH_2)_2—X, wherein X is —OMe, COOH, CN or —SO_2Me, or $R^{2a}$ is 1-triazolyl (e.g., 1,2,3-triazolyl) that is optionally substituted with up to two groups selected from halo, $C_{1-4}$ alkyl, hydroxy-substituted $C_{1-4}$ alkyl, $C_{2-4}$ alkenyl, and $C_{1-4}$ alkoxy, or —SO_2Me.

In some embodiments of these compounds of Formula (A), A1, A2, A3 or A4, $R^{2a}$ is —OMe or —O(CH_2)_2—X, wherein X is —OMe, COOH, CN or —SO_2Me; preferably $R^{2a}$ is —OMe or —OCH_2CH_2CN. $R^1$ in some embodiments of these compounds can be selected from 2-hydroxy-2-propyl, methoxymethyl, ethoxymethyl, methoxy, ethoxy, isopropoxy, cyclopropyl, cyclobutyl, 1-hydroxycyclobutyl, cyclopentyl, tetrahydropyranyl, 4-f, 4-hydroxy-4-tetrahydropyranyl, 4-tetrahydropyranyloxy, and 4-tetrahydropyranyl.

In certain embodiments, the compounds of Formula (A) have the Formula (I):

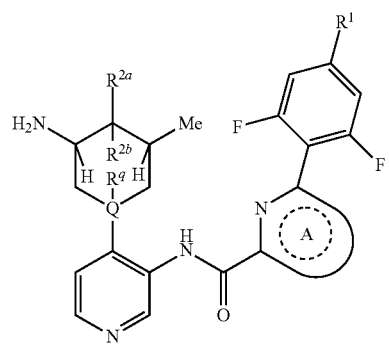

$R^1$ is selected from H, $C_{1-4}$ alkyl, $C_{3-6}$ cycloalkyl, $C_{4-6}$ heterocyclyl, —$(CR'_2)_{1-3}$—OR' and —OR',
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;
one of $R^{2a}$ and $R^{2b}$ is H,
and the other of $R^{2a}$ and $R^{2b}$ is selected from CN, halo, azido, amino, —OR, —O(CH$_2$)$_{1-3}$OR, —NRC(O)R, —NRC(O)OR, —NHSO$_2$R, —SO$_2$R, —OSO$_2$R, —SR, —S(O)R, —OP(O)R$_2$, and triazolyl optionally substituted with up to two groups selected from halo, $C_{1-4}$ alkyl, hydroxy-substituted $C_{1-4}$ alkyl, $C_{3-6}$ cycloalkyl, $C_{1-4}$ alkoxy, and $C_{5-6}$heteroaryl;
where each R is independently $C_{1-4}$ alkyl optionally substituted with up to three groups selected from cyano, halo, hydroxy, carboxy, $C_{1-4}$ alkylsulfonyl, and $C_{1-4}$ alkoxy;
or $R^{2a}$ and $R^{2b}$ taken together form a dialkyl ketal or 5-6 membered cyclic ketal, =O or =N—OR", where R" is H or $C_{1-4}$ alkyl;
ring A is selected from pyridinyl, pyrimidinyl, pyrazinyl, and thiazolyl, each having N positioned as shown in Formula (I); and
Ring A is optionally substituted with 1 or 2 groups selected from halo, CN, $NH_2$, hydroxy, $C_{1-4}$ alkyl, $C_{1-4}$haloalkyl, $C_{1-4}$alkoxy, and $C_{1-4}$haloalkoxy;
or a pharmaceutically acceptable salt thereof.

The following enumerated embodiments represent additional aspects and variations of the invention:

1. A compound of Formula (A)

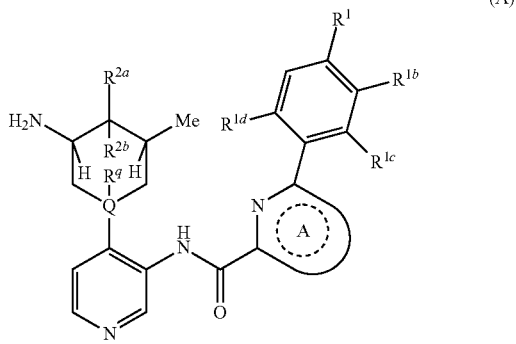

(A)

wherein:
groups attached to the ring containing Q that are depicted inside the ring are all syn to each other, and all groups attached to that ring that are depicted outside the ring are syn to one another;
Q is C or N;
$R^q$ is H when Q is C, and $R^q$ is absent when Q is N;
$R^1$ is selected from H, $C_{1-4}$ alkyl, $C_{3-6}$ cycloalkyl, $C_{4-6}$ heterocyclyl, —$(CR'_2)_{1-3}$—OR' and —OR',
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$haloalkyl, $C_{1-4}$alkoxy, and $C_{1-4}$haloalkoxy;
$R^{1b}$, $R^{1c}$, and $R^{1d}$ are each independently selected from H, halo, OR', R', —(CH$_2$)$_{1-2}$OR', and CONR'$_2$;
one of $R^{2a}$ and $R^{2b}$ is H,
and the other of $R^{2a}$ and $R^{2b}$ is selected from CN, halo, azido, amino, —OR, —O(CH$_2$)$_{1-3}$OR, —NRC(O)R, —NRC(O)OR, —NHSO$_2$R, —SO$_2$R, —OSO$_2$R, —SR, —S(O)R, —OP(O)R$_2$, and 1-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;
where each R is independently $C_{5-6}$heteroaryl or $C_{1-4}$ alkyl optionally substituted with up to three groups selected from cyano, halo, hydroxy, carboxy, $C_{1-4}$ alkylsulfonyl, and $C_{1-4}$ alkoxy;
or $R^{2a}$ and $R^{2b}$ taken together may form a dialkyl ketal or 5-6 membered cyclic ketal, =O or =N—OR", where R" is H or $C_{1-4}$ alkyl;
ring A is selected from pyridinyl, pyrimidinyl, pyrazinyl, and thiazolyl, each having N positioned as shown in Formula (I); and
Ring A is optionally substituted with 1 or 2 groups selected from halo, CN, $NH_2$, hydroxy, $C_{1-4}$ alkyl, $C_{1-4}$haloalkyl, $C_{1-4}$ alkoxy, and $C_{1-4}$haloalkoxy;
or a pharmaceutically acceptable salt thereof 2. The compound of Formula (A) according to embodiment 1, wherein one but not both, of $R^{1b}$ and $R^1$ represents H.
3. The compound of embodiment 1, wherein $R^{1d}$ is F.
4. The compound of embodiment 1 or 2, wherein $R^{1c}$ is F.
5. The compound of any of embodiments 1-3, wherein $R^{1b}$ is H.
6. The compound of any of embodiments 1-3, wherein $R^{1b}$ is H or CONR'$_2$.
7. The compound of any of embodiments 1-6, wherein $R^{2b}$ is H.
8. The compound of any of embodiments 1-7, wherein $R^{2a}$ is —OMe, —SO$_2$Me, —NHCOOMe, or —O(CH$_2$)$_2$—X, wherein X is —OMe, COOH, CN or —SO$_2$Me, or $R^{2a}$ is 1-triazolyl (e.g., 1,2,3-triazolyl) or 1-pyridonyl that is optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, and $C_{1-4}$alkoxy, or —SO$_2$Me.
9. The compound of any of embodiments 1-8, wherein $R^1$ is selected from 2-hydroxy-2-propyl, methoxymethyl, ethoxymethyl, methoxy, ethoxy, isopropoxy, cyclopropyl, cyclobutyl, 1-hydroxycyclobutyl, cyclopentyl, tetrahydropyranyl, 4-F, 4-hydroxy-4-tetrahydropyranyl, 4-tetrahydropyranyloxy, and 4-tetrahydropyranyl.
10. The compound of any of embodiments 1-6, wherein $R^{2b}$ is OMe.
11. The compound of embodiment 1, which is a compound of Formula (I):

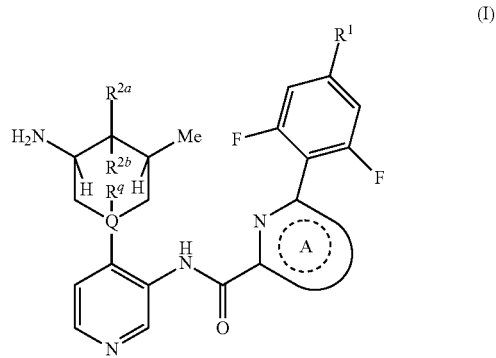

(I)

wherein:
groups attached to the ring containing Q that are depicted inside the ring are all syn to each other, and all groups attached to that ring that are depicted outside the ring are syn to one another;
Q is C or N;
$R^q$ is H when Q is C, and $R^q$ is absent when Q is N;
$R^1$ is selected from H, $C_{1-4}$ alkyl, $C_{3-6}$ cycloalkyl, $C_{4-6}$ heterocyclyl, —$(CR'_2)_{1-3}$—OR' and —OR',
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$haloalkyl, $C_{1-4}$alkoxy, and $C_{1-4}$ haloalkoxy;
one of $R^{2a}$ and $R^{2b}$ is H,
and the other of $R^{2a}$ and $R^{2b}$ is selected from CN, halo, azido, amino, —OR, —O($CH_2$)$_{1-3}$OR, —NRC(O)R, —NRC(O)OR, —NHSO$_2$R, —SO$_2$R, —OSO$_2$R, —SR, —S(O)R, —OP(O)R$_2$, and N-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;
where each R is independently $C_{5-6}$ heteroaryl or $C_{1-4}$ alkyl optionally substituted with up to three groups selected from cyano, halo, hydroxy, carboxy, $C_{1-4}$ alkylsulfonyl, and $C_{1-4}$ alkoxy;
or $R^{2a}$ and $R^{2b}$ taken together may form a dialkyl ketal or 5-6 membered cyclic ketal, =O or =N—OR", where R" is H or $C_{1-4}$ alkyl;
Ring A is selected from pyridinyl, pyrimidinyl, pyrazinyl, and thiazolyl, each having N positioned as shown in Formula (I); and
Ring A is optionally substituted with 1 or 2 groups selected from halo, CN, $NH_2$, hydroxy, $C_{1-4}$ alkyl, $C_{1-4}$haloalkyl, $C_{1-4}$ alkoxy, and $C_{1-4}$haloalkoxy;
or a pharmaceutically acceptable salt thereof
12. The compound of embodiment 11, wherein $R^{2a}$ is H.
13. The compound of embodiment 11, wherein $R^{2b}$ is H.
14. The compound of embodiment 11 or 13, wherein $R^{2a}$ is —NHCOOMe.
15. The compound of embodiment 11 or 13, wherein $R^{2a}$ is —O(CH$_2$)$_2$—CN.
16. The compound of embodiment 11 or 13, wherein $R^{2a}$ is —O(CH$_2$)$_2$—SO$_2$Me.
17. The compound of embodiment 11 or 13, wherein $R^{2a}$ is —OMe.
18. The compound of embodiment 11 or 13, wherein $R^{2a}$ is —SO$_2$Me.
19. The compound of and embodiment 11 or 12, wherein $R^{2b}$ is —OMe.
20. The compound of embodiment 11, wherein $R^{2a}$ and $R^{2b}$ taken together form =O or =N—OR", where R" is H or $C_{1-4}$ alkyl.
21. The compound of any of embodiments 11-20, wherein $R^1$ is selected from H, methyl, ethyl, isopropyl, 2-hydroxy-2-propyl, methoxymethyl, ethoxymethyl, methoxy, ethoxy, isopropoxy, cyclopropyl, cyclobutyl, 1-hydroxycyclobutyl, cyclopentyl, tetrahydrofuranyl, 4-fluoro-4-tetrahydrofuranyl, tetrahydrothiopyran, and 4-tetrahydrothiopyran-1,1-dioxide.
22. The compound of embodiment 21, wherein $R^1$ is selected from H, Me, tetrahydropyran, methoxymethyl, and ethoxymethyl.
23. The compound of any one of the preceding embodiments, wherein Ring A is pyridine, and is optionally substituted with F or amino.
24. The compound of any one of embodiments 11-21, wherein Ring A is a thiazolyl, optionally substituted with amino.
25. The compound of any of embodiments 11-24, wherein $R^{2a}$ is selected from the group consisting of —OR, —OCH$_2$CH$_2$OR, —OCH$_2$CH$_2$CN, —OCH$_2$CH$_2$COOH, —OCH$_2$CH$_2$SO$_2$R, —CN, —NHC(O)OR, —NHC(O)R, N$_3$, NH$_2$, F, —NHSO$_2$R, —SO$_2$R, —SR, —S(O)R, unsubstituted triazole, and triazole substituted with Me, ethyl, cyclopropyl, hydroxymethyl, $C_{24}$ alkenyl, or thienyl;
wherein each R is methyl, ethyl or isopropyl.
26. The compound of any one of embodiments 11-24, wherein $R^{2b}$ is selected from the group consisting of —OR, —OCH$_2$CH$_2$OR, —OCH$_2$CH$_2$CN, —OCH$_2$CH$_2$COOH, —OCH$_2$CH$_2$SO$_2$R, —CN, —NHC(O)OR, —NHC(O)R, N$_3$, NH$_2$, F, —NHSO$_2$R, —SO$_2$R, —SR, —S(O)R, unsubstituted triazole, and triazole substituted with Me, ethyl, cyclopropyl, hydroxymethyl, $C_{24}$ alkenyl, or thienyl;
wherein each R is methyl, ethyl or isopropyl.
27. The compound of embodiment 11, wherein $R^{2a}$ is —SO$_2$Me, —OCH$_2$CH$_2$CN, 1,2,4-triazol-1-yl, —OCH$_2$CH$_2$COOH, —OCH$_2$CH$_2$SO$_2$R, —CN, or —NHC(O)OMe.
28. The compound of embodiment 12, wherein $R^{2b}$ is —OMe, —CN, —OCH$_2$CH$_2$CN, 1,2,4-triazol-1-yl, —OCH$_2$CH$_2$COOH, —OCH$_2$CH$_2$SO$_2$R, —CN, or —NHC(O)OMe.
29. The compound of any of the preceding embodiments, wherein Q is C.
30. The compound of any of embodiments 1-28, wherein Q is N.
31. The compound of any of the preceding embodiments, which is optically active and has a lower IC-50 than its opposite enantiomer on at least one Pim kinase.
32. The compound of embodiment 31, wherein the at least one Pim kinase is Pim2 kinase.
33. The compound of any one of embodiments 11-32, which is an optically active compound of Formula IIa or IIb: or

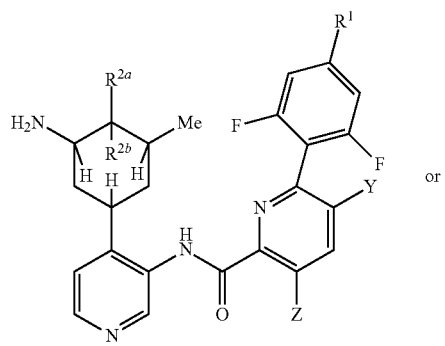

IIa

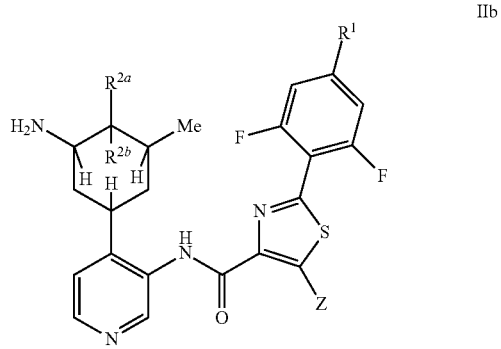

IIb wherein Y is H or F, and Z is H or $NH_2$.

34. The compound of any one of embodiments 11-32, which is an optically active compound of Formula IIIa or IIIb:

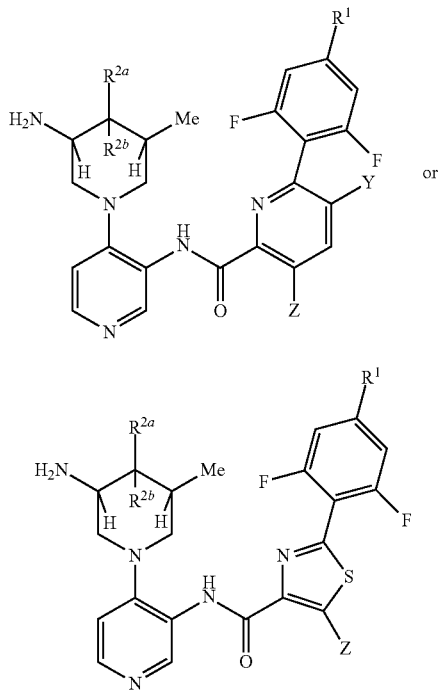

wherein Y is H or F, and Z is H or NH$_2$.

35. The compound of embodiment 33, which is a compound of Formula IIa.
36. The compound of embodiment 33, which is a compound of Formula IIb.
37. The compound of embodiment 34, which is a compound of Formula IIa.
38. The compound of embodiment 34, which is a compound of Formula IIb.
39. A compound selected from the group consisting of the compounds in Table 1 and Table 2, and the pharmaceutically acceptable salts thereof.
40. A pharmaceutical composition comprising a compound of any of embodiments 1-39, admixed with at least one pharmaceutically acceptable excipient.
41. The pharmaceutical composition of embodiment 40 which further comprises an additional agent for treatment of cancer.
42. The pharmaceutical composition of embodiment 41, wherein the additional therapeutic agent is selected from MEK inhibitors, irinotecan, topotecan, gemcitabine, 5-fluorouracil, cytarabine, daunorubicin, PI3 Kinase inhibitors, mTOR inhibitors, DNA synthesis inhibitors, leucovorin, carboplatin, cisplatin, taxanes, tezacitabine, cyclophosphamide, vinca alkaloids, imatinib, anthracyclines, rituximab, lenalidomide, bortezomib and trastuzumab
43. A compound of any of embodiments 1-39 for use in the treatment of a condition that responds to inhibitors of Provirus Integration of Moloney Kinase (PIM Kinase) activity.
44. The compound according to embodiment 43, wherein the condition is a cancer.
45. The compound according to embodiment 44, wherein the cancer is selected from carcinoma of the lungs, pancreas, thyroid, ovaries, bladder, breast, prostate or colon, melanoma, myeloid leukemia, multiple myeloma, erythro leukemia, villous colon adenoma, and osteosarcoma.
46. The compound of embodiment 45, wherein the condition is an autoimmune disorder.
47. A method of treating a disease or condition mediated by PIM kinase, comprising administering to a subject in need thereof a therapeutically effective amount of a compound according to any one of embodiments 1-39, or a pharmaceutically acceptable salt thereof
48. The method of embodiment 47, wherein the disease is selected from carcinoma of the lungs, pancreas, thyroid, ovaries, bladder, breast, prostate or colon, melanoma, myeloid leukemia, multiple myeloma, erythro leukemia, villous colon adenoma, and osteosarcoma; or the disease is an autoimmune disorder.
49. The method of embodiment 48, wherein the disease is an autoimmune disorder.
50. The method of embodiment 49, wherein the autoimmune disorder is selected from Crohn's disease, inflammatory bowel disease, rheumatoid arthritis, and chronic inflammatory diseases.

In some embodiments, at least one substituent for Ar is selected from F, Cl, NH$_2$, Me, Et, OMe, OEt, OCF$_3$, OCHF$_2$, OCH$_2$CF$_3$, CN, CF$_3$, SMe, SOMe, SO$_2$Me, —COOMe, —C(O)Me, —C(Me)$_2$-OH, MeOCH$_2$—, HOCH$_2$—, hydroxyethyl, hydroxyethoxy, methoxyethyl, methoxyethoxy, oxetanyl (e.g., 3-oxetanyl), isopropoxy, tetrahydropyranyloxy (e.g., 4-tetrahydropyranyloxy), cyclopropyl, and CN. At least one substituent for Ar is preferably selected from Me, F, NH$_2$, OMe, MeOCH$_2$—, HOCH$_2$—, hydroxyethyl, hydroxyethoxy, methoxyethyl, methoxyethoxy, and CN.

These compounds may be used in racemic form, or the individual enantiomers may be used, or mixtures of the enantiomers may be used. Each enantiomer can be used, and preferably the compound to be used is the enantiomer that has greater activity as a Pim inhibitor.

The cyclohexyl or piperidine ring in these compounds has three non-hydrogen substituents, not counting its attachment to the pyridinyl ring in Formula I. The invention provides novel combinations of substituents and their relative stereochemical orientation on the cyclohexyl or piperidinyl ring, to provide advantageous biological activities. Advantages provided by preferred compounds include reduced drug-drug interactions, due to reduction of time-dependent Cyp inhibition or pharmacokinetic superiority based on improved clearance and metabolic properties.

In one preferred embodiment of the claimed invention, the compound is of formula IIc or IId, (IIc)

-continued (IId)

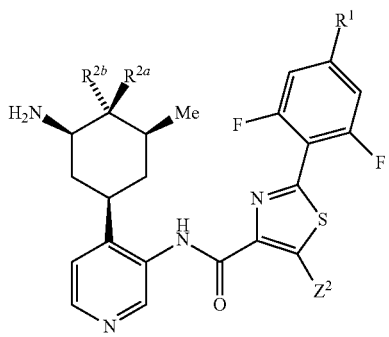

wherein Y is H or F, and $Z^2$ is H or $NH_2$; or. In these compounds, $R^{2a}$ is preferably —OR, —O(CH$_2$)$_{1-3}$OR, —SO$_2$R, or —NRC(O)OR, where each R is independently C$_{14}$ alkyl optionally substituted with cyano, halo, hydroxy, carboxy, C$_{14}$ alkylsulfonyl, or C$_{14}$ alkoxy; and $R^{2b}$ is H. In some such embodiments, $R^{2a}$ is preferably —OR, —O(CH$_2$)$_{1-3}$OR, or —NRC(O)OR, where each R is independently C$_{1-4}$ alkyl optionally substituted with cyano, halo, hydroxy, carboxy, C$_{1-4}$ alkylsulfonyl, or C$_{1-4}$ alkoxy; and $R^{2b}$ is H In some preferred embodiments, $R^{2a}$ is OMe. In these compounds, $R^1$ can be H, Me, 4-tetrahydropyranyl, or 2-hydroxy-2-propyl. In specific embodiments, $R^{2a}$ is —OMe, —OCH$_2$CH$_2$CN, —OCH$_2$CH$_2$OMe, or —OCH$_2$CH$_2$SO$_2$Me or —NHCOOMe, or —N(Me)COOMe. Preferably when $R^{2b}$ is H, $R^1$ is not H.

In another embodiment, the compound is of Formula IIe or IIf:

(IIe)

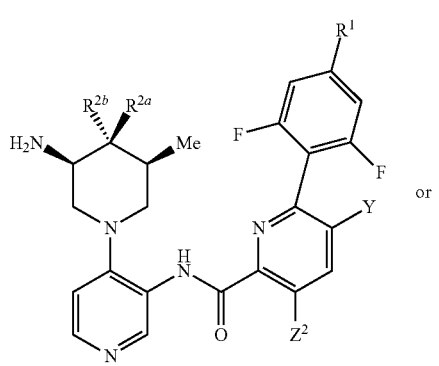

or (IIf)

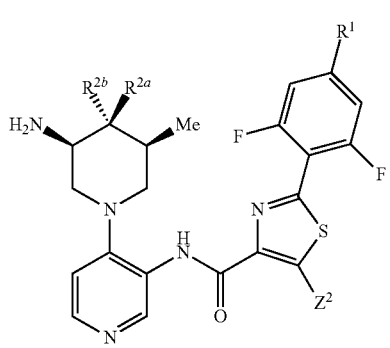

wherein Y is H or F, and $Z^2$ is H or $NH_2$. In these compounds, $R^{2a}$ is preferably —OR, —O(CH$_2$)$_{1-3}$OR, —SO$_2$R, or —NRC(O)OR, where each R is independently C$_{1-4}$ alkyl optionally substituted with cyano, halo, hydroxy, carboxy, C$_{1-4}$ alkylsulfonyl, or C$_{1-4}$ alkoxy; and $R^{2b}$ is H. In some such embodiments, $R^{2a}$ is —OR, —O(CH$_2$)$_{1-3}$OR, or —NRC(O) OR, where each R is independently C$_{1-4}$ alkyl optionally substituted with cyano, halo, hydroxy, carboxy, C$_{1-4}$ alkylsulfonyl, or C$_{1-4}$ alkoxy; and $R^{2b}$ is H In some preferred embodiments, $R^{2a}$ is OMe. In these compounds, $R^1$ can be H, Me, 4-tetrahydropyranyl, or 2-hydroxy-2-propyl. In specific embodiments, $R^{2a}$ is —OMe, —OCH$_2$CH$_2$CN, —OCH$_2$CH$_2$OMe, or —OCH$_2$CH$_2$SO$_2$Me or —NHCOOMe, or —N(Me)COOMe. Preferably when $R^{2b}$ is H, $R^1$ is not H.

Each of the species in Tables 1 and 2 are preferred embodiments of the invention.

For purposes of the present invention, a therapeutically effective dose will generally be a total daily dose administered to a host in single or divided doses may be in amounts, for example, of from 0.001 to 1000 mg/kg body weight daily, typically 0.01 to 10 mg/kg per day, and more preferred from 0.1 to 30 mg/kg body weight daily. Generally, daily dosage amounts of 1 to 4000 mg, or from 5 to 3000, or from 10 to 2000 mg, or from 100 to 2000 mg are anticipated for human subjects. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: MEK inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known therapeutic or anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

In certain presently preferred embodiments of the invention, representative therapeutic agents useful in combination with the compounds of the invention for the treatment of cancer include, for example, MEK inhibitors, irinotecan, topotecan, gemcitabine, 5-fluorouracil, cytarabine, daunorubicin, PI3 Kinase inhibitors, mTOR inhibitors, DNA synthesis inhibitors, leucovorin carboplatin, cisplatin, taxanes, tezacitabine, cyclophosphamide, vinca alkaloids, imatinib (Gleevec), anthracyclines, rituximab, trastuzumab, Revlimid, Velcade, dexamethasone, daunorubicin, cytaribine, clofarabine, Mylotarg, lenalidomide, bortezomib, as well as other cancer chemotherapeutic agents including targeted therapuetics.

The above compounds to be employed in combination with the compounds of the invention will be used in therapeutic amounts as indicated in the *Physicians' Desk Reference* (*PDR*) 47th Edition (1993), which is incorporated herein by reference, or such therapeutically useful amounts as would be known to one of ordinary skill in the art, or provided in prescribing materials such as a drug label for the additional therapeutic agent.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In one embodiment, the invention provides a method of inhibiting Pim1, Pim2 or Pim3 in a human or animal subject. The method includes administering an effective amount of a compound, or a pharmaceutically acceptable salt thereof, of any of the embodiments of compounds of Formula I or II to a subject in need thereof.

The present invention will be understood more readily by reference to the following examples, which are provided by way of illustration and are not intended to be limiting of the present invention.

Synthetic Methods

The compounds of the invention can be obtained through procedures known to those skilled in the art. As shown in Scheme 1, 5-alkyl, 4-hydroxy, 3-aminopiperidines can be prepared and modified to yield 5-alkyl, 4-substituted, 3-aminopiperidinyl pyridine amides VI as follows. Reaction of Garner's aldehyde with (R)-4-benzyl-3-propionyloxazolidin-2-one followed by TBS protection of the resulting alcohol affords compound I. Reduction of the oxazolidinone followed by introduction of the azide group yields intermediate II. Deprotection under acidic conditions reveals the corresponding amino alcohol, which upon protection with the Boc group followed by mesylation of the primary alcohol yields intermediate III. Reduction of the azide affords formation of the piperidine which is subsequently reacted with 4-chloro-3-nitropyridine and following nitro reduction pyridyl aniline IV is obtained. Aniline IV can be coupled with heterocyclic acids, which after silyl group deprotection (Va) and modification of the hydroxyl (activation as mesylate, displacement and potentially further modification of the displaced group) and Boc deprotection can afford target amides VI. Alternatively, aniline IV can be Boc protected, silyl deprotected (Vb), modified at the hydroxyl position and after aniline Boc deprotection (Vc), amide coupling and Boc deprotection, 5-alkyl, 4-substitued, 3-aminopiperidinyl pyridine amides VI can be obtained.

Scheme 1

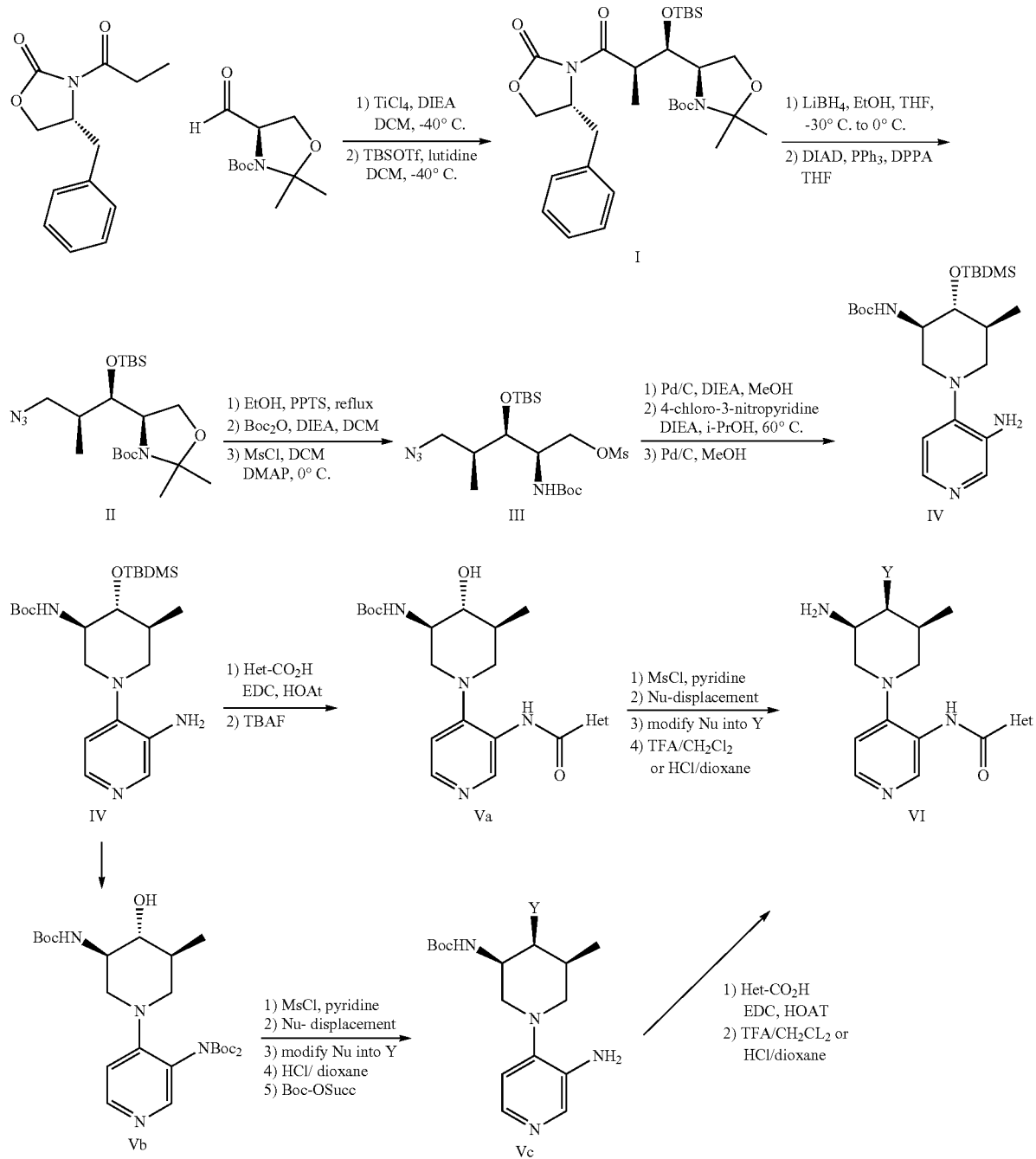

In Scheme 2, synthetic methods to prepare tetrasubstituted aminocyclohexylpyridyl amides X are depicted. Methyl cyclohexanedione can be converted via the monotriflate to the corresponding cyclohexenoneboronate ester which can undergo palladium mediated carbon bond formation with 4-chloro, 3-nitro pyridine to yield nitropyridine substituted cyclohexenone VII. Ketone reduction followed by dehydration yields a cyclohexadiene which upon epoxidation (via bromohydrin formation and HBr elimination), azide epoxide opening, azide reduction and amine Boc protection yields cyclohexenyl Boc amino alcohol nitro pyridyl compound VIII. Nitro pyridyl VIII can be converted to the trans protected amino hydroxy aniline IXa by alcohol protection and alkene and nitro reduction. Alternatively, the alcohol moiety of nitropyridyl VIII can be inverted via a mesylation, cyclization, Boc protection and hydrogenation sequence to provide the all cis substituted cyclohexyl pyridyl aniline IXb, where the cis hydroxy is protected in the form of a cylic carbamate. As described above in Scheme 1 for the preparation of substituted piperidine compounds of the invention, upon amide coupling of the cyclohexyl pyridyl anilines IXa or IXb to heterocyclic acids and subsequent hydroxyl and amine deprotection, substituted cyclohexyl compounds of the invention Xa and Xb can be prepared.

Scheme 2
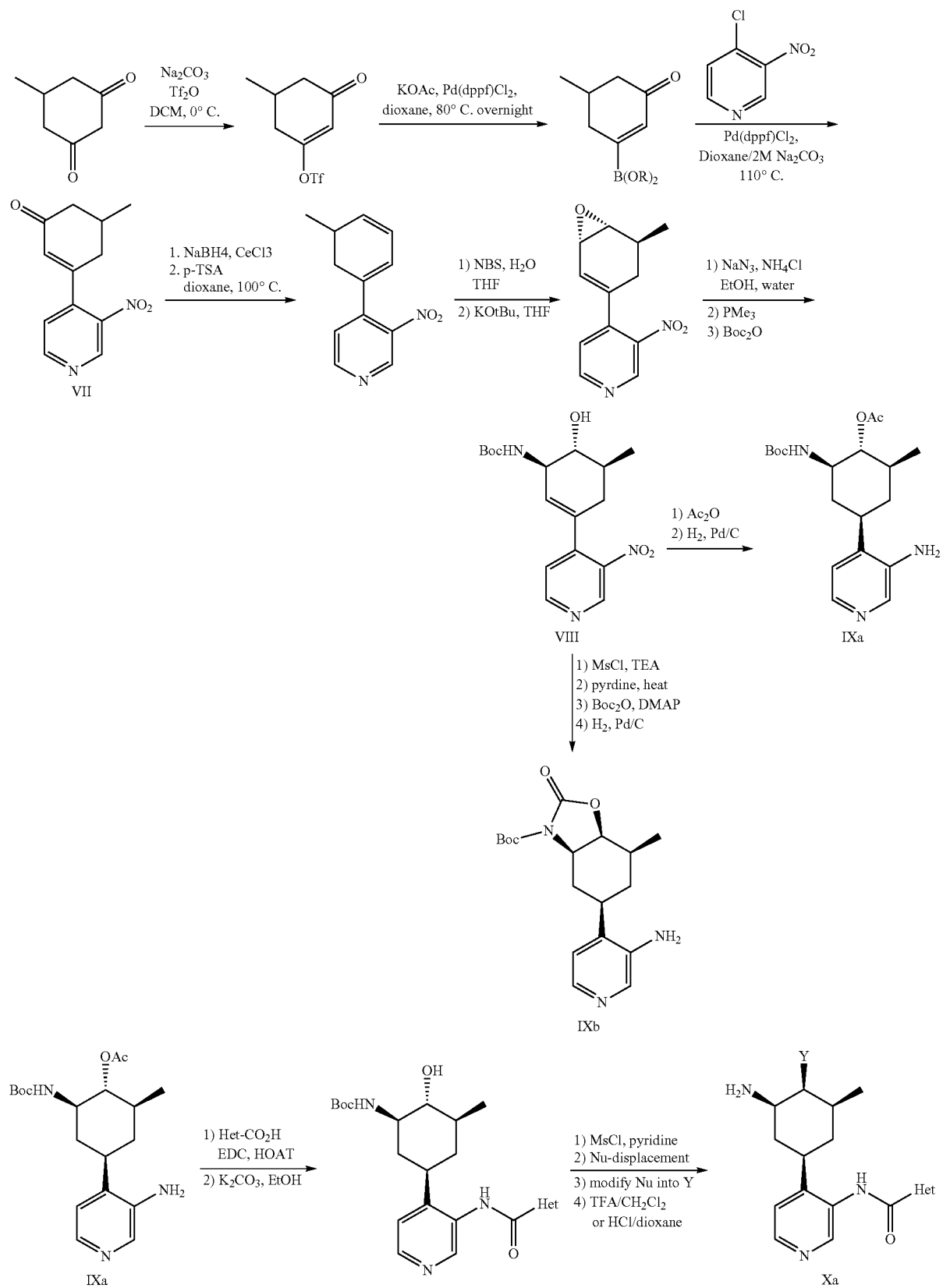

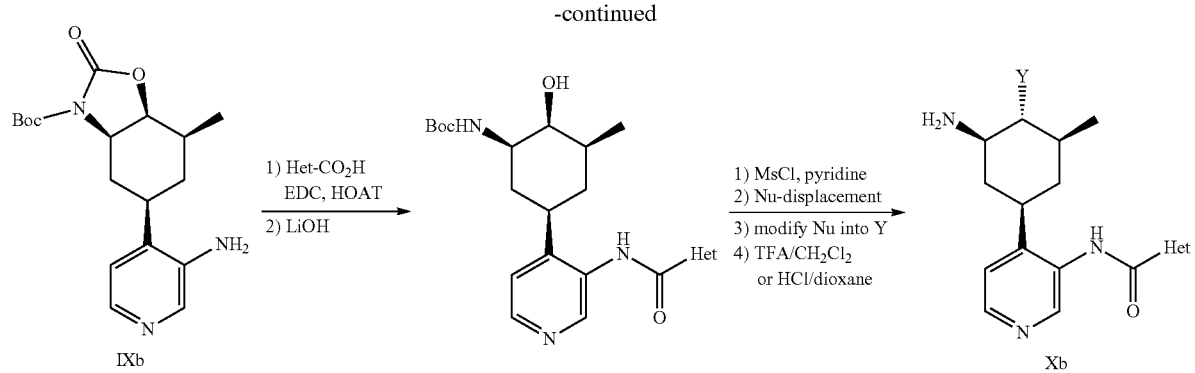

In Scheme 3, additional synthetic methods to prepare tetrasubstituted aminocyclohexylpyridyl amides X are depicted in which the cyclohexyl systems are modified prior to coupling of the aniline to heterocyclic acids. For example, aniline IXa can be Boc protected, acetyl deprotected, modified at the hydroxyl position and after a net aniline Boc deprotection, amide coupling and Boc deprotection, substituted aminocyclohexylpyridyl amides Xa can be obtained. In an alternative manner, the cyclohexenyl Boc amino alcohol nitro pyridyl compound VIII can be modified at the hydroxyl position and after alkene and nitro reduction, amide coupling and Boc deprotection, substituted aminocyclohexylpyridyl amides Xc can be obtained. Additionally, the hydroxyl group of VIII can be inverted via mesylation, intramolecular cyclization, Boc protection and cyclic carbamate opening to yield an alcohol that after processing as described above can yield substituted aminocyclohexylpyridyl amides Xd. For the sequences depicted in Shemes 1-3, the aliphatic amine is primarily protected as a Boc derivative. As one skilled in the art would expect, alternative protecting groups and subsequent deprotection conditions for the amine and hydroxy moieties can be utilized.

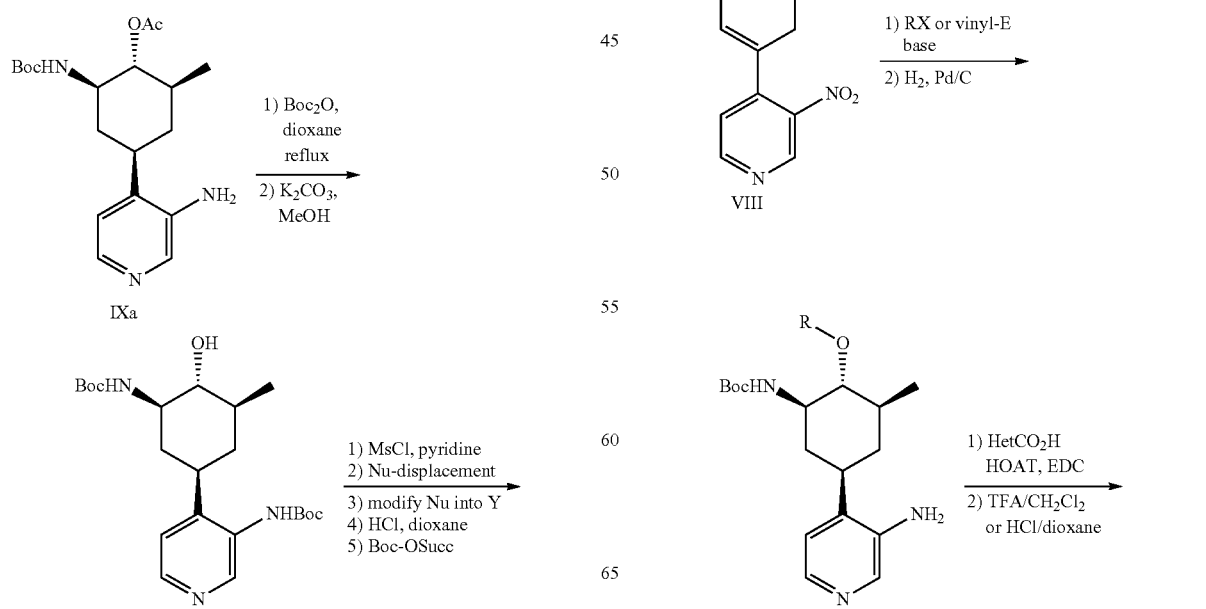

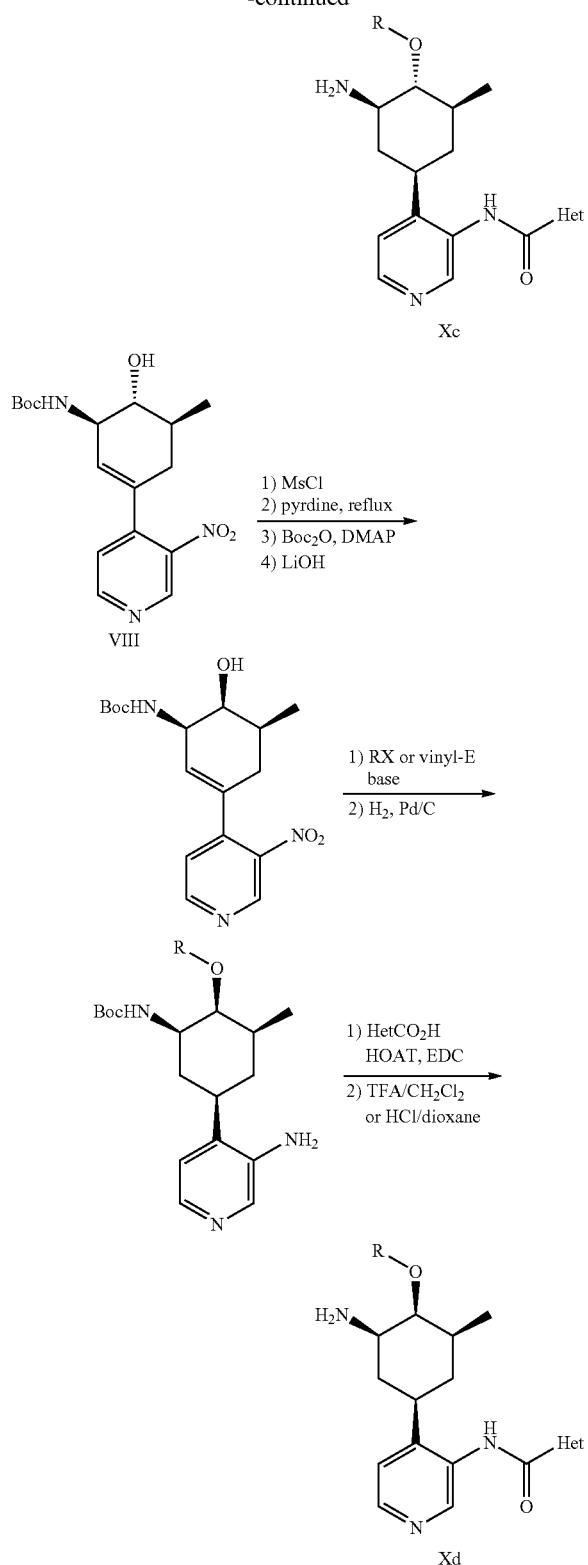

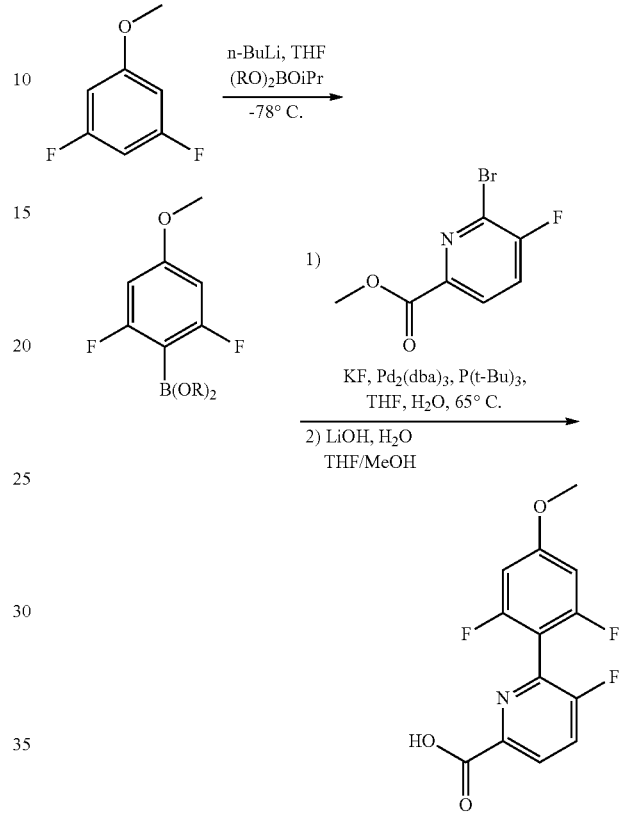

Suzuki coupling with the bromofluoro picolinate ester and subsequent ester hydrolysis yields the fluoro picolinic acid XI.

A representative route to a heterocyclic acid that can be incorporated into compounds VI, Xa-Xd of the invention is depicted in Scheme 4. Lithiation of 5-methoxy, 1,3 difluorobenzene and reaction with 2-isopropoxy-4,4,5,5-tetramethyl-1,3,2-dioxaborolane yields a boranate ester which upon

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18–5 μ, 4.6×50 mm, from Alltech (Deerfield, Ill.). A gradient elution was used (flow 2.5 mL/min), typically starting with 5% acetonitrile/ 95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY UPLC system and a ZQ 2000 system; Column: ACQUITY UPLC HSS-C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

Preparative separations are carried out using a Flash 40 chromatography system and KP-Sil, 60A (Biotage, Charlottesville, Va.), or by flash column chromatography using silica gel (230-400 mesh) packing material on ISCO or Analogix purification systems, or by HPLC using a Waters 2767 Sample Manager, C-18 reversed phase column, 30×50 mm, flow 75 mL/min. Typical solvents employed for the Flash 40 Biotage, ISCO or Analogixsystem for silica gel column chromatography are dichloromethane, methanol, ethyl acetate, hexane, n-heptanes, acetone, aqueous ammonia (or ammonium hydroxide), and triethyl amine. Typical solvents employed for the reverse phase HPLC are varying concentrations of acetonitrile and water with 0.1% trifluoroacetic acid.

Chiral separations of enantiomeric mixtures were performed by the following analytical and preparative general methods:

Chiral SFC-Analytical Method: Chiral compounds were separated on a Waters Supercritical Fluid Chromatography (SFC). The separation used a Chiralpak AD (AS, OD, OJ, IC or IA) 4.6×100 mm column at 40 C temperature at a flow rate of 5 mL/min using an isocratic method. The mobile phase was 15% MeOH (or EtOH or IPA or with 0.1% Diethyl amine) 85% CO2. The detection wavelength was 220 nm (or 250 nm or Diode Array) Chiral SFC-Purification Method: Chiral compounds were separated on a Waters Supercritical Fluid Chromatography (SFC). The separation used a Chiralpak AD (AS, OD, OJ, IC or IA) 21×250 mm column at 40 C temperature at a flow rate of 100 mL/min using an isocratic method. The mobile phase was 15% MeOH (or EtOH or IPA or with 0.1% Diethyl amine) 85% CO2. The detection wavelength was 220 nm (or 250 nm or Diode Array).

Chiral HPLC-Analytical Method: Chiral compounds were separated on a Waters 2695 HPLC system. The separation used a Chiralpak AD (AS, OD, OJ, IC or IA) 4.6×100 mm column at room temperature at a flow rate of 1 mL/min using an isocratic method. The mobile phase was 15% EtOH (or IPA or with 0.1% Diethyl amine): 85% Heptane. The detection wavelength was 220 nm (or 250 nm or Diode Array).

Chiral HPLC-Purification Method: Chiral compounds were separated on a Waters 2767 HPLC system. The separation used a Chiralpak AD (AS, OD, OJ, IC or IA) 21×250 mm column at room temperature at a flow rate of 20 (or 10-15) mL/min using an isocratic method. The mobile phase was 15% EtOH (or IPA or with 0.1% Diethyl amine): 85% Heptane. The detection wavelength was 220 nm (or 250 nm or Diode Array).

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

| ABBREVIATIONS | |
|---|---|
| BINAP | 2,2'-Bis(diphenylphosphino)-1,1'-binaphthalene |
| Boc$_2$O | di-tert-butyl dicarbonate |
| Boc-OSu | N-(tert-Butoxycarbonyloxy)succinimide |
| Cbz-OSu | N-(Benzyloxycarbonyloxy)succinimide |
| DAST | (diethylamino)sulfurtrifluoride |
| DBU | 1,8-Diazabicyclo[5.4.0]undec-7-ene |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| K$_2$CO$_3$ | Potassium carbonate |
| KSAc | Potassium thioacetate |
| Lawesson's reagent | 2,4-bis(4-methoxyphenyl)-1,3,2,4-dithiadiphosphetane-2,4-dithione |
| LiOH | Lithium hydroxide |
| MCPBA | Meta-chloroperbenzoic acid |
| MeCN | Acetonitrile |
| methylDAST | (dimethylamino)sulfurtrifruoride |
| MgSO$_4$ | Magnesium sulfate |
| MeOH | Methanol |
| MsCl | Methane sulfonyl chloride |
| Na$_2$CO$_3$ | sodium carbonate |
| NaCl | Sodium chloride |
| NaHCO$_3$ | sodium bicarbonate |
| NaHMDS | Sodium bis(trimethylsilyl)amide |
| NBS | N-bromosuccinimide |
| NMP | N-methyl-2-pyrrolidone |
| oxone | Potassium peroxymonosulfate |
| p-TSA | para-toluene sulfonic acid |
| Pd$_2$(dba)$_3$ | Tris(dibenzylideneacetone)dipalladium(0) |
| Pd(PPh$_3$)$_4$ | Tetrakis(triphenylphospine)palladium(0) |
| Pd(dppf)Cl$_2$- DCM | Dichloro-(1,2-bis(diphenylphosphino)ethan)-Palladium(II) - dichloromothethane adduct |
| RT or rt | room temperature |
| TBAF | Tetrabutyl ammonium fluoride |
| TBDMSCl | tert-butyldimethylsilylchloride |
| TEA | Triethylamine |
| THF | tetrahydrofuran |

EXAMPLES

Synthesis of 6-bromo-5-fluoropicolinic acid

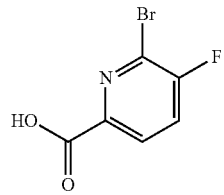

To 2-bromo-3-fluoro-6-methylpyridine (1.0 equiv.) in H₂O (30 mL) was added potassium permanganate (1.0 equiv.). The solution was heated at 100° C. for 5 hours at which time more potassium permanganate (1.0 equiv.) was added. After heating for an additional 48 hours the material was filtered through celite (4 cm×2 inches) and rinsed with H₂O (150 mL). The combined aqueous was acidified with 1N HCl to pH=4, extracted with ethyl acetate (200 mL), washed with NaCl(sat.), dried over MgSO₄, filtered and concentrated to yield 6-bromo-5-fluoropicolinic acid (17%) as a white solid. LCMS (m/z): 221.9 (MH+); LC Rt=2.05 min.

Synthesis of methyl 6-bromo-5-fluoropicolinate

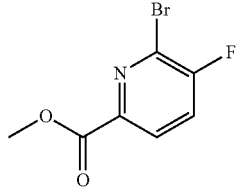

To a solution of 6-bromo-5-fluoropicolinic acid (1.0 equiv.) in methanol (0.2 M) was added H₂SO₄ (4.2 equiv.) and the reaction was stirred at room temperature for two hours. Upon completion of the reaction as monitored by LC/MS, the reaction was diluted with ethyl acetate and quenched slowly with saturated aqueous NaHCO₃. The reaction was poured into a separatory funnel and extracted with ethyl acetate. The organic phase was dried with magnesium sulfate, filtered, and concentrated in vacuo to provide methyl 6-bromo-5-fluoropicolinate as a white solid (>99%). LC/MS=233.9/235.9 (M+H), Rt=0.69 min.
Method 1

Synthesis of methyl 6-(2,6-difluoro-4-methoxyphenyl)-5-fluoropicolinate

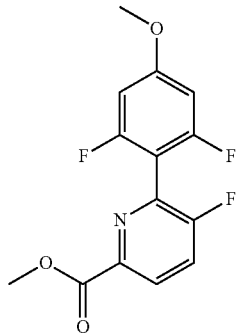 [SMILES: COC(=O)c1ccc(F)c(-c2c(F)cc(OC)cc2F)n1]

To a solution of methyl 6-bromo-5-fluoropicolinate (1.0 equiv.) in THF and water (10:1, 0.1 M) was added 2,6-difluoro-4-methoxyphenylboronic acid (2.5 equiv.) and potassium fluoride (3.3 equiv.). The reaction was degassed with nitrogen, then Pd₂(dba)₃ (0.25 equiv.) and tri-tert-butylphosphine (0.5 equiv.) were added and the reaction was heated to 80° C. for one hour. LC/MS analysis indicated complete conversion of the starting material to product. The reaction was cooled to room temperature, then concentrated in vacuo and fused to silica gel. The crude product was purified by ISCO flash chromatography eluting with ethyl acetate and hexanes (0% to 30% ethyl acetate) to provide methyl 6-(2,6-difluoro-4-methoxyphenyl)-5-fluoropicolinate as a white solid in 85% yield. LC/MS=298.0 (M+H), Rt=0.89 min.
Method 2

Synthesis of 6-(2,6-difluoro-4-methoxyphenyl)-5-fluoropicolinic acid

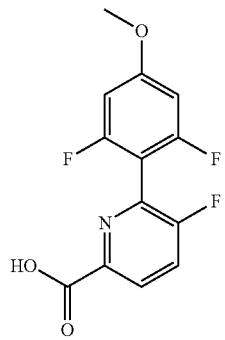 [SMILES: COc1cc(F)c(-c2nc(C(=O)O)ccc2F)c(F)c1]

To a solution of methyl 6-(2,6-difluoro-4-methoxyphenyl)-5-fluoropicolinate (1.0 equiv.) in THF/MeOH (2:1, 0.09 M) was added LiOH (1.5 equiv.) and the reaction was stirred at room temperature for 1 hour. The solution was quenched with 1N HCl, extracted with ethyl acetate, washed with brine, dried with sodium sulfate, filtered and concentrated to give 6-(2,6-difluoro-4-methoxyphenyl)-5-fluoropicolinic acid in 84% yield. LC/MS=284.1 (M+H), Rt=0.76 min.
Method 3

Synthesis of 2-(2,6-difluoro-4-methylphenyl)-4,4,5,5-tetramethyl-1,3,2-dioxaboroane

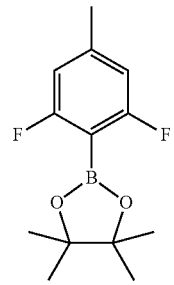 [SMILES: Cc1cc(F)c(B2OC(C)(C)C(C)(C)O2)c(F)c1]

To a solution of 1,3-difluoro-5-methylbenzene (1.0 eq) in dry THF (0.2M) under an atmosphere of N₂ at −78° C. was added n-butyllithium (1 eq, 1.6M in hexanes) slowly keeping the internal temperature below −65° C. The reaction was stirred for 2 hrs at −78° C., followed by the addition of 2-isopropoxy-4,4,5,5-tetramethyl-1,3,2-dioxaborolane (1.15 eq). The reaction was allowed to warm to room temperature. Upon completion, the reaction was quenched with NaHCO₃(sat.) and extracted with EtOAc. The organics were washed with brine, dried over Na₂SO₄, filtered and concentrated to yield 2-(2,6-difluoro-4-methylphenyl)-4,4,5,5-tetramethyl-1,3,2-dioxaboroane as a white solid in 92%. 1H NMR (400 MHz, <cdcl3>) δ ppm 6.67 (dd, J=9.39, 0.78 Hz, 2 H), 2.34 (s, 3 H), 1.38 (s, 12 H).

Synthesis of methyl 6-(2,6-difluoro-4-methylphenyl)-5-fluoropicolinate

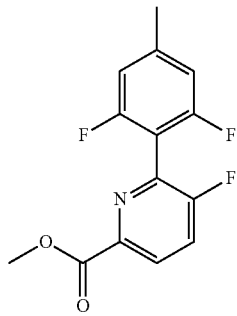 [SMILES: COC(=O)c1ccc(F)c(-c2c(F)cc(C)cc2F)n1]

Method 1 was followed using methyl 6-bromo-5-fluoropicolinate (1.0 equiv.) and 2-(2,6-difluoro-4-methylphenyl)-4,4,5,5-tetramethyl-1,3,2-dioxaboroane (1.75 equiv.) to give methyl 6-(2,6-difluoro-4-methylphenyl)-5-fluoropicolinate as a solid in 85% yield. LC/MS=282.0 (M+H), Rt=0.87 min.

Synthesis of 6-(2,6-difluoro-4-methylphenyl)-5-fluoropicolinic acid

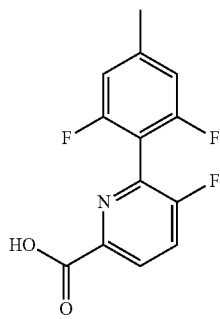

To a solution of methyl 6-(2,6-difluoro-4-methylphenyl)-5-fluoropicolinate (1.0 eq) in THF (0.1M) was added LiOH (5.5 eq, 2M) and allowed to stir at room temperature for 4 hrs. The volatiles were removed in vacuo, and the residual aqueous was acidified with 2M HCl to pH 4. The precipitate was filtered and dried to yield 6-(2,6-difluoro-4-methylphenyl)-5-fluoropicolinic acid as a light yellow solid in 73.5%. LCMS (m/z): 268.0 (MH$^+$), R$_f$=0.76 min.

Synthesis of (2-(3,5-difluorophenyl)propan-2-yloxy)triisopropylsilane

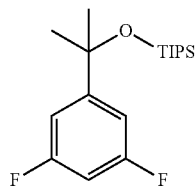

To a solution of 1-(3,5-difluorophenyl)ethanone (1.0 equiv) in THF (0.2 M) at 0° C. was added methylmagnesium bromide (1.0 M in THF, 1.15 equiv). After stirring for 4 hours the reaction was quenched by addition of NH$_4$Cl$_{(sat)}$, diluted with EtOAc, washed with NaCl$_{(sat)}$, dried over MgSO$_4$, filtered, concentrated and purified by ISCO SiO$_2$ chromatography to yield 2-(3,5-difluorophenyl)propan-2-ol. To a solution of 2-(3,5-difluorophenyl)propan-2-ol in CH$_2$Cl$_2$ (0.1 M) at 0° C. was added 2,6 lutidine (6 equiv.) and than triisopropylsilyl trifluoromethanesulfonate (3.0 equiv.). After stirring for 3 hours at 0° C. and six hours at rt the solution was partitioned between EtOAc and NaHCO$_{3(sat)}$, separated, washed with NaCl$_{(sat)}$, dried over MgSO$_4$, filtered, concentrated and purified by ISCO SiO$_2$ chromatography to yield (2-(3,5-difluorophenyl)propan-2-yloxy)triisopropylsilane. (400 MHz, <cdcl3>) δ ppm 1.05-1.08 (m, 21 H) 1.57 (s, 6 H) 6.63 (s, 1 H) 7.00 (dd, J=9.39, 2.35 Hz, 2 H).

Synthesis of (2-(3,5-difluoro-4-(4,4,5,5-tetramethyl-1,3,2-dioxaborolan-2-yl)phenyl)propan-2-yloxy)triisopropylsilane

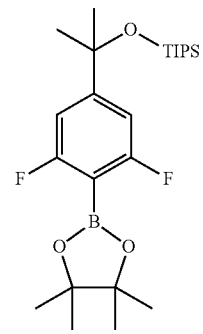

To a solution of (2-(3,5-difluorophenyl)propan-2-yloxy)triisopropylsilane (1.0 eq) in dry THF (0.2M) under an atmosphere of N$_2$ at −78° C. was added n-butyllithium (1 eq, 1.6M in hexanes) slowly keeping the internal temperature below −65° C. The reaction was stirred for 2 hrs at −78° C., followed by the addition of 2-isopropoxy-4,4,5,5-tetramethyl-1,3,2-dioxaborolane (1.15 eq). The reaction was allowed to warm to room temperature. Upon completion, the reaction was quenched with NaHCO$_{3(sat)}$ and extracted with EtOAc. The organics were washed with brine, dried over Na$_2$SO$_4$, filtered and concentrated to yield (2-(3,5-difluoro-4-(4,4,5,5-tetramethyl-1,3,2-dioxaborolan-2-yl)phenyl)propan-2-yloxy)triisopropylsilane in 99%. $^1$H NMR (400 MHz, <cdcl3>) δ ppm 1.03-1.08 (m, 21 H) 1.24 (s, 12 H) 1.38 (s, 3 H) 1.57 (s, 3 H) 6.92-7.03 (m, 2 H).

Synthesis of tert-butyl(3,5-difluorophenoxy)dimethylsilane

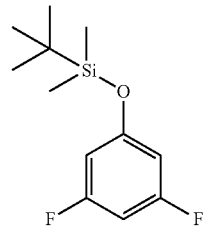 [SMILES: CC(C)(C)[Si](C)(C)Oc1cc(F)cc(F)c1]

To a solution of 3,5-difluorophenol (1.0 equiv.) and imidazole (2.2 equiv.) in DMF (0.8 M) at 0° C. was added TBDMSCl (1.1 equiv.). The ice bath was removed and after stirring for 3 hours the solution was diluted with EtOAc, washed with water, brine, dried over MgSO$_4$, filtered, concentrated and purified by SiO$_2$ chromatography to yield tert-butyl(3,5-difluorophenoxy)dimethylsilane in 73% yield. $^1$H NMR (400 MHz, <cdcl3>) δ ppm 0.23 (s, 6 H) 0.99 (s, 9 H) 6.33-6.40 (m, 2 H) 6.44 (tt 1 H).

Synthesis of tert-butyl(3,5-difluoro-4-(4,4,5,5-tetramethyl-1,3,2-dioxaborolan-2-yl)phenoxy)dimethylsilane

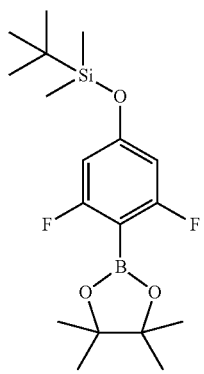 [SMILES: CC1(C)OB(c2c(F)cc(O[Si](C)(C)C(C)(C)C)cc2F)OC1(C)C]

To a solution of tert-butyl(3,5-difluorophenoxy)dimethylsilane (1.0 eq) in dry THF (0.2M) under an atmosphere of N$_2$ at −78° C. was added n-butyllithium (1 eq, 1.6M in hexanes) slowly keeping the internal temperature below −65° C. The reaction was stirred for 1 hr at −78° C., followed by the addition of 2-isopropoxy-4,4,5,5-tetramethyl-1,3,2-dioxaborolane (2.1 eq). The reaction was allowed to warm to room temperature. Upon completion, the reaction was quenched with NaHCO$_3$ $_{(sat)}$ and extracted with EtOAc. The organics were washed with brine, dried over Na$_2$SO$_4$, filtered and concentrated to yield tert-butyl(3,5-difluoro-4-(4,4,5,5-tetramethyl-1,3,2-dioxaborolan-2-yl)phenoxy)dimethylsilane in 91% yield. $^1$H NMR (400 MHz, <cdcl3>) δ ppm 0.21 (s, 6 H) 0.97 (s, 9 H) 1.37 (s, 12 H) 6.33 (d, J=9.39 Hz, 2 H).

Synthesis of methyl 6-(2,6-difluoro-4-hydroxyphenyl)-5-fluoropicolinate

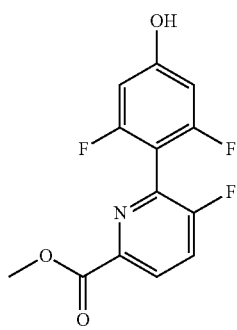 [SMILES: COC(=O)c1ccc(F)c(-c2c(F)cc(O)cc2F)n1]

Method 1 was followed using methyl 6-bromo-5-fluoropicolinate (1.0 equiv.) and tert-butyl(3,5-difluoro-4-(4,4,5,5-tetramethyl-1,3,2-dioxaborolan-2-yl)phenoxy)dimethylsilane (1.75 equiv.) to give methyl 6-(2,6-difluoro-4-hydroxyphenyl)-5-fluoropicolinate in 65% yield. The reaction was heated for an additional 30 minutes at 100° C. in the microwave to drive to completion the deprotection of the TBDMS group. LC/MS=283.9 (M+H), Rt=0.69 min.

Synthesis of methyl 6-(4-(2-(tert-butyldimethylsilyloxy)ethoxy)-2,6-difluorophenyl)-5-fluoropicolinate

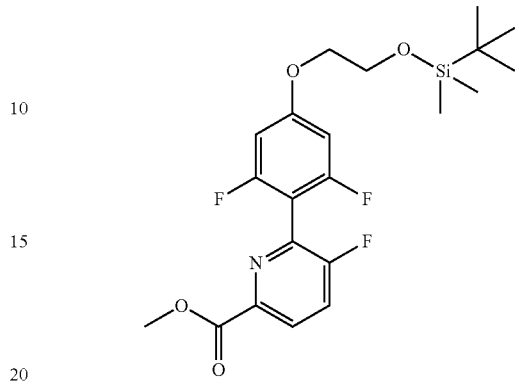

To a solution of methyl 6-(2,6-difluoro-4-hydroxyphenyl)-5-fluoropicolinate (1.0 equiv.) and potassium carbonate (4.0 equiv.) in DMF (0.4 M) was added (2-bromoethoxy)(tert-butyl)dimethylsilane (2 equiv.). After stirring for 72 hours at rt the heterogeneous solution was diluted with water, extracted with EtOAc, dried over MgSO$_4$, filtered, concentrated and purified by ISCO SiO$_2$ chromatography to yield methyl 6-(4-(2-(tert-butyldimethylsilyloxy)ethoxy)-2,6-difluorophenyl)-5-fluoropicolinate in 74% yield. LC/MS=442.1 (M+H), R$_t$=1.22 min.

Synthesis of 6-(4-(2-(tert-butyldimethylsilyloxy)ethoxy)-2,6-difluorophenyl)-5-fluoropicolinic acid

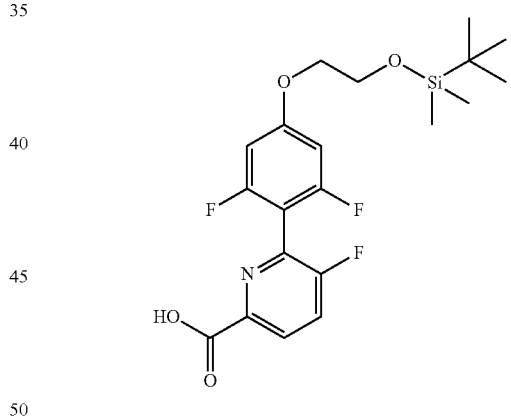

Method 2 was followed using methyl 6-(4-(2-(tert-butyldimethylsilyloxy)ethoxy)-2,6-difluorophenyl)-5-fluoropicolinate to give 6-(4-(2-(tert-butyldimethylsilyloxy)ethoxy)-2,6-difluorophenyl)-5-fluoropicolinic acid in 94% yield. LC/MS=428.1 (M+H), R$_t$=1.13 min.

Synthesis of 1,3-difluoro-5-(2-methoxyethoxyl)benzene

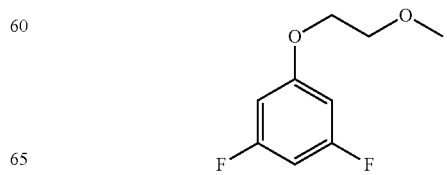

To a solution of 3,5-difluorophenol (1.0 equiv.), 2-methoxyethanol (3.0 equiv.) and triphenylphosphine (3.0 equiv) in THF (0.1 M) was added DIAD (3.0 equiv.). After stirring at rt for 18 hours, the volatiles were removed in vacuo and the residue was purified by SiO$_2$ chromatography to yield 1,3-difluoro-5-(2-methoxyethoxyl)benzene in 95% yield. $^1$H NMR (400 MHz, <cdcl3>) δ ppm 6.41-6.47 m (3 H), 4.08 (t, 2H), 3.74 (t, 2H), 3.45 (s, 3 H).

Synthesis of 2-(2,6-difluoro-4-(2-methoxyethoxyl)phenyl)-4,4,5,5-tetramethyl-1,3,2-dioxaborolane

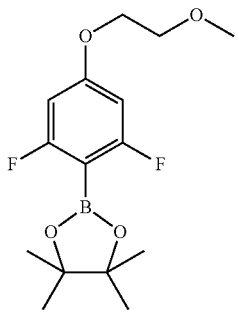 [SMILES: COCCOc1cc(F)c(B2OC(C)(C)C(C)(C)O2)c(F)c1]

To a solution of 1,3-difluoro-5-(2-methoxyethoxyl)benzene (1.0 eq) in dry THF (0.2M) under an atmosphere of N$_2$ at −78° C. was added n-butyllithium (1 eq, 1.6M in hexanes) slowly keeping the internal temperature below −65° C. The reaction was stirred for 1 hr at −78° C., followed by the addition of 2-isopropoxy-4,4,5,5-tetramethyl-1,3,2-dioxaborolane (2.1 eq). The reaction was allowed to warm to room temperature. Upon completion, the reaction was quenched with NaHCO$_3$ $_{(sat)}$ and extracted with EtOAc. The organics were washed with brine, dried over Na$_2$SO$_4$, filtered and concentrated to yield 2-(2,6-difluoro-4-(2-methoxyethoxyl)phenyl)-4,4,5,5-tetramethyl-1,3,2-dioxaborolane. $^1$H NMR (400 MHz, <cdcl3>) δ ppm 6.42 (d, 2 H), 4.10 (m, 2H), 3.74 (m, 2H), 3.44 (s, 3 H), 1.37 (s, 12 H).

Synthesis of methyl 6-(2,6-difluoro-4-(2-methoxyethoxyl)phenyl)-5-fluoropicolinate

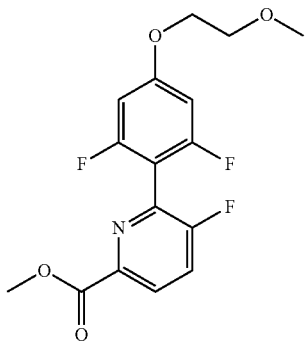

Method 1 was followed using methyl 6-bromo-5-fluoropicolinate (1.0 equiv.) and 2-(2,6-difluoro-4-(2-methoxyethoxyl)phenyl)-4,4,5,5-tetramethyl-1,3,2-dioxaborolane (1.75 equiv.) at 80° C. for 1 hour to give methyl 6-(2,6-difluoro-4-(2-methoxyethoxyl)phenyl)-5-fluoropicolinate in 95% yield. LC/MS=341.9 (M+H), R$_t$=0.89 min.

Synthesis of 6-(2,6-difluoro-4-(2-methoxyethoxyl)phenyl)-5-fluoropicolinic acid

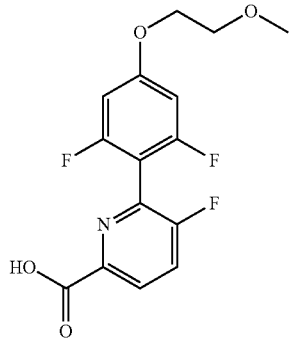 [SMILES: COCCOc1cc(F)c(-c2nc(C(=O)O)ccc2F)c(F)c1]

Method 2 was followed using methyl 6-(2,6-difluoro-4-(2-methoxyethoxyl)phenyl)-5-fluoropicolinate to give 6-(2,6-difluoro-4-(2-methoxyethoxyl)phenyl)-5-fluoropicolinic acid in 98% yield. LC/MS=327.9 (M+H), R$_t$=0.71 min.

Synthesis of meth 6-(2,6-difluoro-4-(2-hydroxypropan-2-yl)phenyl)-5-fluoropicolinate

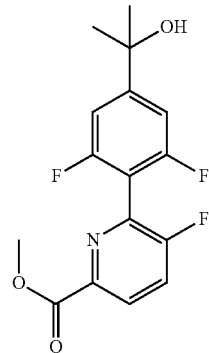 [SMILES: COC(=O)c1ccc(F)c(-c2c(F)cc(C(C)(C)O)cc2F)n1]

Method 1 was followed using methyl 6-bromo-5-fluoropicolinate (1.0 equiv.) and (2-(3,5-difluoro-4-(4,4,5,5-tetramethyl-1,3,2-dioxaborolan-2-yl)phenyl)propan-2-yloxy)triisopropylsilane (1.6 equiv.) at 100° C. for 30 min in the microwave to give methyl 6-(2,6-difluoro-4-(2-hydroxypropan-2-yl)phenyl)-5-fluoropicolinate in 90% yield. LC/MS=325.9 (MH$^+$), R$_t$=0.81 min. 1H NMR (400 MHz, <cdcl3>) δ ppm 1.59 (s, 6 H), 4.00 (s, 3 H), 7.15 (d, J=9.00 Hz, 2 H), 7.62-7.68 (m, 1 H), 8.23-8.29 (m, 1 H).

Synthesis of 6-(2,6-difluoro-4-(2-hydroxypropan-2-yl)phenyl)-5-fluoropicolinic acid

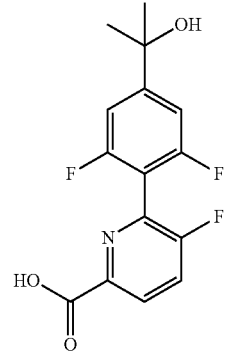 [SMILES: CC(C)(O)c1cc(F)c(-c2nc(C(=O)O)ccc2F)c(F)c1]

Method 2 was followed using methyl 6-(2,6-difluoro-4-(2-hydroxypropan-2-yl)phenyl)-5-fluoropicolinate to give 6-(2,6-difluoro-4-(2-hydroxypropan-2-yl)phenyl)-5-fluoropicolinic acid in 94% yield. LC/MS=312.0 (MH$^+$), R$_f$=0.69 min.

Synthesis of 4-(3,5-difluorophenyl)tetrahydro-2H-pyran-4-ol

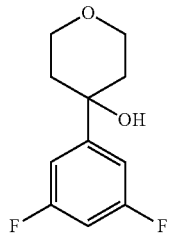 [SMILES: OC1(c2cc(F)cc(F)c2)CCOCC1]

To a solution of 1-bromo-3,5-difluorobenzene (1.6 equiv.) in THF (0.26 M) under Ar was added Mg turnings (1.6 equiv.). A reflux condenser was attached and the solution was submerged in a 90° C. oil bath and refluxed for two hours. The dihydro-2H-pyran-4(3H)-one (1.0 equiv.) was added in THF via syringe. The solution was left stirring at rt under Ar for 5 hrs. The reaction solution was quenched by addition of NH$_4$Cl$_{(sat)}$ and the solution was extracted with EtOAc, washed with NaCl$_{(sat)}$, dried over MgSO$_4$, filtered, concentrated and purified by ISCO SiO$_2$ chromatography (0-100% EtOAc/n-heptanes gradient) to yield 4-(3,5-difluorophenyl)tetrahydro-2H-pyran-4-ol in 71% yield. $^1$H NMR (400 MHz, CHLOROFORM-d) δ ppm 1.59-1.68 (m, 3 H), 2.07-2.19 (m, 2 H), 3.87-3.93 (m, 4 H), 6.72 (tt, J=8.75, 2.20 Hz, 1 H), 6.97-7.06 (m, 2 H).

Synthesis of 4-(3,5-difluorophenyl)-3,6-dihydro-2H-pyran

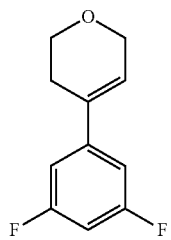 [SMILES: Fc1cc(F)cc(C2=CCOCC2)c1]

4-(3,5-difluorophenyl)tetrahydro-2H-pyran-4-ol (1.0 equiv.) was dissolved in DCM (0.2 M) and cooled to 0° C. TEA (2.8 equiv.) was added to the solution, followed by MsCl (1.3 equiv.). The reaction was stirred at rt for 2 hrs. The solution was cooled to 0° C. and DBU (3.0 equiv.) was added. The reaction was stirred at rt for 18 hrs. The solution was concentrated and the residue was purified by SiO$_2$ chromatography (0-100% EtOAc in Heptanes) to afford 4-(3,5-difluorophenyl)-3,6-dihydro-2H-pyran in 38% yield.

$^1$H NMR (400 MHz, <cdcl3>) δ ppm 2.42-2.49 (m, 2 H), 3.93 (t, J=5.48 Hz, 2 H), 4.32 (q, J=2.74 Hz, 2 H), 6.16-6.22 (m, 1 H), 6.70 (tt, J=8.80, 2.35 Hz, 1 H), 6.85-6.94 (m, 2 H).

Synthesis of 4-(3,5-difluorophenyl)tetrahydro-2H-pyran

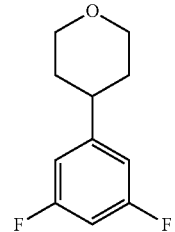 [SMILES: Fc1cc(F)cc(C2CCOCC2)c1]

To a solution of 4-(3,5-difluorophenyl)-3,6-dihydro-2H-pyran (1.0 equiv.) in methanol (0.2 M) was added 10% Pd/C (0.05 equiv.). The reaction was placed under an atmosphere of hydrogen and stirred for 18 hours. Upon completion, the solution was filtered over a pad of Celite, the pad was washed with DCM, the filtrate was concentrated in vacuo to give 4-(3,5-difluorophenyl)tetrahydro-2H-pyran in 71% yield. $^1$H NMR (400 MHz, <cdcl3>) δ ppm 1.76 (br. s., 4 H), 2.75 (br. s., 1 H), 3.50 (br. s., 2 H), 4.08 (d, J=9.78 Hz, 2 H), 6.56-6.94 (m, 3 H). cl Synthesis of 2-(2,6-difluoro-4-(tetrahydro-2H-pyran-4-yl)phenyl)-4,4,5,5-tetramethyl-1,3,2-dioxaborolane

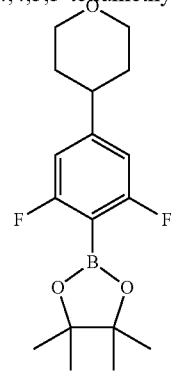

Method 3 was followed using 2-isopropoxy-4,4,5,5-tetramethyl-1,3,2-dioxaborolane (2.2 equiv.), butyllithium (1.1 equiv.) and 4-(3,5-difluorophenyl)tetrahydro-2H-pyran (1.0 equiv.) to give 2-(2,6-difluoro-4-(tetrahydro-2H-pyran-4-yl)phenyl)-4,4,5,5-tetramethyl-1,3,2-dioxaborolane in 100% yield. $^1$H NMR (400 MHz, <cdcl3>) δ ppm 1.16-1.19 (m, 12 H), 1.65-1.74 (m, 4 H), 2.60-2.75 (m, 1 H), 3.37-3.51 (m, 2 H), 4.01 (dt, J=11.54, 3.42 Hz, 2 H), 6.67 (d, J=8.22 Hz, 2 H).

Synthesis of methyl 6-(2,6-difluoro-4-(tetrahydro-2H-pyran-4-yl)phenyl)-5-fluoropicolinate

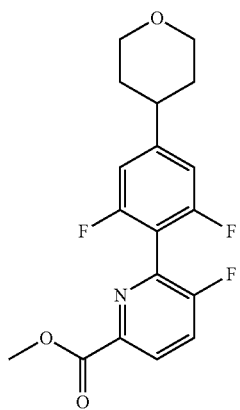

Method 1 was followed using methyl 6-bromo-5-fluoropicolinate (1.0 equiv.) and 2-(2,6-difluoro-4-(tetrahydro-2H-pyran-4-yl)phenyl)-4,4,5,5-tetramethyl-1,3,2-dioxaborolane (3.0 equiv.) at 100° C. for 20 min in microwave to give methyl 6-(2,6-difluoro-4-(tetrahydro-2H-pyran-4-yl)phenyl)-5-fluoropicolinate in 59% yield. LC/MS=352.2 (MH$^+$), R$_t$=0.92 min.

Synthesis of 6-(2,6-difluoro-4-(tetrahydro-2H-pyran-4-yl)phenyl)-5-fluoropicolinic acid

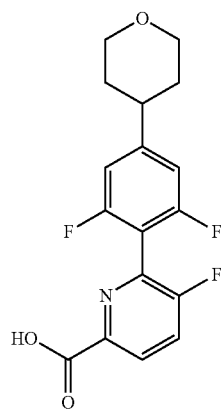

Method 2 was followed using methyl 6-(2,6-difluoro-4-(tetrahydro-2H-pyran-4-yl)phenyl)-5-fluoropicolinate to give 6-(2,6-difluoro-4-(tetrahydro-2H-pyran-4-yl)phenyl)-5-fluoropicolinic acid in 71% yield. LC/MS=338.1 (MH$^+$), R$_t$=0.80 min.

Synthesis of 4-(3,5-difluoro-4-(4,4,5,5-tetramethyl-1,3,2-dioxaborolan-2-yl)phenyl)tetrahydro-2H-pyran-4-ol

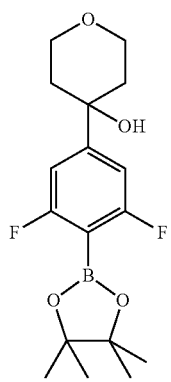 [SMILES: CC1(C)OB(c2c(F)cc(C3(O)CCOCC3)cc2F)OC1(C)C]

Method 3 was followed using 2-isopropoxy-4,4,5,5-tetramethyl-1,3,2-dioxaborolane (2.5 equiv.), butyllithium (2.4 equiv.) and 4-(3,5-difluorophenyl)tetrahydro-2H-pyran-4-ol (1.0 equiv.) to give 4-(3,5-difluoro-4-(4,4,5,5-tetramethyl-1,3,2-dioxaborolan-2-yl)phenyl)tetrahydro-2H-pyran-4-ol in 97% yield. $^1$H NMR (400 MHz, <cdcl3>) δ ppm 1.32-1.42 (m, 12 H), 1.56-1.65 (m, 2H), 2.11 (d, J=3.13 Hz, 2 H), 3.86-3.92 (m, 4 H), 6.99 (d, J=9.00 Hz, 2 H).

Synthesis of methyl 6-(2,6-difluoro-4-(4-hydroxytetrahydro-2H-pyran-4-yl)phenyl)-5-fluoropicolinate

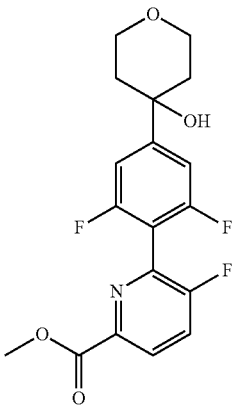 [SMILES: COC(=O)c1ccc(F)c(-c2c(F)cc(C3(O)CCOCC3)cc2F)n1]

Method 1 was followed using methyl 6-bromo-5-fluoropicolinate (1.0 equiv.) and 4-(3,5-difluoro-4-(4,4,5,5-tetramethyl-1,3,2-dioxaborolan-2-yl)phenyl)tetrahydro-2H-pyran-4-ol (1.8 equiv.) at to give methyl 6-(2,6-difluoro-4-(4-hydroxytetrahydro-2H-pyran-4-yl)phenyl)-5-fluoropicolinate in 72% yield. LC/MS=368.0 (MH$^+$), R$_t$=0.75 min.

Synthesis of 6-(2,6-difluoro-4-(4-hydroxytetrahydro-2H-pyran-4-yl)phenyl)-5-fluoropicolinic acid

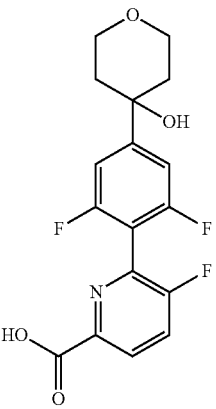 [SMILES: O=C(O)c1ccc(F)c(-c2c(F)cc(C3(O)CCOCC3)cc2F)n1]

Method 2 was followed using methyl 6-(2,6-difluoro-4-(4-hydroxytetrahydro-2H-pyran-4-yl)phenyl)-5-fluoropicolinate to give 6-(2,6-difluoro-4-(4-hydroxytetrahydro-2H-pyran-4-yl)phenyl)-5-fluoropicolinic acid in 69% yield. LC/MS=354.0 (MH$^+$), R$_t$=0.64 min.

Synthesis of methyl 6-(2,6-difluoro-4-(4-fluorotetrahydro-2H-pyran-4-yl)phenyl)-5-fluoropicolinate

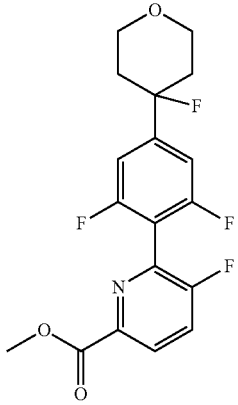 [SMILES: COC(=O)c1ccc(F)c(-c2c(F)cc(C3(F)CCOCC3)cc2F)n1]

To a solution of methyl 6-(2,6-difluoro-4-(4-hydroxytetrahydro-2H-pyran-4-yl)phenyl)-5-fluoropicolinate (1.0 equiv.) in CH$_2$Cl$_2$ (0.04 M) at −78° C. under Ar was added methylDAST (2.0 equiv.). After addition, the solution was stirred under Ar at −78° C. for 10 minutes and then the bath was removed. The reaction was allowed to warm up to rt and quenched by addition of NaHCO$_{3(sat.)}$. The solution was diluted with EtOAc, washed with NaHCO$_{3(sat)}$, NaCl$_{(sat)}$, dried over MgSO$_4$, filtered, concentrated, purified by ISCO SiO$_2$ chromatography (0-100 EtOAc/n-heptanes) to yield methyl 6-(2,6-difluoro-4-(4-fluorotetrahydro-2H-pyran-4-yl)phenyl)-5-fluoropicolinate in 100% yield. LC/MS=370.0 (MH$^+$), R$_t$=0.94 min.

Synthesis of 6-(2,6-difluoro-4-(4-fluorotetrahydro-2H-pyran-4-yl)phenyl)-5-fluoropicolinic acid

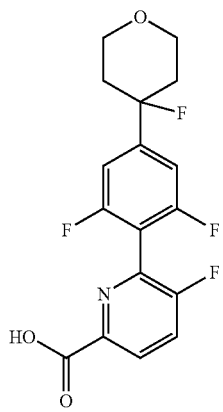

Method 2 was followed using methyl 6-(2,6-difluoro-4-(4-fluorotetrahydro-2H-pyran-4-yl)phenyl)-5-fluoropicolinate to give 6-(2,6-difluoro-4-(4-fluorotetrahydro-2H-pyran-4-yl)phenyl)-5-fluoropicolinic acid in 95% yield. LC/MS=355.9 (MH$^+$), R$_t$=0.81 min.

Synthesis of 1-(3,5-difluorophenyl)cyclobutanol

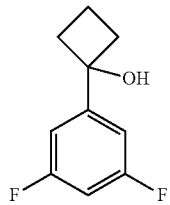 [SMILES: OC1(c2cc(F)cc(F)c2)CCC1]

To a solution of 1-bromo-3,5-difluorobenzene (1.0 equiv.) in THF (0.26 M) under Ar was added Mg turnings (1.6 equiv.). A reflux condenser was attached and the solution was submerged in a 90° C. oil bath and refluxed for two hours. The cyclobutanone (1.0 equiv.) was added in THF via syringe. The solution was left stirring at rt under Ar for 5 hrs. The reaction solution was quenched by addition of NH$_4$Cl$_{(sat)}$ and the solution was extracted with EtOAc, washed with NaCl$_{(sat)}$, dried over MgSO$_4$, filtered, concentrated and purified by ISCO SiO$_2$ chromatography (0-100% EtOAc/n-heptanes gradient) to yield 1-(3,5-difluorophenyl)cyclobutanol in 54% yield. $^1$H NMR (400 MHz, CHLOROFORM-d) δ ppm 1.69-1.83 (m, 1 H), 2.03-2.13 (m, 1 H), 2.31-2.43 (m, 2 H), 2.45-2.56 (m, 2 H), 6.71 (tt, J=8.80, 2.35 Hz, 1 H), 6.98-7.07 (m, 2 H).

Synthesis of 1-(3,5-difluoro-4-(4,4,5,5-tetramethyl-1,3,2-dioxaborolan-2-yl)phenyl)cyclobutanol

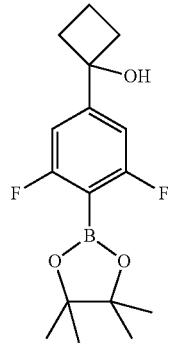 [SMILES: CC1(C)OB(c2c(F)cc(C3(O)CCC3)cc2F)OC1(C)C]

Method 3 was followed using 2-isopropoxy-4,4,5,5-tetramethyl-1,3,2-dioxaborolane (2.5 equiv.), butyllithium (2.4 equiv.) and 1-(3,5-difluorophenyl)cyclobutanol (1.0 equiv.) to give 1-(3,5-difluoro-4-(4,4,5,5-tetramethyl-1,3,2-dioxaborolan-2-yl)phenyl)cyclobutanol in 100% yield. $^1$H NMR (400 MHz, <cdcl3>) δ ppm 1.23-1.25 (m, 12 H), 1.69-1.82 (m, 1 H), 2.05-2.12 (m, 1 H), 2.37 (br. s., 2 H), 2.47 (br. s., 2 H), 7.00 (d, J=8.80 Hz, 2 H).

Synthesis of methyl 6-(2,6-difluoro-4-(1-hydroxycyclobutyl)phenyl)-5-fluoropicolinate

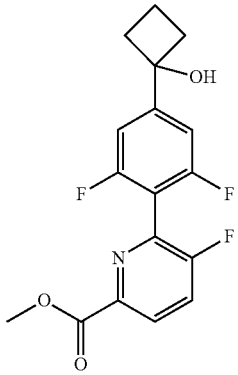 [SMILES: COC(=O)c1ccc(F)c(-c2c(F)cc(C3(O)CCC3)cc2F)n1]

Method 1 was followed using methyl 6-bromo-5-fluoropicolinate (1.0 equiv.) and 1-(3,5-difluoro-4-(4,4,5,5-tetramethyl-1,3,2-dioxaborolan-2-yl)phenyl)cyclobutanol (1.6 equiv.) at 100° C. for 30 min in microwave to give methyl 6-(2,6-difluoro-4-(1-hydroxycyclobutyl)phenyl)-5-fluoropicolinate in 71% yield. LC/MS=338.0 (MH$^+$), R$_t$=0.85 min.

Synthesis of 6-(2,6-difluoro-4-(1-hydroxycyclobutyl)phenyl)-5-fluoropicolinic acid

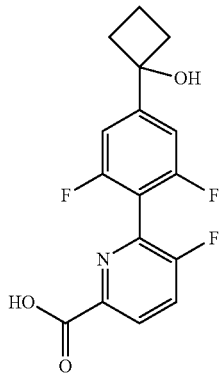 [SMILES: O=C(O)c1ccc(F)c(-c2c(F)cc(C3(O)CCC3)cc2F)n1]

Method 2 was followed using methyl 6-(2,6-difluoro-4-(1-hydroxycyclobutyl)phenyl)-5-fluoropicolinate to give 6-(2,6-difluoro-4-(1-hydroxycyclobutyl)phenyl)-5-fluoropicolinic acid in 90% yield. LC/MS=323.9 (MH+), R$_t$=0.74 min.

Synthesis of 4-(3,5-difluorophenoxyl)tetrahydro-2H-pyran

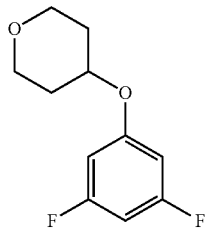 [SMILES: Fc1cc(F)cc(OC2CCOCC2)c1]

To a solution of 3,5-difluorophenol (1.0 equiv.), tetrahydro-2H-pyran-4-ol (1.2 equiv.), and triphenylphosphine (2.0 equiv.) in THF (0.33 M) at 0° C. was added DIAD (2.0 equiv.) dropwise. The reaction mixture was stirred at rt overnight. The mixture was concentrated and purified by flash chromatography over silica gel (heptanes:ethyl acetate gradient) to give 4-(3,5-difluorophenoxyl)tetrahydro-2H-pyran in 90% yield. $^1$H NMR (400 MHz, <cdcl3>) δ ppm 1.72-1.84 (m, 2H), 1.96-2.09 (m, 2 H), 3.59 (ddd, J=11.64, 8.31, 3.52 Hz, 2 H), 3.90-4.04 (m, 2 H), 4.44 (tt, J=7.78, 3.77 Hz, 1 H), 6.32-6.53 (m, 3 H).

Synthesis of 2-(2,6-difluoro-4-((tetrahydro-2H-pyran-4-yl)oxy)phenyl)-4,4,5,5-tetramethyl-1,3,2-dioxaborolane

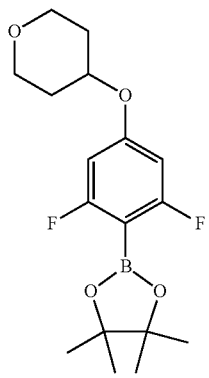 [SMILES: CC1(C)OB(c2c(F)cc(OC3CCOCC3)cc2F)OC1(C)C]

Method 3 was followed using 2-isopropoxy-4,4,5,5-tetramethyl-1,3,2-dioxaborolane (1.5 equiv.), butyllithium (1.3 equiv.) and 4-(3,5-difluorophenoxyl)tetrahydro-2H-pyran (1.0 equiv.) to give 2-(2,6-difluoro-4-((tetrahydro-2H-pyran-4-yl)oxy)phenyl)-4,4,5,5-tetramethyl-1,3,2-dioxaborolane in 33% yield. $^1$H NMR (400 MHz, <cdcl3>) δ ppm 1.21-1.34 (m, 12 H), 1.78 (dtd, J=12.72, 8.31, 8.31, 3.91 Hz, 2 H), 1.93-2.09 (m, 2 H), 3.59 (ddd, J=11.64, 8.31, 3.13 Hz, 2 H), 3.89-4.01 (m, 2 H), 4.48 (tt, J=7.78, 3.77 Hz, 1 H), 6.40 (d, J=9.39 Hz, 2 H).

Synthesis of methyl 6-(2,6-difluoro-4-((tetrahydro-2H-pyran-4-yl)oxy)phenyl)-5-fluoropicolinate

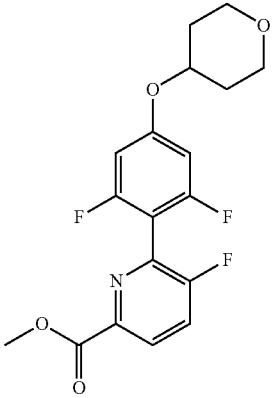 [SMILES: COC(=O)c1ccc(F)c(-c2c(F)cc(OC3CCOCC3)cc2F)n1]

Method 1 was followed using methyl 6-bromo-5-fluoropicolinate (1.0 equiv.) and 2-(2,6-difluoro-4-((tetrahydro-2H-pyran-4-yl)oxy)phenyl)-4,4,5,5-tetramethyl-1,3,2-dioxaborolane (1.5 equiv.) at 100° C. for 30 min in microwave to give methyl 6-(2,6-difluoro-4-((tetrahydro-2H-pyran-4-yl)oxy)phenyl)-5-fluoropicolinate in 77% yield. LC/MS=368.0 (MH+), Rt=0.95 min.

Synthesis of 6-(2,6-difluoro-4-((tetrahydro-2H-pyran-4-yl)oxy)phenyl)-5-fluoropicolinic acid

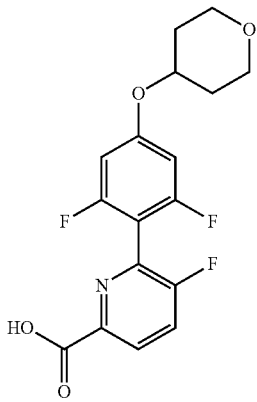 [SMILES: O=C(O)c1ccc(F)c(-c2c(F)cc(OC3CCOCC3)cc2F)n1]

Method 2 was followed using methyl 6-(2,6-difluoro-4-((tetrahydro-2H-pyran-4-yl)oxy)phenyl)-5-fluoropicolinate to give 6-(2,6-difluoro-4-((tetrahydro-2H-pyran-4-yl)oxy)phenyl)-5-fluoropicolinic acid in 100% yield. LC/MS=353.9 (MH+), R$_t$=0.82 min.

Synthesis of methyl 6-(4-(ethoxymethyl)-2,6-difluorophenyl)-5-fluoropicolinate

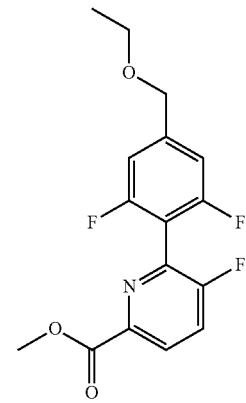 [SMILES: CCOCc1cc(F)c(-c2nc(C(=O)OC)ccc2F)c(F)c1]

To a solution of methyl 6-(2,6-difluoro-4-(hydroxymethyl)phenyl)-5-fluoropicolinate (1.0 equiv.) in DMF (0.20 M) (colorless) at 0° C. was added sodium hydride (1.2 equiv.) and the reaction was stirred at 0° C. for 2 min. Ethyl iodide (1.2 equiv.) was added and the reaction was allowed to warm to room temperature. After 1 h, additional 1.0 equiv. of NaH was added and stirred for 15 mi. Reaction was quenched by the addition of sat. Ammonium chloride. The aqueous was acidified with conc HCl to pH3 and extracted with ethyl acetate three times. The organics were combined, dried with MgSO$_4$, filtered and concentrated. The crude mixture was used as is. LC/MS=326.0 (MH$^+$), R$_f$=0.94 min.

Synthesis of 6-(4-(ethoxymethyl)-2,6-difluorophenyl)-5-fluoropicolinic acid

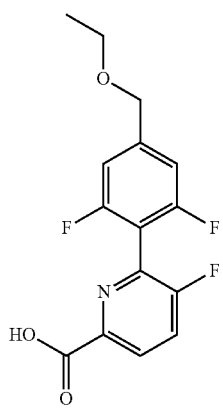

Method 2 was followed using methyl 6-(4-(ethoxymethyl)-2,6-difluorophenyl)-5-fluoropicolinate to give 6-(4-(ethoxymethyl)-2,6-difluorophenyl)-5-fluoropicolinic acid. LC/MS=311.9 (MH$^+$), R$_f$=0.82 min.

Synthesis of 1,3-difluoro-5-isopropoxybenzene

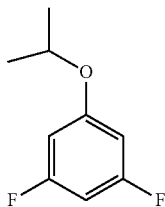

To a solution of 3,5-difluorophenol (1.0 equiv.) in DMF (0.26 M) was added potassium carbonate (2.2 equiv.) followed by 2-iodopropane (1.1 equiv.) and the reaction was stirred overnight at room temperature. The reaction was poured into a separatory funnel and diluted with a 3:1 (v/v) solution of EtOAc:heptanes. The organic phase was washed with water, then sat'd NaHCO$_3$. The remaining organic phase was dried over MgSO$_4$, filtered and concentrated in vacuo to provide 1,3-difluoro-5-isopropoxybenzene in 88% yield. $^1$H NMR (400 MHz, <cdcl3>) δ ppm 1.33 (d, J=6.26 Hz, 6 H), 4.48 (dt, J=11.93, 6.16 Hz, 1 H), 6.31-6.47 (m, 3 H).

Synthesis of 2-(2,6-difluoro-4-isopropoxyphenyl)-4,4,5,5-tetramethyl-1,3,2-dioxaborolane

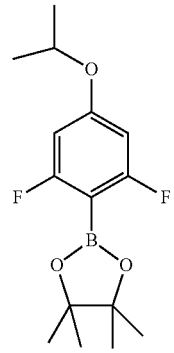 [SMILES: CC(C)Oc1cc(F)c(B2OC(C)(C)C(C)(C)O2)c(F)c1]

Method 3 was followed using 2-isopropoxy-4,4,5,5-tetramethyl-1,3,2-dioxaborolane (2.2 equiv.), butyllithium (1.2 equiv.) and 1,3-difluoro-5-isopropoxybenzene (1.0 equiv.) to give 2-(2,6-difluoro-4-isopropoxyphenyl)-4,4,5,5-tetramethyl-1,3,2-dioxaborolane in 99% yield. $^1$H NMR (400 MHz, <cdcl3>) δ ppm 1.24 (s, 12 H), 1.31-1.33 (m, 6 H), 4.43-4.56 (m, 1 H), 6.31-6.44 (m, 2 H).

Synthesis of methyl 6-2,6-difluoro-4-isopropoxyphenyl)-5-fluoropicolinate

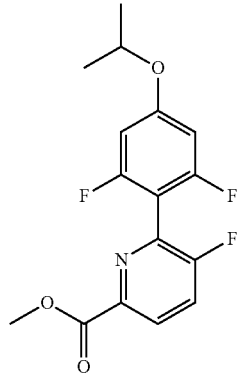 [SMILES: COC(=O)c1ccc(F)c(-c2c(F)cc(OC(C)C)cc2F)n1]

Method 1 was followed using methyl 6-bromo-5-fluoropicolinate (0.8 equiv.) and 2-(2,6-difluoro-4-isopropoxyphenyl)-4,4,5,5-tetramethyl-1,3,2-dioxaborolane (1.0 equiv.) at 70° C. for 1 hour to give methyl 6-(2,6-difluoro-4-isopropoxyphenyl)-5-fluoropicolinate. LC/MS=325.9 (MH+), Rt=1.04 min.

Synthesis of 6-(2,6-difluoro-4-isopropoxyphenyl)-5-fluoropicolinic acid

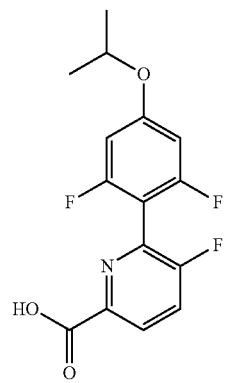 [SMILES: CC(C)Oc1cc(F)c(-c2nc(C(=O)O)ccc2F)c(F)c1]

Method 2 was followed using methyl 6-(2,6-difluoro-4-isopropoxyphenyl)-5-fluoropicolinate to give 6-(2,6-difluoro-4-isopropoxyphenyl)-5-fluoropicolinic acid. LC/MS=311.9 (MH+), Rt=0.92 min.

Synthesis of 3-(3,5-difluorophenyl)oxetane

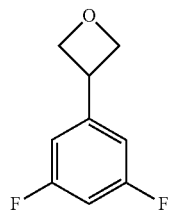 [SMILES: Fc1cc(F)cc(C2COC2)c1]

3,5-difluorophenylboronic acid (2.0 equiv.), (1R,2R)-2-aminocyclohexanol (0.06 equiv.), NaHMDS (2.0 equiv.), and nickel(II) iodide (0.06 equiv.) were dissolved in 2-propanol (0.35 M). The mixture was degassed with $N_2$, stirred at rt for 10 min and then a solution of 3-iodooxetane (1.0 equiv.) in 2-Propanol (0.70 M) was added. The mixture was sealed and heated at 80° C. in the microwave for 20 min. The mixture was filtered through celite, eluting with EtOH and concentrated. The crude residue was purified by ISCO $SiO_2$ chromatography eluting with 0-100% EtOAc in Heptanes to afford 3-(3,5-difluorophenyl)oxetane in 63% yield. $^1$H NMR (400 MHz, <cdcl3>) δ 6.88-6.96 (m, 2H), 6.72 (tt, J=2.20, 8.95 Hz, 1H), 5.08 (dd, J=6.26, 8.22 Hz, 2H), 4.71 (t, J=6.26 Hz, 2H), 4.14-4.24 (m, 1H).

Synthesis of 2-(2,6-difluoro-4-(oxetan-3-yl)phenyl)-4,4,5,5-tetramethyl-1,3,2-dioxaborolane

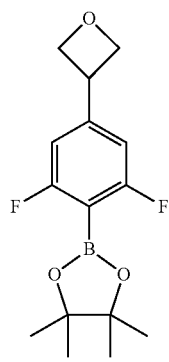 [SMILES: CC1(C)OB(c2c(F)cc(C3COC3)cc2F)OC1(C)C]

Method 3 was followed using 2-isopropoxy-4,4,5,5-tetramethyl-1,3,2-dioxaborolane (1.3 equiv.), butyllithium (1.1 equiv.) and 3-(3,5-difluorophenyl)oxetane (1.0 equiv.) to give 2-(2,6-difluoro-4-(oxetan-3-yl)phenyl)-4,4,5,5-tetramethyl-1,3,2-dioxaborolane. $^1$H NMR (400 MHz, <cdcl3>) δ ppm 6.90 (d, J=8.22 Hz, 2H), 5.07 (dd, J=6.06, 8.41 Hz, 2H), 4.70 (t, J=6.26 Hz, 2H), 4.13-4.23 (m, 1H), 1.39 (s, 12H).

Synthesis of methyl 6-(2,6-difluoro-4-(oxetan-3-yl)phenyl)-5-fluoropicolinate

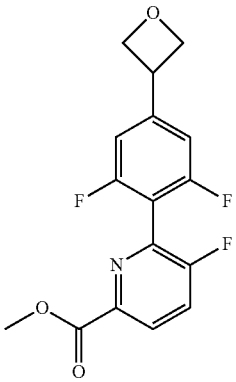 [SMILES: COC(=O)c1ccc(F)c(-c2c(F)cc(C3COC3)cc2F)n1]

Method 1 was followed using methyl 6-bromo-5-fluoropicolinate (1.2 equiv.) and 2-(2,6-difluoro-4-(oxetan-3-yl)phenyl)-4,4,5,5-tetramethyl-1,3,2-dioxaborolane (1.0 equiv.) at 80° C. for 15 min in microwave to give methyl 6-(2,6-difluoro-4-(oxetan-3-yl)phenyl)-5-fluoropicolinate in 47% yield. LC/MS=324.0 (MH+), Rt=0.75 min.

Synthesis of 6-(2,6-difluoro-4-(oxetan-3-yl)phenyl)-5-fluoropicolinic acid

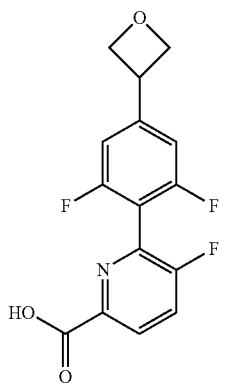 [SMILES: O=C(O)c1ccc(F)c(-c2c(F)cc(C3COC3)cc2F)n1]

Method 2 was followed using methyl 6-(2,6-difluoro-4-(oxetan-3-yl)phenyl)-5-fluoropicolinate to give 6-(2,6-difluoro-4-(oxetan-3-yl)phenyl)-5-fluoropicolinic acid in 71% yield. LC/MS=309.9 (MH+), Rt=0.69 min.

Synthesis of methyl 2',6,6'-trifluoro-4'-(trifluoromethylsulfonyloxy)biphenyl-3-carboxylate

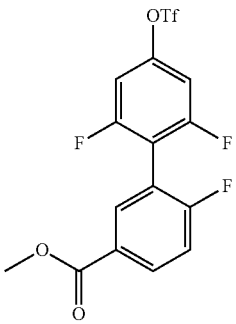 [SMILES: COC(=O)c1ccc(F)c(-c2c(F)cc(OS(=O)(=O)C(F)(F)F)cc2F)c1]

To a solution of methyl 2',6,6'-trifluoro-4'-hydroxybiphenyl-3-carboxylate (1.0 equiv.) in DCM (0.35 M) at 0° C. was added pyridine (1.5 equiv.) and allowed to stir for 5 mins, followed by the addition of Triflic Anhydride (1.1 equiv.). The reaction was allowed to stir warming to RT. The reaction was quenched with NaHCO$_{3(sat)}$, extracted in DCM and the organics were washed with water and brine. The organics were dried over Na$_2$SO$_4$, filtered, and concentrated to yield methyl 2',6,6'-trifluoro-4'-(trifluoromethylsulfonyloxy)biphenyl-3-carboxylate in 81% yield.

Synthesis of methyl 6-(4-(3,6-dihydro-2H-thiopyran-4-yl)-2,6-difluorophenyl)-5-fluoropicolinate

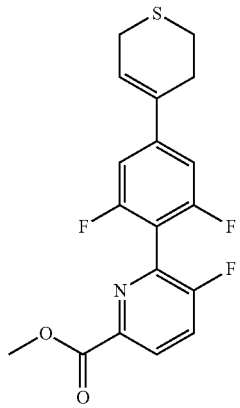 [SMILES: COC(=O)c1ccc(F)c(-c2c(F)cc(C3=CCSCC3)cc2F)n1]

To a degassed solution of methyl 6-(2,6-difluoro-4-(trifluoromethylsulfonyloxy)phenyl)-5-fluoropicolinate (1.0 equiv.) and 3,6-dihydro-2H-thiopyran-4-ylboronic acid (1.5 equiv.) in DME/2M Na$_2$CO$_3$ (3/1, 0.10 M) was added PdCl2(dppf).CH$_2$Cl$_2$ adduct (0.10 equiv.). The reaction was heated to 90° C. in an oil bath for 15 min. The reaction mixture was partitioned with water and EtOAc; the organics were dried over MgSO$_4$, filtered, and concentrated. The crude was purified via ISCO SiO$_2$ chromatography. Pure fractions were combined and concentrated to yield methyl 6-(4-(3,6-dihydro-2H-thiopyran-4-yl)-2,6-difluorophenyl)-5-fluoropicolinate in 60% yield. LC/MS=366.1 (M+H), Rt=1.00 min.

Synthesis of methyl 6-(4-(1,1-dioxido-3,6-dihydro-2H-thiopyran-4-yl)-2,6-difluorophenyl)-5-fluoropicolinate

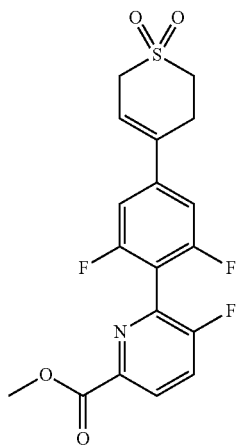 [SMILES: COC(=O)c1ccc(F)c(-c2c(F)cc(C3=CCS(=O)(=O)CC3)cc2F)n1]

To a solution of methyl 6-(4-(3,6-dihydro-2H-thiopyran-4-yl)-2,6-difluorophenyl)-5-fluoropicolinate (1.0 equiv.) in DCM (0.10 M) at rt was added oxone (6.0 equiv.) in one portion. The resulting mixture was stirred at RT overnight, and then refluxed at 40° C. for 4 hrs. 10.0 equiv. of oxone were added and the reaction was allowed to stir at 40° C. over the weekend. The reaction mixture was then diluted with DCM and washed with water the aqueous layer was then separated and extracted with DCM. The combined organic were then dried over MgSO$_4$ and concentrated in vacuo to yield methyl 6-(4-(1,1-dioxido-3,6-dihydro-2H-thiopyran-4-yl)-2,6-difluorophenyl)-5-fluoropicolinate in 100% yield. LC/MS=398.0 (M+H), Rt=0.76 min.

Synthesis of 6-(4-(1,1-dioxido-3,6-dihydro-2H-thiopyran-4-yl)-2,6-difluorophenyl)-5-fluoropicolinic acid

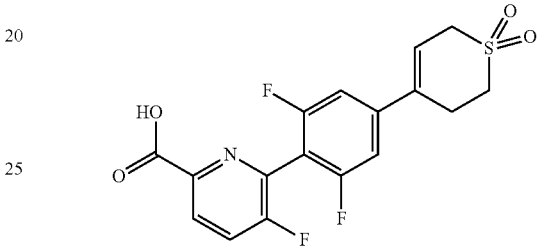

Method 2 was followed using methyl 6-(4-(1,1-dioxido-3,6-dihydro-2H-thiopyran-4-yl)-2,6-difluorophenyl)-5-fluoropicolinate to give 6-(4-(1,1-dioxidotetrahydro-2H-thiopyran-4-yl)-2,6-difluorophenyl)-5-fluoropicolinic acid in 74% yield. LC/MS=384.0 (M+H), Rt=0.64 min.

Synthesis of 6-(4-(1,1-dioxidotetrahydro-2H-thiopyran-4-yl)-2,6-difluorophenyl)-5-fluoropicolinic acid

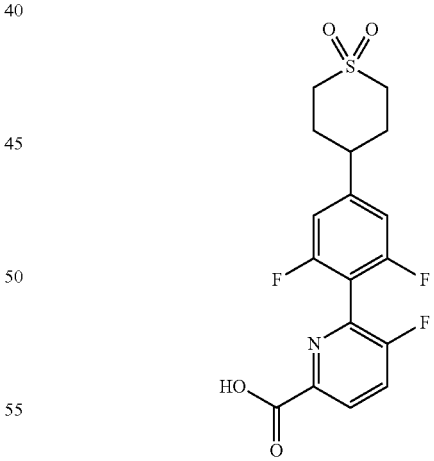

To a degassed solution of 6-(4-(1,1-dioxido-3,6-dihydro-2H-thiopyran-4-yl)-2,6-difluorophenyl)-5-fluoropicolinic acid (1.0 equiv.) in EtOH (0.10 M) was added Pd/C (0.1 equiv.). The mixture was stirred at rt under H$_2$ for 16 hrs. Add Pd/C (0.1 equiv.) and the reaction was stirred for additional 16 hrs. The reaction was filtered and concentrated to yield 6-(4-(1,1-dioxidotetrahydro-2H-thiopyran-4-yl)-2,6-difluorophenyl)-5-fluoropicolinic acid in 100% yield. LC/MS=386.0 (M+H), Rt=0.64 min.

Synthesis of methyl 6-(2,6-difluoro-4-(prop-1-en-2-yl)phenyl)-5-fluoropicolinate

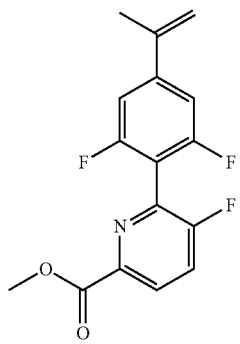 [SMILES: C=C(C)c1cc(F)c(-c2nc(C(=O)OC)ccc2F)c(F)c1]

To a degassed solution of methyl 6-(2,6-difluoro-4-(trifluoromethylsulfonyloxy)phenyl)-5-fluoropicolinate (1.0 equiv.) in DME/2M Na$_2$CO$_3$ (3/1, 0.09 M) was added 4,4,5,5-tetramethyl-2-(prop-1-en-2-yl)-1,3,2-dioxaborolane (1.5 equiv.) and PdCl2(dppf)-CH$_2$Cl$_2$Adduct (0.1 equiv.). The reaction was heated to 90° C. in an oil bath for 15 min. The mixture was cooled to rt and partitioned between water and ethyl acetate. The organic phase was dried with sodium sulfate, filtered and concentrated. The crude material was purified via silica gel column chromatography (Analogix, eluting with 0-100% ethyl acetate). The pure fractions were concentrated to yield methyl 6-(2,6-difluoro-4-(prop-1-en-2-yl)phenyl)-5-fluoropicolinate. LC/MS=308.2 (M+H), Rt=0.99 min. $^1$H NMR (400 MHz, <cdcl3>) δ ppm 2.15 (s, 3 H), 4.01 (s, 3 H), 5.23 (s, 1 H), 5.47 (s, 1 H), 7.11 (d, J=9.39 Hz, 2 H), 7.65 (t, J=8.41 Hz, 1 H), 8.26 (dd, J=8.61, 3.91 Hz, 1 H).

Synthesis of methyl 6-(2,6-difluoro-4-isopropylphenyl)-5-fluoropicolinate

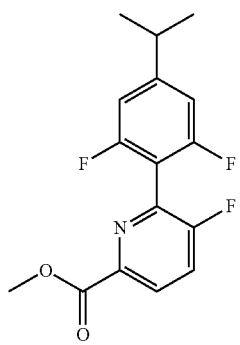 [SMILES: COC(=O)c1ccc(F)c(-c2c(F)cc(C(C)C)cc2F)n1]

To a degassed solution of methyl 6-(2,6-difluoro-4-(prop-1-en-2-yl)phenyl)-5-fluoropicolinate (1.0 equiv.) in MeOH (0.09 M) was added Pd/C (0.1 equiv.) and the reaction was stirred at rt under an atmosphere of hydrogen. After overnight stirring, filtered through a pad of Celite and washed with Methanol. The filtrate was concentrated and dried under vacuo to give methyl 6-(2,6-difluoro-4-isopropylphenyl)-5-fluoropicolinate. LC/MS=310.0 (M+H), Rt=1.00 min.

Synthesis of 6-(2,6-difluoro-4-isopropylphenyl)-5-fluoropicolinic acid

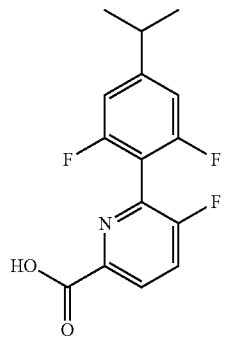 [SMILES: CC(C)c1cc(F)c(-c2nc(C(=O)O)ccc2F)c(F)c1]

Method 2 was followed using methyl 6-(2,6-difluoro-4-isopropylphenyl)-5-fluoropicolinate to give 6-(2,6-difluoro-4-isopropylphenyl)-5-fluoropicolinic acid in 100% yield. LC/MS=296.2 (M+H), Rt=0.89 min.

Synthesis of ethyl 2-(2,6-difluorophenyl)thiazole-4-carboxylate

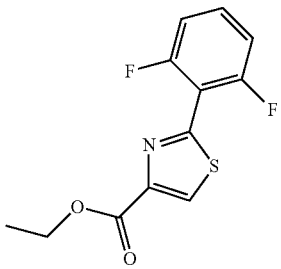 [SMILES: CCOC(=O)c1csc(-c2c(F)cccc2F)n1]

A solution of 2,6-difluorobenzothioamide (1.0 eq) and ethylbromopyruvate (1.0 eq.) in ethanol (1.0 M) was heated in the microwave at 130° C. for 30 minutes. Upon removal of volatiles in vacuo, ethyl acetate was added and the solution was washed with Na$_2$CO$_{3(sat.)}$, with NaCl$_{(sat)}$, was dried over MgSO$_4$, filtered and concentrated yielding ethyl 2-(2,6-difluorophenyl)thiazole-4-carboxylate (84%). LCMS (m/z): 270.1 (MH$^+$); LC R$_t$=3.79 min.

Synthesis of 2-(2,6-difluorophenyl)thiazole-4-carboxylic acid

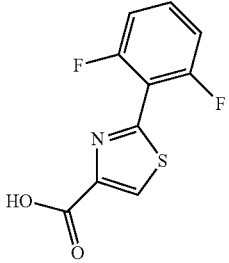 [SMILES: O=C(O)c1csc(-c2c(F)cccc2F)n1]

To a solution of ethyl 2-(2,6-difluorophenyl)thiazole-4-carboxylate (1.0 eq.) in 2:1 THF/MeOH (0.17 M) was added 1.0 M LiOH (2.0 eq.). After standing for 16 hours, 1.0 M HCl (2.0 eq.) was added and the THF/MeOH was removed in vacuo. The resulting solid was filtered, rinsed with H$_2$O and dried, yielding 2-(2,6-difluorophenyl)thiazole-4-carboxylic acid (88%) as a crusty solid. LCMS (m/z): 251.1 (MH+); LC R$_t$=2.68 min.

Synthesis of ethyl 2-amino-2-cyanoacetate

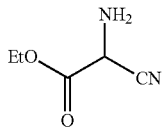

To a solution of ethyl 2-cyano-2-(hydroxyimino)acetate (1 eq) in ethanol (1.4 M) was added PtO$_2$ (0.05 eq) and the solution was put under an H$_2$ atmosphere (4 bar) in a steel bomb and was stirred overnight. The reaction was filtered through a pad of celite, rinsing with CH$_2$Cl$_2$ and upon removal of volatiles in vacuo ethyl 2-amino-2-cyanoacetate was obtained in 89% yield. LC/MS (m/z): 129.0 (MH+), R$_t$: 0.25 min.

Synthesis of ethyl 2-cyano-2-(2,6-difluorobenzamido)acetate

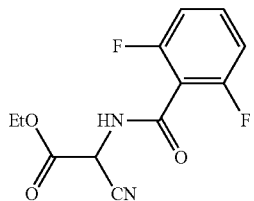 [SMILES: CCOC(=O)C(C#N)NC(=O)c1c(F)cccc1F]

To a solution of ethyl 2-amino-2-cyanoacetate (1 eq) in 6 mL of dichloromethane was added pyridine (1.5 eq) and 2,6-difluorobenzoyl chloride (1 eq) at 0° C. The reaction mixture was stirred at room temperature for 3 hours. The mixture was diluted with ethyl acetate, washed with brine, then dried over anhydrous MgSO$_4$, filtered, and concentrated in vacuo. The crude residue was purified by flash chromatography (EtOAc: hexanes=1:1) to give the titled compound (84%). LC/MS (m/z): 269.1 (MH+), R$_t$: 0.69 min.

Synthesis of ethyl 5-amino-2-(2,6-difluorophenyl)thiazole-4-carboxylate

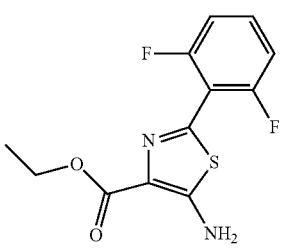 [SMILES: CCOC(=O)c1nc(-c2c(F)cccc2F)sc1N]

To a solution of the ethyl 2-cyano-2-(2,6-difluorobenzamido)acetate (1 eq) in pyridine (0.1 M) was added Lawesson's reagent (1.5 eq.). The mixture was stirred at reflux under Ar for 18 hours. Solvents were removed under reduced pressure. The crude residue was purified by flash chromatography (EtOAc:hexanes=1:1) to give the ethyl 5-amino-2-(2,6-difluorophenyl)thiazole-4-carboxylate in 25% yield. LC/MS (m/z): 284.9 (MH+), R$_t$: 0.76 min.

Synthesis of 5-((tert-butoxycarbonyl)amino)-2-(2,6-difluorophenyl)thiazole-4-carboxylic acid

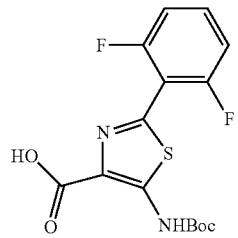 [SMILES: CC(C)(C)OC(=O)Nc1sc(-c2c(F)cccc2F)nc1C(=O)O]

To a solution of the ethyl 5-amino-2-(2,6-difluorophenyl)thiazole-4-carboxylate (1 eq) in CH$_2$Cl$_2$ (0.1 M) was added Boc$_2$O (1.2 eq.) and DMAP (0.05 eq.). Upon stirring for 1 hour the volatiles were removed in vacuo, THF (0.1 M) and 2.0 M LiOH$_{(aq.)}$ (5 equiv) were added and the solution was stirred at 55° C. for 2 days. The volatiles were removed in vacuo and the remaining aqueous solution was adjusted to pH 5 by addition of 2 M HCl. The resulting solid was filtered, rinsed with H$_2$O and pumped on to yield 5-((tert-butoxycarbonyl)amino)-2-(2,6-difluorophenyl)thiazole-4-carboxylic acid 25% yield. LC/MS (m/z): 357.1 (MH+), R$_t$: 0.97 min.

Synthesis of Methyl 3-amino-5-fluoropicolinate

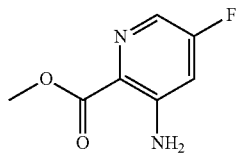

To a steel bomb reactor, 2-bromo-5-fluoropyridin-3-amine (1.0 equiv.), triethylamine (1.6 equiv.), Pd(BINAP)Cl$_2$ (0.0015 equiv.) and anhydrous methanol (0.4 M solution) were added. After degassed by nitrogen stream for 15 min, the steel bomb reactor was closed and filled with CO gas up to 60 psi. The reactor was then heated to 100° C. After 3 h, more Pd catalyst (0.0015 equiv.) was added and the reaction mixture was re-heated to the same temperature for 3 h. After cooling down to room temperature, a brown precipitate was filtered off and the filtrate was extracted with EtOAc, which was washed with water and brine, dried over anhydrous sodium sulfate, and filtered. After removing volatile materials, the crude yellow product was obtained and used for the next step without further purification (40%). LCMS (m/z): 271.2 (MH+); LC R$_t$=3.56 min.

Synthesis of Methyl 3-amino-6-bromo-5-fluoropicolinate

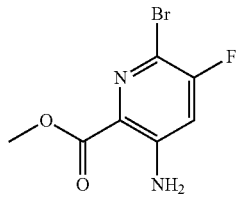

To a solution of methyl 3-amino-5-fluoropicolinate (1.0 equiv.) in acetonitrile (0.3 M solution) was added NBS (1.1 equiv.) for 2 minutes at room temperature. After quenched with water, the reaction mixture was extracted with EtOAc. The crude product was purified by silica column chromatography (20% to 50% EtOAc in hexanes) to give methyl 3-amino-6-bromo-5-fluoropicolinate (41%). LCMS (m/z): 249.1 (MH$^+$); LC R$_t$=2.80 min.

Synthesis of methyl 3-amino-6-(2,6-difluorophenyl)-5-fluoropicolinate

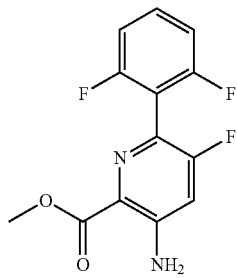 [SMILES: COC(=O)c1nc(-c2c(F)cccc2F)c(F)cc1N]

Method 1 was followed using methyl 3-amino-6-bromo-5-fluoropicolinate (1.0 equiv.) and 2,6-difluorophenylboronic acid (1.3 equiv.) and Pd(dppf)Cl$_2$-DCM (0.05 equiv.) to give methyl 3-amino-6-(2,6-difluorophenyl)-5-fluoropicolinate in 94% yield. LCMS (m/z): 283.0 (MH$^+$), R$_t$=0.76 min.

Synthesis of 3-amino-6-(2,6-difluorophenyl)-5-fluoropicolinic acid

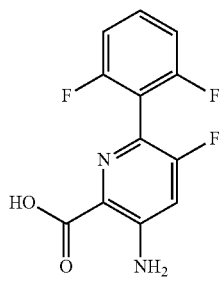

Method 2 was followed using methyl 3-amino-6-(2,6-difluorophenyl)-5-fluoropicolinate (1.0 equiv.) and LiOH (1.0 equiv.) to give 3-amino-6-(2,6-difluorophenyl)-5-fluoropicolinic acid in 79% yield. LCMS (m/z): 269.0 (MH$^+$), R$_t$=0.79 min.

Synthesis of 2-(2,6-difluorophenyl)pyrimidine-4-carboxylic acid

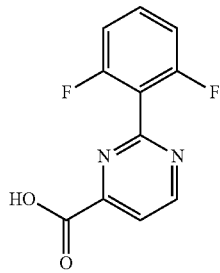 [SMILES: O=C(O)c1ccnc(-c2c(F)cccc2F)n1]

To a solution of 2-chloropyrimidine-4-carboxylic acid (1.0 equiv.) in DME and 2M Na$_2$CO$_3$ (3:1, 0.25 M) was added 2,6-difluorophenylboronic acid (1.3 equiv.) and Pd(dppf)Cl$_2$-DCM (0.05 equiv.) in a microwave vial. The vial was heated in the microwave at 120° C. for 30 minutes. The mixture was diluted with ethyl acetate and 1N NaOH was added. The organic phase was separated and extracted three more times with 1N NaOH and once with 6N NaOH. The combined aqueous phases were filtered and acidified to pH 1 by the addition of concentrated HCl and extracted with ethyl acetate. The organic layer was dried over magnesium sulfate, filtered, and concentrated to give 2-(2,6-difluorophenyl)pyrimidine-4-carboxylic acid in 81%. LCMS (m/z): 237.0 (MH$^+$), R$_t$=0.54 min.

Synthesis of 5-amino-2-(2,6-difluorophenyl)pyrimidine-4-carboxylic acid

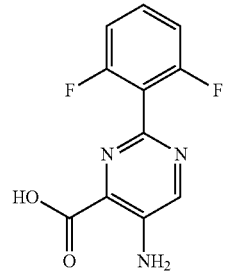 [SMILES: Nc1cnc(-c2c(F)cccc2F)nc1C(=O)O]

A 2.68 M NaOEt in EtOH solution (3 eq) was added to an ice-bath cooled mixture of 2,6-difluorobenzimidamide hydrochloride (2 eq) in EtOH (0.1 M). The resulting mixture was allowed to warm to rt and stirred under N$_2$ for 30 min. To the reaction mixture was added drop wise a solution of mucobromic acid (1 eq) in EtOH and the reaction was heated in a 50° C. oil bath for 2.5 hr. After cooling to rt the reaction mixture was concentrated in vacuo. H$_2$O and 1.0 N NaOH were added and the aqueous mixture was washed with EtOAc. The aqueous phase was acidified to pH=4 with 1.0 N HCl then extracted with EtOAc. Combined organic extracts were washed once with brine, then dried over anhydrous Na$_2$SO$_4$, filtered, and concentrated in vacuo to give 5-bromo-2-(2,6-difluorophenyl)pyrimidine-4-carboxylic acid. The crude product was used for the next step without further purification. LC/MS (m/z): 316.9 (MH$^+$). LC: R$_t$: 2.426 min.

CuSO$_4$ (0.1 eq) was added to a mixture of 5-bromo-2-(2,6-difluorophenyl)pyrimidine-4-carboxylic acid (1 eq) and 28% aqueous ammonium hydroxide solution in a microwave reaction vessel. The reaction mixture was heated in a microwave reactor at 110° C. for 25 min. The reaction vessel was cooled in dry ice for 30 min then unsealed and concentrated in vacuo. To the resulting solids was added 1.0 N HCl and the mixture was extracted with EtOAc. Combined organic extracts were washed once with brine, then dried over anhydrous Na$_2$SO$_4$, filtered, and concentrated in vacuo to give 5-amino-2-(2,6-difluorophenyl)pyrimidine-4-carboxylic acid. The crude product was used for the next step without further purification. LCMS (m/z): 252.0 (MH$^+$), R$_t$=2.0 min.

Synthesis of 2-(2,6-difluorophenyl)-3-fluoro-6-methylpyridine

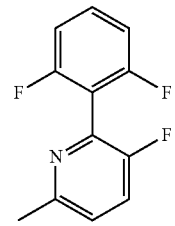 [SMILES: Cc1ccc(F)c(-c2c(F)cccc2F)n1]

To a solution of 2-bromo-3-fluoro-6-methylpyridine (1.0 equiv.) in THF and Water (10:1, 0.2 M) was added 2,6-difluorophenylboronic acid (2.0 equiv.) and potassium fluoride (3.3 equiv.). The reaction was degassed for 10 minutes, then $Pd_2(dba)_3$ (0.05 equiv.) was added, followed by tri-t-butylphosphine (0.1 equiv.). The reaction was stirred to 60° C. for 1 hour at which point, all starting material was consumed as indicated by LC/MS. The reaction was allowed to cool to room temperature, partitioned with ethyl acetate and water, the organic phase was dried with sodium sulfate, filtered, and concentrated. The crude material was diluted in EtOH to 0.1 M, and 0.5 equiv. of $NaBH_4$ was added to reduce the dba. The reaction was stirred for one hour at room temperature, then quenched with water and concentrated under vacuo to remove the ethanol. The product was extracted in ether, washed with brine, the organics were dried over sodium sulfate, filtered, and concentrated. The crude material was loaded on silica gel and purified via column chromatography (ISCO) eluting with hexanes and ethyl acetate (0%-10% ethyl acetate). The pure fractions were combined, and concentrated to yield 2-(2,6-difluorophenyl)-3-fluoro-6-methylpyridine as a light yellow oil in 86% yield. LC/MS=224.0 (M+H), $R_t$=0.84 min.

Synthesis of 6-(2,6-difluorophenyl)-5-fluoropicolinic acid

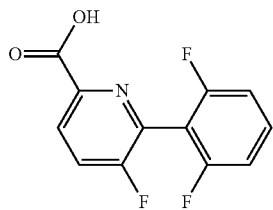 [SMILES: O=C(O)c1ccc(F)c(-c2c(F)cccc2F)n1]

To a solution of 2-(2,6-difluorophenyl)-3-fluoro-6-methylpyridine (1.0 equiv.) in water (0.05 M) was added $KMnO_4$ (2.0 equiv.) and the reaction was heated to reflux overnight. Another 2.0 equiv. of $KMnO_4$ were added and stirred at reflux for another 8 hours. The solution was cooled to room temperature, filtered through Celite and washed with water. The filtrate was acidified with 6N HCl to pH=3, the white precipitate was filtered. The filtrate was further acidified to pH=1 and filtered again. The filtrate was extracted with ethyl acetate until no more product was in the aqueous layer. The organic phase was washed with brine and dried over magnesium sulfate, filtered, and concentrated. The residue was dissolved in ethyl acetate, washed with 1N NaOH, the aqueous layer was acidified to pH=1 and the white crystals were filtered. The combined products yielded 6-(2,6-difluorophenyl)-5-fluoropicolinic acid in 32% yield as a white solid. LC/MS=254.0 (M+H), $R_t$=0.71 min.

Synthesis of methyl 3-amino-6-(2-fluoro-5-isopropylcabamoyl)phenyl)-picolinate

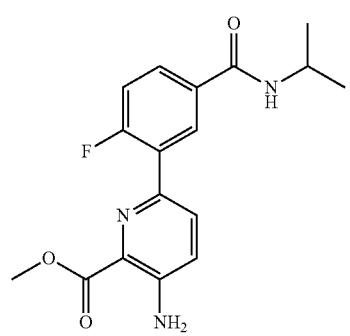 [SMILES: COC(=O)c1nc(-c2cc(C(=O)NC(C)C)ccc2F)ccc1N]

A solution of methyl 3-amino-6-bromopicolinate (1.0 equiv.), N-isopropyl 3-borono-4-fluorobenzamide (1.1 equiv.), and $Pd(dppf)Cl_2$-DCM (0.15 equiv.) in DME/2M $Na_2CO_3$ (3:1), at a concentration of 0.5 M, was stirred at 120° C. for 1.5 hours. The reaction was filtered and washed with EtOAc. The organic was partitioned with $H_2O$ (25 mL), washed with $NaCl_{(sat)}$ (25 mL), dried over $MgSO_4$, and the volatiles were removed in vacuo. The residue was diluted in EtOAc and passed through a silica gel plug and the volatiles were removed in vacuo yielding methyl 3-amino-6-(2-fluoro-5-isopropylcabamoyl)-phenyl)picolinate (60%). LCMS (m/z): 332.2 (MH$^+$); LC $R_t$=2.9 min.

Synthesis of 3-amino-6-(2-fluoro-5-isopropylcabamoyl)phenyl)picolinic acid

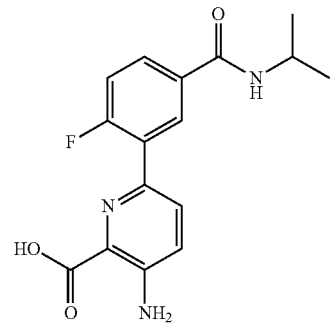 [SMILES: CC(C)NC(=O)c1ccc(F)c(-c2ccc(N)c(C(=O)O)n2)c1]

To a solution of methyl 3-amino-6-(2-fluoro-5-isopropylcabamoyl)phenyl)picolinate (1.0 equiv) in THF (0.5M), was added 1M LiOH (4.0 equiv). After stirring for 4 hours at 60° C., 1 N HCl (4.0 equiv.) was added and the THF was removed in vacuo. The resulting solid was filtered and rinsed with cold $H_2O$ (3×20 mL) to yield 3-amino-6-(2-fluoro-5-isopropylcabamoyl)phenyl)picolinic acid (98%). LCMS (m/z): 318.1 (MH$^+$); LC $R_t$=2.4 min.

Synthesis of (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate

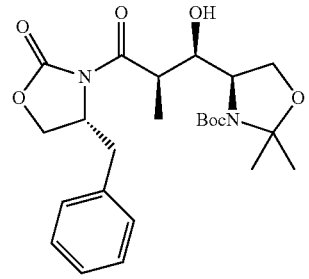 [SMILES: C[C@@H](C(=O)N1C(=O)OC[C@H]1Cc1ccccc1)[C@@H](O)[C@H]1COC(C)(C)N1C(=O)OC(C)(C)C]

To a solution of (R)-4-benzyl-3-propionyloxazolidin-2-one (1.0 equiv.) in DCM (0.13 M) was added $TiCl_4$ (1.0 equiv.) at −40° C. The mixture was stirred at −40° C. for 10 min (yellow suspension), then DIPEA (2.5 equiv.) was added (dark red solution) and stirred at 0° C. for 20 min. (R)-tert-butyl 4-formyl-2,2-dimethyloxazolidine-3-carboxylate (1.0 equiv.) in DCM (0.5 M) was then added dropwise and the resulting mixture was stirred for 1.5 hours. The reaction was quenched by the addition of aqueous ammonium chloride and the mixture was extracted with ethyl acetate. The organic phase was separated, washed with brine, dried with magnesium sulfate, filtered, and concentrated. The residue was purified via column chromatography eluting with ethyl acetate and hexanes (1:4) to give (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate as the major product (5:2) in 58% yield. LC/MS=363.3 (M+H-Boc), Rt=1.09 min.

Synthesis of (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate

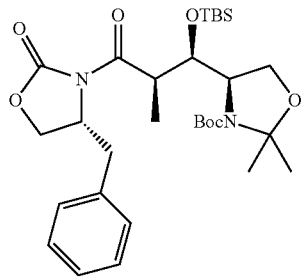 [SMILES: C[C@@H](C(=O)N1C(=O)OC[C@H]1Cc1ccccc1)[C@@H](O[Si](C)(C)C(C)(C)C)[C@H]1COC(C)(C)N1C(=O)OC(C)(C)C]

To a solution of (R)-tert-butyl 4-((1R,2R)-3-((R)-4-benzyl-2-oxooxazolidin-3-yl)-1-hydroxy-2-methyl-3-oxopropyl)-2,2-dimethyloxazolidine-3-carboxylate (1.0 equiv.) and lutidine (1.8 equiv.) in DCM (0.1M) was added TBSOTf (1.4 equiv.) at −40° C. The reaction mixture was stirred at −40° C. for 2 hours. The solution was diluted with ethyl acetate and washed with sat. NaHCO$_3$, sat. NaCl, dried with magnesium sulfate, filtered, and concentrated. The residue was purified by silica gel column chromatography eluting with ethyl acetate and hexanes (1:4) to give (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate as the major product (5:2) in 83% yield. LC/MS=577.3 (M+H), Rt=1.33 min (Frac 65%-95% method).

Synthesis of (R)-tert-butyl 4-((1R,2S)-1-(tert-butyldimethylsilyloxy)-3-hydroxy-2-methylpropyl)-2,2-dimethyloxazolidine-3-carboxylate

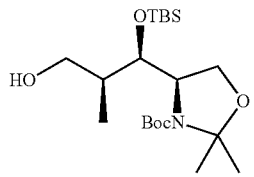 [SMILES: C[C@@H](CO)[C@@H](O[Si](C)(C)C(C)(C)C)[C@H]1COC(C)(C)N1C(=O)OC(C)(C)C]

To a solution of (R)-tert-butyl 4-((1R,2R)-3-((R)-4-benzyl-2-oxooxazolidin-3-yl)-1-(tert-butyldimethylsilyloxy)-2-methyl-3-oxopropyl)-2,2-dimethyloxazolidine-3-carboxylate (1.0 equiv.) and ethanol (3.0 equiv.) in THF (0.09 M) was added LiBH$_4$ (3.0 equiv.) at −30° C. The reaction mixture was allowed to warm up to 0° C. and stirred at that temperature for 3 hours. The solution was then diluted with diethyl ether and 1N NaOH was added. The resulting mixture was extracted with ethyl acetate, the organic layer was separated, washed with sat. NaCl, dried over magnesium sulfate, filtered, and concentrated. The residue was purified via silica gel column chromatography eluting with ethyl acetate and hexanes (1:4) to give (R)-tert-butyl 4-((1R,2S)-1-(tert-butyldimethylsilyloxy)-3-hydroxy-2-methylpropyl)-2,2-dimethyloxazolidine-3-carboxylate as the major product (5:2 ratio) in 71% yield. LC/MS=304.3 (M+H-Boc), Rt=0.95 min (Frac 65%-95% method).

Synthesis of (R)-tert-butyl 4-((1R,2S)-3-azido-1-(tert-butyldimethylsilyloxy)-2-methylpropyl)-2,2-dimethyloxazolidine-3-carboxylate

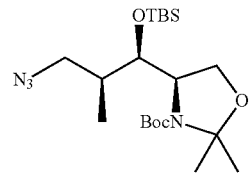

To a solution of (R)-tert-butyl 4-((1R,2S)-1-(tert-butyldimethylsilyloxy)-3-hydroxy-2-methylpropyl)-2,2-dimethyloxazolidine-3-carboxylate (1.0 equiv.), DIAD (2.0 equiv.), and PPh$_3$ (2.0 equiv.) in THF (0.18 M) was added DPPA (2.0 equiv., 1M solution in THF). The reaction mixture was stirred at room temperature overnight. Upon removal of the volatiles under vacuo, the residue was purified by silica gel column chromatography eluting with ethyl acetate and hexanes (1:6) to give (R)-tert-butyl 4-((1R,2S)-3-azido-1-(tert-butyldimethylsilyloxy)-2-methylpropyl)-2,2-dimethyloxazolidine-3-carboxylate as the major product (5:2) in 86% yield. LC/MS=329.3 (M+H-Boc), Rt=1.40 min (Frac 65%-95% method).

Synthesis of tert-butyl (2R,3R,4S)-5-azido-3-(tert-butyldimethylsilyloxy)-1-hydroxy-4-methylpentan-2-ylcarbamate

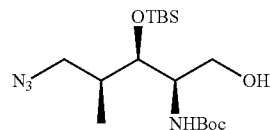 [SMILES: C[C@@H](CN=[N+]=[N-])[C@@H](O[Si](C)(C)C(C)(C)C)[C@@H](CO)NC(=O)OC(C)(C)C]

To a solution of (R)-tert-butyl 4-((1R,2S)-3-azido-1-(tert-butyldimethylsilyloxy)-2-methylpropyl)-2,2-dimethyloxazolidine-3-carboxylate (1.0 equiv.) in EtOH (0.1 M) was added PPTS (1.3 equiv.) and the mixture was refluxed for 2 days. The volatiles were removed under vacuo, the residue was dissolved in DCM (0.1 M) and DIEA (1.5 equiv.) and Boc$_2$O (1.0 equiv.) were added to the reaction mixture. The solution was stirred for 3 hours at room temperature. The solvents were removed under reduced pressure and the residue was diluted with ethyl acetate, washed with water, aqueous NaHSO$_4$, aqueous NaHCO$_3$, sat. NaCl, the organic phase was dried with magnesium sulfate, filtered, and concentrated. The residue was purified via silica gel column chromatography eluting with ethyl acetate and hexanes (1:3) to give tert-butyl (2R,3R,4S)-5-azido-3-(tert-butyldimethylsilyloxy)-1-hydroxy-4-methylpentan-2-ylcarbamate as the major isomer (5:2) in 70% yield. LC/MS=289.3 (M+H-Boc), Rt=0.76 min (Frac 65%-95% method).

Synthesis of (2R,3R,4S)-5-azido-2-(tert-butoxycarbonylamino)-3-(tert-butyldimethylsilyloxy)-4-methylpentyl methanesulfonate

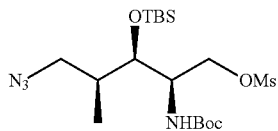 [SMILES: C[C@@H](CN=[N+]=[N-])[C@@H](O[Si](C)(C)C(C)(C)C)[C@@H](COS(C)(=O)=O)NC(=O)OC(C)(C)C]

To a solution of tert-butyl (2R,3R,4S)-5-azido-3-(tert-butyldimethylsilyloxy)-1-hydroxy-4-methylpentan-2-ylcarbamate (1.0 equiv.) in pyridine (0.2 M) was added MsCl (1.3 equiv.) followed by DMAP (catalytic amount) at 0° C. The mixture was stirred at that temperature for 1 hour. The solution was diluted with ether and ethyl acetate (4:1), washed with aq. NaHSO$_4$, sat. NaHCO$_3$, brine, dried over magnesium sulfate, filtered, and concentrated. The residue was purified by silica gel column chromatography eluting with ethyl acetate and hexanes (1:3) to give (2R,3R,4S)-5-azido-2-(tert-butoxycarbonylamino)-3-(tert-butyldimethylsilyloxy)-4-methylpentyl methanesulfonate as the major isomer (5:2) in 90% yield. LC/MS=367.3 (M+H-Boc), Rt=0.81 min (Frac 65%-95% method).

Synthesis of tert-butyl (3R,4R,5S)-4-(tert-butyldimethylsilyloxy)-5-methylpiperidin-3-ylcarbamate

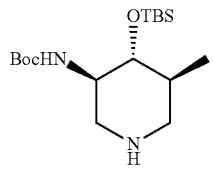 [SMILES: C[C@H]1CNC[C@@H](NC(=O)OC(C)(C)C)[C@@H]1O[Si](C)(C)C(C)(C)C]

A solution of (2R,3R,4S)-5-azido-2-(tert-butoxycarbonylamino)-3-(tert-butyldimethylsilyloxy)-4-methylpentyl methanesulfonate in MeOH (0.09 M) was degassed with nitrogen for 20 min. DIEA (2.5 equiv.) was added, followed by 10% Pd/C (0.1 equiv.). The reaction mixture was stirred under a hydrogen balloon for 2 hours. The solution was filtered and the filtrate was concentrated under vacuo to afford tert-butyl (3R,4R,5S)-4-(tert-butyldimethylsilyloxy)-5-methylpiperidin-3-ylcarbamate as the major isomer (5:2) in >99% yield. LC/MS=345.2 (M+H-Boc), Rt=0.95 and 0.99 min.

Synthesis of tert-butyl (3R,4R,5S)-4-(tert-butyldimethylsilyloxy)-5-methyl-1-(3-nitropyridin-4-yl)piperidin-3-ylcarbamate

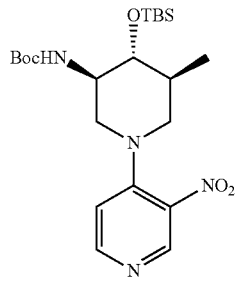

To a solution of tert-butyl (3R,4R,5S)-4-(tert-butyldimethylsilyloxy)-5-methylpiperidin-3-ylcarbamate (1.0 equiv.) in i-PrOH (0.09 M) was added DIEA (2.5 equiv.) and 4-chloro-3-nitropyridine (1.5 equiv.). The reaction mixture was stirred at 60° C. for 2 hours. The volatiles were removed under vacuo, the residue was diluted with ethyl acetate and washed with sat. NaCl. The organic phase was dried with magnesium sulfate, filtered, and concentrated. The crude material was purified by silica gel column chromatography eluting with ethyl acetate and hexanes (1:2) to give tert-butyl (3R,4R,5S)-4-(tert-butyldimethylsilyloxy)-5-methyl-1-(3-nitropyridin-4-yl)piperidin-3-ylcarbamate in 76% yield. LC/MS=467.3 (M+H), Rt=1.09 min.

Synthesis of tert-butyl (3R,4R,5S)-1-(3-aminopyridin-4-yl)-4-(tert-butyldimethylsilyloxy)-5-methylpiperidin-3-ylcarbamate

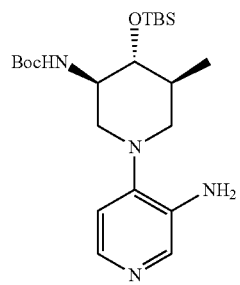 [SMILES: C[C@H]1CN(c2ccncc2[N+](=O)[O-])C[C@@H](NC(=O)OC(C)(C)C)[C@@H]1O[Si](C)(C)C(C)(C)C]

A solution of tert-butyl (3R,4R,5S)-4-(tert-butyldimethylsilyloxy)-5-methyl-1-(3-nitropyridin-4-yl)piperidin-3-ylcarbamate (1.0 equiv.) in MeOH (0.05 M) was degassed with nitrogen for 20 min. 10% Pd/C (0.2 equiv.) was added to the mixture and the solution was stirred under a hydrogen balloon for 3 hours. The reaction was filtered and the filtrate was concentrated under reduced pressure to give tert-butyl (3R,4R,5S)-1-(3-aminopyridin-4-yl)-4-(tert-butyldimethylsilyloxy)-5-methylpiperidin-3-ylcarbamate as the desired product in 94% yield. LC/MS=437.4 (M+H), Rt=1.08 min. $^1$H-NMR (300 MHz, CDCl$_3$): δ 8.01 (s, 1H), 7.95 (d, J=6.0 Hz, 1H), 6.76 (d, J=6.0 Hz, 1H), 4.44 (br s, 1H), 3.74 (br s, 2H), 3.59-3.55 (m, 1H), 3.25-3.13 (m, 2H), 2.47-2.35 (m, 2H), 1.89 (br s, 2H), 1.44 (s, 9H), 1.04 (d, J=6.0, 3H), 0.92 (s, 9H), 0.13 (d, J=9.0, 6H).

Synthesis of 5-methyl-3-oxocyclohex-1-enyltrifluoromethanesulfonate

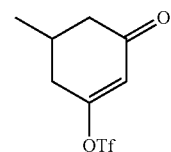

To a solution of 5-methylcyclohexane-1,3-dione (1.0 equiv.) in DCM (0.5M) was added Na$_2$CO$_3$ (1.1 equiv.) and cooled to 0° C. Added Tf$_2$O (1.0 equiv.) in DCM (5.0 M) dropwise over 1 hr at 0° C. under a nitrogen atmosphere. Upon addition, the reaction was stirred for 1 hr at room temperature (dark red solution). The solution was filtered and the filtrate was quenched by careful addition of saturated NaHCO$_3$ with vigorous stirring until pH=7. The solution was transferred to a separatory funnel and the layers were separated. The organic layer was washed with brine, dried with Na$_2$SO$_4$, filtered, concentrated under vacuo and dried under high vacuum for 15 min to yield 5-methyl-3-oxocyclohex-1- enyl trifluoromethanesulfonate as light yellow oil in 78% yield. The triflate decomposes upon storage and should be used immediately for the next reaction. LC/MS=259.1/300.1 (M+H and M+CH₃CN); Rt=0.86 min, LC=3.84 min. ¹H-NMR (400 MHz, CDCl₃) δ ppm: 6.05 (s, 1H), 2.70 (dd, J=17.2, 4.3, 1H), 2.53 (dd, J=16.6, 3.7, 1H), 2.48-2.31 (m, 2H), 2.16 (dd, J=16.4, 11.7, 1H), 1.16 (d, J=5.9, 3H).

Synthesis of 5-methyl-3-(4,4,5,5-tetramethyl-1,3,2-dioxaborolan-2-yl)cyclohex-2-enone

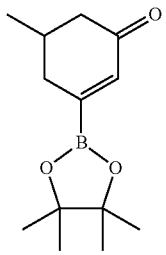 [SMILES: CC1CC(=O)C=C(B2OC(C)(C)C(C)(C)O2)C1]

To a solution of 5-methyl-3-oxocyclohex-1-enyl trifluoromethanesulfonate (1.0 equiv.) in degassed dioxane (0.7 M) was added bis(pinacolato)diboron (2.0 equiv.), KOAc (3.0 equiv.), and Pd(dppf)Cl₂-DCM (0.03 equiv.). The reaction was heated to 80° C. for 10 h then cooled to room temperature and filtered through a coarse frit glass funnel The cake was rinsed with more dioxane and the filtrate solution was used for the next step without further purification. LC/MS=155.1 (M+H of boronic acid); Rt=0.41 min, LC=1.37 min.

Synthesis of 5-methyl-3-(3-nitropyridin-4-yl)cyclohex-2-enone

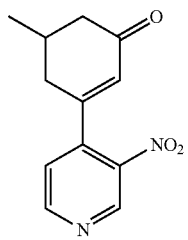 [SMILES: CC1CC(=O)C=C(c2ccncc2[N+](=O)[O-])C1]

To a solution of 5-methyl-3-(4,4,5,5-tetramethyl-1,3,2-dioxaborolan-2-yl)cyclohex-2-enone (1.0 equiv.) in degassed dioxane (0.5 M) and 2M Na₂CO₃ (2 equiv.) was added 4-chloro-3-nitropyridine (1.3 equiv.) and Pd(dppf)Cl₂-DCM (0.05 equiv.). The reaction was placed under a reflux condenser and heated in an oil bath to 110° C. for 1 h. Cooled to room temperature, filtered through a pad of Celite, washed the pad with ethyl acetate and concentrated the filtrate under vacuo. The residue was further pumped at 80° C. on a rotary evaporator for one hour to remove boronate by-products (M+H=101) via sublimation. The residue was partitioned between brine and ethyl acetate, and the layers were separated, the aqueous phase was further extracted with ethyl acetate (4×), the organics were combined, dried over sodium sulfate, filtered, and concentrated. The crude was purified via silica gel chromatography loading in DCM and eluting with 2-50% ethyl acetate and hexanes. The pure fractions were concentrated in vacuo to yield an orange oil. The oil was placed under high vacuum (~500 mtorr) with seed crystals overnight to yield an orange solid. The solid was further purified via trituration in hexanes to yield 5-methyl-3-(3-nitropyridin-4-yl)cyclohex-2-enone (48% 2 steps). LC/MS=233.2 (M+H); Rt=0.69 min, LC=2.70 min. ¹H-NMR (400 MHz, CdCl₃) δ ppm: 9.31 (s, 1H), 8.88 (d, J=5.1, 1H), 7.30 (d, J=5.1, 1H), 6.00 (d, J=2.4, 1H), 2.62 (dd, J=16.4, 3.5, 1H), 2.53-2.34 (m, 3H), 2.23 (dd, J=16.1, 11.7, 1H), 1.16 (d, J=6.3, 3H).

Synthesis of cis-(+/−)-5-methyl-3-(3-nitropyridin-4-yl)cyclohex-2-enol

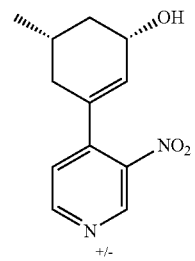

To a solution of 5-methyl-3-(3-nitropyridin-4-yl)cyclohex-2-enone (1.0 equiv.) in EtOH (0.3 M) was added CeCl₃-7H₂O (1.2 equiv.). The reaction was cooled to 0° C., then NaBH₄ (1.2 equiv.) was added in portions. Stirred for 1 h at 0° C., then quenched by adding water, concentrated to remove the EtOH, added EtOAc, extracted the organics, washed with brine, then dried with Na₂SO₄, filtered and concentrated to yield cis-(+/−)-5-methyl-3-(3-nitropyridin-4-yl)cyclohex-2-enol (94%). LC/MS=235.2 (M+H), LC=2.62 min.

Synthesis of (+/−)-4-(5-methylcyclohexa-1,3-dienyl)-3-nitropyridine

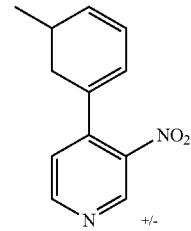 [SMILES: CC1C=CC=C(c2ccncc2[N+](=O)[O-])C1]

To a solution of (+/−)-5-methyl-3-(3-nitropyridin-4-yl)cyclohex-2-enol (1.0 equiv.) in dioxane (0.1M) was added p-TSA (1.0 equiv.), and the reaction was stirred at 100° C. for 3 h. The solution was cooled to room temperature, then passed through a pad of neutral alumina eluting with EtOAc to yield (+/−)-4-(5-methylcyclohexa-1,3-dienyl)-3-nitropyridine as a yellow oil in 68% yield. LC/MS=217.1 (M+H), LC=3.908 min.

Synthesis of (+/−)-6-bromo-5-methyl-3-(3-nitropyridin-4-yl)cyclohex-2-enol

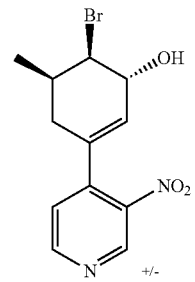 [SMILES: C[C@@H]1CC(c2ccncc2[N+](=O)[O-])=C[C@@H](O)[C@@H]1Br]

To a solution of 4-(5-methylcyclohexa-1,3-dienyl)-3-nitropyridine (1.0 equiv.) in THF and water (1:1, 0.13 M) was added NBS (1.5 equiv.) and the reaction was stirred at room temperature for 30 min. Upon completion, ethyl acetate and water were added to the reaction, the organic phase was dried with brine, then sodium sulfate, filtered, and concentrated. The crude material was purified via silica gel column chromatography eluting with ethyl acetate and hexanes (1:1) to give (+/−)-6-bromo-5-methyl-3-(3-nitropyridin-4-yl)cyclohex-2-enol as a yellow oil in 80% yield. LC/MS=315.0/313.0 (M+H), LC=2.966 min.

Synthesis of (+/−)-2-azido-6-methyl-4-(3-nitropyridin-4-yl)cyclohex-3-enol

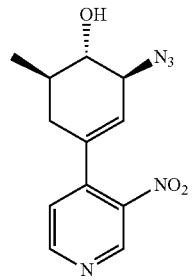 [SMILES: C[C@@H]1CC(c2ccncc2[N+](=O)[O-])=C[C@H](N=[N+]=[N-])[C@H]1O]

To a solution of (+/−)-6-bromo-5-methyl-3-(3-nitropyridin-4-yl)cyclohex-2-enol (1.0 equiv.) in THF (0.1 M) was added potassium tert-butoxide (1.5 equiv.). The reaction turned from orange to black almost immediately. By TLC, the formation of product is clean in 30 min. Quenched by adding saturated ammonium chloride and ethyl acetate. The organic phase was dried with brine, then sodium sulfate, filtered, and concentrated. The crude product was dissolved in ethanol and water (3:1, 0.1 M), and ammonium chloride (2.0 equiv) and sodium azide (2.0 equiv.) were added. The dark orange reaction was stirred at room temperature overnight. The conversion to product is clean as indicated by LC/MS. The reaction was concentrated to remove the ethanol, ethyl acetate and water were added, and the organic phase was dried with sodium sulfate, filtered, and concentrated. The crude material was purified via silica gel column chromatography eluting with ethyl acetate and hexanes (1:1) to give (+/−)-2-azido-6-methyl-4-(3-nitropyridin-4-yl)cyclohex-3-enol in 55% yield. LC/MS=276.0 (M+H), LC=2.803 min.

Synthesis of (+/−)-tert-butyl 6-hydroxy-5-methyl-3-(3-nitropyridin-4-yl)cyclohex-2-enylcarbamate

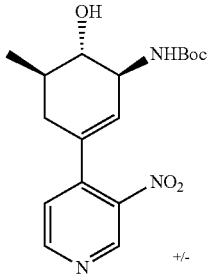 [SMILES: C[C@@H]1CC(c2ccncc2[N+](=O)[O-])=C[C@H](NC(=O)OC(C)(C)C)[C@H]1O]

To a solution of (+/−)-2-azido-6-methyl-4-(3-nitropyridin-4-yl)cyclohex-3-enol (1.0 equiv.) in pyridine and ammonium hydroxide (8:1, 0.08 M) was added trimethylphosphine (3.0 equiv.) and the brown solution was stirred at room temperature for 2 h. Upon completion, EtOH was added and the solution was concentrated in vacuo. More ethanol was added and the reaction was concentrated again. Dioxane and sat. NaHCO$_3$ (1:1, 0.08 M) were added to the crude, followed by Boc$_2$O (1.0 equiv.). Stirred the reaction mixture at room temperature for 2 h, then added water and ethyl acetate. The organic phase was dried with MgSO$_4$, and concentrated. The crude product was purified via silica gel column chromatography eluting with ethyl acetate and hexanes (1:1) to afford (+/−)-tert-butyl 6-hydroxy-5-methyl-3-(3-nitropyridin-4-yl)cyclohex-2-enylcarbamate (59%). LC/MS=350.1 (M+H), Rt: 0.76 min.

Synthesis of (+/−)-2-(tert-butoxycarbonylamino)-6-methyl-4-(3-nitropyridin-4-yl)cyclohex-3-enyl acetate

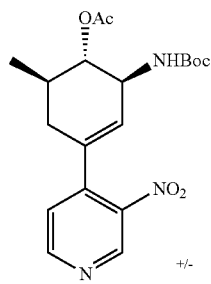 [SMILES: CC(=O)O[C@H]1[C@H](C)CC(c2ccncc2[N+](=O)[O-])=C[C@@H]1NC(=O)OC(C)(C)C]

To a solution of (+/−)-tert-butyl 6-hydroxy-5-methyl-3-(3-nitropyridin-4-yl)cyclohex-2-enylcarbamate (1.0 equiv.) in pyridine (0.1 M) was added Ac$_2$O (2.0 equiv.) and the reaction was stirred at room temperature overnight. Upon completion, the reaction was concentrated to dryness, then worked-up with ethyl acetate and water. The organic phase was dried with brine, then sodium sulfate, filtered, and concentrated to give (+/−)-2-(tert-butoxycarbonylamino)-6-methyl-4-(3-nitropyridin-4-yl)cyclohex-3-enyl acetate in 94% yield. LC/MS=392.2 (M+H), Rt=0.94 min.

Synthesis of (1S,2S,4S,6R)-4-(3-aminopyridin-4-yl)-2-((tert-butoxycarbonyl)amino)-6-methylcyclohexyl acetate and (1R,2R,4R,6S)-4-(3-aminopyridin-4-yl)-2-((tert-butoxycarbonyl)amino)-6-methylcyclohexyl acetate

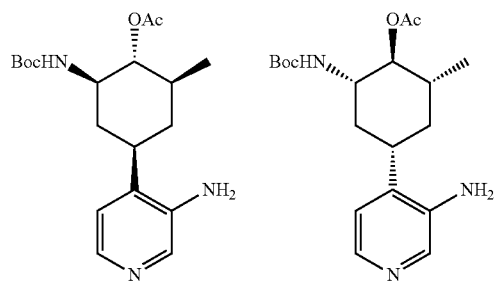 [SMILES: CC(=O)O[C@@H]1[C@@H](C)C[C@@H](c2ccncc2N)C[C@H]1NC(=O)OC(C)(C)C ; CC(=O)O[C@H]1[C@H](C)C[C@H](c2ccncc2N)C[C@@H]1NC(=O)OC(C)(C)C]

To a degassed solution of (+/−)-2-(tert-butoxycarbonylamino)-6-methyl-4-(3-nitropyridin-4-yl)cyclohex-3-enyl acetate (1.0 equiv.) in MeOH and EtOAc (1:1, 0.1 M) was added 10% Pd/C (0.1 equiv.) and the reaction was stirred at room temperature under a hydrogen balloon for 3 days. Upon completion, the solution was filtered through a pad of Celite, the pad was washed with ethyl acetate and the filtrate was concentrated. The crude material contained about 10% of the undesired isomer. The crude was dissolved in ethyl acetate (~20%) and hexanes and heated until all dissolved. The solution was allowed to sit at room temperature for 2 days. The precipitate was then collected to give (+/−)-4-(3-aminopyridin-4-yl)-2-(tert-butoxycarbonylamino)-6-methylcyclohexyl acetate as the pure product in 59% yield. LC/MS=364.3

(M+H), Rt=0.63 min. The racemic material was resolved using an AD-H chiral column (20% i-PrOH/80% n-heptanes, 20 mL/min flow rate) to (1S,2S,4S,6R)-4-(3-aminopyridin-4-yl)-2-((tert-butoxycarbonyl)amino)-6-methylcyclohexyl acetate (peak#1, R$_f$=3.76 min on AD-H chiral analytical column, 20% i-PrOH/80% n-heptanes, 1 mL/min) and (1R,2R,4R,6S)-4-(3-aminopyridin-4-yl)-2-((tert-butoxycarbonyl)amino)-6-methylcyclohexyl acetate (peak#2, R$_f$=6.79 min on AD-H chiral analytical column, 20% i-PrOH/80% n-heptanes, 1 mL/min)

Synthesis of 2-(tert-butoxycarbonylamino)-6-methyl-4-(3-nitropyridin-4-yl)cyclohex-3-enyl methanesulfonate

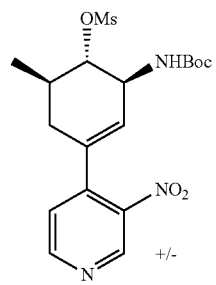

To a solution of tert-butyl 6-hydroxy-5-methyl-3-(3-nitropyridin-4-yl)cyclohex-2-enylcarbamate (1.0 equiv.) in DCM (0.09 M) was added triethylamine (1.5 equiv.) and the reaction was cooled to 0° C. MsCl (1.2 equiv.) was added to the reaction and stirred for 3 h. Another 1.0 equiv. of MsCl was added to the reaction and stirred for another 2 h. Worked up the reaction by adding water, the organic phase was dried with brine, sodium sulfate, and concentrated. The crude product was purified via silica gel column chromatography eluting with ethyl acetate and hexanes (1:1) to afford 2-(tert-butoxycarbonylamino)-6-methyl-4-(3-nitropyridin-4-yl)cyclohex-3-enyl methanesulfonate as a white foam in 65% yield. LC/MS=428.2 (M+H), LC: 3.542 min.

Synthesis of (+/−)-tert-butyl 7-methyl-5-(3-nitropyridin-4-yl)-2-oxo-3a,6,7,7a-tetrahydrobenzo[d]oxazole-3(2H)-carboxylate

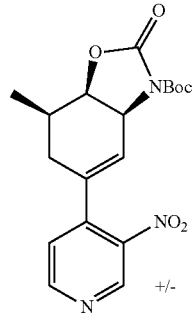 [SMILES: C[C@@H]1CC(c2ccncc2[N+](=O)[O-])=C[C@H]2[C@@H]1OC(=O)N2C(=O)OC(C)(C)C]

A solution of (+/−)-2-(tert-butoxycarbonylamino)-6-methyl-4-(3-nitropyridin-4-yl)cyclohex-3-enyl methanesulfonate (1.0 equiv.) in pyridine (0.2 M) was heated in the microwave at 110° C. for 10 min. The orange reaction was then concentrated under vacuo, the crude was dissolved in ethyl acetate and water, the organic phase was dried with sodium sulfate and concentrated under vacuo. The crude material was dissolved in DCM (0.2 M), triethylamine (1.8 equiv.) was added, followed by Boc$_2$O (1.2 equiv.). The reaction was stirred for 40 min, then concentrated to dryness. The crude material was purified via silica gel column chromatography eluting with hexane and ethyl acetate (1:1) to afford (+/−)-tert-butyl 7-methyl-5-(3-nitropyridin-4-yl)-2-oxo-3a,6,7,7a-tetrahydrobenzo[d]oxazole-3(2H)-carboxylate as a white foam in 66% yield. LC/MS=376.0 (M+H), LC: 3.424 min.

Synthesis of (+/−)-tert-butyl 5-(3-aminopyridin-4-yl)-7-methyl-2-oxohexahydrobenzo[d]oxazole-3(2H)-carboxylate

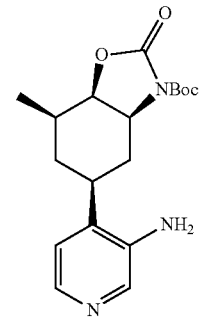 [SMILES: C[C@@H]1C[C@H](c2ccncc2N)C[C@H]2[C@@H]1OC(=O)N2C(=O)OC(C)(C)C]

To a degassed solution of (+/−)-tert-butyl 7-methyl-5-(3-nitropyridin-4-yl)-2-oxo-3a,6,7,7a-tetrahydrobenzo[d]oxazole-3(2H)-carboxylate (1.0 equiv.) in MeOH and EtOAc (1:1, 0.1 M) was added 10% Pd/C (0.1 equiv.). The reaction was stirred under a hydrogen balloon overnight. Upon completion, the solution was filtered through a pad of Celite and the pad was washed with ethyl acetate. The filtrate was concentrated under vacuo to give (+/−)-tert-butyl 5-(3-aminopyridin-4-yl)-7-methyl-2-oxohexahydrobenzo[d]oxazole-3(2H)-carboxylate as the desired product as a yellow foam in 93% yield. LC/MS=348.1 (M+H), Rt=055 min.

Synthesis of tert-butyl (1R,2R,3S,5R)-5-(3-(6-(2,6-difluorophenyl)-5-fluoropicolinamido)pyridin-4-yl)-2-hydroxy-3-methylcyclohexylcarbamate

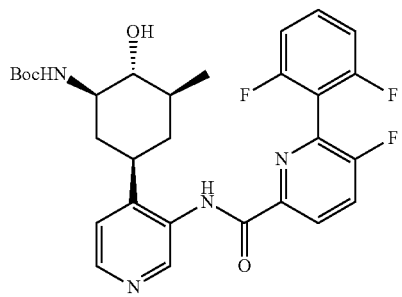 [SMILES: C[C@H]1C[C@@H](c2ccncc2NC(=O)c2ccc(F)c(-c3c(F)cccc3F)n2)C[C@@H](NC(=O)OC(C)(C)C)[C@@H]1O]

To a solution of (1R,2R,4R,6S)-4-(3-aminopyridin-4-yl)-2-(tert-butoxycarbonylamino)-6-methylcyclohexyl acetate (1.0 equiv.) in DMF/Ethanol (1/5, 0.05 M) was added 6-(2,6-difluorophenyl)-5-fluoropicolinic acid (1.3 equiv.), aza-HOBt (1.3 equiv.) and EDC (1.3 equiv.). The mixture was stirred at rt for 6 hrs. The solution was diluted with EtOAc, washed with H$_2$O, 1N NaOH, NaCl (sat.), dried over MgSO4, filtered and concentrated to yield crude protected amide. The material was dissolved in EtOH (0.45 M), Cs$_2$CO$_3$ (1.0 equiv.) was added and the solution was submerged in a 60° C. oil bath and stirred for 90 mins. The volatiles were removed in vacuo; the residue was partitioned between with EtOAc and H$_2$O. The organic layer was washed with NaCl$_{(sat)}$, dried over MgSO$_4$, filtered, concentrated and pumped on to yield tert-butyl (1R,2R,3S,5R)-5-(3-(6-(2,6-difluorophenyl)-5-fluoropicolinamido)pyridin-4-yl)-2-hydroxy-3-methylcyclohexylcarbamate in 99% yield. LC/MS (m/z)=557.3 (MH+), $R_t$=0.80 min.

Synthesis of (1R,2R,4R,6S)-2-amino-4-(3-(6-(2,6-difluorophenyl)-5-fluoropicolinamido)pyridin-4-yl)-6-methylcyclohexyl methanesulfonate

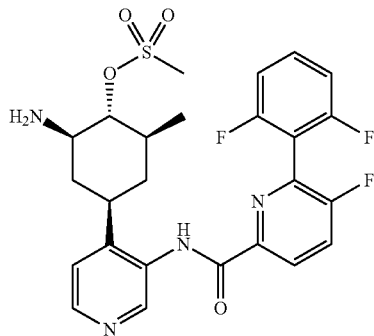 [SMILES: C[C@H]1C[C@@H](c2ccncc2NC(=O)c2ccc(F)c(-c3c(F)cccc3F)n2)C[C@@H](N)[C@@H]1OS(C)(=O)=O]

To a solution of tert-butyl (1R,2R,3S,5R)-5-(3-(6-(2,6-difluorophenyl)-5-fluoropicolinamido)pyridin-4-yl)-2-hydroxy-3-methylcyclohexylcarbamate (1.0 equiv.) in $CH_2Cl_2$ was added TEA (4.0 equiv.) and MsCl (2.0 equiv.). The capped solution was stirred for 5 minutes and then the homogeneous solution was left standing at rt for 16 hrs. The volatiles were removed in vacuo, the residue was dissolved in DMSO, purified by RP HPLC and the product fractions were lyophilized directly. The Boc protected product was treated with 25% $TFA/CH_2Cl_2$ for 20 minutes at which time the volatiles were removed in vacuo and the residue was dissolved in DMSO and purified by RP-HPLC. The product fractions were lyophilized directly to yield (1R,2R,4R,6S)-2-amino-4-(3-(6-(2,6-difluorophenyl)-5-fluoropicolinamido)pyridin-4-yl)-6-methylcyclohexyl methanesulfonate in 31% yield. LC/MS (m/z)=535.2 (MH+), $R_t$=0.61 min.

Synthesis of tert-butyl (1R,2S,3S,5R)-5-(3-(6-(2,6-difluorophenyl)-5-fluoropicolinamido)pyridin-4-yl)-2-hydroxy-3-methylcyclohexylcarbamate

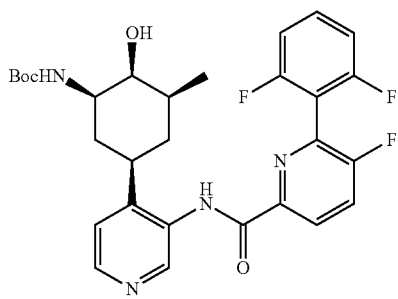 [SMILES: C[C@H]1C[C@@H](c2ccncc2NC(=O)c2ccc(F)c(-c3c(F)cccc3F)n2)C[C@@H](NC(=O)OC(C)(C)C)[C@H]1O]

To a solution of (3aR,5R,7S,7aS)-tert-butyl 5-(3-aminopyridin-4-yl)-7-methyl-2-oxohexahydrobenzo[d]oxazole-3(2H)-carboxylate (1.0 equiv.) in DMF (0.2 M) was added 6-(2,6-difluorophenyl)-5-fluoropicolinic acid (1.3 equiv.), aza-HOBt (1.3 equiv.) and EDC (1.3 equiv.). The mixture was stirred at rt for 16 hrs. The solution was diluted with EtOAc, washed with $H_2O$, 1N NaOH, $NaCl_{(sat)}$, dried over $MgSO_4$, filtered and concentrated to yield crude protected amide. The material was dissolved in EtOH (0.45 M), $Cs_2CO_3$ (1.0 equiv.) was added and the solution was submerged in a 60° C. oil bath and stirred for 90 mins The volatiles were removed in vacuo; the residue was partitioned between with EtOAc and $H_2O$. The organic layer was washed with $NaCl_{(sat)}$, dried over $MgSO_4$, filtered, concentrated and pumped on to yield tert-butyl (1R,2S,3S,5R)-5-(3-(6-(2,6-difluorophenyl)-5-fluoropicolinamido)pyridin-4-yl)-2-hydroxy-3-methylcyclohexylcarbamate in 100% yield. LC/MS (m/z)=557.3 (MH+), $R_t$=0.83 min.

Synthesis of (1S,2R,4R,6S)-2-amino-4-(3-(6-(2,6-difluorophenyl)-5-fluoropicolinamido)pyridin-4-yl)-6-methylcyclohexyl methanesulfonate

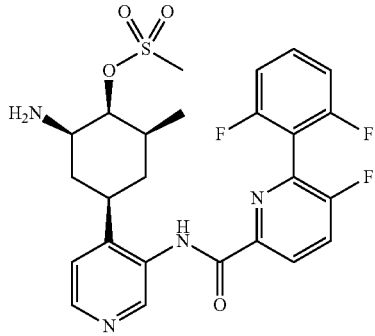 [SMILES: C[C@H]1C[C@@H](c2ccncc2NC(=O)c2ccc(F)c(-c3c(F)cccc3F)n2)C[C@@H](N)[C@H]1OS(C)(=O)=O]

To a solution of tert-butyl (1R,2S,3S,5R)-5-(3-(6-(2,6-difluorophenyl)-5-fluoropicolinamido)pyridin-4-yl)-2-hydroxy-3-methylcyclohexylcarbamate (1.0 equiv.) in pyridine (0.12 M) was added MsCl (7.0 equiv.). The capped solution was stirred for 5 minutes and then the homogeneous solution was left standing at rt for 16 hrs. The volatiles were removed in vacuo and the residue was partitioned between EtOAc and $H_2O$. The organic layer was washed with $H_2O$, 10% $CuSO_4$, $H_2O$, $Na_2CO_{3(sat)}$, $NaCl_{(sat)}$, dried over $MgSO_4$, filtered, concentrated and purified by ISCO chromatography. The Boc protected product was treated with 25% $TFA/CH_2Cl_2$ for 20 minutes at which time the volatiles were removed in vacuo and the residue was dissolved in DMSO and purified by RP-HPLC. The product fractions were lyophilized directly to yield (1S,2R,4R,6S)-2-amino-4-(3-(6-(2,6-difluorophenyl)-5-fluoropicolinamido)pyridin-4-yl)-6-methylcyclohexyl methanesulfonate in 45% yield. LC/MS (m/z)=535.2 (MH+), $R_t$=0.60 min.

Synthesis of (1S,2R,4R,6S)-2-amino-4-(3-(6-(2,6-difluorophenyl)-5-fluoropicolinamido)pyridin-4-yl)-6-methylcyclohexyl dimethylphosphinate

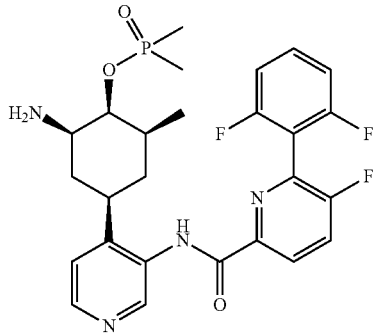 [SMILES: C[C@H]1C[C@@H](c2ccncc2NC(=O)c2ccc(F)c(-c3c(F)cccc3F)n2)C[C@@H](N)[C@H]1OP(C)(C)=O]

To a solution of tert-butyl (1R,2S,3S,5R)-5-(3-(6-(2,6-difluorophenyl)-5-fluoropicolinamido)pyridin-4-yl)-2-hydroxy-3-methylcyclohexylcarbamate (1.0 equiv.) in pyridine (0.05 M) was added phosphonic chloride (5.0 equiv.). The capped homogeneous solution was left stirring at rt for 1 hr.

The volatiles were removed in vacuo and the residue was partitioned between EtOAc and H₂O. The organic layer was washed with H₂O, 10% CuSO₄, Na₂CO₃$_{(sat)}$, NaCl$_{(sat)}$, dried over MgSO₄, filtered, concentrated to yield crude Boc protected product. The Boc group was removed by treating with 25% TFA/CH₂Cl₂ for 30 minutes at which time the volatiles were removed in vacuo and the residue was dissolved in DMSO and purified by RP-HPLC. The product fractions were lyophilized directly to yield (1S,2R,4R,6S)-2-amino-4-(3-(6-(2,6-difluorophenyl)-5-fluoropicolinamido)pyridin-4-yl)-6-methylcyclohexyl dimethylphosphinate in 43% yield. LC/MS (m/z)=533.3 (MH⁺), R$_t$=0.59 min.

Synthesis of (1R,2R,4R,6S)-2-amino-4-(3-(6-(2,6-difluorophenyl)-5-fluoropicolinamido)pyridin-4-yl)-6-methylcyclohexyl dimethylphosphinate

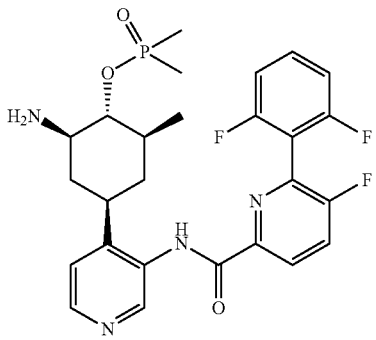 [SMILES: C[C@H]1C[C@@H](c2ccncc2NC(=O)c2ccc(F)c(-c3c(F)cccc3F)n2)C[C@@H](N)[C@@H]1OP(C)(C)=O]

To a solution of tert-butyl (1R,2R,3S,5R)-5-(3-(6-(2,6-difluorophenyl)-5-fluoropicolinamido)pyridin-4-yl)-2-hydroxy-3-methylcyclohexylcarbamate (1.0 equiv.) in pyridine (0.05 M) was added phosphonic chloride (5.0 equiv.). The capped homogeneous solution was left stirring at rt for 1 hr. The volatiles were removed in vacuo and the residue was partitioned between EtOAc and H₂O. The organic layer was washed with H₂O, 10% CuSO₄, Na₂CO₃$_{(sat)}$, NaCl$_{(sat)}$, dried over MgSO₄, filtered, concentrated to yield crude Boc protected product. The Boc group was removed by treating with 25% TFA/CH₂Cl₂ for 30 minutes at which time the volatiles were removed in vacuo and the residue was dissolved in DMSO and purified by RP-HPLC. The product fractions were lyophilized directly to yield (1R,2R,4R,6S)-2-amino-4-(3-(6-(2,6-difluorophenyl)-5-fluoropicolinamido)pyridin-4-yl)-6-methylcyclohexyl dimethylphosphinate in 43% yield. LC/MS (m/z)=533.3 (MH⁺), R$_t$=0.60 min.

Synthesis of S-(1S,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate

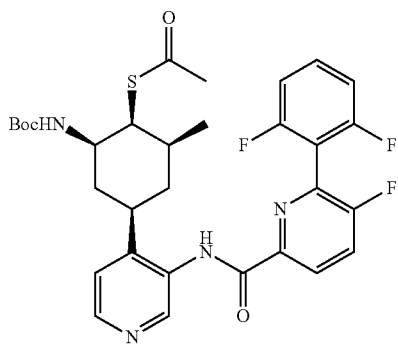 [SMILES: CC(=O)S[C@H]1[C@@H](C)C[C@@H](c2ccncc2NC(=O)c2ccc(F)c(-c3c(F)cccc3F)n2)C[C@H]1NC(=O)OC(C)(C)C]

To a solution of (1R,2R,4R,6S)-2-(tert-butoxycarbonylamino)-4-(3-(6-(2,6-difluorophenyl)-5-fluoropicolinamido)pyridin-4-yl)-6-methylcyclohexyl methanesulfonate (1.0 equiv.) in DMF (0.19 M) was added KSAc (3.0 equiv.). The capped solution was left stirring at rt for 20 hrs. The solution was partitioned between EtOAc and H₂O. The organic layer was washed with H₂O, Na₂CO₃$_{(sat)}$, NaCl$_{(sat)}$, dried over MgSO₄, filtered, concentrated and purified by ISCO SiO₂ chromatography to yield S-(1S,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate in 35% yield. LC/MS (m/z)=615.2 (MH⁺), R$_t$=0.95 min.

Synthesis of tert-butyl (1R,2S,3S,5R)-5-(3-(6-(2,6-difluorophenyl)-5-fluoropicolinamido)pyridin-4-yl)-3-methyl-2-(methylthio)cyclohexylcarbamate

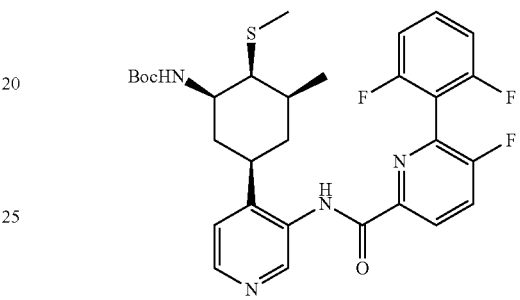

To a solution of S-(1S,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate (1.0 equiv.) in MeOH (0.07 M) was added K₂CO₃ (3.0 equiv.). The heterogeneous solution was capped and left stirring at rt for 1 hr. Methyl iodide (1.5 equiv.) was added and stirred at rt for 10 min. The volatiles were removed in vacuo and the residue was partitioned between EtOAc and H₂O. The organic layer was washed with NaCl$_{(sat)}$, dried over MgSO₄, filtered, concentrated and purified by ISCO SiO₂ chromatography to yield tert-butyl (1R,2S,3S,5R)-5-(3-(6-(2,6-difluorophenyl)-5-fluoropicolinamido) pyridin-4-yl)-3-methyl-2-(methylthio) cyclohexylcarbamate in 78% yield. LC/MS (m/z)=587.2 (MH⁺), R$_t$=1.00 min.

Synthesis of N-(4-((1R,3R,4S,5S)-3-amino-5-methyl-4-(methylthio)cyclohexyl)pyridin-3-yl)-6-(2,6-difluorophenyl)-5-fluoropicolinamide

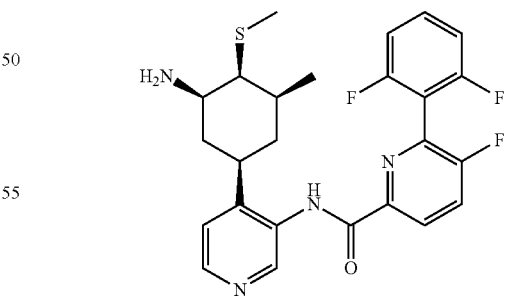

To a solution of HCl (30.0 equiv.) in dioxane was added to tert-butyl (1R,2S,3S,5R)-5-(3-(6-(2,6-difluorophenyl)-5-fluoropicolinamido)pyridin-4-yl)-3-methyl-2-(methylthio) cyclohexylcarbamate (1.0 equiv.). The solution was capped and left standing at rt for 1 hr. The volatiles were removed in vacuo, dissolved in DMSO and purified by reverse phase HPLC to yield N-(4-((1R,3R,4S,5S)-3-amino-5-methyl-4-

(methylthio)cyclohexyl)pyridin-3-yl)-6-(2,6-difluorophenyl)-5-fluoropicolinamide in 94% yield. LC/MS (m/z)=487.2 (MH+), R$_t$=0.65 min. $^1$H NMR (400 MHz, <dmso>) δ ppm 10.44 (s, 1H), 8.58 (d, J=4.0, 1H), 8.47 (d, J=4.0, 1H), 8.34 (dd, J=8.0, 4.0, 1H), 8.20 (dd, J=8.0, 8.0, 1H), 8.20 (dd, J=16.0, 4.0, 1H), 7.67-7.74 (m, 1H), 7.36 (dd, J=8.0, 8.0, 2H), 7.26 (d, J=4.0, 1H), 2.85-2.95 (m, 2H), 2.18 (s, 3H), 1.88-1.98 (m, 1H), 1.74-1.84 (m, 1H), 1.48-1.56 (m, 1H), 1.38-1.48 (m, 1H), 1.18-1.28 (m, 1H), 1.02 (d, J=8.0, 3H).

Synthesis of tert-butyl (1R,2S,3S,5R)-5-(3-(6-(2,6-difluorophenyl)-5-fluoropicolinamido)pyridin-4-yl)-3-methyl-2-((R)-methylsulfinyl)cyclohexylcarbamate and tert-butyl (1R,2S,3S,5R)-5-(3-(6-(2,6-difluorophenyl)-5-fluoropicolinamido)pyridin-4-yl)-3-methyl-2-(methylsulfonyl)cyclohexylcarbamate

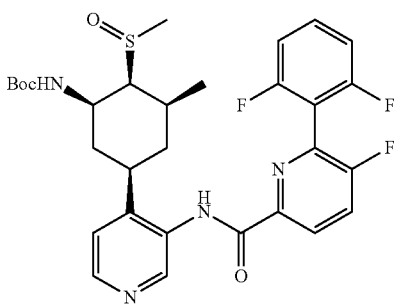

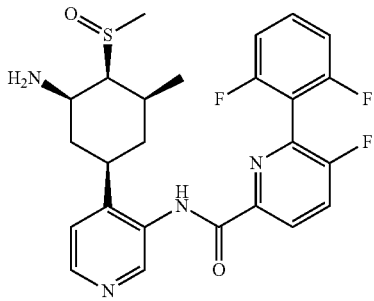 [SMILES: C[C@H]1C[C@@H](c2ccncc2NC(=O)c2ccc(F)c(-c3c(F)cccc3F)n2)C[C@@H](N)[C@H]1S(C)=O]

To a solution of tert-butyl (1R,2S,3S,5R)-5-(3-(6-(2,6-difluorophenyl)-5-fluoropicolinamido)pyridin-4-yl)-3-methyl-2-(methylthio)cyclohexylcarbamate (1.0 equiv.) in CH$_2$Cl$_2$ (0.10 M) in a 0° C. bath was added mCPBA (1.2 equiv.). The capped solution was left stirring at rt for 1 hr. cyclohexene (10.0 equiv.) was added to quench any remaining mCBPA and after stirring for 5 minutes the solution was directly loaded onto ISCO SiO$_2$ column and purified to yield tert-butyl (1R,2S,3S,5R)-5-(3-(6-(2,6-difluorophenyl)-5-fluoropicolinamido)pyridin-4-yl)-3-methyl-2-((R)-methylsulfinyl)cyclohexylcarbamate in 31% yield, LC/MS=603.2 (MH+), Rt=0.66 min; and tert-butyl (1R,2S,3S,5R)-5-(3-(6-(2,6-difluorophenyl)-5-fluoropicolinamido)pyridin-4-yl)-3-methyl-2-(methylsulfonyl)cyclohexylcarbamate in 37% yield. LC/MS (m/z)=619.2 (MH+), R$_t$=0.88 min.

Synthesis of N-(4-((1R,3R,4S,5S)-3-amino-5-methyl-4-((R)-methylsulfinyl)cyclohexyl)pyridin-3-yl)-6-(2,6-difluorophenyl)-5-fluoropicolinamide To a solution of tert-butyl (1R,2S,3S,5R)-5-(3-(6-(2,6-difluorophenyl)-5-fluoropicolinamido)pyridin-4-yl)-3-methyl-2-((R)-methylsulfinyl)cyclohexylcarbamate in DCM (0.10 M) was added TFA (30.0 equiv.). The solution was capped and left standing at rt for 1 hr. The volatiles were removed in vacuo; the residue was dissolved in DMSO and purified by reverse phase HPLC. The product fractions were lyophilized directly to yield N-(4-((1R,3R,4S,5S)-3-amino-5-methyl-4-((R)-methylsulfinyl)cyclohexyl)pyridin-3-yl)-6-(2,6-difluorophenyl)-5-fluoropicolinamide in 54% yield. LC/MS (m/z)=503.2 (MH+), R$_t$=0.57 min. $^1$H NMR (400 MHz, <dmso>) δ ppm 10.48 (s, 1H), 8.58 (d, J=4.0, 1H), 8.50 (d, J=4.0, 1H), 8.34 (dd, J=8.0, 4.0, 1H), 8.20 (dd, J=8.0, 8.0, 1H), 8.20 (dd, J=16.0, 4.0, 1H), 7.67-7.74 (m, 1H), 7.42 (d, J=4.0, 1H), 7.36 (dd, J=8.0, 8.0, 2H), 3.40-3.42 (m, 1H), 3.06-3.20 (m, 1H), 2.92 (s, 3H), 2.06-2.20 (m, 1H), 1.95-2.04 (m, 2H), 1.70-1.80 (m, 1H), 1.56-1.70 (m, 1H), 0.86 (d, J=8.0, 3H).

Synthesis of N-(4-((1R,3R,4S,5S)-3-amino-5-methyl-4-(methylsulfonyl)cyclohexyl)pyridin-3-yl)-6-(2,6-difluorophenyl)-5-fluoropicolinamide

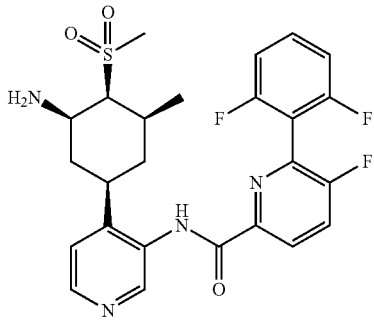 [SMILES: C[C@H]1C[C@@H](c2ccncc2NC(=O)c2ccc(F)c(-c3c(F)cccc3F)n2)C[C@@H](N)[C@H]1S(C)(=O)=O]

To a solution of tert-butyl (1R,2S,3S,5R)-5-(3-(6-(2,6-difluorophenyl)-5-fluoropicolinamido)pyridin-4-yl)-3-methyl-2-(methylsulfonyl)cyclohexylcarbamate in DCM (0.02 M) was added TFA (30.0 equiv.). The solution was capped and left standing at rt for 1 hr. The volatiles were removed in vacuo; the residue was dissolved in DMSO and purified by reverse phase HPLC. The product fractions were lyophilized directly to yield N-(4-((1R,3R,4S,5S)-3-amino-5-methyl-4-(methylsulfonyl)cyclohexyl)pyridin-3-yl)-6-(2,6-difluorophenyl)-5-fluoropicolinamide in 73% yield. LC/MS (m/z)= 519.2 (MH+), R$_t$=0.58 min. 1H NMR (400 MHz, <dmso>) δ ppm 10.52 (s, 1H), 8.51-8.54 (m, 2H), 8.34 (dd, J=8.0, 4.0, 1H), 8.20 (dd, J=8.0, 8.0, 1H), 8.15 (dd, J=16.0, 4.0, 1H), 7.67-7.74 (m, 1H), 7.36 (dd, J=8.0, 8.0, 2H), 7.28 (d, J=4.0, 1H), 3.77-3.79 (m, 1H), 3.18 (s, 3H), 3.02-3.20 (m, 1H), 1.94-2.40 (m, 5H), 1.57-1.62 (m, 1H), 1.24 (d, J=8.0, 3H).

Synthesis of tert-butyl (1R,2S,3S,5R)-5-(3-(6-(2,6-difluorophenyl)-5-fluoropicolinamido)pyridin-4-yl)-2-(2-methoxyethylthio)-3-methylcyclohexylcarbamate

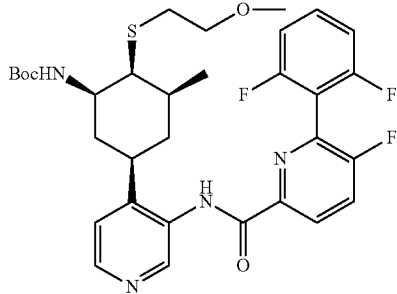 [SMILES: COCCS[C@H]1[C@@H](C)C[C@@H](c2ccncc2NC(=O)c2ccc(F)c(-c3c(F)cccc3F)n2)C[C@H]1NC(=O)OC(C)(C)C]

To a solution of S-(1S,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate (1.0 equiv.) in MeOH (0.04 M) was added K$_2$CO$_3$ (3.0 equiv.). The heterogeneous solution was capped and left stirring at rt for 1 hr. 1-bromo-2-methoxyethane (7.0 equiv.) was added and stirred at rt for 6 hrs. Quench the reaction with diisopropylamine and the volatiles were removed in vacuo and the residue was partitioned between EtOAc and H$_2$O. The organic layer was washed with NaCl$_{(sat)}$, dried over MgSO$_4$, filtered, concentrated and purified by ISCO SiO$_2$ chromatography to yield tert-butyl (1R,2S,3S,5R)-5-(3-(6-(2,6-difluorophenyl)-5-fluoropicolinamido)pyridin-4-yl)-2-(2-methoxyethylthio)-3-methylcyclohexylcarbamate in 63% yield. LC/MS (m/z)=631.2 (MH$^+$), R$_t$=0.98 min.

Synthesis of N-(4-((1R,3R,4S,5S)-3-amino-4-((2-methoxyethyl)sulfonyl)-5-methylcyclohexyl)pyridin-3-yl)-6-(2,6-difluorophenyl)-5-fluoropicolinamide

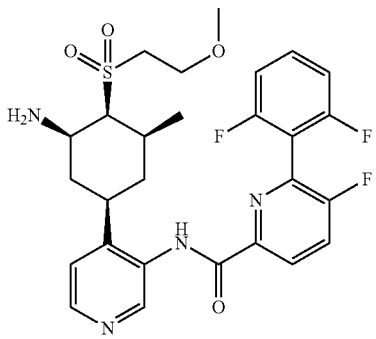 [SMILES: COCCS(=O)(=O)[C@@H]1[C@H](N)C[C@H](c2ccncc2NC(=O)c2ccc(F)c(-c3c(F)cccc3F)n2)C[C@@H]1C]

To a solution of tert-butyl (1R,2S,3S,5R)-5-(3-(6-(2,6-difluorophenyl)-5-fluoropicolinamido)pyridin-4-yl)-2-(2-methoxyethylthio)-3-methylcyclohexylcarbamate (1.0 equiv.) in THF (0.04 M) in a 0° C. bath was added oxone (2.0 equiv.) as a solution in H$_2$O. The solution was left stirring at rt for 5 hrs. The solution was diluted with EtOAc, washed with H$_2$O, NaCl$_{(sat)}$, dried over MgSO$_4$, filtered, concentrated to yield Boc protected product. The material was treated with 25% TFA/CH$_2$Cl$_2$ for 30 minutes, at which time the volatiles were removed in vacuo, the residue was dissolved in DMSO and purified by reverse phase HPLC. The product fractions were lyophilized directly to yield N-(4-((1R,3R,4S,5S)-3-amino-4-(2-methoxyethyl)sulfonyl)-5-methylcyclohexyl)pyridin-3-yl)-6-(2,6-difluorophenyl)-5-fluoropicolinamide in 76% yield. LC/MS (m/z)=563.3 (MH$^+$), R$_t$=0.62 min. $^1$H NMR (400 MHz, <dmso>) δ ppm 10.52 (s, 1H), 8.53 (s, 1H), 8.50 (d, J=4.0, 1H), 8.35 (dd, J=8.0, 4.0, 1H), 8.20 (t, J=8.0, 1H), 7.80 (bs, 2H), 7.70 (quintet, J=8.0, 1H), 7.36 (t, J=8.0, 2H), 7.31 (d, J=4.0, 1H), 3.82-3.88 (m, 2H), 3.73-3.78 (m, 2H), 3.55-3.61 (m, 1H), 3.42-3.49 (m, 1H), 3.31 (s, 3H), 3.06-3.16 (m, 1H), 1.92-2.18 (m, 4H), 1.54-1.64 (m, 1H), 1.22 (d, J=4.0, 3H).

Synthesis of tert-butyl (1R,2S,3S,5R)-2-(2-(tert-butyldimethylsilyloxy)ethylthio)-5-(3-(6-(2,6-difluorophenyl)-5-fluoropicolinamido)pyridin-4-yl)-3-methylcyclohexylcarbamate

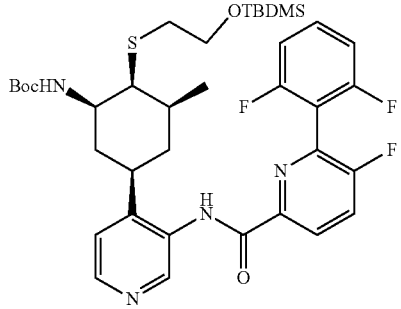 [SMILES: C[C@H]1C[C@@H](c2ccncc2NC(=O)c2ccc(F)c(-c3c(F)cccc3F)n2)C[C@@H](NC(=O)OC(C)(C)C)[C@H]1SCCO[Si](C)(C)C(C)(C)C]

To a solution of S-(1S,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate (1.0 equiv.) in MeOH (0.04 M) was added K$_2$CO$_3$ (5.0 equiv.). The heterogeneous solution was capped and left stirring at rt for 1 hr. (2-bromoethoxy)(tert-butyl)dimethylsilane (7.0 equiv.) was added and stirred at rt for 6 hrs. Quench the reaction with diisopropylamine and the volatiles were removed in vacuo and the residue was partitioned between EtOAc and H$_2$O. The organic layer was washed with NaCl$_{(sat)}$, dried over MgSO$_4$, filtered, concentrated. The residue was dissolved in DMF (0.05 M) and imidazole (20.0 equiv.) and TBDMSCl (7.0 equiv.) were added. After stirring at rt for 1 hr, the solution was partitioned between EtOAc and H$_2$O. The organic layer was washed with NaCl$_{(sat)}$, dried over MgSO$_4$, filtered, concentrated and purified by ISCO SiO$_2$ chromatography to yield tert-butyl (1R,2S,3S,5R)-2-(2-(tert-butyldimethylsilyloxy)ethylthio)-5-(3-(6-(2,6-difluorophenyl)-5-fluoropicolinamido)pyridin-4-yl)-3-methylcyclohexylcarbamate in 57% yield. LC/MS (m/z)=731.4 (MH$^+$), R$_t$=1.27 min.

Synthesis of N-(4-((1R,3R,4S,5S)-3-amino-4-(2-hydroxyethylsulfonyl)-5-methylcyclohexyl)pyridin-3-yl)-6-(2,6-difluorophenyl)-5-fluoropicolinamide

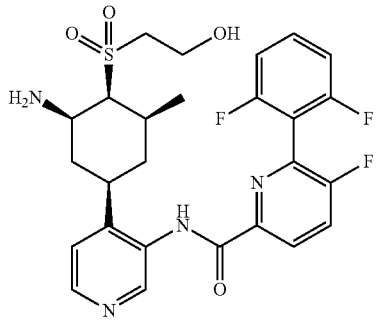 [SMILES: C[C@H]1C[C@@H](c2ccncc2NC(=O)c2ccc(F)c(-c3c(F)cccc3F)n2)C[C@@H](N)[C@H]1S(=O)(=O)CCO]

To a solution of tert-butyl (1R,2S,3S,5R)-2-(2-(tert-butyldimethylsilyloxy)ethylthio)-5-(3-(6-(2,6-difluorophenyl)-5-fluoropicolinamido)pyridin-4-yl)-3-methylcyclohexylcarbamate (1.0 equiv.) in THF (0.04 M) in a 0° C. bath was added oxone (2.0 equiv.) as a solution in H$_2$O. The solution was left stirring at rt for 48 hrs. The solution was diluted with EtOAc, washed with H$_2$O, Na$_2$CO$_{3(sat)}$, NaCl$_{(sat)}$, dried over MgSO$_4$, filtered, concentrated to yield Boc protected product. The material was treated with 25% TFA/CH$_2$Cl$_2$ for 30 minutes, at which time the volatiles were removed in vacuo, the residue was dissolved in DMSO and purified by reverse phase HPLC. The product fractions were lyophilized directly to N-(4-((1R,3R,4S,5S)-3-amino-4-(2-hydroxyethylsulfonyl)-5-methylcyclohexyl)pyridin-3-yl)-6-(2,6-difluorophenyl)-5-fluoropicolinamide in 44% yield. LC/MS (m/z)=549.6 (MH$^+$), R$_t$=0.58 min. $^1$H NMR (400 MHz, <dmso>) δ ppm 10.51 (s, 1H), 8.53 (s, 1H), 8.51 (d, J=4.0, 1H), 8.33 (dd, J=8.0, 4.0, 1H), 8.20 (t, J=8.0, 1H), 8.09 (broad doublet, J=4.0, 2H), 7.65-7.75 (m, 1H), 7.36 (t, J=8.0, 2H), 7.30 (d, J=8.0, 1H), 3.84-4.02 (m, 3H), 3.58-3.68 (m, 1H), 3.43-3.53 (m, 1H), 3.28-3.36 (m, 1H), 3.04-3.14 (m, 1H), 1.92-2.18 (m, 4 H), 1.56-1.63 (m, 1H), 1.24 (d, J=8.0, 3H).

Synthesis of S-(1R,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate

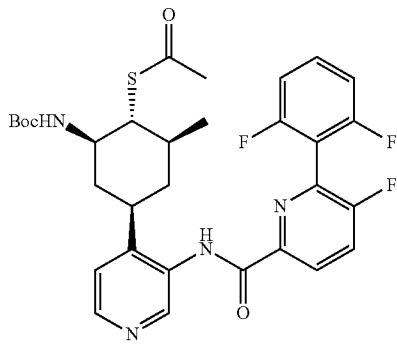 [SMILES: CC(=O)S[C@@H]1[C@@H](C)C[C@@H](c2ccncc2NC(=O)c2ccc(F)c(-c3c(F)cccc3F)n2)C[C@H]1NC(=O)OC(C)(C)C]

To a solution of (1S,2R,4R,6S)-2-(tert-butoxycarbonylamino)-4-(3-(6-(2,6-difluorophenyl)-5-fluoropicolinamido)pyridin-4-yl)-6-methylcyclohexyl methanesulfonate (1.0 equiv.) in DMF (0.25 M) was added KSAc (6.0 equiv.). The capped solution was left stirring at rt for 20 hrs. The solution was partitioned between EtOAc and H$_2$O. The organic layer was washed with H$_2$O, Na$_2$CO$_{3(sat)}$, NaCl$_{(sat)}$, dried over MgSO$_4$, filtered, concentrated and purified by ISCO SiO$_2$ chromatography to yield S-(1R,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate in 50% yield. LC/MS (m/z)=615.2 (MH$^+$), R$_t$=0.96 min.

Synthesis of tert-butyl (1R,2R,3S,5R)-5-(3-(6-(2,6-difluorophenyl)-5-fluoropicolinamido)pyridin-4-yl)-3-methyl-2-(methylthio)cyclohexylcarbamate

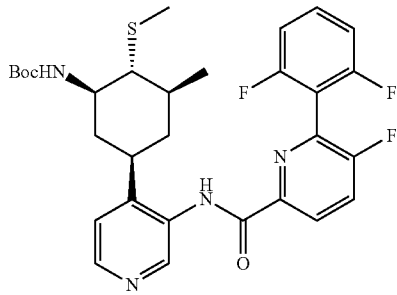 [SMILES: CS[C@@H]1[C@@H](C)C[C@@H](c2ccncc2NC(=O)c2ccc(F)c(-c3c(F)cccc3F)n2)C[C@H]1NC(=O)OC(C)(C)C]

To a solution of S-(1R,2R,4R,6S)-2-(tert-butoxycarbonylamino)-4-(3-(6-(2,6-difluorophenyl)-5-fluoropicolinamido)pyridin-4-yl)-6-methylcyclohexyl ethanethioate (1.0 equiv.) in MeOH (0.07 M) was added K$_2$CO$_3$ (3.0 equiv.). The heterogeneous solution was capped and left stirring at rt for 1 hr. Methyl iodide (1.5 equiv.) was added and stirred at rt for 10 min. The volatiles were removed in vacuo and the residue was partitioned between EtOAc and H$_2$O. The organic layer was washed with NaCl$_{(sat)}$, dried over MgSO$_4$, filtered, concentrated and purified by ISCO SiO$_2$ chromatography to yield tert-butyl (1R,2R,3S,5R)-5-(3-(6-(2,6-difluorophenyl)-5-fluoropicolinamido)pyridin-4-yl)-3-methyl-2-(methylthio)cyclohexylcarbamate in 72% yield. LC/MS (m/z)=587.2 (MH$^+$), R$_t$=0.96 min.

Synthesis of N-(4-((1R,3R,4R,5S)-3-amino-5-methyl-4-(methylthio)cyclohexyl)pyridin-3-yl)-6-(2,6-difluorophenyl)-5-fluoropicolinamide

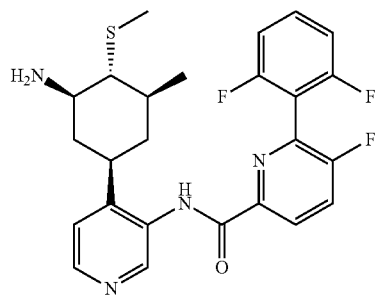 [SMILES: CS[C@H]1[C@H](N)C[C@H](c2ccncc2NC(=O)c2ccc(F)c(-c3c(F)cccc3F)n2)C[C@@H]1C]

To a solution of HCl (30.0 equiv.) in dioxane was added to tert-butyl (1R,2R,3S,5R)-5-(3-(6-(2,6-difluorophenyl)-5-fluoropicolinamido)pyridin-4-yl)-3-methyl-2-(methylthio)cyclohexylcarbamate (1.0 equiv.). The solution was capped and left standing at rt for 1 hr. The volatiles were removed in vacuo, dissolved in DMSO and purified by reverse phase HPLC to yield N-(4-((1R,3R,4R,5S)-3-amino-5-methyl-4-(methylthio)cyclohexyl)pyridin-3-yl)-6-(2,6-difluorophenyl)-5-fluoropicolinamide in 43% yield. LC/MS (m/z)=487.2 (MH$^+$), R$_t$=0.65 min.

Synthesis of N-(4-((1R,3R,4R,5S)-3-amino-5-methyl-4-((S)-methylsulfinyl)cyclohexyl)pyridin-3-yl)-6-(2,6-difluorophenyl)-5-fluoropicolinamide and N-(4-((1R,3R,4R,5S)-3-amino-5-methyl-4-((R)-methylsulfinyl)cyclohexyl)pyridin-3-yl)-6-(2,6-difluorophenyl)-5-fluoropicolinamide

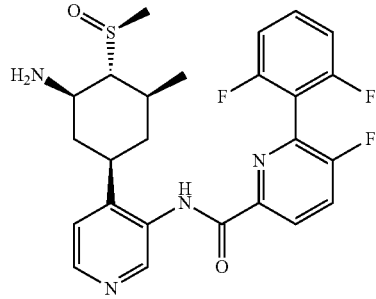

-continued

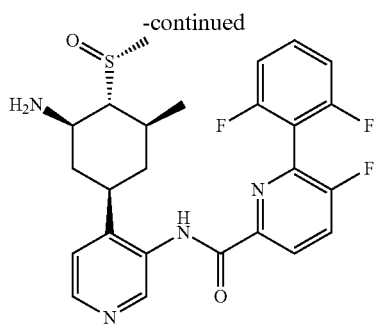

To a solution of tert-butyl (1R,2R,3S,5R)-5-(3-(6-(2,6-difluorophenyl)-5-fluoropicolinamido)pyridin-4-yl)-3-methyl-2-(methylthio)cyclohexylcarbamate (1.0 equiv.) in THF (0.05 M) in a 0° C. bath was added the oxone (1.0 equiv.) as a solution in H$_2$O. The solution was left stirring at 0° C. for 5 mins. The solution was diluted with EtOAc, washed with H$_2$O, NaCl$_{(sat)}$, dried over MgSO$_4$, filtered, concentrated to yield Boc protected product. The material was treated with 25% TFA/CH$_2$Cl$_2$ for 30 minutes, at which time the volatiles were removed in vacuo, the residue was dissolved in DMSO and purified by reverse phase HPLC. The product fractions were lyophilized directly to yield N-(4-((1R,3R,4R,5S)-3-amino-5-methyl-4-((S)-methylsulfinyl)cyclohexyl)pyridin-3-yl)-6-(2,6-difluorophenyl)-5-fluoropicolinamide in 33% yield, LC/MS=503.2 (MH+), Rt=0.58 min; and N-(4-((1R,3R,4R,5S)-3-amino-5-methyl-4-((R)-methylsulfinyl)cyclohexyl)pyridin-3-yl)-6-(2,6-difluorophenyl)-5-fluoropicolinamide in 37% yield. LC/MS (m/z)=503.2 (MH$^+$), R$_f$=0.60 min.

Synthesis of N-(4-((1R,3R,4R,5S)-3-amino-5-methyl-4-(methylsulfonyl)cyclohexyl)pyridin-3-yl)-6-(2,6-difluorophenyl)-5-fluoropicolinamide

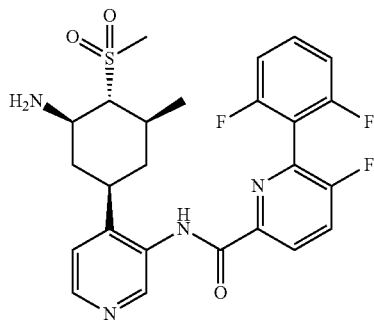 [SMILES: C[C@H]1C[C@@H](c2ccncc2NC(=O)c2ccc(F)c(-c3c(F)cccc3F)n2)C[C@@H](N)[C@@H]1S(C)(=O)=O]

To a solution of tert-butyl (1R,2R,3S,5R)-5-(3-(6-(2,6-difluorophenyl)-5-fluoropicolinamido)pyridin-4-yl)-3-methyl-2-(methylthio)cyclohexylcarbamate (1.0 equiv.) in THF (0.04 M) in a 0° C. bath was added the oxone (2.0 equiv.) as a solution in H$_2$O. The solution was left stirring at rt for 5 hrs. The solution was diluted with EtOAc, washed with H$_2$O, NaCl$_{(sat)}$, dried over MgSO$_4$, filtered, concentrated to yield Boc protected product. The material was treated with 25% TFA/CH$_2$Cl$_2$ for 30 minutes, at which time the volatiles were removed in vacuo, the residue was dissolved in DMSO and purified by reverse phase HPLC. The product fractions were lyophilized directly to yield N-(4-((1R,3R,4R,5S)-3-amino-5-methyl-4-(methylsulfonyl)cyclohexyl)pyridin-3-yl)-6-(2,6-difluorophenyl)-5-fluoropicolinamide in 68% yield. LC/MS (m/z)=519.2 (MH$^+$), R$_f$=0.60 min. $^1$H NMR (400 MHz, <dmso>) δ ppm 10.44 (s, 1H), 8.60 (d, J=8.0, 1H), 8.48 (d, J=4.0, 1H), 8.34 (dd, J=8.0, 4.0, 1H), 8.20 (dd, J=8.0, 8.0, 1H), 8.00 (dd, J=16.0, 4.0, 1H), 7.67-7.74 (m, 1H), 7.34-7.38 (m, 3H), 3.14 (s, 3H), 3.02-3.12 (m, 2H), 2.18-2.24 (m, 1H), 1.84-1.96 (m, 3H), 1.62-1.72 (m, 1H), 1.38-1.48 (m, 1H), 1.18 (d, J=4.0, 3H).

Synthesis of (+/−)-tert-butyl ((1R,2R,3S,5R)-5-(3-((tert-butoxycarbonyl)amino)pyridin-4-yl)-2-hydroxy-3-methylcyclohexyl)carbamate

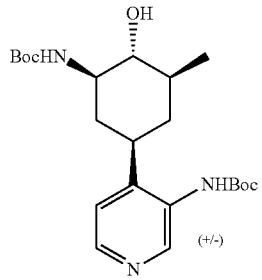 [SMILES: C[C@H]1C[C@@H](c2ccncc2NC(=O)OC(C)(C)C)C[C@@H](NC(=O)OC(C)(C)C)[C@@H]1O]

A solution of (+/−)-(1R,2R,4R,6S)-4-(3-aminopyridin-4-yl)-2-(tert-butoxycarbonylamino)-6-methylcyclohexyl acetate (1.0 equiv.) and Boc$_2$O (2.1 equiv.) in dioxane (0.34 M) was submerged in an 120° C. oil bath, fitted with a condenser and left stirring under Ar for 6 hrs. The reaction was cooled to rt and the volatiles were removed in vacuo. The residue was dissolved in EtOH (0.34 M), K$_2$CO$_3$ (10.0 equiv.) was added, a refluxing head was attached and the heterogeneous solution was submerged in an 50° C. oil bath and left stirring for 24 hrs. The reaction was cooled to rt. The volatiles were removed in vacuo and the residue was partitioned between EtOAc and H$_2$O. The organic layer was washed with Na$_2$CO$_{3(sat)}$, NaCl$_{(sat)}$, dried over MgSO$_4$, filtered, and concentrated. The residue was dissolved in CH$_2$Cl$_2$/Heptane and left standing. The solid that form was sonciated, filtered, rinsed with CH$_2$Cl$_2$ and pumped on to yield (+/−)-tert-butyl ((1R,2R,3S,5R)-5-(3-((tert-butoxycarbonyl)amino)pyridin-4-yl)-2-hydroxy-3-methylcyclohexyl)carbamate in 85% yield. LC/MS (m/z)=422.3 (MH$^+$), R$_f$=0.65 min.

Synthesis of (+/−)-(1R,2R,4R,6S)-2-(tert-butoxycarbonylamino)-4-(3-(tert-butoxycarbonylamino)pyridin-4-yl)-6-methylcyclohexyl methanesulfonate

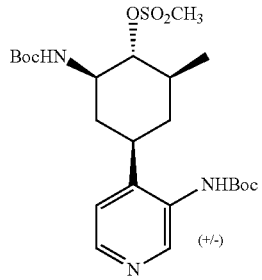

To a solution of (+/−)-tert-butyl ((1R,2R,3S,5R)-5-(3-((tert-butoxycarbonyl)amino)pyridin-4-yl)-2-hydroxy-3-methylcyclohexyl)carbamate (1.0 equiv.) in pyridine (0.17 M) was added MsCl (5.0 equiv.). The capped solution was stirred for 5 minutes and then the homogeneous solution was left standing at rt for 16 hrs. The volatiles were removed in vacuo and the residue was partitioned between EtOAc and H$_2$O. The organic layer was washed with H$_2$O, 10% CuSO$_4$, H$_2$O, Na$_2$CO$_{3(sat)}$, NaCl$_{(sat)}$, dried over MgSO$_4$, filtered, concentrated and purified by ISCO SiO$_2$ chromatography to yield (+/−)-(1R,2R,4R,6 S)-2-(tert-butoxycarbonylamino)-4-(3-(tert-butoxycarbonylamino)pyridin-4-yl)-6-methylcyclohexyl methanesulfonate in 59% yield. LC/MS (m/z)=500.3 (MH⁺), R_t=0.74 min.

Synthesis of (+/−)S-((1S,2R,4R,6S)-2-((tert-butoxycarbonyl)amino)-4-(3-((tert-butoxycarbonyl)amino)pyridin-4-yl)-6-methylcyclohexyl) ethanethioate

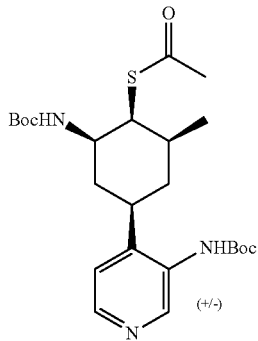 [SMILES: CC(=O)S[C@H]1[C@@H](C)C[C@@H](c2ccncc2NC(=O)OC(C)(C)C)C[C@H]1NC(=O)OC(C)(C)C]

To a solution of (+/−)-(1R,2R,4R,6S)-2-(tert-butoxycarbonylamino)-4-(3-(tert-butoxycarbonylamino)pyridin-4-yl)-6-methylcyclohexyl methanesulfonate (1.0 equiv.) in DMF (0.25 M) was added potassium thioacetate (6.0 equiv.). The mixture was stirred for 6 hours in a 60° C. bath under Ar. Upon cooling and the residue was partitioned between EtOAc and H₂O. The organic layer was washed with H₂O (3x), Na₂CO₃(sat), NaCl(sat), dried over MgSO₄, filtered, concentrated and purified by ISCO SiO₂ chromatography to yield (+/−)S-((1S,2R,4R,6S)-2-((tert-butoxycarbonyl)amino)-4-(3-((tert-butoxycarbonyl)amino)pyridin-4-yl)-6-methylcyclohexyl) ethanethioate in 87% yield. LC/MS (m/z)=480.3 (MH⁺), R_t=0.82 min.

Synthesis of (+/−)tert-butyl ((1R,2S,3S,5R)-5-(3-aminopyridin-4-yl)-3-methyl-2-(methylsulfonyl)cyclohexyl)carbamate

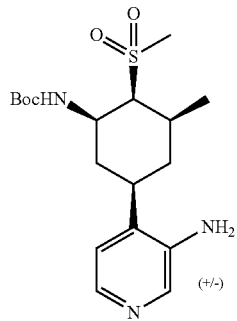 [SMILES: C[C@H]1C[C@@H](c2ccncc2N)C[C@@H](NC(=O)OC(C)(C)C)[C@H]1S(C)(=O)=O]

To a solution of (+/−)S-((1S,2R,4R,6S)-2-((tert-butoxycarbonyl)amino)-4-(3-((tert-butoxycarbonyl)amino)pyridin-4-yl)-6-methylcyclohexyl) ethanethioate (1.0 equiv.) in MeOH (0.09 M) was added potassium carbonate (3.0 equiv.). The mixture was stirred for 15 minutes at which time methyl iodide (1.1 eq.) was added and the solution was stirred at rt for 15 minutes. The volatiles were removed in vacuo and the residue was partitioned between EtOAc and H₂O. The organic layer was washed with H₂O, NaCl(sat), dried over MgSO₄, filtered, concentrated and purified by ISCO SiO₂ chromatography to yield the methyl sulfide product in 99% yield. LC/MS (m/z)=452.3 (MH⁺), R_t=0.87 min. To a solution of methyl sulfide (1.0 eq.) in THF (0.05 M) at rt was added an aqueous solution of oxone (2.2 eq.) dropwise over 10 minutes. After stirring at rt for 1 hour the solution was partitioned between EtOAc and H₂O. The organic layer was washed with H₂O, NaCl(sat), dried over MgSO₄, filtered, concentrated to yield the bis Boc protected methyl sulfone product in 95% yield. LC/MS (m/z)=484.2 (MH⁺), R_t=0.77 min. The bis boc protected cyclohexyl sulfone (1.0 equiv) was treated with 4M HCl in dioxane for 3 hours to removed both Boc groups. Upon removal of the volatiles in vacuo, the residue was suspended in 1:1 dioxane/Na₂CO₃(sat) and N-(tert-Butoxycarbonyloxy)succinimide (1.2 eq.) was added. After stirring for 1 hour, additional N-(tert-Butoxycarbonyloxy)succinimide (1.2 eq.) was added. After stirring for an additional 2 hours the solution was extracted with CH₂Cl₂, the combined organic layers were washed with H₂O, NaCl(sat), dried over MgSO₄, filtered, concentrated and purified by ISCO SiO₂ chromatography to yield the (+/−)tert-butyl ((1R,2S,3S,5R)-5-(3-aminopyridin-4-yl)-3-methyl-2-(methylsulfonyl)cyclohexyl)carbamate in 56% yield. LC/MS (m/z)=384.3 (MH⁺), R_t=0.57 min. Chiral purification was completed via SFC (20% EtOH/80% n-heptanes, 20 mL/min, OJ column) to isolate the pure enantiomers. The second peak correlated with tert-butyl ((1R,2S,3S,5R)-5-(3-aminopyridin-4-yl)-3-methyl-2-(methylsulfonyl)cyclohexyl)carbamate.

Synthesis of tert-butyl (1R,2S,3S,5R)-5-(3-aminopyridin-4-yl)-3-methyl-2-(1H-1,2,4-triazol-1-yl)cyclohexylcarbamate and tert-butyl (1S,2R,3R,5S)-5-(3-aminopyridin-4-yl)-3-methyl-2-(1H-1,2,4-triazol-1-yl)cyclohexylcarbamate

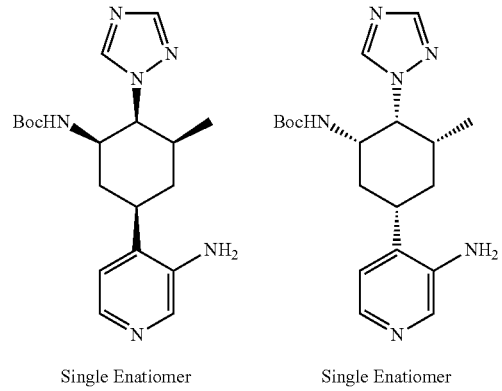 [SMILES: C[C@H]1C[C@@H](c2ccncc2N)C[C@@H](NC(=O)OC(C)(C)C)[C@H]1n1cncn1 ; C[C@@H]1C[C@H](c2ccncc2N)C[C@H](NC(=O)OC(C)(C)C)[C@@H]1n1cncn1]

Single Enatiomer    Single Enatiomer

A solution of (+/−)-(1R,2R,4R,6S)-2-(tert-butoxycarbonylamino)-4-(3-(tert-butoxycarbonylamino)pyridin-4-yl)-6-methylcyclohexyl methanesulfonate (1.0 equiv.), 1H-1,2,4-triazole (3.0 equiv.) and Cs₂CO₃ (3.0 equiv.) in DMF (0.15 M) was stirred at 80° C. for 5 hrs. The volatiles were removed in vacuo and the residue was partitioned between EtOAc and H₂O. The organic layer was washed with Na₂CO₃(sat), NaCl(sat), dried over MgSO₄, filtered, concentrated and purified by RP HPLC, followed by free basing by partitioning between an equal volume of EtOAc and Na₂CO₃, separating, washing with NaCl(sat), drying over MgSO₄, filtering, concentrating. Purification was completed via SFC (20% MeOH, 100 mL/min, AD column) to yield tert-butyl (1R,2S,3S,5R)-5-(3-aminopyridin-4-yl)-3-methyl-2-(1H-1,2,4-triazol-1-yl)cyclohexylcarbamate (19% yield, 99% ee) and tert-butyl (1S,2R,3R,5S)-5-(3-aminopyridin-4-yl)-3-methyl-2-(1H-1,2,4- triazol-1-yl)cyclohexylcarbamate (19% yield, 99% ee). LC/MS (m/z)=373.3 (MH+), $R_t$=0.54 min.

Synthesis of tert-butyl tert-butoxycarbonyl(4-((3R, 4R,5S)-3-((tert-butoxycarbonyl)amino)-4-((tert-butyldimethysilyl)oxy)-5-methylpiperidin-1-yl)pyridin-3-yl)carbamate

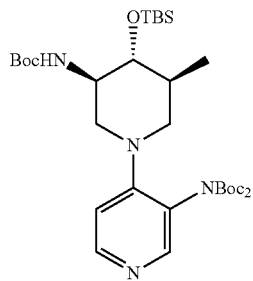

To a solution of tert-butyl (3R,4R,5S)-1-(3-aminopyridin-4-yl)-4-(tert-butyldimethylsilyloxy)-5-methylpiperidin-3-ylcarbamate (1.0 equiv.) in $CH_2Cl_2$ (0.50 M) at RT was added $Boc_2O$ (6.0 equiv.), followed by DMAP (2.0 equiv.). The resulting mixture was stirred at RT for 16 hrs. The reaction mixture was then diluted with EtOAc and water. The organic layer was washed with Brine, dried over $MgSO_4$, concentrated and purified by flash column chromatography to yield tert-butyl tert-butoxycarbonyl(4-((3R,4R,5S)-3-((tert-butoxycarbonyl)amino)-4-((tert-butyldimethylsilyl)oxy)-5-methylpiperidin-1-yl)pyridin-3-yl)carbamate in 57% yield. LC/MS (m/z)=637.3 (MH+), $R_t$=1.17 min.

Synthesis of tert-butyl tert-butoxycarbonyl(4-((3R, 4R,5S)-3-((tert-butoxycarbonyl)amino)-4-hydroxy-5-methylpiperidin-1-yl)pyridin-3-yl)carbamate

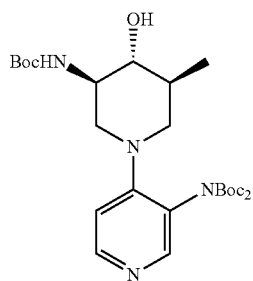

To a solution of tert-butyl tert-butoxycarbonyl(4-((3R, 4R,5S)-3-((tert-butoxycarbonyl)amino)-4-((tert-butyldimethylsilyl)oxy)-5-methylpiperidin-1-yl)pyridin-3-yl)carbamate (1.0 equiv.) in THF (0.20 M) at RT was added TBAF (1.0 equiv.). The resulting mixture was stirred at rt for 4 hrs. The reaction mixture was then diluted with EtOAc and water. The organic layer was washed with Brine, dried over $MgSO_4$, concentrated and purified by flash column chromatography to yield tert-butyl tert-butoxycarbonyl(4-((3R,4R,5S)-3-((tert-butoxycarbonyl)amino)-4-hydroxy-5-methylpiperidin-1-yl) pyridin-3-yl)carbamate in 87% yield. LC/MS (m/z)=523.4 (MH+), $R_t$=0.72 min. $^1$H NMR (400 MHz, <cdcl3>) δ ppm 1.03 (d, J=6.65 Hz, 3 H), 1.34-1.51 (m, 54 H), 1.72-1.87 (m, 1 H), 2.05 (s, 1 H), 2.46-2.57 (m, 1 H), 2.69 (t, J=11.35 Hz, 1H), 2.78-2.94 (m, 1 H), 3.00-3.14 (m, 1 H), 3.45 (d, J=12.52 Hz, 1 H), 3.53-3.76 (m, 1H), 4.63 (d, J=6.26 Hz, 1 H), 6.88 (d, J=5.48 Hz, 3 H), 8.13 (s, 3 H), 8.26-8.36 (m, 3 H).

Synthesis of (3R,4R,5S)-1-(3-(bis(tert-butoxycarbonyl)amino)pyridin-4-yl)-3-((tert-butoxycarbonyl) amino)-5-methylpiperidin-4-yl methanesulfonate

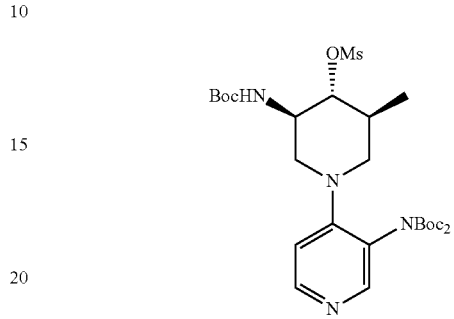

To a solution of tert-butyl tert-butoxycarbonyl(4-((3R,4R, 5S)-3-((tert-butoxycarbonyl)amino)-4-hydroxy-5-methylpiperidin-1-yl)pyridin-3-yl)carbamate (1.0 equiv.) in DCM (0.20 M) was added TEA (1.7 equiv.), followed by MsCl (1.3 equiv.). The capped solution was stirred at rt for 90 mins. The reaction mixture was quenched with $NaHCO_{3(sat)}$, and extracted with EtOAc. The organic layer was washed with $NaCl_{(sat)}$, dried over $MgSO_4$, filtered, concentrated to yield (3R,4R,5S)-1-(3-(bis(tert-butoxycarbonyl)amino)pyridin-4-yl)-3-((tert-butoxycarbonyl)amino)-5-methylpiperidin-4-yl methanesulfonate in 99% yield. LC/MS (m/z)=601.3 (MH+), $R_t$=0.83 min.

Synthesis of tert-butyl (3R,4S,5S)-1-(3-aminopyridin-4-yl)-5-methyl-4-(1H-1,2,4-triazol-1-yl)piperidin-3-ylcarbamate

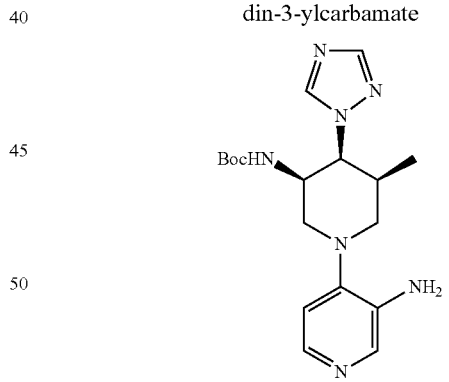

A solution of (3R,4R,5S)-3-(tert-butoxycarbonylamino)-1-(3-(tert-butoxycarbonylamino)pyridin-4-yl)-5-methylpiperidin-4-yl methanesulfonate (1.0 equiv.), 1H-1,2,4-triazole (3.0 equiv.) and $Cs_2CO_3$ (3.0 equiv.) in DMF (0.17 M) was stirred at 90° C. for 3 hrs. The mixture was diluted with DMF, filtered and purified by RP HPLC, followed by free basing by partitioning between an equal volume of EtOAc and $Na_2CO_3$, separating, washing with $NaCl_{(sat)}$, drying over $MgSO_4$, filtering, concentrating to yield tert-butyl (3R,4S,5S)-1-(3-aminopyridin-4-yl)-5-methyl-4-(1H-1,2,4-triazol-1-yl)piperidin-3-ylcarbamate in 8% yield. LC/MS (m/z)=374.3 (MH+), $R_t$=0.53 min.

Synthesis of tert-butyl ((1R,2S,3S,5R)-5-(3-aminopyridin-4-yl)-3-methyl-2-(2-oxopyridin-1(2H)-yl)cyclohexyl)carbamate, tert-butyl ((1S,2R,3R,5S)-5-(3-aminopyridin-4-yl)-3-methyl-2-(2-oxopyridin-1(2H)-yl)cyclohexyl)carbamate, tert-butyl ((1R,2S,3S,5R)-5-(3-aminopyridin-4-yl)-3-methyl-2-(pyridin-2-yloxy)cyclohexyl)carbamate and tert-butyl al S,2R,3R,5S)-5-(3-aminopyridin-4-yl)-3-methyl-2-(pyridin-2-yloxy)cyclohexyl)carbamate

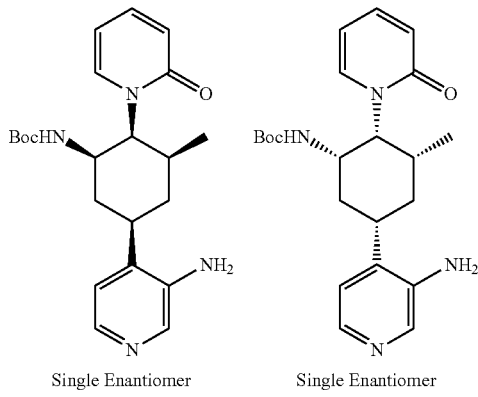

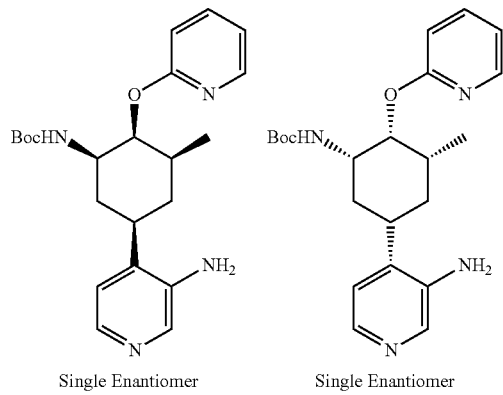

To a solution of (1R,2R,4R,6S)-2-(tert-butoxycarbonylamino)-4-(3-(tert-butoxycarbonylamino)pyridin-4-yl)-6-methylcyclohexyl methanesulfonate (1.0 equiv.) Cs$_2$CO$_3$ (3.0 equiv.) in DMF (0.15 M) was added pyridin-2-ol (1.0 equiv). The mixture was stirred at 70° C. for 5 hrs. The reaction was worked up with EtOAc and Brine. The organic layer was concentrated and was treated with 4N HCl (30.0 equiv.) in Dioxane for 2 hrs at which time the volatiles were removed in vacuo. The redisue was dissolved in THF (0.15 M) and tert-butyl 2,5-dioxopyrrolidin-1-yl carbonate (1.5 equiv.) was added, followed by DIEA (3.0 equiv.). After stirring at rt for 3 hrs, the reaction was quenched with sat. NaHCO$_3$ and extracted with EtOAc. The organic layer was washed with Brine, dried over Na$_2$SO$_4$ and concentrated. The crude was purified by prep HPLC to yield two major peaks. The fractions of the first product peak was combined and neutralized with sat. NaHCO$_3$ and extracted with EtOAc. The organic layer was washed with Brine, dried over Na$_2$SO$_4$ and concentrated. Purification was completed via SFC (20% (MeOH with 10% DEA), 100 mL/min, AD column) to yield tert-butyl ((1R,2S,3S,5R)-5-(3-aminopyridin-4-yl)-3-methyl-2-(2-oxopyridin-1(2H)-yl)cyclohexyl)carbamate (8% yield, 99% ee) and tert-butyl ((1S,2R,3R,5S)-5-(3-aminopyridin-4-yl)-3-methyl-2-(2-oxopyridin-1(2H)-yl)cyclohexyl)carbamate (9% yield, 99% ee). LC/MS (m/z)=399.2 (MH$^+$), R$_t$=0.60 min. $^1$H NMR (400 MHz, <dmso>) δ ppm 0.72 (s, 3 H), 1.30 (s, 9 H), 1.63-1.81 (m, 2 H), 1.89-2.00 (m, 2 H), 2.02-2.18 (m, 2 H), 3.04-3.13 (m, 1 H), 4.03-4.12 (m, 1 H), 4.91-5.02 (m, 1 H), 5.04-5.13 (m, 2 H), 6.17-6.26 (m, 1 H), 6.31-6.41 (m, 1 H), 6.98-7.07 (m, 1 H), 7.32-7.41 (m, 2 H), 7.68-7.74 (m, 1H), 7.74-7.82 (m, 1 H), 7.85-7.90 (m, 1 H). The fractions of the second product peak was combined and neutralized with sat. NaHCO$_3$ and extracted with EtOAc. The organic layer was washed with Brine, dried over Na$_2$SO$_4$ and concentrated. Purification was completed via SFC (20% (MeOH with 10% DEA), 100 mL/min, AD column) to yield tert-butyl ((1R,2S,3S,5R)-5-(3-aminopyridin-4-yl)-3-methyl-2-(pyridin-2-yloxy)cyclohexyl)carbamate (14% yield, 99% ee) and tert-butyl ((1S,2R,3R,5S)-5-(3-aminopyridin-4-yl)-3-methyl-2-(pyridin-2-yloxy)cyclohexyl)carbamate (15% yield, 99% ee). LC/MS (m/z)=399.2 (MH$^+$), R$_t$=0.65 min. $^1$H NMR (400 MHz, <cdcl3>) δ ppm 0.95 (d, J=6.65 Hz, 3 H), 1.35-1.78 (m, 12 H), 1.97-2.08 (m, 2 H), 2.76 (t, J=11.93 Hz, 1 H), 3.72 (br. s., 2 H), 3.88 (d, J=4.70 Hz, 1 H), 5.43 (d, J=7.43 Hz, 1 H), 5.59 (br. s., 1H), 6.79-6.94 (m, 2H), 7.08 (d, J=5.09 Hz, 1 H), 7.56-7.65 (m, 1 H), 7.98-8.17 (m, 3 H).

Synthesis of tert-butyl ((1R,2S,3S,5R)-5-(3-((tert-butoxycarbonyl)amino)pyridin-4-yl)-2-azido-3-methylcyclohexyl)carbamate and tert-butyl ((1S,2R,3R,5S)-5-(3-((tert-butoxycarbonyl)amino)pyridin-4-yl)-2-azido-3-methylcyclohexyl)carbamate

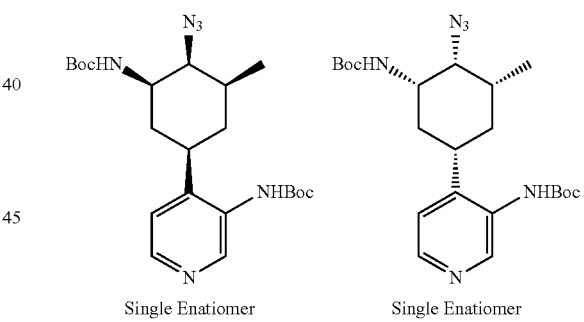

To a solution of (+/−)-(1R,2R,4R,6S)-2-(tert-butoxycarbonylamino)-4-(3-(tert-butoxycarbonylamino)pyridin-4-yl)-6-methylcyclohexyl methanesulfonate (1.0 equiv.) in DMF (0.13 M) was added NaN$_3$ (1.0 equiv.). The solution was submerged in an 80° C. oil bath and left stirring under Ar for 16 hrs. The solution was cooled to rt and left stirring under Ar overnight. The solution was partitioned between EtOAc and H$_2$O. The organic layer was washed with Na$_2$CO$_{3(sat)}$, NaCl$_{(sat)}$, dried over MgSO$_4$, filtered, concentrated and purified by ISCO SiO$_2$ chromatography. Purification was completed via SFC (15% IPA, 100 mL/min, IA column) to yield tert-butyl ((1R,2S,3S,5R)-5-(3-((tert-butoxycarbonyl)amino)pyridin-4-yl)-2-azido-3-methylcyclohexyl)carbamate (21% yield, 99% ee) and tert-butyl ((1S,2R,3R,5S)-5-(3-((tert-butoxycarbonyl)amino)pyridin-4-yl)-2-azido-3-methylcyclohexyl)carbamate (22% yield, 99% ee). LC/MS (m/z)=447.3 (MH$^+$), R$_t$=0.86 min.

Synthesis of tert-butyl (1R,2S,3S,5R)-5-(3-aminopyridin-4-yl)-2-azido-3-methylcyclohexylcarbamate

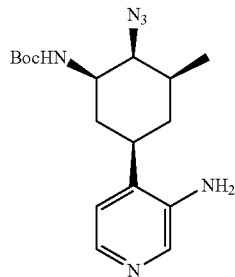 [SMILES: C[C@H]1C[C@@H](c2ccncc2N)C[C@@H](NC(=O)OC(C)(C)C)[C@H]1N=[N+]=[N-]]

A solution of 4 M HCl in dioxane (30.0 equiv.) was added to tert-butyl ((1R,2S,3S,5R)-5-(3-((tert-butoxycarbonyl)amino)pyridin-4-yl)-2-azido-3-methylcyclohexyl)carbamate (1.0 equiv.). The solution started to go homogeneous for a few minutes, but then a ppt formed and the solution went very thick. After sitting at rt for 1 hour, the volatiles were removed in vacuo and the solid was pumped on for 5 minutes on the high vac. To the residue was added CH$_2$Cl$_2$ (0.15 M), TEA (5.0 equiv.) and Boc$_2$O (1.0 equiv.). The solution was left stirring at rt for 1 hr. The volatiles were removed in vacuo and the residue was partitioned between EtOAc and H$_2$O. The organic layer was washed with Na$_2$CO$_{3(sat)}$, NaCl$_{(sat)}$, dried over MgSO$_4$, filtered, concentrated and purified by ISCO SiO$_2$ chromatography to yield tert-butyl (1R,2S,3S,5R)-5-(3-aminopyridin-4-yl)-2-azido-3-methylcyclohexylcarbamate in 57% yield. LC/MS (m/z)=347.3 (MH$^+$), R$_t$=0.70 min. $^1$H NMR (400 MHz, CHLOROFORM-d) δ ppm 1.13 (d, J=6.65 Hz, 3 H), 1.43-1.58 (m, 11 H), 1.79 (d, J=12.52 Hz, 1 H), 1.95 (d, J=6.26 Hz, 1 H), 2.60 (br. s., 1 H), 3.61 (br. s., 2 H), 3.77-3.91 (m, 2 H), 4.78 (d, J=7.43 Hz, 1 H), 6.96 (d, J=4.70 Hz, 1 H), 7.97-8.07 (m, 2 H).

Synthesis of tert-butyl (1S,2R,3R,5S)-5-(3-aminopyridin-4-yl)-2-azido-3-methylcyclohexylcarbamate

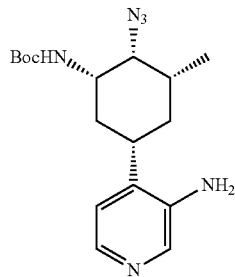 [SMILES: C[C@@H]1C[C@H](c2ccncc2N)C[C@H](NC(=O)OC(C)(C)C)[C@@H]1N=[N+]=[N-]]

A solution of 4 M HCl in dioxane (30.0 equiv.) was added to tert-butyl ((1S,2R,3R,5S)-5-(3-((tert-butoxycarbonyl)amino)pyridin-4-yl)-2-azido-3-methylcyclohexyl)carbamate (1.0 equiv.). The solution started to go homogeneous for a few minutes, but then a ppt formed and the solution went very thick. After sitting at rt for 1 hour, the volatiles were removed in vacuo and the solid was pumped on for 5 minutes on the high vac. To the residue was added CH$_2$Cl$_2$ (0.15 M), TEA (5.0 equiv.) and Boc$_2$O (1.0 equiv.). The solution was left stirring at rt for 1 hr. The volatiles were removed in vacuo and the residue was partitioned between EtOAc and H$_2$O. The organic layer was washed with Na$_2$CO$_{3(sat)}$, NaCl$_{(sat)}$, dried over MgSO$_4$, filtered, concentrated to yield tert-butyl (1S,2R,3R,5S)-5-(3-aminopyridin-4-yl)-2-azido-3-methylcyclohexylcarbamate in 98% yield. LC/MS (m/z)=347.3 (MH$^+$), R$_t$=0.71 min.

Synthesis of tert-butyl (1S,2R,3R,5S)-2-azido-5-(3-(6-(2,6-difluorophenyl)-5-fluoropicolinamido)pyridin-4-yl)-3-methylcyclohexylcarbamate

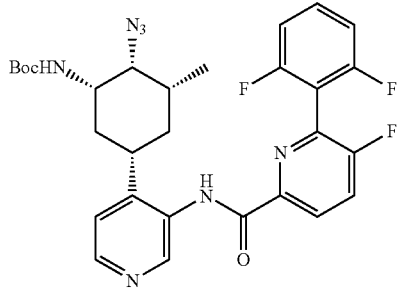 [SMILES: C[C@@H]1C[C@H](c2ccncc2NC(=O)c2ccc(F)c(-c3c(F)cccc3F)n2)C[C@H](NC(=O)OC(C)(C)C)[C@@H]1N=[N+]=[N-]]

EDC (2.0 equiv.) and HOAt (2.0 equiv.) was added to a solution of tert-butyl (1S,2R,3R,5S)-5-(3-aminopyridin-4-yl)-2-azido-3-methylcyclohexyl carbamate (1.0 equiv.) and 6-(2,6-difluorophenyl)-5-fluoropicolinic acid (1.5 equiv.) in DMF (0.08 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography to yield tert-butyl (1S,2R,3R,5S)-2-azido-5-(3-(6-(2,6-difluorophenyl)-5-fluoropicolinamido)pyridin-4-yl)-3-methylcyclohexyl carbamate in 31% yield. LC/MS (m/z)=582.3 (MH$^+$), R$_t$=1.00 min.

Synthesis of tert-butyl (1R,2S,3S,5R)-2-azido-5-(3-(6-(2,6-difluorophenyl)-5-fluoropicolinamido)pyridin-4-yl)-3-methylcyclohexylcarbamate

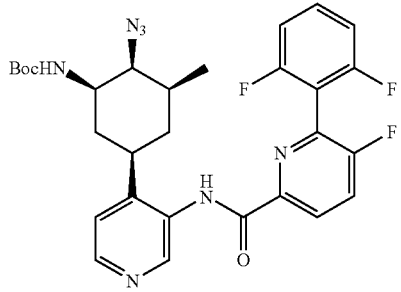 [SMILES: C[C@H]1C[C@@H](c2ccncc2NC(=O)c2ccc(F)c(-c3c(F)cccc3F)n2)C[C@@H](NC(=O)OC(C)(C)C)[C@H]1N=[N+]=[N-]]

EDC (2.0 equiv.) and HOAt (2.0 equiv.) was added to a solution of tert-butyl (1R,2S,3S,5R)-5-(3-aminopyridin-4-yl)-2-azido-3-methylcyclohexylcarbamate (1.0 equiv.) and 6-(2,6-difluorophenyl)-5-fluoropicolinic acid (1.5 equiv.) in DMF (0.08 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography to yield tert-butyl (1R,2S,3S,5R)-2-azido-5-(3-(6-(2,6-difluorophenyl)-5-fluoropicolinamido)pyridin-4-yl)-3-methylcyclohexylcarbamate 59% yield. LC/MS (m/z)=582.3 (MH$^+$), R$_t$=0.97 min.

Synthesis of tert-butyl (1R,2S,3S,5R)-2-amino-5-(3-(6-(2,6-difluorophenyl)-5-fluoropicolinamido)pyridin-4-yl)-3-methylcyclohexylcarbamate

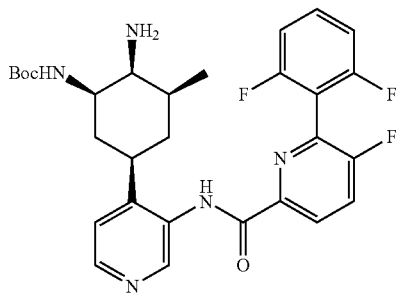 [SMILES: C[C@H]1C[C@@H](c2ccncc2NC(=O)c2ccc(F)c(-c3c(F)cccc3F)n2)C[C@@H](NC(=O)OC(C)(C)C)[C@H]1N]

Degass a solution of tert-butyl (1R,2S,3S,5R)-2-azido-5-(3-(6-(2,6-difluorophenyl)-5-fluoropicolinamido)pyridin-4-yl)-3-methylcyclohexylcarbamate (1.0 equiv.) in MeOH/EtOAc (3/1, 0.04 M). To this solution was added Pd/C (0.2 equiv.) and purge with Ar and $H_2$. The mixture was stirred under $H_2$ for 16 hrs. Filter the mixture over cetlite and wash the cake with MeOH. Concentrate the filtrate to yield tert-butyl (1R,2S,3S,5R)-2-amino-5-(3-(6-(2,6-difluorophenyl)-5-fluoropicolinamido)pyridin-4-yl)-3-methylcyclohexylcarbamate in 100% yield). LC/MS (m/z)=556.3 (MH$^+$), $R_t$=0.73 min.

Method 4

Synthesis of ethyl (1S,2R,4R,6S)-2-amino-4-(3-(6-(2,6-difluorophenyl)-5-fluoropicolinamido)pyridin-4-yl)-6-methylcyclohexylcarbamate

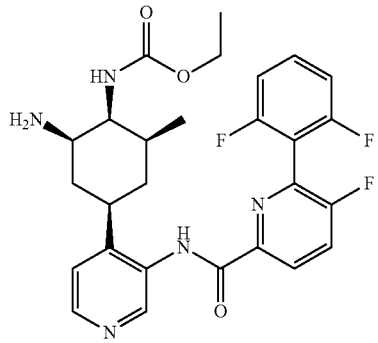 [SMILES: CCOC(=O)N[C@@H]1[C@H](N)C[C@H](c2ccncc2NC(=O)c2ccc(F)c(-c3c(F)cccc3F)n2)C[C@@H]1C]

To a solution of tert-butyl (1R,2S,3S,5R)-2-amino-5-(3-(6-(2,6-difluorophenyl)-5-fluoropicolinamido)pyridin-4-yl)-3-methylcyclohexylcarbamate (1.0 equiv.) in $CH_2Cl_2$ (0.03 M) at 0° C. was added DIEA (3.0 equiv.) and then ETHYL CHLOFORMATE (1.0 equiv.). The homogeneous solution was left standing at 0° C. at for 4 hrs. Neutralize the reaction with sat. $NaHCO_3$ solution. The solution was partitioned between EtOAc and $H_2O$. The organic layer was washed with $Na_2CO_{3(sat)}$, $NaCl_{(sat)}$, dried over $MgSO_4$, filtered, concentrated and purified by ISCO $SiO_2$ chromatography. The Boc protected product was treated with 25% TFA/ $CH_2Cl_2$ for 20 minutes at which time the volatiles were removed in vacuo and the residue was dissolved in DMSO and purified by RP-HPLC. The product fractions were lyophilized directly to yield ethyl (1S,2R,4R,6S)-2-amino-4-(3-(6-(2,6-difluorophenyl)-5-fluoropicolinamido)pyridin-4-yl)-6-methylcyclohexylcarbamate in 14% yield. LC/MS (m/z)=528.2 (MH$^+$), $R_t$=0.65 min.

Synthesis of isopropyl (1S,2R,4R,6S)-2-amino-4-(3-(6-(2,6-difluorophenyl)-5-fluoropicolinamido)pyridin-4-yl)-6-methylcyclohexylcarbamate

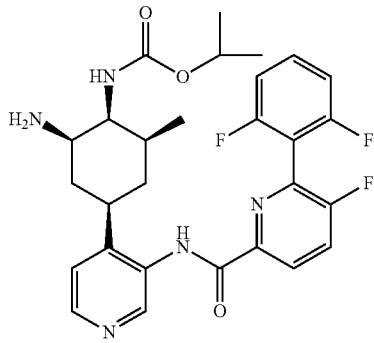 [SMILES: CC(C)OC(=O)N[C@@H]1[C@H](N)C[C@H](c2ccncc2NC(=O)c2ccc(F)c(-c3c(F)cccc3F)n2)C[C@@H]1C]

Method 4 was followed using tert-butyl (1R,2S,3S,5R)-2-amino-5-(3-(6-(2,6-difluorophenyl)-5-fluoropicolinamido)pyridin-4-yl)-3-methylcyclohexyl carbamate and isopropyl carbonochloridate to give isopropyl (1S,2R,4R,6S)-2-amino-4-(3-(6-(2,6-difluorophenyl)-5-fluoropicolinamido)pyridin-4-yl)-6-methyl cyclohexylcarbamate in 6% yield. LC/MS (m/z)=542.3 (MH$^+$), $R_t$=0.68 min.

Synthesis of N-(4-((1R,3R,4S,5S)-3-amino-5-methyl-4-propionamidocyclohexyl)pyridin-3-yl)-6-(2,6-difluorophenyl)-5-fluoropicolinamide

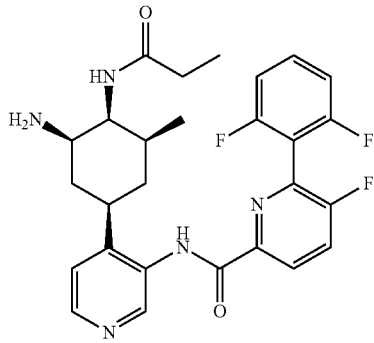 [SMILES: CCC(=O)N[C@@H]1[C@H](N)C[C@H](c2ccncc2NC(=O)c2ccc(F)c(-c3c(F)cccc3F)n2)C[C@@H]1C]

Method 4 was followed using tert-butyl (1R,2S,3S,5R)-2-amino-5-(3-(6-(2,6-difluorophenyl)-5-fluoropicolinamido)pyridin-4-yl)-3-methylcyclohexyl carbamate, TEA and propionyl chloride to give N-(4-((1R,3R,4S,5S)-3-amino-5-methyl-4-propionamidocyclohexyl)pyridin-3-yl)-6-(2,6-difluorophenyl)-5-fluoropicolinamide in 8% yield. LC/MS (m/z)=512.1 (MH$^+$), $R_t$=0.62 min.

Synthesis of N-(4-((1R,3R,4S,5S)-3-amino-4-isobutyramido-5-methylcyclohexyl)pyridin-3-yl)-6-(2,6-difluorophenyl)-5-fluoropicolinamide

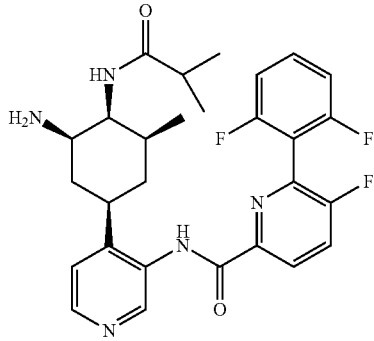 [SMILES: CC(C)C(=O)N[C@@H]1[C@H](N)C[C@H](c2ccncc2NC(=O)c2ccc(F)c(-c3c(F)cccc3F)n2)C[C@@H]1C]

Method 4 was followed using tert-butyl (1R,2S,3S,5R)-2-amino-5-(3-(6-(2,6-difluorophenyl)-5-fluoropicolinamido)pyridin-4-yl)-3-methylcyclohexyl carbamate, TEA and isobutyryl chloride to give N-(4-((1R,3R,4S,5S)-3-amino-4-isobutyramido-5-methylcyclohexyl)pyridin-3-yl)-6-(2,6-difluorophenyl)-5-fluoropicolinamide in 16% yield. LC/MS (m/z)=526.3 (MH$^+$), R$_t$=0.66 min.

Synthesis of N-(4-((1R,3R,4S,5S)-3-amino-4-(2-methoxyacetamido)-5-methylcyclohexyl)pyridin-3-yl)-6-(2,6-difluorophenyl)-5-fluoropicolinamide

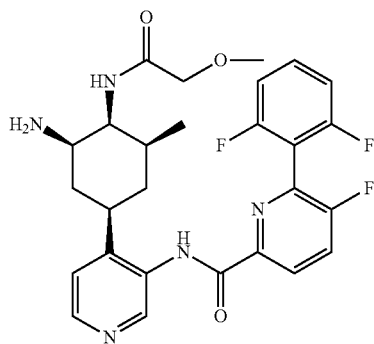 [SMILES: COCC(=O)N[C@@H]1[C@H](N)C[C@H](c2ccncc2NC(=O)c2ccc(F)c(-c3c(F)cccc3F)n2)C[C@@H]1C]

Method 4 was followed using tert-butyl (1R,2S,3S,5R)-2-amino-5-(3-(6-(2,6-difluorophenyl)-5-fluoropicolinamido)pyridin-4-yl)-3-methylcyclohexyl carbamate, TEA and 2-methoxyacetyl chloride to give N-(4-((1R,3R,4S,5S)-3-amino-4-(2-methoxyacetamido)-5-methylcyclohexyl)pyridin-3-yl)-6-(2,6-difluorophenyl)-5-fluoropicolinamide in 24% yield. LC/MS (m/z)=528.2 (MH$^+$), R$_t$=0.62 min.

Synthesis of N-(4-((1R,3R,4R,5S)-4-acetamido-3-amino-5-methylcyclohexyl)pyridin-3-yl)-6-(2,6-difluorophenyl)-5-fluoropicolinamide

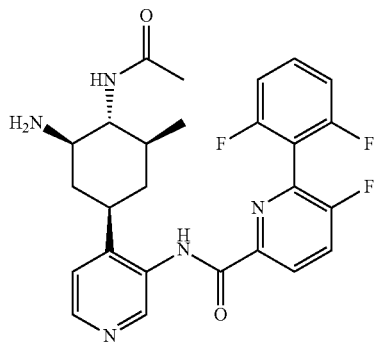 [SMILES: CC(=O)N[C@H]1[C@H](N)C[C@H](c2ccncc2NC(=O)c2ccc(F)c(-c3c(F)cccc3F)n2)C[C@@H]1C]

Method 4 was followed using tert-butyl ((1R,2R,3S,5R)-2-amino-5-(3-(6-(2,6-difluorophenyl)-5-fluoropicolinamido)pyridin-4-yl)-3-methylcyclohexyl)carbamate and acetic anhydride to give N-(4-((1R,3R,4R,5S)-4-acetamido-3-amino-5-methylcyclohexyl)pyridin-3-yl)-6-(2,6-difluorophenyl)-5-fluoropicolinamide in 13% yield. LC/MS (m/z)=498.3 (MH$^+$), R$_t$=0.58 min.

Method 5

Synthesis of N-(4-((1R,3R,4S,5S)-3-amino-5-methyl-4-(methylsulfonamido)cyclohexyl)pyridin-3-yl)-6-(2,6-difluorophenyl)-5-fluoropicolinamide and N-(4-((1S,3S,4R,5R)-3-amino-5-methyl-4-(methylsulfonamido)cyclohexyl)pyridin-3-yl)-6-(2,6-difluorophenyl)-5-fluoropicolinamide

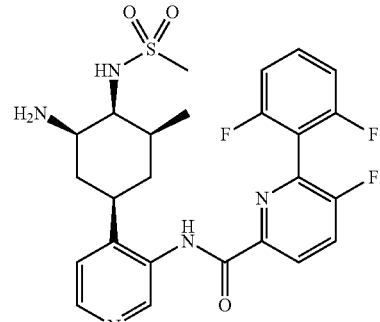

Single Enantiomer

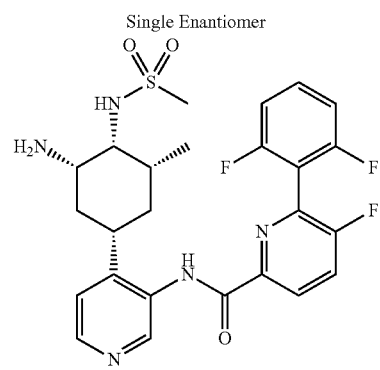

Single Enantiomer

To a solution of (+/−)-tert-butyl (1R,2S,3S,5R)-2-amino-5-(3-(6-(2,6-difluorophenyl)-5-fluoropicolinamido)pyridin-4-yl)-3-methylcyclohexyl carbamate (1.0 equiv.) in CH$_2$Cl$_2$ (0.03 M) at 0° C. was added DIEA (3.0 equiv.) and then METHANESULFONYL CHLORIDE (1.5 equiv.). The homogeneous solution was left standing at 0° C. at for 2 hrs. Neutralize the reaction with sat. NaHCO$_3$ solution. The solution was partitioned between EtOAc and H$_2$O. The organic layer was washed with Na$_2$CO$_{3(sat)}$, NaCl$_{(sat)}$, dried over MgSO$_4$, filtered, concentrated and purified by ISCO SiO$_2$ chromatography. Purification was completed via SFC (MeOH, 100 mL/min, OD column) to yield tert-butyl (1R,2S,3S,5R)-5-(3-(6-(2,6-difluorophenyl)-5-fluoropicolinamido)pyridin-4-yl)-3-methyl-2-(methylsulfonamido)cyclohexylcarbamate (14% yield, 99% ee) and tert-butyl (1S,2R,3R,5S)-5-(3-(6-(2,6-difluorophenyl)-5-fluoropicolinamido)pyridin-4-yl)-3-methyl-2-(methylsulfonamido)cyclohexylcarbamate (13% yield, 99% ee). LC/MS (m/z)=634.3 (MH$^+$), R$_t$=0.86 min. Each Boc protected enantiomer was treated respectively with 25% TFA/CH$_2$Cl$_2$ for 20 minutes at which time the volatiles were removed in vacuo and the residue was dissolved in DMSO and purified by RP-HPLC to yield N-(4-((1R,3R,4S,5S)-3-amino-5-methyl-4-(methylsulfonamido)cyclohexyl)pyridin-3-yl)-6-(2,6-difluorophenyl)-5-fluoropicolinamide in 94% yield; N-(4-((1S,3S,4R,5R)-3-amino-5-methyl-4-(methylsulfonamido)cyclohexyl)pyridin-3-yl)-6-(2,6-difluorophenyl)-5-fluoropicolinamide in 97% yield. LC/MS (m/z)=534.2 (MH$^+$), R$_t$=0.59 min.

Synthesis of N-(4-(((1R,3R,4S,5S)-4-acetamido-3-amino-5-methylcyclohexyl)pyridin-3-yl)-6-(2,6-difluorophenyl)-5-fluoropicolinamide and N-(4-(((1S,3S,4R,5R)-4-acetamido-3-amino-5-methylcyclohexyl)pyridin-3-yl)-6-(2,6-difluorophenyl)-5-fluoropicolinamide

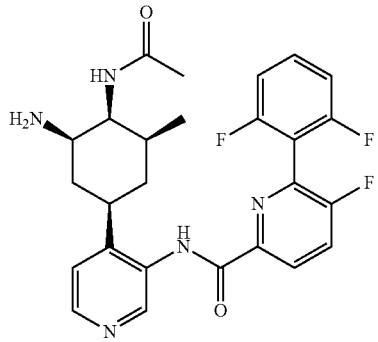

Single Enantiomer

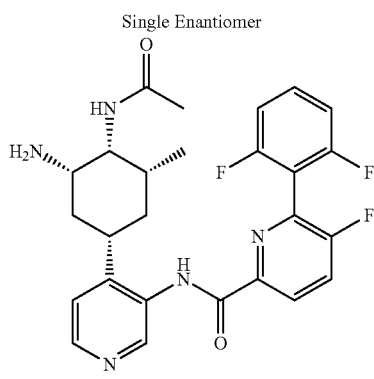

Single Enantiomer

Method 5 was followed using (+/−)-tert-butyl (1R,2S,3S,5R)-2-amino-5-(3-(6-(2,6-difluorophenyl)-5-fluoropicolinamido)pyridin-4-yl)-3-methylcyclohexyl carbamate and acetic anhydride to give N-(4-(((1R,3R,4S,5S)-4-acetamido-3-amino-5-methylcyclohexyl)pyridin-3-yl)-6-(2,6-difluorophenyl)-5-fluoropicolinamide in 20% yield; N-(4-(((1S,3S,4R,5R)-4-acetamido-3-amino-5-methylcyclohexyl)pyridin-3-yl)-6-(2,6-difluorophenyl)-5-fluoropicolinamide in 25% yield. LC/MS (m/z)=498.2 (MH$^+$), R$_t$=0.59 min.

Synthesis of methyl (1R,2S,4S,6R)-2-amino-4-(3-(6-(2,6-difluorophenyl)-5-fluoropicolinamido)pyridin-4-yl)-6-methylcyclohexylcarbamate and methyl (1S,2R,4R,6S)-2-amino-4-(3-(6-(2,6-difluorophenyl)-5-fluoropicolinamido)pyridin-4-yl)-6-methylcyclohexylcarbamate

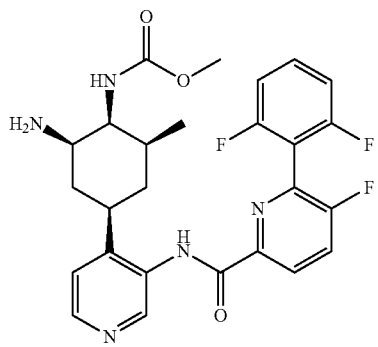

Single Enantiomer

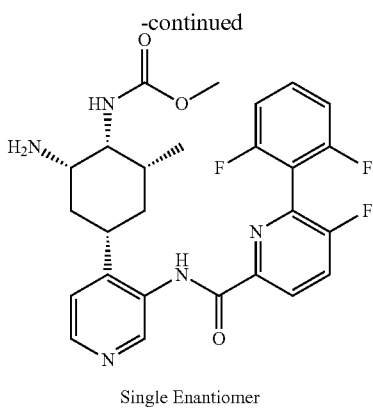

Single Enantiomer

Method 5 was followed using (+/−)-tert-butyl (1R,2S,3S,5R)-2-amino-5-(3-(6-(2,6-difluorophenyl)-5-fluoropicolinamido)pyridin-4-yl)-3-methylcyclohexyl carbamate and methyl carbonochloridate to give methyl (1R,2S,4S,6R)-2-amino-4-(3-(6-(2,6-difluorophenyl)-5-fluoropicolinamido)pyridin-4-yl)-6-methylcyclohexylcarbamate in 9% yield; methyl (1S,2R,4R,6S)-2-amino-4-(3-(6-(2,6-difluorophenyl)-5-fluoropicolinamido)pyridin-4-yl)-6-methylcyclohexylcarbamate in 10% yield. LC/MS (m/z)=514.2 (MH$^+$), R$_t$=0.62 min.

Synthesis of (+/−)-(1S,2R,6S)-2-((tert-butoxycarbonyl)amino)-6-methyl-4-(3-nitropyridin-4-yl)cyclohex-3-en-1-yl methanesulfonate

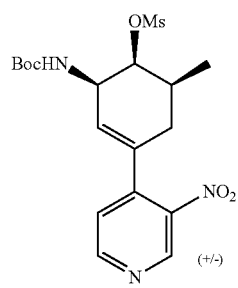 [SMILES: C[C@H]1CC(c2ccncc2[N+](=O)[O-])=C[C@@H](NC(=O)OC(C)(C)C)[C@H]1OS(C)(=O)=O]

To a solution of (+/−)-tert-butyl ((1R,5S,6S)-6-hydroxy-5-methyl-3-(3-nitropyridin-4-yl)cyclohex-2-en-1-yl)carbamate (1.0 equiv.) in pyridine (0.20 M) was added MsCl (5.0 equiv.). The capped solution was stirred for 5 minutes and then the homogeneous solution was left standing at rt for 16 hrs. The volatiles were removed in vacuo and the residue was partitioned between EtOAc and H$_2$O. The organic layer was washed with 10% CuSO$_4$, H$_2$O, Na$_2$CO$_{3(sat)}$, NaCl$_{(sat)}$, dried over MgSO$_4$, filtered, concentrated and purified by ISCO SiO$_2$ chromatography to yield (+/−)-(1S,2R,6S)-2-((tert-butoxycarbonyl)amino)-6-methyl-4-(3-nitropyridin-4-yl)cyclohex-3-en-1-yl methanesulfonate in 46% yield. LC/MS (m/z)=428.2 (MH$^+$), R$_t$=0.89 min.

Synthesis of (+/−)-(1S,2R,4R,6S)-4-(3-aminopyridin-4-yl)-2-((tert-butoxycarbonyl)amino)-6-methylcyclohexyl methanesulfonate

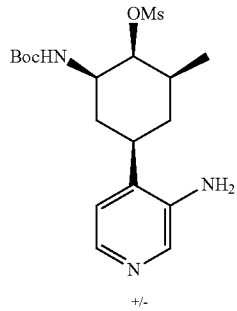 [SMILES: C[C@H]1C[C@@H](c2ccncc2N)C[C@@H](NC(=O)OC(C)(C)C)[C@H]1OS(C)(=O)=O]

Degass a solution of (+/−)-(1S,2R,6S)-2-((tert-butoxycarbonyl)amino)-6-methyl-4-(3-nitropyridin-4-yl)cyclohex-3-en-1-yl methanesulfonate (1.0 equiv.) in Ethanol (0.20 M). To this solution was added Pd/C (0.2 equiv.) and purge with Ar and H$_2$. The mixture was stirred under H$_2$ for 16 hrs. Filter the mixture over cetlite and wash the cake with MeOH. Concentrate the filtrate to yield (+/−)-(1S,2R,4R,6S)-4-(3-aminopyridin-4-yl)-2-((tert-butoxycarbonyl)amino)-6-methylcyclohexyl methanesulfonate in 49% yield. LC/MS (m/z)=400.3 (MH$^+$), R$_t$=0.62 min.

Synthesis of (+/−)-tert-butyl ((1R,2R,3S,5R)-5-(3-aminopyridin-4-yl)-2-azido-3-methylcyclohexyl)carbamate

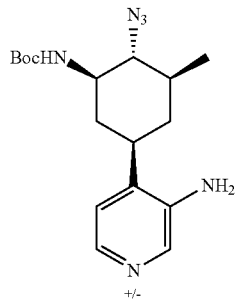 [SMILES: C[C@H]1C[C@@H](c2ccncc2N)C[C@@H](NC(=O)OC(C)(C)C)[C@@H]1N=[N+]=[N-]]

To a solution of (+/−)-(1S,2R,4R,6S)-4-(3-aminopyridin-4-yl)-2-((tert-butoxycarbonyl)amino)-6-methylcyclohexyl methanesulfonate (1.0 equiv.) in DMF (0.20 M) was added NaN$_3$ (7.0 equiv.). The solution was submerged in a 70° C. oil bath and left stirring under Ar for 4 hrs. The solution was cooled to rt and left stirring under Ar overnight. The solution was partitioned between EtOAc and H$_2$O. The organic layer was washed with Na$_2$CO$_{3(sat)}$, NaCl$_{(sat)}$, dried over MgSO$_4$, filtered, concentrated to yield (+/−)-tert-butyl ((1R,2R,3S,5R)-5-(3-aminopyridin-4-yl)-2-azido-3-methyl cyclohexyl)carbamate in 87% yield. LC/MS (m/z)=347.3 (MH$^+$), R$_t$=0.68 min.

Synthesis of (+/−)-tert-butyl ((1R,2R,3S,5R)-2-amino-5-(3-(6-(2,6-difluorophenyl)-5-fluoropicolinamido)pyridin-4-yl)-3-methylcyclohexyl)carbamate

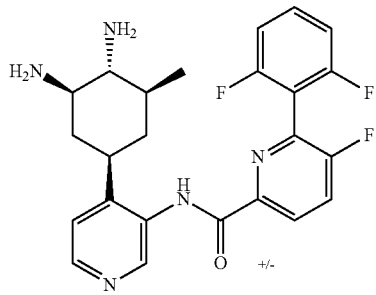 [SMILES: C[C@H]1C[C@@H](c2ccncc2NC(=O)c2ccc(F)c(-c3c(F)cccc3F)n2)C[C@@H](N)[C@@H]1N]

EDC (2.0 equiv.) and HOAt (2.0 equiv.) was added to a solution of (+/−)-tert-butyl ((1R,2R,3S,5R)-5-(3-aminopyridin-4-yl)-2-azido-3-methyl cyclohexyl)carbamate (1.0 equiv.) and 6-(2,6-difluorophenyl)-5-fluoropicolinic acid (1.5 equiv.) in DMF (0.20 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography. To a degassed a solution of the azide (1.0 equiv.) in 2-propanol (0.10 M) was added Pd/C (0.2 equiv.). The mixture was stirred under H$_2$ for 48 hrs. Filter the mixture over cetlite and wash the cake with MeOH. Concentrate the filtrate to yield (+/−)-tert-butyl ((1R,2R,3S,5R)-2-amino-5-(3-(6-(2,6-difluorophenyl)-5-fluoropicolinamido)pyridin-4-yl)-3-methylcyclohexyl)carbamate in 35% yield. LC/MS (m/z)=556.3 (MH$^+$), R$_t$=0.64 min.

Synthesis of N-(4-((1R,3R,4R,5S)-3-amino-5-methyl-4-(methylsulfonamido)cyclohexyl)pyridin-3-yl)-6-(2,6-difluorophenyl)-5-fluoropicolinamide and N-(4-((1S,3S,4S,5R)-3-amino-5-methyl-4-(methylsulfonamido)cyclohexyl)pyridin-3-yl)-6-(2,6-difluorophenyl)-5-fluoropicolinamide

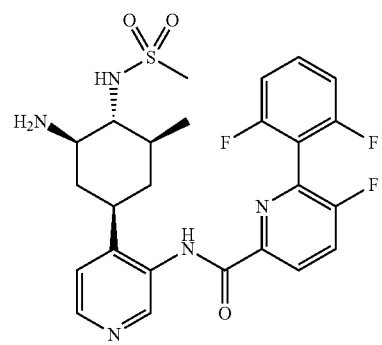

Single Enantiomer

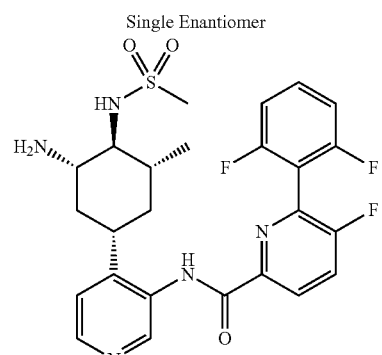

Single Enantiomer

Method 5 was followed using (+/−)-tert-butyl (1R,2R,3S,5R)-2-amino-5-(3-(6-(2,6-difluorophenyl)-5-fluoropicolinamido)pyridin-4-yl)-3-methylcyclohexylcarbamate and methanesulfonyl chloride to give N-(4-((1R,3R,4R,5S)-3-amino-5-methyl-4-(methylsulfonamido)cyclohexyl)pyridin-3-yl)-6-(2,6-difluorophenyl)-5-fluoropicolinamide in 13% yield; N-(4-((1S,3S,4S,5R)-3-amino-5-methyl-4-(methylsulfonamido)cyclohexyl)pyridin-3-yl)-6-(2,6-difluorophenyl)-5-fluoropicolinamide in 14% yield. LC/MS (m/z)=534.2 (MH$^+$), R$_t$=0.58 min.

Synthesis of tert-butyl (1R,3S,5R)-5-(3-(6-(2,6-difluorophenyl)-5-fluoropicolinamido)pyridin-4-yl)-3-methyl-2-oxocyclohexylcarbamate

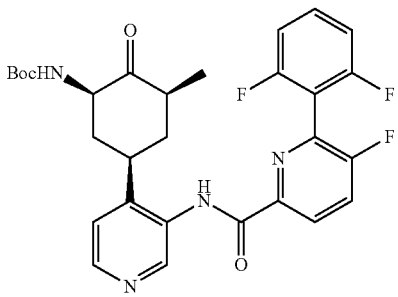 [SMILES: C[C@H]1C[C@@H](c2ccncc2NC(=O)c2ccc(F)c(-c3c(F)cccc3F)n2)C[C@@H](NC(=O)OC(C)(C)C)C1=O]

To a solution of tert-butyl (1R,2R,3S,5R)-5-(3-(6-(2,6-difluorophenyl)-5-fluoropicolinamido)pyridin-4-yl)-2-hydroxy-3-methylcyclohexylcarbamate (1.0 equiv.) in DCM (0.10 M) was added Dess-MartinPeriodinane (1.2 equiv.). The flask was capped and the homogeneous solution was left stirring at rt for 3 hrs. The solution was partitioned between EtOAc and 1:1 10% $Na_2S_2O_3$/$NaHCO_3$ (sat.). The organic layer was washed with NaCl(sat.), dried over $MgSO_4$, filtered and concentrated, and purified by ISCO $SiO_2$ chromatography to yield tert-butyl (1R,3S,5R)-5-(3-(6-(2,6-difluorophenyl)-5-fluoropicolinamido)pyridin-4-yl)-3-methyl-2-oxocyclohexylcarbamate in 83% yield. LC/MS (m/z)=555.4 (MH$^+$), $R_t$=0.87 min.

Synthesis of N-(4-((1R,3R,5S,E)-3-amino-4-(methoxyimino)-5-methylcyclohexyl)pyridin-3-yl)-6-(2,6-difluorophenyl)-5-fluoropicolinamide and N-(4-((1R,3R,5S,Z)-3-amino-4-(methoxyimino)-5-methylcyclohexyl)pyridin-3-yl)-6-(2,6-difluorophenyl)-5-fluoropicolinamide

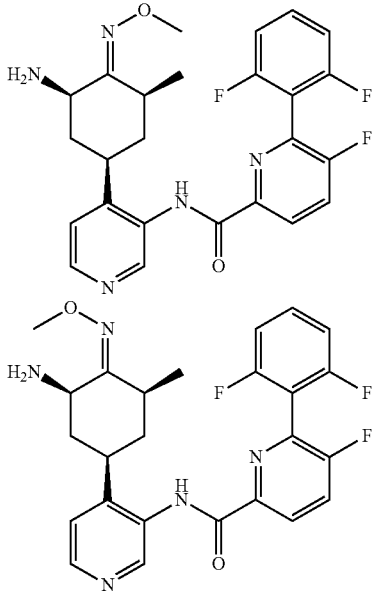

A solution of methoxylamine-HCl (1.0 equiv.) and tert-butyl (1R,3S,5R)-5-(3-(6-(2,6-difluorophenyl)-5-fluoropicolinamido)pyridin-4-yl)-3-methyl-2-oxocyclohexylcarbamate (1.0 equiv.) in EtOH/pyridine (1/1, 0.01 M) was capped and left standing at rt for 16 hrs. The volatiles were removed in vacuo and the residue was partitioned between EtOAc and $Na_2CO_3$ (sat.). The organic layer was washed with NaCl$_{(sat)}$, dried over $MgSO_4$, filtered, concentrated. The Boc group was removed with 25% TFA/$CH_2Cl_2$. After 45 minutes, the volatiles were removed in vacuo and the residue was pumped on for 5 minutes, dissolved in $CH_2Cl_2$ and neutralized with TEA. The volatiles were removed in vacuo and after pumping the residue was dissolved in DMSO and purified by RP-HPLC to yield N-(4-((1R,3R,5S,E)-3-amino-4-(methoxyimino)-5-methylcyclohexyl)pyridin-3-yl)-6-(2,6-difluorophenyl)-5-fluoropicolinamide in 16% yield. LC/MS (m/z)=484.2 (MH$^+$), $R_t$=0.64 min. $^1$H NMR (400 MHz, DMSO-d6) δ ppm 10.49 (s, 1H), 8.57 (s, 1H), 8.47 (d, J=4.0, 1H), 8.35 (dd, J=8.0, 4.0, 1H), 8.25 (broad doublet, J=4.0, 2H), 8.20 (t, J=8.0, 1H), 7.67-7.74 (m, 1H), 7.42 (d, J=8.0, 1H), 7.36 (t, J=8.0, 2H), 4.04-4.08 (m, 1H), 3.79 (s, 3H), 3.23-3.29 (m, 1H), 2.39-2.45 (m, 1H), 2.11 (d, J=8.0, 1H), 2.10 (d, J=8.0, 1H), 1.90 (q, J=12, 1H), 1.40 (q, J=12, 1H), 1.01 (d, J=4.0, 3H); and N-(4-((1R,3R,5S,Z)-3-amino-4-(methoxyimino)-5-methylcyclohexyl)pyridin-3-yl)-6-(2,6-difluorophenyl)-5-fluoropicolinamide in 27% yield. LC/MS (m/z)=484.2 (MH$^+$), $R_t$=0.66 min. $^1$H NMR (400 MHz, DMSO-d6) δ ppm 10.48 (s, 1H), 8.57 (s, 1H), 8.47 (d, J=4.0, 1H), 8.35 (dd, J=8.0, 4.0, 1H), 8.20 (t, J=8.0, 1H), 8.08 (broad singlet, 2H), 7.67-7.74 (m, 1H), 7.42 (d, J=8.0, 1H), 7.36 (t, J=8.0, 2H), 3.88-3.92 (m, 1H), 3.80 (s, 3H), 3.22-3.28 (m, 1H), 2.51-2.58 (m, 1H), 2.25 (d, J=12.0, 1H), 1.86 (d, J=12.0, 1H), 1.70 (q, J=12, 1H), 1.62 (q, J=12, 1H), 1.34 (d, J=4.0, 3H).

Synthesis of N-(4-((1R,3R,5S,Z)-3-amino-4-(hydroxyimino)-5-methylcyclohexyl)pyridin-3-yl)-6-(2,6-difluorophenyl)-5-fluoropicolinamide

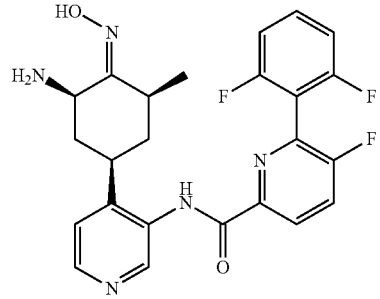 [SMILES: C[C@H]1C[C@@H](c2ccncc2NC(=O)c2ccc(F)c(-c3c(F)cccc3F)n2)C[C@@H](N)/C1=N\O]

A solution of hydroxylamine-HCl (4.0 equiv.) and tert-butyl (1R,3S,5R)-5-(3-(6-(2,6-difluorophenyl)-5-fluoropicolinamido)pyridin-4-yl)-3-methyl-2-oxocyclohexylcarbamate (1.0 equiv.) in EtOH/pyridine (1/1, 0.01 M) was capped and left standing at rt for 16 hrs. The volatiles were removed in vacuo and the residue was partitioned between EtOAc and $Na_2CO_{3(sat.)}$. The organic layer was washed with NaCl$_{(sat)}$, dried over $MgSO_4$, filtered, concentrated. The Boc group was removed with 25% TFA/$CH_2Cl_2$. After 45 minutes, the volatiles were removed in vacuo and after pumping the residue was dissolved in DMSO and purified by RP-HPLC to yield N-(4-((1R,3R,5 S,Z)-3-amino-4-(hydroxyimino)-5-methylcyclohexyl)pyridin-3-yl)-6-(2,6-difluorophenyl)-5-fluoropicolinamide in 14% yield. LC/MS (m/z)=470.3 (MH$^+$), $R_t$=0.60 min. $^1$H NMR (300 MHz, DMSO-d6) δ ppm 10.94 (s, 1H), 10.49 (s, 1H), 8.60 (s, 1H), 8.48 (d, J=4.0, 1H), 8.35 (dd, J=8.0, 4.0, 1H), 8.20 (t, J=8.0, 1 H), 8.02 (broad doublet, J=4.0, 2H), 7.67-7.74 (m, 1H), 7.42 (d, J=4.0, 1H), 7.36 (t, J=8.0, 2H), 4.24 (m, 1H), 3.82-3.86 (m, 1H), 3.21-3.27 (m, 1H), 2.50-2.55 (m, 1H), 2.24 (d, J=12.0, 1H), 1.86 (d, J=16.0, 1H), 1.68 (q, J=12.0, 1H), 1.59 (q, J=12.0, 1H), 1.40 (d, J=8.0, 3H).

Synthesis of N-(4-((1R,3R,5S)-3-amino-5-methyl-4-oxocyclohexyl)pyridin-3-yl)-6-(2,6-difluorophenyl)-5-fluoropicolinamide

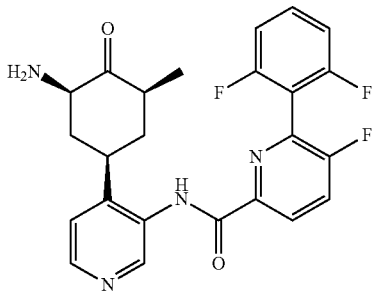 [SMILES: C[C@H]1C[C@@H](c2ccncc2NC(=O)c2ccc(F)c(-c3c(F)cccc3F)n2)C[C@@H](N)C1=O]

Tert-butyl (1R,3S,5R)-5-(3-(6-(2,6-difluorophenyl)-5-fluoropicolinamido)pyridin-4-yl)-3-methyl-2-oxocyclohexylcarbamate was treated with 25% TFA/CH$_2$Cl$_2$ for 30 minutes. The volatiles were removed in vacuo, the residue was dissolved in DMSO and purified by reverse phase HPLC to yield N-(4-((1R,3R,5S)-3-amino-5-methyl-4-oxocyclohexyl)pyridin-3-yl)-6-(2,6-difluorophenyl)-5-fluoropicolinamide in 98% yield. LC/MS (m/z)=455.1 (MH$^+$), R$_t$=0.57 min. $^1$H NMR (300 MHz, DMSO-d6) δ ppm 10.55 (s, 1H), 8.55 (s, 1H), 8.47 (d, J=4.0, 1H), 8.37 (dd, J=8.0, 4.0, 1H), 8.21 (t, J=8.0, 1H), 8.16 (broad doublet, J=4.0, 2H), 7.67-7.74 (m, 1H), 7.40 (d, J=8.0, 1H), 7.36 (t, J=8.0, 2H), 4.20-4.26 (m, 1H), 3.50-3.70 (m, 2H), 2.76-2.82 (m, 1H), 2.49-2.54 (m, 1H), 2.32-2.36 (m, 1H), 2.16-2.18 (m, 1H), 1.91 (q, J=12, 1H), 1.65 (q, J=12, 1H), 0.97 (d, J=8.0, 3H).

Synthesis of (+/−)-tert-butyl ((1R,5S,6R)-6-methoxy-5-methyl-3-(3-nitropyridin-4-yl)cyclohex-2-en-1-yl)carbamate

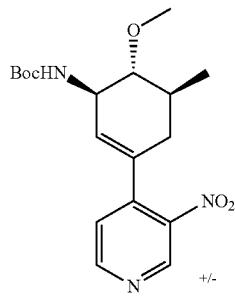 [SMILES: CO[C@@H]1[C@@H](C)CC(c2ccncc2[N+](=O)[O-])=C[C@H]1NC(=O)OC(C)(C)C]

(+/−)-Tert-butyl (1R,5S,6R)-6-hydroxy-5-methyl-3-(3-nitropyridin-4-yl)cyclohex-2-enylcarbamate (1.0 equiv.) was suspended in iodomethane (100.0 equiv.). Silver oxide (6.0 equiv.) was added to the mixture and the reaction vessel was wrapped in foil (kept dark) and allowed to stir 45° C. for 10 hrs. The reaction was diluted with THF and filtered through a pad of celite. The celite cake was further washed with MeOH. The organics were concentrated and the crude was taken up in DCM, washed with NaHCO$_{3(aq)}$, dried over Na$_2$SO$_4$, filtered and concentrated. The crude was loaded onto silica gel and purified via ISCO to yield (+/−)-tert-butyl ((1R,5S,6R)-6-methoxy-5-methyl-3-(3-nitropyridin-4-yl)cyclohex-2-en-1-yl)carbamate in 35% yield. LC/MS (m/z)=364.1 (MH$^+$), R$_t$=0.89 min.

Method 6

Synthesis of tert-butyl ((1S,2S,3R,5S)-5-(3-aminopyridin-4-yl)-2-methoxy-3-methylcyclohexyl)carbamate and tert-butyl ((1R,2R,3S,5R)-5-(3-aminopyridin-4-yl)-2-methoxy-3-methylcyclohexyl)carbamate

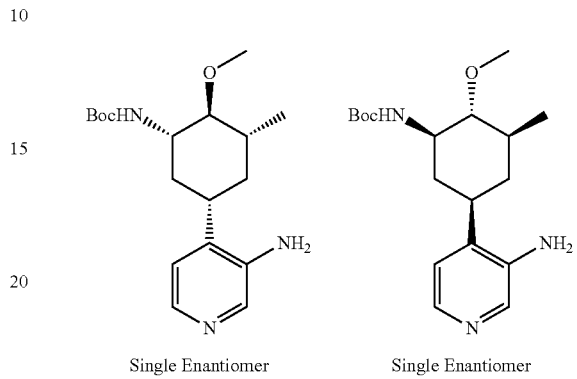

Single Enantiomer      Single Enantiomer

To a solution of (+/−)-tert-butyl ((1R,5S,6R)-6-methoxy-5-methyl-3-(3-nitropyridin-4-yl)cyclohex-2-en-1-yl)carbamate (1.0 equiv.) in degassed EtOH (0.10 M) was added Pd/C (0.1 equiv.). The mixture was purged with H$_2$, and allowed to to stir under an atm of H$_2$ overnight at RT. The reaction was filtered through a pad of celite and the cake was washed with MeOH. The organics were concentrated and purified by ISCO SiO$_2$ chromatography. Purification was completed via SFC (30% MeOH, 100 mL/min, AD column) to yield tert-butyl S,2S,3R,5S)-5-(3-aminopyridin-4-yl)-2-methoxy-3-methylcyclohexyl)carbamate (15% yield, 99% ee) and tert-butyl ((1R,2R,3S,5R)-5-(3-aminopyridin-4-yl)-2-methoxy-3-methylcyclohexyl)carbamate (12% yield, 99% ee). LC/MS (m/z)=336.3 (MH$^+$), R$_t$=0.58 min.

Synthesis of (+/−)-tert-butyl a 1R,5S,6S)-6-hydroxy-5-methyl-3-(3-nitropyridin-4-yl)cyclohex-2-en-1-yl) carbamate

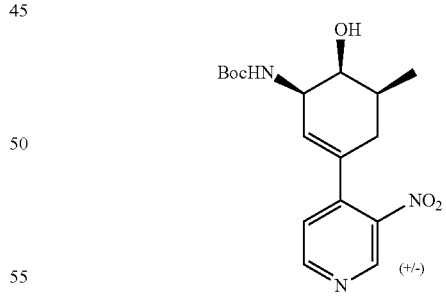

To a solution of (+/−)-(3aR,7S,7aS)-tert-butyl 7-methyl-5-(3-nitropyridin-4-yl)-2-oxo-3a,6,7,7a-tetrahydrobenzo[d]oxazole-3(2H)-carboxylate (1.0 equiv.) in THF (0.20 M) was added 2M LiOH (3.0 equiv.) was added. The mixture was stirred overnight 20 hrs at 22° C. The mixture was diluted with EtOAc and NaHCO$_{3(aq.)}$. The layers were separated and the aqueous was extracted with EtOAc. The combined organics were washed with brine, dried over Na$_2$SO$_4$, filtered, and concentrated. The golden foam was purified by ISCO chromatography to afford (+/−)-tert-butyl ((1R,5S,6S)-6-hydroxy-5-methyl-3-(3-nitropyridin-4-yl)cyclohex-2-en-1-yl) carbamate in 83% yield. LC/MS (m/z)=350.2 (MH+), R$_t$=0.82 min.

Synthesis of (+/−)-tert-butyl (1R,5S,6S)-6-(2-cyano-ethoxy)-5-methyl-3-(3-nitropyridin-4-yl)cyclohex-2-enylcarbamate

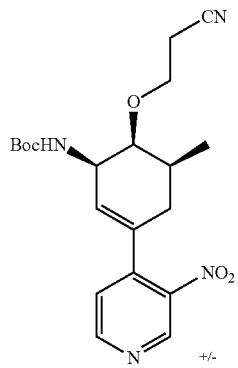 [SMILES: C[C@H]1CC(c2ccncc2[N+](=O)[O-])=C[C@@H](NC(=O)OC(C)(C)C)[C@H]1OCCC#N]

A mixture of (+/−)-Tert-butyl (1R,5S,6S)-6-hydroxy-5-methyl-3-(3-nitropyridin-4-yl)cyclohex-2-enylcarbamate (1.0 equiv.), acrylonitrile (30.0 equiv.) and CESIUM CARBONATE (1.2 equiv.) in t-BuOH (0.57 M) was stirred at 35° C. for 3 hrs. The reaction was cooled to room temperature, followed by the addition of NaHCO$_{3(aq)}$ and water. The mixture was extracted with EtOAc and the combined organics were dried over MgSO$_4$, filtered, and concentrated. The sample was purified by ISCO SiO$_2$ chromatography to yield (+/−)-tert-butyl (1R,5S,6S)-6-(2-cyanoethoxy)-5-methyl-3-(3-nitropyridin-4-yl)cyclohex-2-enylcarbamate in 94% yield. LC/MS (m/z)=403.3 (MH+), R$_t$=0.92 min. $^1$H NMR (400 MHz, CHLOROFORM-d) δ ppm 1.13 (d, J=6.46 Hz, 3 H), 1.46 (s, 9 H), 1.99-2.18 (m, 2 H), 2.20-2.36 (m, 1 H), 2.65 (t, J=6.06 Hz, 2 H), 3.68 (br. s., 1 H), 3.88 (t, J=5.99 Hz, 2 H), 4.51 (br. s., 1 H), 4.99 (d, J=9.15 Hz, 1 H), 5.39 (br. s., 1 H), 7.25 (d, J=4.99 Hz, 1 H), 8.73 (d, J=4.94 Hz, 1 H), 9.10 (s, 1 H).

Synthesis of tert-butyl ((1S,2R,3R,5S)-5-(3-aminopyridin-4-yl)-2-(2-cyanoethoxy)-3-methylcyclohexyl)carbamate and tert-butyl ((1R,2S,3S,5R)-5-(3-aminopyridin-4-yl)-2-(2-cyanoethoxy)-3-methylcyclohexyl)carbamate

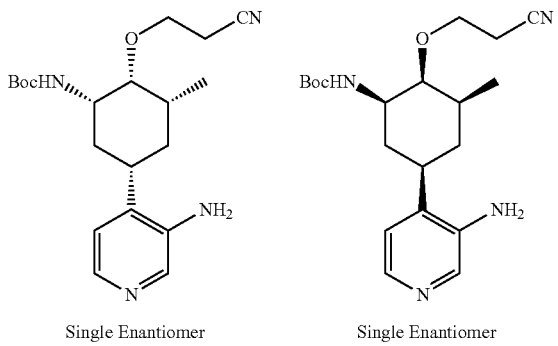 [SMILES: C[C@@H]1C[C@H](c2ccncc2N)C[C@H](NC(=O)OC(C)(C)C)[C@@H]1OCCC#N ; C[C@H]1C[C@@H](c2ccncc2N)C[C@@H](NC(=O)OC(C)(C)C)[C@H]1OCCC#N]

Method 6 was followed using (+/−)-tert-butyl (1R,5S,6S)-6-(2-cyanoethoxy)-5-methyl-3-(3-nitropyridin-4-yl)cyclohex-2-enylcarbamate with SFC (15% EtOH, 100 mL/min, OJ column) to yield tert-butyl ((1S,2R,3R,5S)-5-(3-aminopyridin-4-yl)-2-(2-cyanoethoxy)-3-methylcyclohexyl)carbamate (31% yield, 99% ee) and tert-butyl ((1R,2S,3S,5R)-5-(3-aminopyridin-4-yl)-2-(2-cyanoethoxy)-3-methylcyclohexyl) carbamate (26% yield, 99% ee). LC/MS (m/z)=375.3 (MH+), R$_t$=0.65 min.

Synthesis of (+/−)-tert-butyl ((1R,5S,6S)-6-methoxy-5-methyl-3-(3-nitropyridin-4-yl)cyclohex-2-en-1-yl) carbamate

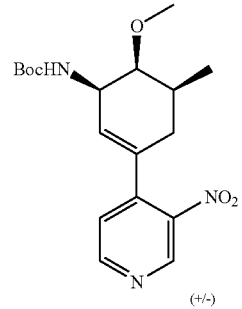 [SMILES: CO[C@H]1[C@@H](C)CC(c2ccncc2[N+](=O)[O-])=C[C@H]1NC(=O)OC(C)(C)C]

To a solution of (+/−)-tert-butyl ((1R,5S,6S)-6-hydroxy-5-methyl-3-(3-nitropyridin-4-yl)cyclohex-2-en-1-yl)carbamate (1.0 equiv.) in MeI (100.0 equiv.) was added Ag$_2$O (5.5 equiv.). A reflux condenser was attached and the heterogeneous solution under Ar was submerged in a 50° C. bath and the reaction was gently refluxing for 6 hrs. The solids were filtered, rinsed with CH$_2$Cl$_2$. The volatiles were removed in vacuo, the residue was partitioned between CH$_2$Cl$_2$ and NaHCO$_{3(sat.)}$. The organic layer was dried over MgSO$_4$, filtered, concentrated and purified by ISCO SiO$_2$ chromatography to yield (+/−)-tert-butyl ((1R,5 S,6S)-6-hydroxy-5-methyl-3-(3-nitropyridin-4-yl)cyclohex-2-en-1-yl)carbamate in 59% yield. LC/MS (m/z)=364.5 (MH+), Rt=1.02 min. $^1$H NMR (400 MHz, <cdcl3>) δ ppm 1.11 (d, J=6.65 Hz, 3 H), 1.46 (s, 9 H), 1.95-2.13 (m, 2 H), 2.18-2.28 (m, 1 H), 3.47 (d, J=3.52 Hz, 1 H), 3.57 (s, 3 H), 4.45 (d, J=7.83 Hz, 1 H), 5.01 (d, J=9.39 Hz, 1 H), 5.44 (br. s., 1 H), 7.24 (s, 1 H), 8.71 (d, J=5.09 Hz, 1 H), 9.08 (s, 1 H).

Synthesis of tert-butyl a 1S,2R,3R,5S)-5-(3-aminopyridin-4-yl)-2-methoxy-3-methylcyclohexyl) carbamate and tert-butyl a 1R,2S,3S,5R)-5-(3-aminopyridin-4-yl)-2-methoxy-3-methylcyclohexyl) carbamate

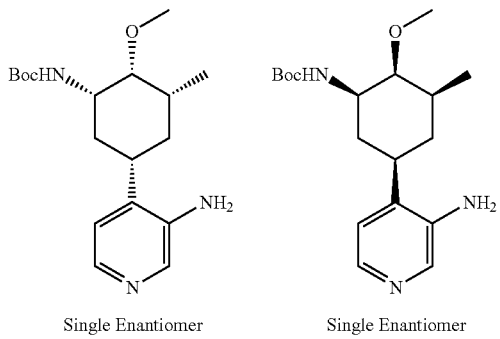 [SMILES: CO[C@@H]1[C@H](C)C[C@H](c2ccncc2N)C[C@@H]1NC(=O)OC(C)(C)C ; CO[C@H]1[C@@H](C)C[C@@H](c2ccncc2N)C[C@H]1NC(=O)OC(C)(C)C]

To a degassed solution of (+/−)-tert-butyl ((1R,5S,6S)-6-hydroxy-5-methyl-3-(3-nitropyridin-4-yl)cyclohex-2-en-1-yl)carbamate (1.0 equiv.) in i-PrOH (0.07 M) was added Pd/C (0.1 equiv.). The solution was degassed and purged to H$_2$ and left stirring under a balloon of H$_2$ at rt for 16 hrs. The solution was degassed and purged to Ar, diluted with CH$_2$Cl$_2$, filtered through a pad of celite, concentrated and purified by ISCO SiO$_2$ chromatography. Purification was completed via SFC (20% MeOH, 100 mL/min, AD column) to yield tert-butyl ((1S,2R,3R,5S)-5-(3-aminopyridin-4-yl)-2-methoxy-3-methylcyclohexyl)carbamate (42% yield, 99% ee) and tert-butyl ((1R,2S,3S,5R)-5-(3-aminopyridin-4-yl)-2-methoxy-3-methylcyclohexyl)carbamate (39% yield, 99% ee). LC/MS (m/z)=336.2 (MH$^+$), R$_t$=0.67 min. $^1$H NMR (400 MHz, <cdcl3>) δ ppm 1.08 (d, J=7.04 Hz, 3 H), 1.43-1.49 (m, 10 H), 1.52-1.64 (m, 2 H), 1.70-1.81 (m, 2 H), 2.52-2.64 (m, 1 H), 3.39 (br. s., 1 H), 3.52-3.57 (m, 3 H), 3.62 (br. s., 2 H), 3.66-3.75 (m, 1 H), 4.75-4.87 (m, 1 H), 6.98 (d, J=5.09 Hz, 1 H), 7.95-8.05 (m, 2 H).

Synthesis of (+/−)-tert-butyl (1R,5S,6S)-6-ethoxy-5-methyl-3-(3-nitropyridin-4-yl)cyclohex-2-enylcarbamate

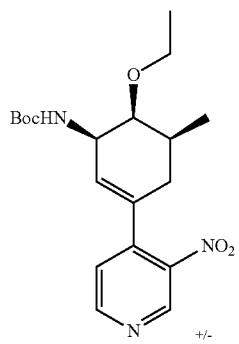 [SMILES: CCO[C@H]1[C@@H](C)CC(c2ccncc2[N+](=O)[O-])=C[C@H]1NC(=O)OC(C)(C)C]

(+/−)-Tert-butyl (1R,5 S,6S)-6-hydroxy-5-methyl-3-(3-nitropyridin-4-yl)cyclohex-2-enylcarbamate (1.0 equiv.) was suspended in iodoethane (100.0 equiv.). Silver oxide (6.0 equiv.) was added to the mixture and the reaction vessel was wrapped in foil (kept dark) and allowed to stir 55° C. for 10 hrs. The reaction was diluted with THF and filtered through a pad of celite. The celite cake was further washed with MeOH. The organics were concentrated and the crude was taken up in DCM, washed with NaHCO$_3$ (aq), dried over Na$_2$SO$_4$, filtered and concentrated. The crude was loaded onto silica gel and purified via ISCO to yield (+/−)-tert-butyl (1R,5S,6S)-6-ethoxy-5-methyl-3-(3-nitropyridin-4-yl)cyclohex-2-enylcarbamate in 31% yield. LC/MS (m/z)=378.1 (MH$^+$), R$_t$=0.99 min.

Synthesis of tert-butyl ((1S,2R,3R,5S)-5-(3-aminopyridin-4-yl)-2-ethoxy-3-methylcyclohexyl)carbamate and tert-butyl a 1R,2S,3S,5R)-5-(3-aminopyridin-4-yl)-2-ethoxy-3-methylcyclohexyl)carbamate

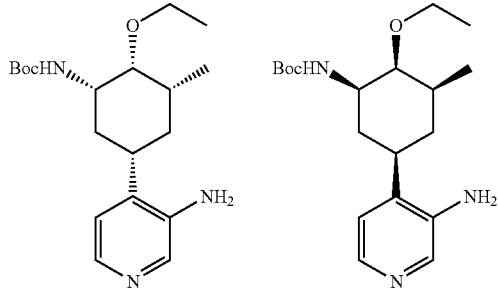

Single Enantiomer        Single Enantiomer

Method 6 was followed using (+/−)-tert-butyl (1R,5S,6S)-6-ethoxy-5-methyl-3-(3-nitropyridin-4-yl)cyclohex-2-enylcarbamate with Chiral HPLC (Heptane/EtOH=90/10, 20 mL/min, IC column) to yield tert-butyl a 1S,2R,3R,5S)-5-(3-aminopyridin-4-yl)-2-ethoxy-3-methylcyclohexyl)carbamate (33% yield, 99% ee) and tert-butyl ((1R,2S,3S,5R)-5-(3-aminopyridin-4-yl)-2-ethoxy-3-methylcyclohexyl) carbamate (28% yield, 99% ee). LC/MS (m/z)=350.2 (MH$^+$), R$_t$=0.72 min.

Synthesis of (+/−)-methyl 3-((1R,2R,6S)-2-(tert-butoxycarbonylamino)-6-methyl-4-(3-nitropyridin-4-yl)cyclohex-3-enyloxy)propanoate

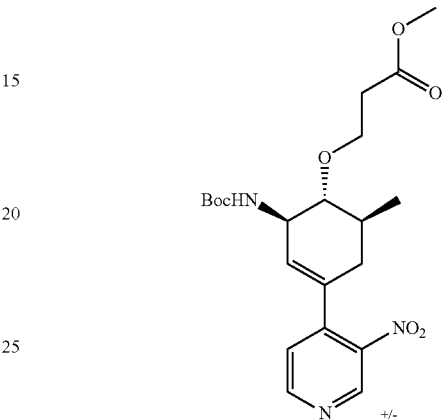

A mixture of (+/−)-tert-butyl (1R,5S,6R)-6-hydroxy-5-methyl-3-(3-nitropyridin-4-yl)cyclohex-2-enylcarbamate (1.0 equiv.), methyl acrylate (30.0 equiv.) and CESIUM CARBONATE (1.2 equiv.) in t-BuOH (0.38 M) was stirred at 35° C. for 16 hrs. The reaction was cooled to room temperature, followed by the addition of NaHCO$_{300}$ and water. The mixture was extracted with EtOAc and the combined organics were dried over MgSO$_4$, filtered, and concentrated. The sample was purified by ISCO chromatography to yield (+/−)-methyl 341R,2R,6S)-2-(tert-butoxycarbonylamino)-6-methyl-4-(3-nitropyridin-4-yl)cyclohex-3-enyloxy)propanoate in 48% yield. LC/MS (m/z)=436.1 (MH$^+$), R$_t$=0.91 min.

Synthesis of (+/−)-methyl 3-((1R,2R,4R,6S)-4-(3-aminopyridin-4-yl)-2-(tert-butoxycarbonylamino)-6-methylcyclohexyloxy)propanoate

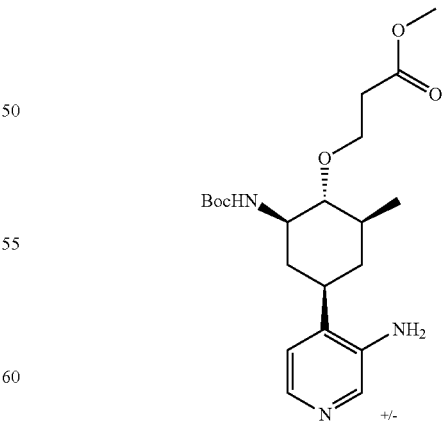

To a solution of (+/−)-methyl 3-((1R,2R,6S)-2-(tert-butoxycarbonylamino)-6-methyl-4-(3-nitropyridin-4-yl)cyclohex-3-enyloxy)propanoate (1.0 equiv.) in degassed EtOH (0.07 M) was added Pd/C (0.3 equiv.). The mixture was purged with H$_2$, and allowed to stir under H$_2$ overnight at RT. The reaction was filtered through a pad of celite and the cake was washed with MeOH. The organics were concentrated and purified by ISCO SiO$_2$ chromatography to yield (+/−)-methyl 3-((1R,2R,4R,6S)-4-(3-aminopyridin-4-yl)-2-(tert-butoxycarbonylamino)-6-methylcyclohexyloxy)propanoate in 100% yield. LC/MS (m/z)=408.2 (MH$^+$), R$_t$=0.62 min.

Synthesis of methyl 3-((1R,2R,4R,6S)-2-(tert-butoxycarbonylamino)-4-(3-(6-(2,6-difluorophenyl)-5-fluoropicolinamido)pyridin-4-yl)-6-methylcyclohexyloxy)propanoate and methyl 3-(((1S,2S,4S,6R)-2-((tert-butoxycarbonyl)amino)-4-(3-(6-(2,6-difluorophenyl)-5-fluoropicolinamido)pyridin-4-yl)-6-methylcyclohexyl)oxy) propanoate

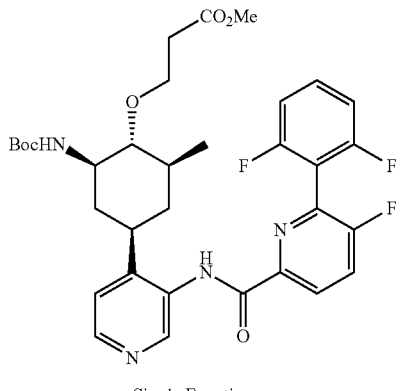

Single Enantiomer

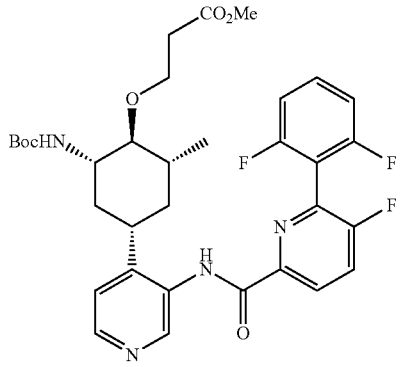

Single Enantiomer

EDC (2.0 equiv.) and HOAt (2.0 equiv.) was added to a solution of (+/−)-methyl 3-((1R,2R,4R,6S)-4-(3-aminopyridin-4-yl)-2-(tert-butoxycarbonylamino)-6-methylcyclohexyloxy) propanoate (1.0 equiv.) and 6-(2,6-difluorophenyl)-5-fluoropicolinic acid (1.5 equiv.) in DMF (0.08 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography. Purification was completed via SFC (20% IPA, 20 mL/min, AD column) to yield methyl 3-(1R,2R,4R,6S)-2-(tert-butoxycarbonylamino)-4-(3-(6-(2,6-difluorophenyl)-5-fluoropicolinamido)pyridin-4-yl)-6-methylcyclohexyloxy)propanoate (22% yield, 99% ee) and methyl 3-(((1S,2S,4S,6R)-2-((tert-butoxycarbonyl)amino)-4-(3-(6-(2,6-difluorophenyl)-5-fluoropicolinamido)pyridin-4-yl)-6-methylcyclohexyl)oxy) propanoate (21% yield, 99% ee). LC/MS (m/z)=643.4 (MH$^+$), R$_t$=0.92 min.

Synthesis of 3-((1R,2R,4R,6S)-2-amino-4-(3-(6-(2,6-difluorophenyl)-5-fluoropicolinamido)pyridin-4-yl)-6-methylcyclohexyloxy)propanoic acid

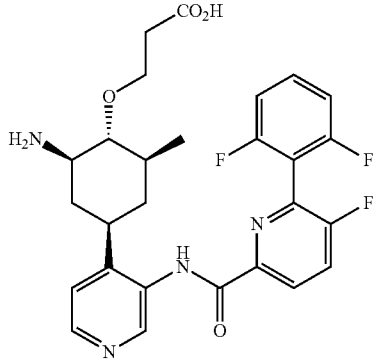 [SMILES: C[C@H]1C[C@@H](c2ccncc2NC(=O)c2ccc(F)c(-c3c(F)cccc3F)n2)C[C@@H](N)[C@@H]1OCCC(=O)O]

To a solution of methyl 3-((1R,2R,4R,6S)-2-(tert-butoxycarbonylamino)-4-(3-(6-(2,6-difluorophenyl)-5-fluoropicolinamido)pyridin-4-yl)-6-methylcyclohexyloxy) propanoate (1.0 equiv.) was added 4 M HCl (40.0 equiv.) in dioxane. After stirring at rt overnight, the mixture was concentrated and dissolved in MeOH (0.05 M). LiOH (20.0 equiv.) was added. After stirred 10 min at rt, the mixture was concentrated, neutralized with HCl to PH 7 and extracted with EtOAc/t-Butanol (1/1). The organic layer was wash with brine, dried over MgSO$_4$, filtered, and concentrated. The sample was purified by RP HPLC to yield 3-((1R,2R,4R,6S)-2-amino-4-(3-(6-(2,6-difluorophenyl)-5-fluoropicolinamido)pyridin-4-yl)-6-methylcyclohexyloxy) propanoic acid in 34% yield. LC/MS (m/z)=529.3 (MH$^+$), R$_t$=0.63 min.

Synthesis of (+/−)-tert-butyl (1R,5S,6S)-5-methyl-6-(2-(methylsulfonyl)ethoxy)-3-(3-nitropyridin-4-yl)cyclohex-2-enylcarbamate

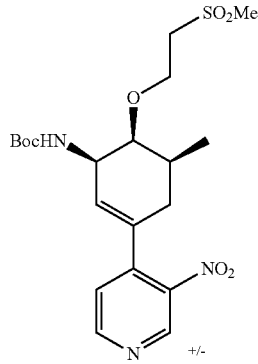 [SMILES: C[C@H]1CC(c2ccncc2[N+](=O)[O-])=C[C@@H](NC(=O)OC(C)(C)C)[C@H]1OCCS(C)(=O)=O]

A mixture of (+/−)-Tert-butyl (1R,5 S,6S)-6-hydroxy-5-methyl-3-(3-nitropyridin-4-yl)cyclohex-2-enylcarbamate (1.0 equiv.), methylsulfonylethene (30.0 equiv.) and CESIUM CARBONATE (1.2 equiv.) in t-BuOH (0.22 M) was stirred at 22° C. for 5 hrs. The reaction was cooled to room temperature, followed by the addition of NaHCO$_{3(aq)}$ and water. The mixture was extracted with EtOAc and the combined organics were dried over MgSO$_4$, filtered, and concentrated. The sample was purified by ISCO chromatography to yield (+/−)-tert-butyl (1R,5S,6S)-5-methyl-6-(2-(methylsulfonyl)ethoxy)-3-(3-nitropyridin-4-yl)cyclohex-2-enylcarbamate in 84% yield. LC/MS (m/z)=456.2 (MH$^+$), $R_t$=0.87 min. $^1$H NMR (400 MHz, CHLOROFORM-d) δ ppm 1.10 (d, J=6.60 Hz, 3 H), 1.47 (s, 9 H), 1.92-2.16 (m, 2 H), 2.17-2.32 (m, 1 H), 2.93-3.00 (m, 1 H), 3.09 (s, 3 H), 3.18 (d, J=14.87 Hz, 1 H), 3.38-3.52 (m, 1 H), 3.63 (d, J=2.40 Hz, 1 H), 3.95-4.06 (m, 1 H), 4.21 (td, J=9.84, 2.42 Hz, 1 H), 4.56 (d, J=7.58 Hz, 1 H), 5.58 (br. s., 1 H), 5.66 (d, J=9.44 Hz, 1 H), 7.20 (d, J=4.99 Hz, 1 H), 8.73 (d, J=4.99 Hz, 1 H), 9.05 (s, 1 H).

Synthesis of (+/−)-tert-butyl (1R,2S,3S,5R)-5-(3-aminopyridin-4-yl)-3-methyl-2-(2-(methylsulfonyl)ethoxy)cyclohexylcarbamate

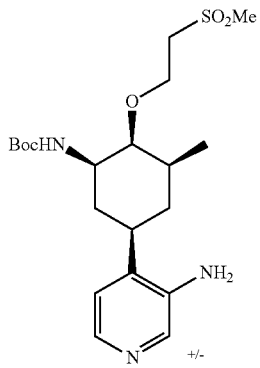 [SMILES: C[C@H]1C[C@@H](c2ccncc2N)C[C@@H](NC(=O)OC(C)(C)C)[C@H]1OCCS(C)(=O)=O]

To a solution of (+/−)-tert-butyl (1R,5S,6S)-5-methyl-6-(2-(methylsulfonyl)ethoxy)-3-(3-nitropyridin-4-yl)cyclohex-2-enylcarbamate (1.0 equiv.) in degassed EtOH (0.17 M) was added Pd/C (0.3 equiv.). The mixture was purged with H$_2$, and allowed to stir under H$_2$ overnight at RT. The reaction was filtered through a pad of celite and the cake was washed with MeOH. The organics were concentrated and purified by ISCO SiO$_2$ chromatography to yield (+/−)-tert-butyl (1R,2S,3S,5R)-5-(3-aminopyridin-4-yl)-3-methyl-2-(2-(methylsulfonyl)ethoxy)cyclohexylcarbamate in 55% yield. LC/MS (m/z)=428.2 (MH$^+$), $R_t$=0.59 min. $^1$H NMR (400 MHz, CHLOROFORM-d) δ ppm 1.07 (d, J=6.85 Hz, 3 H), 1.46 (s, 9 H), 1.72-1.88 (m, 2 H), 2.62 (tt, J=12.23, 3.30 Hz, 1 H), 3.08 (s, 3 H), 3.21 (d, J=14.62 Hz, 1 H), 3.35-3.47 (m, 1 H), 3.58 (br. s., 1 H), 3.64 (br. s., 2 H), 3.70-3.86 (m, 1 H), 3.94-4.10 (m, 1 H), 4.10-4.22 (m, 1 H), 5.43 (d, J=9.00 Hz, 1 H), 6.89 (d, J=5.04 Hz, 1 H), 7.98 (d, J=4.99 Hz, 1 H), 8.03 (s, 1 H).

Synthesis of tert-butyl (1S,2R,3R,5S)-5-(3-(6-(2,6-difluorophenyl)-5-fluoropicolinamido)pyridin-4-yl)-3-methyl-2-(2-(methylsulfonyl)ethoxy)cyclohexylcarbamate and tert-butyl (1R,2S,3S,5R)-5-(3-(6-(2,6-difluorophenyl)-5-fluoropicolinamido)pyridin-4-yl)-3-methyl-2-(2-(methylsulfonyl)ethoxy)cyclohexylcarbamate

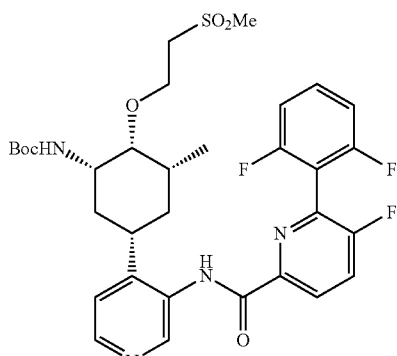

Single Enantiomer

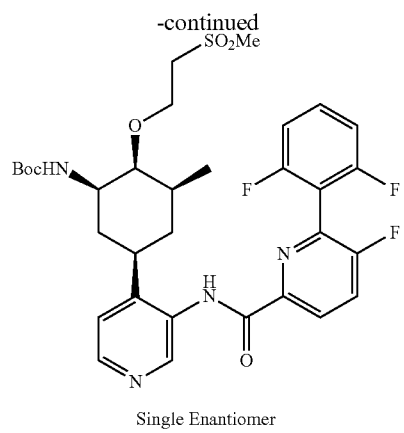

Single Enantiomer

EDC (2.0 equiv.) and HOAt (2.0 equiv.) were added to a solution of (+/−)-tert-butyl (1R,2S,3S,5R)-5-(3-aminopyridin-4-yl)-3-methyl-2-(2-(methylsulfonyl)ethoxy)cyclohexylcarbamate (1.0 equiv.) and 6-(2,6-difluorophenyl)-5-fluoropicolinic acid (1.5 equiv.) in DMF (0.08 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography. Purification was completed via SFC (50% MeOH, 100 mL/min, IC column) to yield tert-butyl (1S,2R,3R,5S)-5-(3-(6-(2,6-difluorophenyl)-5-fluoropicolinamido)pyridin-4-yl)-3-methyl-2-(2-(methylsulfonyl)ethoxy)cyclohexylcarbamate (48% yield, 99% ee) and tert-butyl (1R,2S,3S,5R)-5-(3-(6-(2,6-difluorophenyl)-5-fluoropicolinamido)pyridin-4-yl)-3-methyl-2-(2-(methylsulfonyl) ethoxy)cyclohexylcarbamate (48% yield, 99% ee). LC/MS (m/z)=663.2 (MH$^+$), $R_t$=0.88 min. $^1$H NMR (400 MHz, <cdcl3>) δ ppm 0.95 (d, J=6.75 Hz, 3 H), 1.45 (s, 8 H), 1.50-1.84 (m, 5 H), 2.80-2.95 (m, 1 H), 3.08 (s, 3 H), 3.14-3.29 (m, 1 H), 3.32-3.45 (m, 1 H), 3.56 (br. s., 1 H), 3.63-3.77 (m, 1 H), 3.95-4.08 (m, 1 H), 4.12 (q, J=7.12 Hz, 1 H), 5.36 (d, J=8.56 Hz, 1 H), 7.04-7.18 (m, 3 H), 7.50 (tt, J=8.47, 6.35 Hz, 1 H), 7.77 (t, J=8.56 Hz, 1 H), 8.33-8.46 (m, 2 H), 9.26 (s, 1 H), 9.81 (s, 1 H).

Synthesis of (+/−)-tert-butyl (1R,2S,3S,5R)-5-(3-aminopyridin-4-yl)-2-cyano-3-methylcyclohexylcarbamate

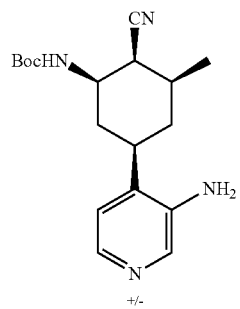 [SMILES: C[C@H]1C[C@@H](c2ccncc2N)C[C@@H](NC(=O)OC(C)(C)C)[C@H]1C#N]

To a solution of (+/−)-(1R,2R,4R,6S)-2-(tert-butoxycarbonylamino)-4-(3-(tert-butoxycarbonylamino)pyridin-4-yl)-6-methylcyclohexyl methanesulfonate (1.0 equiv.) in DMF (0.20 M) was added NaCN (5.0 equiv.). The solution was submerged in an 85° C. oil bath and left stirring under Ar for 16 hrs. The solution was cooled to rt and left stirring under Ar overnight. The solution was partitioned between EtOAc and H₂O. The organic layer was washed with Na₂CO₃(sat), NaCl(sat), dried over MgSO₄, filtered, concentrated. To a solution of the bis-Boc product (10 equiv.) in DCM (0.20 M) was added TFA (62.0 equiv.). The mixture was stirred at ambient temperature for 40 min and concentrated and neutralized with saturated aqueous sodium bicarbonate. Dioxane (0.15 M) and Boc₂O (4.0 equiv.) were added. The reaction mixture was stirred vigorously at ambient temperature for 16 hrs. Volatiles were removed in vacuo. The aqueous phase was extracted with 10:1 DCM: MeOH. The combined extracts were dried over sodium sulfate, filtered, and concentrated. The crude material was purified by ISCO chromatography over silica gel to give (+/−)-tert-butyl (1R,2S,3S,5R)-5-(3-aminopyridin-4-yl)-2-cyano-3-methylcyclohexylcarbamate in 20% yield. LC/MS (m/z)=331.2 (MH⁺), $R_t$=0.62 min.

Synthesis of tert-butyl (1R,2S,3S,5R)-2-cyano-5-(3-(6-(2,6-difluorophenyl)-5-fluoropicolinamido)pyridin-4-yl)-3-methylcyclohexylcarbamate and tert-butyl (1S,2R,3R,5S)-2-cyano-5-(3-(6-(2,6-difluorophenyl)-5-fluoropicolinamido)pyridin-4-yl)-3-methylcyclohexylcarbamate

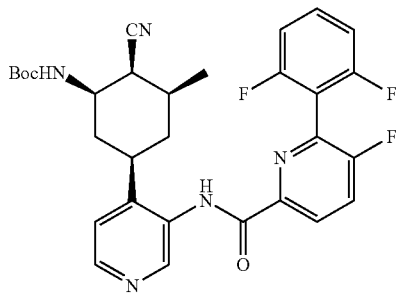

Single Enantiomer

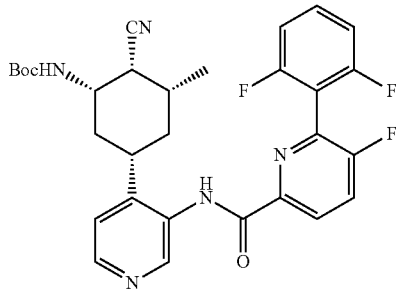

Single Enantiomer

EDC (1.1 equiv.) and HOAt (1.1 equiv.) were added to a solution of (+/−)-tert-butyl (1R,2S,3S,5R)-5-(3-aminopyridin-4-yl)-2-cyano-3-methylcyclohexylcarbamate (1.0 equiv.) and 6-(2,6-difluorophenyl)-5-fluoropicolinic acid (1.5 equiv.) in DMF (0.11 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO₂ chromatography. Purification was completed via SFC (15% IPA, 100 mL/min, IA column) to yield tert-butyl (1R,2S,3S,5R)-2-cyano-5-(3-(6-(2,6-difluorophenyl)-5-fluoropicolinamido)pyridin-4-yl)-3-methylcyclohexylcarbamate (25% yield, 99% ee) and tert-butyl (1S,2R,3R,5S)-2-cyano-5-(3-(6-(2,6-difluorophenyl)-5-fluoropicolinamido)pyridin-4-yl)-3-methylcyclohexylcarbamate (27% yield, 99% ee). LC/MS (m/z)= 566.2 (MH⁺), $R_t$=0.90 min.

Synthesis of tert-butyl (1R,2S,3S,5R)-5-(3-(6-(2,6-difluorophenyl)-5-fluoropicolinamido)pyridin-4-yl)-3-methyl-2-(1H-1,2,3-triazol-1-yl)cyclohexylcarbamate

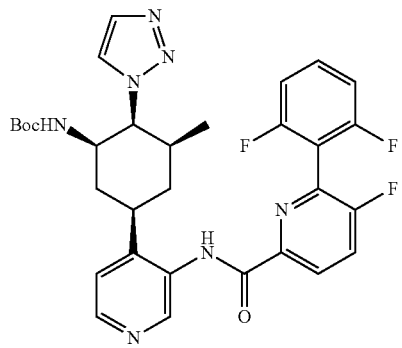 [SMILES: C[C@H]1C[C@@H](c2ccncc2NC(=O)c2ccc(F)c(-c3c(F)cccc3F)n2)C[C@@H](NC(=O)OC(C)(C)C)[C@H]1n1ccnn1]

A solution of tert-butyl (1R,2S,3S,5R)-2-azido-5-(3-(6-(2,6-difluorophenyl)-5-fluoropicolinamido)pyridin-4-yl)-3-methylcyclohexylcarbamate (1.0 equiv.) in vinyl acetate (0.06 M) to give a suspension was heated in microwave at 160° C. for 1 hr. The reaction was concentrated to yield tert-butyl (1R,2S,3S,5R)-5-(3-(6-(2,6-difluorophenyl)-5-fluoropicolinamido)pyridin-4-yl)-3-methyl-2-(1H-1,2,3-triazol-1-yl)cyclohexylcarbamate in 50% yield. LC/MS (m/z)=608.3 (MH⁺), $R_t$=0.89 min.

Synthesis of (+/−)-tert-butyl ((1R,2S,3S,5R)-5-(3-((tert-butoxycarbonyl)amino)pyridin-4-yl)-2-amino-3-methylcyclohexyl)carbamate

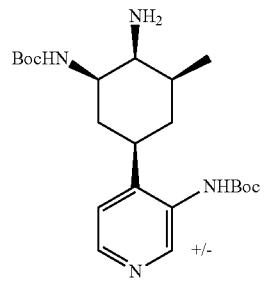 [SMILES: C[C@H]1C[C@@H](c2ccncc2NC(=O)OC(C)(C)C)C[C@@H](NC(=O)OC(C)(C)C)[C@H]1N]

To a degassed a solution of (+/−)-tert-butyl ((1R,2S,3S,5R)-5-(3-((tert-butoxycarbonyl)amino)pyridin-4-yl)-2-azido-3-methylcyclohexyl)carbamate (1.0 equiv.) in ethanol (0.10 M) was added Pd/C (0.2 equiv.). The mixture was stirred under H₂ for 4 hrs. Filter the mixture over cetlite and wash the cake with MeOH. Concentrate the filtrate to yield (+/−)-tert-butyl ((1R,2S,3S,5R)-5-(3-((tert-butoxycarbonyl)amino)pyridin-4-yl)-2-amino-3-methylcyclohexyl)carbamate in 88% yield. LC/MS (m/z)=421.3 (MH⁺), $R_t$=0.58 min.

Synthesis of (+/−)-tert-butyl ((1R,2S,3S,5R)-5-(3-((tert-butoxycarbonyl)amino)pyridin-4-yl)-3-methyl-2-(methylamino)cyclohexyl)carbamate

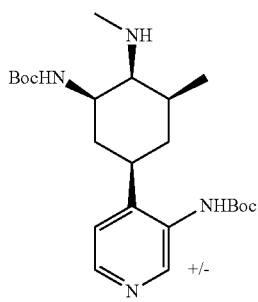 [SMILES: CN[C@H]1[C@@H](C)C[C@@H](c2ccncc2NC(=O)OC(C)(C)C)C[C@H]1NC(=O)OC(C)(C)C]

To a solution of (+/−)-tert-butyl ((1R,2S,3S,5R)-5-(3-((tert-butoxycarbonyl)amino)pyridin-4-yl)-2-amino-3-methylcyclohexyl)carbamate (1.0 equiv.) in MeOH (0.10 M) was added benzaldehyde (1.3 equiv.). After 3 hrs, sodium cyanotrihydroborate (2.5 equiv.) was added and the mixture was stirred at rt for 16 hrs. The reaction mixture was quenched by the addition of water, and volatiles were removed in vacuo. The mixture was extracted with ethyl acetate. The combined organic phases were dried with sodium sulfate, filtered and concentrated. The residue was dissolved in MeOH (0.10 M) and paraformaldehyde (5.0 equiv.) was added. After 16 hrs, sodium cyanotrihydroborate (5.0 equiv.) was added and the mixture was left stirred at rt for 16 hrs. The reaction was quenched by the addition of water, and volatiles were removed in vacuo. The mixture was extracted with DCM. The combined organic phases were dried with sodium sulfate, filtered, concentrated and purified by ISCO Chromatography. The product was dissolved in MeOH (0.10 M) and treated with Pd(OH)$_2$ (0.50 equiv.) under H$_2$ for 5 hrs at RT. The reaction was filtered through a pad of celite and the cake was washed with MeOH. The organics were concentrated to yield (+/−)-tert-butyl ((1R,2S,3S,5R)-5-(3-((tert-butoxycarbonyl)amino)pyridin-4-yl)-3-methyl-2-(methylamino)cyclohexyl)carbamate in 75% yield. LC/MS (m/z)=435.2 (MH$^+$), R$_t$=0.64 min.

Synthesis of (+/−)-methyl ((1S,2R,4R,6S)-4-(3-aminopyridin-4-yl)-2-((tert-butoxycarbonyl)amino)-6-methylcyclohexyl)(methyl)carbamate

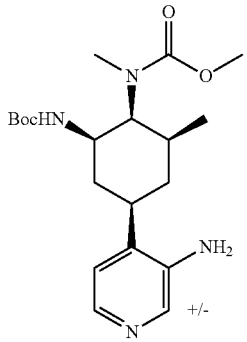 [SMILES: COC(=O)N(C)[C@H]1[C@@H](C)C[C@@H](c2ccncc2N)C[C@H]1NC(=O)OC(C)(C)C]

To a solution of (+/−)-tert-butyl a 1R,2S,3S,5R)-5-(3-((tert-butoxycarbonyl)amino)pyridin-4-yl)-3-methyl-2-(methylamino)cyclohexyl)carbamate (1.0 equiv.) in DCM (0.05 M) at 0° C. was added DIEA (3.0 equiv.) and then methyl chloroformate (1.5 equiv.). The homogeneous solution was left standing at 0° C. at for 4 hrs. The reaction was quenched partitioned between NaHCO$_3$ solution and EtOAc. The organic layer was washed with Brine, dried over Na$_2$SO$_4$, concentrated and purified by ISCO chromatography. The product was treated with 4 M HCl in dioxane (30.0 equiv.) at rt for 1 hour. The volatiles were removed in vacuo and the solid was pumped on for 5 minutes on the high vac. To the residue was added CH$_2$Cl$_2$ (0.15 M), DIEA (5.0 equiv.) and tert-butyl 2,5-dioxopyrrolidin-1-yl carbonate (1.6 equiv.). The solution was left stirring at rt for 1 hr. The volatiles were removed in vacuo and the residue was partitioned between EtOAc and H$_2$O. The organic layer was washed with Na$_2$CO$_{3(sat)}$, NaCl$_{(sat)}$, dried over MgSO$_4$, filtered, concentrated and purified by ISCO SiO$_2$ chromatography to yield (+/−)-methyl ((1S,2R,4R,6S)-4-(3-aminopyridin-4-yl)-2-((tert-butoxycarbonyl)amino)-6-methylcyclohexyl)(methyl)carbamate in 20% yield. LC/MS (m/z)=393.2 (MH$^+$), R$_t$=0.60 min.

Synthesis of methyl ((1S,2R,4R,6S)-2-((tert-butoxycarbonyl)amino)-4-(3-(6-(2,6-difluorophenyl)-5-fluoropicolinamido)pyridin-4-yl)-6-methylcyclohexyl)(methyl)carbamate and methyl ((1R,2A,4S,6R)-2-((tert-butoxycarbonyl)amino)-4-(3-(6-(2,6-difluorophenyl)-5-fluoropicolinamido)pyridin-4-yl)-6-methylcyclohexyl)(methyl)carbamate

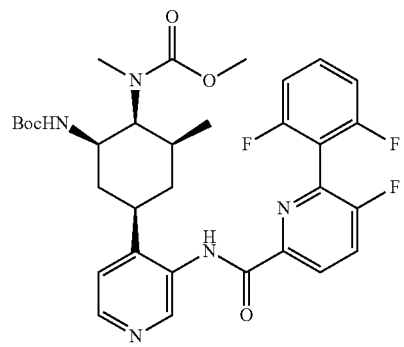

Single Enantiomer

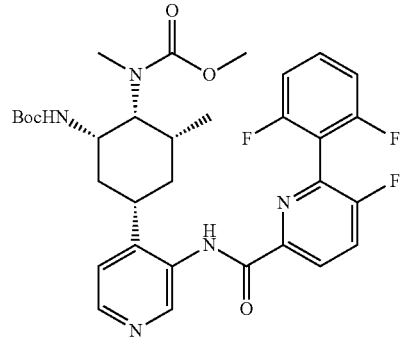

Single Enantiomer

EDC (1.1 equiv.) and HOAt (1.1 equiv.) were added to a solution of (+/−)-methyl ((1S,2R,4R,6S)-4-(3-aminopyridin-4-yl)-2-((tert-butoxycarbonyl)amino)-6-methylcyclohexyl)(methyl)carbamate (1.0 equiv.) and 6-(2,6-difluorophenyl)-5-fluoropicolinic acid (1.5 equiv.) in DMF (0.05 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO$_2$ chromatography. Purification was completed via SFC (40% EtOH, 100 mL/min, IC column) to yield methyl ((1S,2R,4R,6S)-2-((tert-butoxycarbonyl)amino)-4-(3-(6-(2,6-difluorophenyl)-5-fluoropicolinamido)pyridin-4-yl)-6-methylcyclohexyl)(methyl)carbamate (15% yield, 99% ee) and methyl ((1R,2S,4S,6R)-2-((tert-butoxycarbonyl)amino)-4-(3-(6-(2,6-difluorophenyl)-5-fluoropicolinamido)pyridin-4-yl)-6-methylcyclohexyl)(methyl)carbamate (15% yield, 99% ee). LC/MS (m/z)=628.3 (MH$^+$), R$_t$=0.89 min.

Synthesis of tert-butyl (3R,4S,5S)-1-(3-(6-(2,6-difluorophenyl)-5-fluoropicolinamido)pyridin-4-yl)-5-methyl-4-(1H-1,2,3-triazol-1-yl)piperidin-3-ylcarbamate

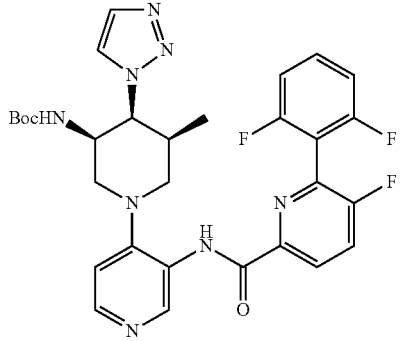 [SMILES: C[C@H]1CN(c2ccncc2NC(=O)c2ccc(F)c(-c3c(F)cccc3F)n2)C[C@@H](NC(=O)OC(C)(C)C)[C@H]1n1ccnn1]

A solution of tert-butyl (3R,4S,5S)-4-azido-1-(3-(6-(2,6-difluorophenyl)-5-fluoropicolinamido)pyridin-4-yl)-5-methylpiperidin-3-ylcarbamate (1.0 equiv.) in vinyl acetate (0.06 M) to give a suspension was heated at 110° C. for 88 hrs. The reaction was concentrated and purified by ISCO chromatography to yield tert-butyl (3R,4S,5S)-1-(3-(6-(2,6-difluorophenyl)-5-fluoropicolinamido)pyridin-4-yl)-5-methyl-4-(1H-1,2,3-triazol-1-yl)piperidin-3-ylcarbamate in 48% yield. LC/MS (m/z)=609.3 (MH$^+$), R$_t$=0.83 min.

Synthesis of tert-butyl (3R,4S,5S)-1-(3-(6-(2,6-difluorophenyl)-5-fluoropicolinamido)pyridin-4-yl)-5-methyl-4-(4-(thiophen-3-yl)-1H-1,2,3-triazol-1-yl)piperidin-3-ylcarbamate

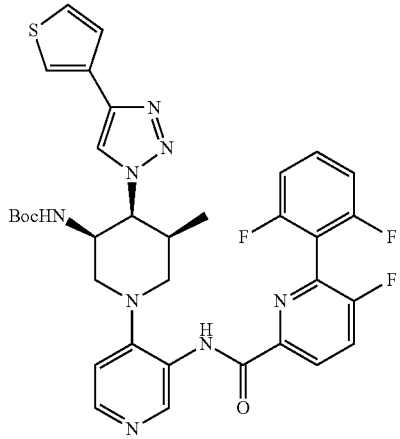 [SMILES: C[C@H]1CN(c2ccncc2NC(=O)c2ccc(F)c(-c3c(F)cccc3F)n2)C[C@@H](NC(=O)OC(C)(C)C)[C@H]1n1cc(-c2ccsc2)nn1]

In a high pressure vial was added tert-butyl (3R,4S,5S)-4-azido-1-(3-(6-(2,6-difluorophenyl)-5-fluoropicolinamido)pyridin-4-yl)-5-methylpiperidin-3-ylcarbamate (1.0 equiv.), copper in charcoal (0.4 equiv.), 3-ethynyl thiophene (5.0 equiv.) and triethylamine (1.0 equiv.), in dioxane (0.09 M) to give a black suspension. The pressure tube was sealed and the mixture was stirred with heating to 100° C. overnight. The reaction was cooled to RT, filtered through celite, concentrated to yield tert-butyl (3R,4S,5S)-1-(3-(6-(2,6-difluorophenyl)-5-fluoropicolinamido)pyridin-4-yl)-5-methyl-4-(4-(thiophen-3-yl)-1H-1,2,3-triazol-1-yl)piperidin-3-ylcarbamate in 48% yield. LC/MS (m/z)=691.2 (MH$^+$), R$_t$=0.98 min.

Synthesis of tert-butyl (3R,4S,5S)-1-(3-(6-(2,6-difluorophenyl)-5-fluoropicolinamido)pyridin-4-yl)-5-methyl-4-(4-methyl-1H-1,2,3-triazol-1-yl)piperidin-3-ylcarbamate

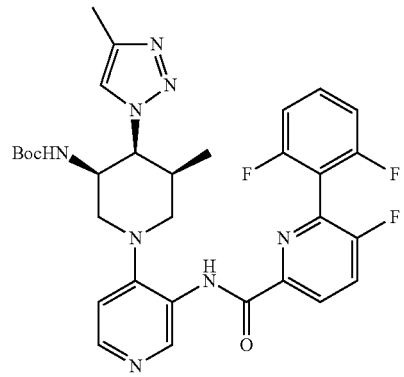 [SMILES: Cc1cn([C@H]2[C@@H](C)CN(c3ccncc3NC(=O)c3ccc(F)c(-c4c(F)cccc4F)n3)C[C@H]2NC(=O)OC(C)(C)C)nn1]

In a high pressure vial was added tert-butyl (3R,4S,5S)-4-azido-1-(3-(6-(2,6-difluorophenyl)-5-fluoropicolinamido)pyridin-4-yl)-5-methylpiperidin-3-ylcarbamate (1.0 equiv.), copper in charcoal (0.2 equiv.), prop-1-yne (10.0 equiv.) and triethylamine (1.5 equiv.), in dioxane (0.15 M) to give a black suspension. The pressure tube was sealed and the mixture was stirred with heating to 60° C. for 48 hrs. The reaction was cooled to RT, filtered through celite, concentrated to yield tert-butyl (3R,4S,5S)-1-(3-(6-(2,6-difluorophenyl)-5-fluoropicolinamido)pyridin-4-yl)-5-methyl-4-(4-methyl-1H-1,2,3-triazol-1-yl)piperidin-3-ylcarbamate in 95% yield. LC/MS (m/z)=623.2 (MH$^+$), R$_t$=0.87 min.

Synthesis of tert-butyl (3R,4S,5S)-1-(3-(6-(2,6-difluorophenyl)-5-fluoropicolinamido)pyridin-4-yl)-4-(4-(methoxymethyl)-1H-1,2,3-triazol-1-yl)-5-methylpiperidin-3-ylcarbamate

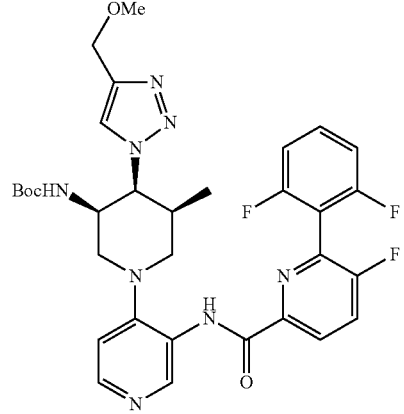 [SMILES: COCc1cn([C@H]2[C@@H](C)CN(c3ccncc3NC(=O)c3ccc(F)c(-c4c(F)cccc4F)n3)C[C@H]2NC(=O)OC(C)(C)C)nn1]

In a high pressure vial was added tert-butyl (3R,4S,5S)-4-azido-1-(3-(6-(2,6-difluorophenyl)-5-fluoropicolinamido)pyridin-4-yl)-5-methylpiperidin-3-ylcarbamate (1.0 equiv.), copper in charcoal (0.2 equiv.), 3-methoxyprop-1-yne (1.5 equiv.) and triethylamine (1.5 equiv.), in dioxane (0.20 M) to give a black suspension. The pressure tube was sealed and the mixture was stirred with heating to 70° C. for 16 hrs. The reaction was cooled to RT, filtered through celite, concentrated to yield tert-butyl (3R,4S,5S)-1-(3-(6-(2,6-difluorophenyl)-5-fluoropicolinamido)pyridin-4-yl)-4-(4-(methoxymethyl)-1H-1,2,3-triazol-1-yl)-5-methylpiperidin-3-ylcarbamate in 95% yield. LC/MS (m/z)=653.2 (MH+), $R_t$=0.86 min.

Synthesis of tert-butyl ((3S,4S,5R)-1-(3-((tert-butoxycarbonyl)amino)pyridin-4-yl)-4-cyano-5-methylpiperidin-3-yl)carbamate

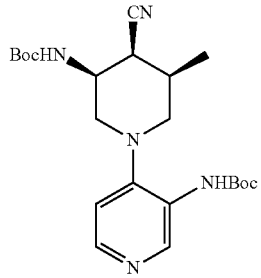 [SMILES: C[C@H]1CN(c2ccncc2NC(=O)OC(C)(C)C)C[C@@H](NC(=O)OC(C)(C)C)[C@H]1C#N]

To a solution of (3R,4R,5S)-1-(3-(bis(tert-butoxycarbonyl)amino)pyridin-4-yl)-3-(tert-butoxycarbonylamino)-5-methylpiperidin-4-yl methanesulfonate (1.0 equiv.) in DMF (0.10 M) was added NaCN (5.0 equiv.). The mixture was stirred at 80° C. for 6 hrs and partitioned between EtOAc and $H_2O$. The organic layer was washed $NaCl_{(sat)}$, dried over $MgSO_4$, filtered, concentrated and purified by ISCO $SiO_2$ chromatography to yield tert-butyl ((3S,4S,5R)-1-(3-((tert-butoxycarbonyl)amino)pyridin-4-yl)-4-cyano-5-methylpiperidin-3-yl)carbamate in 5% yield. LC/MS (m/z)=432.2 (MH+), $R_t$=0.73 min.

Synthesis of tert-butyl (3S,4S,5R)-1-(3-aminopyridin-4-yl)-4-cyano-5-methylpiperidin-3-ylcarbamate

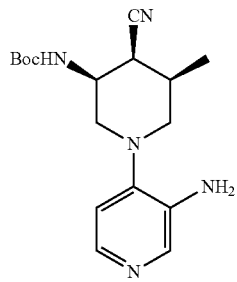 [SMILES: C[C@H]1CN(c2ccncc2N)C[C@@H](NC(=O)OC(C)(C)C)[C@H]1C#N]

Tert-butyl ((3S,4S,5R)-1-(3-((tert-butoxycarbonyl)amino)pyridin-4-yl)-4-cyano-5-methylpiperidin-3-yl)carbamate (1.0 equiv.) was treated with 4 M HCl in dioxane (30.0 equiv.) at rt for 1 hour. The volatiles were removed in vacuo and the solid was pumped on for 5 minutes on the high vac. To the residue was added $CH_2Cl_2$ (0.05 M), DIEA (5.0 equiv.) and Boc-OSu (1.6 equiv.). The solution was left stirring at rt for 1 hr. The volatiles were removed in vacuo and the residue was partitioned between EtOAc and $H_2O$. The organic layer was washed with $Na_2CO_{3(sat)}$, $NaCl_{(sat)}$, dried over $MgSO_4$, filtered, concentrated to yield tert-butyl (3S,4S,5R)-1-(3-aminopyridin-4-yl)-4-cyano-5-methylpiperidin-3-ylcarbamate in 100% yield. LC/MS (m/z)=332.1 (MH+), $R_t$=0.59 min.

Synthesis of tert-butyl (4-((3R,4S,5S)-4-azido-3-((tert-butoxycarbonyl)amino)-5-methylpiperidin-1-yl)pyridin-3-yl)(tert-butoxycarbonyl)carbamate

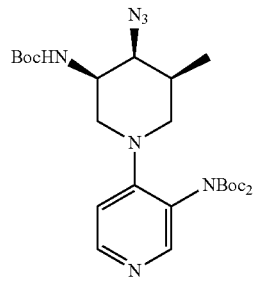

To a solution of (3R,4R,5S)-1-(3-(bis(tert-butoxycarbonyl)amino)pyridin-4-yl)-3-((tert-butoxycarbonyl)amino)-5-methylpiperidin-4-yl methanesulfonate (1.0 equiv.) in DMF (0.13 M) was added $NaN_3$ (5.0 equiv.). The solution was submerged in an 80° C. oil bath and left stirring under Ar for 24 hrs. The solution was cooled to rt and left stirring under Ar overnight. The solution was partitioned between EtOAc and $H_2O$. The organic layer was washed with $Na_2CO_{3(sat)}$, $NaCl_{(sat)}$, dried over $MgSO_4$, filtered, concentrated to yield tert-butyl (4-((3R,4S,5S)-4-azido-3-((tert-butoxycarbonyl)amino)-5-methylpiperidin-1-yl)pyridin-3-yl)(tert-butoxycarbonyl)carbamate in 60% yield. LC/MS (m/z)= 548.4 (MH+), $R_t$=0.94 min. $^1$H NMR (400 MHz, <cdcl3>) δ ppm 0.97-1.13 (m, 3 H), 1.33-1.52 (m, 30 H), 2.03-2.19 (m, 1 H), 2.66-2.87 (m, 2 H), 3.16 (dd, J=12.72, 2.15 Hz, 1 H), 3.22-3.32 (m, 1 H), 3.81-4.01 (m, 2 H), 4.78 (d, J=9.00 Hz, 1 H), 6.76-6.88 (m, 1 H), 8.05-8.18 (m, 1 H), 8.26-8.37 (m, 1 H).

Synthesis of tert-butyl ((3R,4S,5S)-1-(3-aminopyridin-4-yl)-4-azido-5-methylpiperidin-3-yl)carbamate

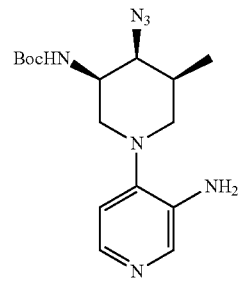 [SMILES: C[C@H]1CN(c2ccncc2N)C[C@@H](NC(=O)OC(C)(C)C)[C@H]1N=[N+]=[N-]]

A solution of 4 M HCl in dioxane (30.0 equiv.) was added to tert-butyl (4-((3R,4S,5S)-4-azido-3-((tert-butoxycarbonyl)amino)-5-methylpiperidin-1-yl)pyridin-3-yl)(tert-butoxycarbonyl)carbamate (1.0 equiv.). The solution started to go homogeneous for a few minutes, but then a ppt formed and the solution went very thick. After sitting at rt for 1 hour, the volatiles were removed in vacuo and the solid was pumped on for 5 minutes on the high vac. To the residue was added $CH_2Cl_2$ (0.11 M), TEA (5.0 equiv.) and $Boc_2O$ (1.0 equiv.). The solution was left stirring at rt for 1 hr. The volatiles were removed in vacuo and the residue was partitioned between EtOAc and $H_2O$. The organic layer was washed with $Na_2CO_{3(sat)}$, $NaCl_{(sat.)}$, dried over $MgSO_4$, filtered, concentrated and purified by ISCO $SiO_2$ chromatography to yield tert-butyl ((3R,4S,5S)-1-(3-aminopyridin-4-yl)-4-azido-5-methylpiperidin-3-yl)carbamate in 33% yield. LC/MS (m/z)=348.2 (MH⁺), R_t=0.70 min. ¹H NMR (400 MHz, CHLOROFORM-d) δ ppm 1.02-1.18 (m, 3 H), 1.36-1.54 (m, 10 H), 2.19 (qd, J=6.91, 3.91 Hz, 1 H), 2.57 (q, J=10.96 Hz, 2 H), 2.96 (d, J=9.00 Hz, 1 H), 3.20 (dd, J=11.15, 3.72 Hz, 1 H), 3.55-3.73 (m, 2 H), 3.90 (br. s., 1 H), 4.01 (br. s., 1 H), 4.81 (d, J=8.61 Hz, 1 H), 6.72-6.83 (m, 1 H), 7.96 (d, J=5.09 Hz, 1 H), 8.02 (s, 1 H).

Synthesis of tert-butyl ((3R,4S,5S)-4-amino-1-(3-(6-(2,6-difluorophenyl)-5-fluoropicolinamido)pyridin-4-yl)-5-methylpiperidin-3-yl)carbamate

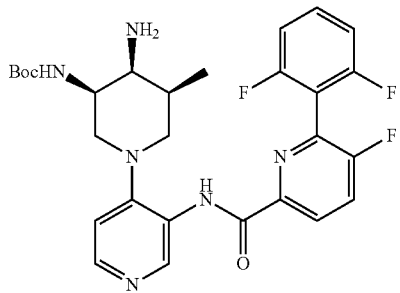 [SMILES: C[C@H]1CN(c2ccncc2NC(=O)c2ccc(F)c(-c3c(F)cccc3F)n2)C[C@@H](NC(=O)OC(C)(C)C)[C@H]1N]

EDC (1.5 equiv.) and HOAt (1.5 equiv.) were added to a solution of tert-butyl ((3R,4S,5S)-1-(3-aminopyridin-4-yl)-4-azido-5-methylpiperidin-3-yl)carbamate (1.0 equiv.) and 6-(2,6-difluorophenyl)-5-fluoropicolinic acid (1.3 equiv.) in DMF (0.20 M). The mixture was stirred at ambient temperature overnight. The reaction mixture was diluted with water and extracted with ethyl acetate. The combined extracts were washed sequentially with 1M aqueous sodium hydroxide and brine, dried over sodium sulfate, filtered, concentrated and purified by ISCO SiO₂ chromatography. To a degassed a solution of the azide (1.0 equiv.) in 2-propanol (0.10 M) was added Pd/C (0.2 equiv.). The mixture was stirred under H₂ for 48 hrs. Filter the mixture over cetlite and wash the cake with MeOH. Concentrate the filtrate to yield tert-butyl ((3R,4S,5S)-4-amino-1-(3-(6-(2,6-difluorophenyl)-5-fluoropicolinamido)pyridin-4-yl)-5-methylpiperidin-3-yl)carbamate in 58% yield. LC/MS (m/z)=557.1 (MH⁺), R_t=0.69 min.

Synthesis of N-(4-((3R,4S,5S)-4-acetamido-3-amino-5-methylpiperidin-1-yl)pyridin-3-yl)-6-(2,6-difluorophenyl)-5-fluoropicolinamide

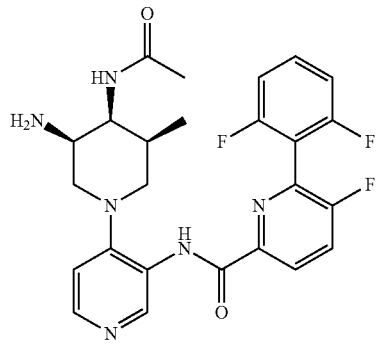 [SMILES: CC(=O)N[C@@H]1[C@H](N)CN(c2ccncc2NC(=O)c2ccc(F)c(-c3c(F)cccc3F)n2)C[C@@H]1C]

Method 4 was followed using tert-butyl ((3R,4S,5S)-4-amino-1-(3-(6-(2,6-difluorophenyl)-5-fluoropicolinamido)pyridin-4-yl)-5-methylpiperidin-3-yl)carbamate and acetic anhydride to give N-(4-((3R,4S,5S)-4-acetamido-3-amino-5-methylpiperidin-1-yl)pyridin-3-yl)-6-(2,6-difluorophenyl)-5-fluoropicolinamidein 40% yield. LC/MS (m/z)=499.1 (MH⁺), R_t=0.58 min.

Synthesis of N-(4-((3R,4S,5S)-3-amino-5-methyl-4-(methylsulfonamido)piperidin-1-yl)pyridin-3-yl)-6-(2,6-difluorophenyl)-5-fluoropicolinamide

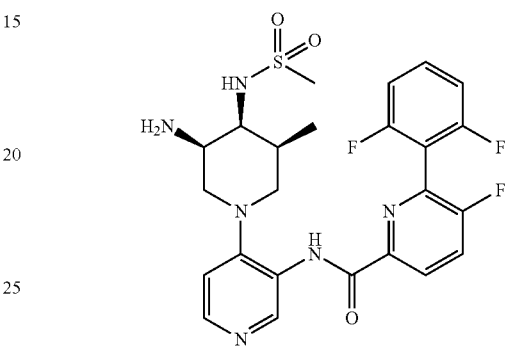

Method 4 was followed using tert-butyl ((3R,4S,5S)-4-amino-1-(3-(6-(2,6-difluorophenyl)-5-fluoropicolinamido)pyridin-4-yl)-5-methylpiperidin-3-yl)carbamate and methanesulfonyl chloride to give N-(4-((3R,4S,5S)-3-amino-5-methyl-4-(methylsulfonamido)piperidin-1-yl)pyridin-3-yl)-6-(2,6-difluorophenyl)-5-fluoropicolinamide in 28% yield. LC/MS (m/z)=535.0 (MH⁺), R_t=0.58 min.

Synthesis of di-tert-butyl (4-((3R,4S,5S)-3-((tert-butoxycarbonyl)amino)-5-methyl-4-(methylamino)piperidin-1-yl)pyridin-3-yl)iminodicarbonate

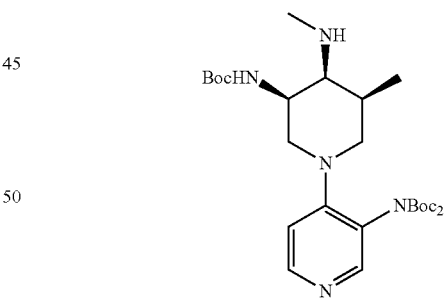

To a solution of di-tert-butyl 4-((3R,4S,5S)-4-azido-3-(tert-butoxycarbonylamino)-5-methylpiperidin-1-yl)pyridin-3-yliminodicarbonate (1.0 equiv.) in DCM (0.14 M) at rt was added PMe₃ (2.0 equiv.). After stirring at rt for 2 hr, PARAFORMALDEHYDE (5.0 equiv.) was added and the mixture was stirred at rt for another 2.5 hrs. The reaction was added MeOH (0.14 M), cooled to 0° C. and added NaBH₄ (5.0 equiv.). After 30 min at rt, the reaction was quenched with sat. NaHCO₃ and extract with EtOAc to yield di-tert-butyl 4-((3R,4S,5S)-3-(tert-butoxycarbonylamino)-5-methyl-4-(methylamino)piperidin-1-yl)pyridin-3-yliminodicarbonate in 85% yield. LC/MS (m/z)=536.3 (MH⁺), R_t=0.61 min.

Synthesis of methyl ((3R,4S,5S)-1-(3-aminopyridin-4-yl)-3-((tert-butoxycarbonyl)amino)-5-methylpiperidin-4-yl)(methyl)carbamate

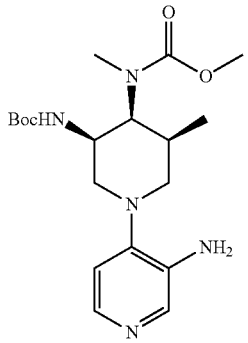 [SMILES: COC(=O)N(C)[C@H]1[C@@H](C)CN(c2ccncc2N)C[C@H]1NC(=O)OC(C)(C)C]

To a solution of di-tert-butyl 4-((3R,4S,5S)-3-(tert-butoxycarbonylamino)-5-methyl-4-(methylamino)piperidin-1-yl)pyridin-3-yliminodicarbonate (1.0 equiv.) in DCM (0.10 M) was added DIEA (3.0 equiv.) the reaction mixture was then cooled to 0° C. To this solution was added methyl chloroformate (1.2 equiv.). The resulting mixture was at RT for 50 min. The reaction mixture was quenched with NaHCO₃ and diluted with EtOAc. The aqeuous layer was separated and extracted with EtOAc, the combined organics were then dried over MgSO₄ and concentrated in vacuo. 4 M HCl (43.0 equiv.) in dioxane was added to the residue. After 1hr, the volatile was removed in vacuo. To the solution of the residue in DCM (0.10 M) at 0° C. was added DIEA (3.0 equiv.) and BocOSu (1.0 equiv.). After 60 min at rt, The reaction mixture was quenched with NaHCO₃ and diluted with EtOAc. The aqueous layer was separated and extracted with EtOAc, the combined organics were then dried over MgSO₄ and concentrated in vacuo to yield a yellow residue, which was purified by ISCO SiO₂ chromatography to yield methyl ((3R,4S,5S)-1-(3-aminopyridin-4-yl)-3-((tert-butoxycarbonyl)amino)-5-methylpiperidin-4-yl)(methyl)carbamate in 44% yield. LC/MS (m/z)=394.2 (MH⁺), $R_t$=0.59 min. ¹H NMR (400 MHz, <cdcl3>) δ ppm 1.06 (d, J=7.04 Hz, 3 H), 1.40-1.52 (m, 10 H), 2.28-2.42 (m, 1 H), 2.89 (d, J=4.70 Hz, 2 H), 3.08 (dd, J=11.93 Hz, 4.50 Hz, 1 H), 3.15 (s, 3 H), 3.47 (dd, J=11.15, 4.11 Hz, 1 H), 3.67-3.79 (m, 5 H), 4.13-4.23 (m, 1 H), 4.56-4.77 (m, 1 H), 6.80 (d, J=5.09 Hz, 1 H), 7.97 (d, J=5.48 Hz, 1 H), 8.04 (s, 1 H).

Synthesis of tert-butyl ((3R,4S,5S)-1-(3-aminopyridin-4-yl)-5-methyl-4-(N-methylacetamido)piperidin-3-yl)carbamate

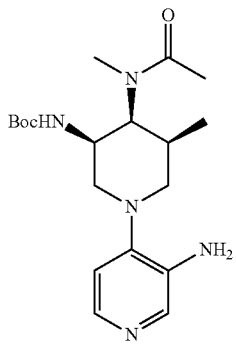 [SMILES: CC(=O)N(C)[C@H]1[C@@H](C)CN(c2ccncc2N)C[C@H]1NC(=O)OC(C)(C)C]

To a solution of di-tert-butyl 4-((3R,4S,5S)-3-(tert-butoxycarbonylamino)-5-methyl-4-(methylamino)piperidin-1-yl)pyridin-3-yliminodicarbonate (1.0 equiv.) in DCM (0.10 M) was added DIEA (3.0 equiv.) the reaction mixture was then cooled to 0° C. To this solution was added acetic anhydride (1.2 equiv.). The resulting mixture was at RT for 50 min. The reaction mixture was quenched with NaHCO₃ and diluted with EtOAc. The aqeuous layer was separated and extracted with EtOAc, the combined organics were then dried over MgSO₄ and concentrated in vacuo. 4 M HCl (43.0 equiv.) in Dioxane was added to the residue. After 1hr, the volatile was removed in vacuo. To the solution of the residue in DCM (0.10 M) at 0° C. was added DIEA (3.0 equiv.) and BocOSu (1.0 equiv.). After 60 min at rt, The reaction mixture was quenched with NaHCO₃ and diluted with EtOAc. The aqeuous layer was separated and extracted with EtOAc, the combined organics were then dried over MgSO₄ and concentrated in vacuo to yield a yellow residue, which was purified by SiO₂ chromatography to yield tert-butyl ((3R,4S,5S)-1-(3-aminopyridin-4-yl)-5-methyl-4-(N-methylacetamido)piperidin-3-yl)carbamate in 60% yield. LC/MS (m/z)=378.2 (MH⁺), $R_t$=0.50 min. ¹HNMR (400 MHz, <cdcl3>) δ ppm 1.06 (d, J=7.83 Hz, 3 H), 1.39-1.50 (m, 9 H), 2.20 (br. s., 3 H), 2.34-2.48 (m, 1 H), 2.84-3.28 (m, 6 H), 3.77 (d, J=18.00 Hz, 2 H), 4.19-4.62 (m, 1 H), 6.82 (d, J=5.09 Hz, 1 H), 7.97 (br. s., 1 H), 8.05 (br. s., 1 H).

Synthesis of tert-butyl tert-butoxycarbonyl(4-43R,4S,5S)-3-((tert-butoxycarbonyl)amino)-4-(4-hydroxymethyl)-1H-1,2,3-triazol-1-yl)-5-methylpiperidin-1-yl)pyridin-3-yl)carbamate

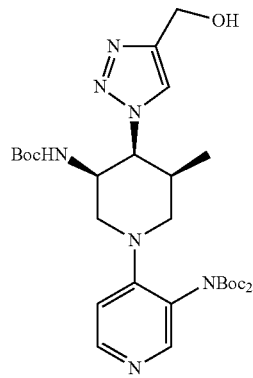

In a round-bottom flask was added tert-butyl (4-((3R,4S,5S)-4-azido-3-((tert-butoxycarbonyl)amino)-5-methylpiperidin-1-yl)pyridin-3-yl)(tert-butoxycarbonyl) carbamate (1.0 equiv.), copper in charcoal (0.02 equiv.) and propargyl alcohol (1.0 equiv.) in t-BuOH/H₂O (0.15 M) to give a blue solution. And sodium ascorbate (0.1 equiv.) was added. The mixture was stirred at rt for 16 hrs. The reaction was diluted with H₂O and cooled to 0° C., then filtered, and the precipitate was collected to yield tert-butyl tert-butoxycarbonyl(4-((3R,4S,5S)-3-((tert-butoxycarbonyl)amino)-4-(4-(hydroxymethyl)-1H-1,2,3-triazol-1-yl)-5-methylpiperidin-1-yl)pyridin-3-yl)carbamate in 85% yield. LC/MS (m/z)=604.3 (MH⁺), $R_t$=0.69 min.

Synthesis of tert-butyl (3R,4S,5S)-1-(3-aminopyridin-4-yl)-4-(4-(hydroxymethyl)-1H-1,2,3-triazol-1-yl)-5-methylpiperidin-3-ylcarbamate

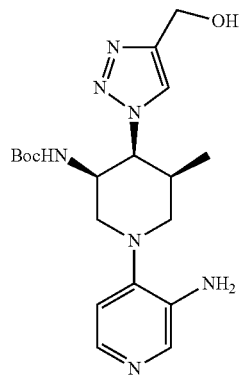 [SMILES: C[C@H]1CN(c2ccncc2N)C[C@@H](NC(=O)OC(C)(C)C)[C@H]1n1cc(CO)nn1]

To di-tert-butyl 4-((3R,4S,5S)-3-(tert-butoxycarbonylamino)-4-(4-(hydroxymethyl)-1H-1,2,3-triazol-1-yl)-5-methylpiperidin-1-yl)pyridin-3-yliminodicarbonate (1.0 equiv.) was added 4 M HCl (30.0 equiv.) in dioxane. After 1 hr, the volatile was removed in vacuo. To the solution of the residue in DCM (0.10 M) at 0° C. was added DIEA (30.0 equiv.) and BocOSu (1.0 equiv.). After 4 hrs at rt, the reaction mixture was quenched with NaHCO$_3$ and diluted with EtOAc. The aqeuous layer was separated and extracted with EtOAc, the combined organics were then dried over MgSO$_4$ and concentrated in vacuo to yield a yellow residue, which was purified by ISCO SiO$_2$ chromatography to yield tert-butyl (3R,4S,5S)-1-(3-aminopyridin-4-yl)-4-(4-(hydroxymethyl)-1H-1,2,3-triazol-1-yl)-5-methylpiperidin-3-ylcarbamate in 57% yield. LC/MS (m/z)=404.3 (MH$^+$), R$_t$=0.47 min.

Synthesis of N-(4-((3R,4S,5S)-3-amino-4-(4-(hydroxymethyl)-1H-1,2,3-triazol-1-yl)-5-methylpiperidin-1-yl)pyridin-3-yl)-6-(2,6-difluorophenyl)-5-fluoropicolinamide

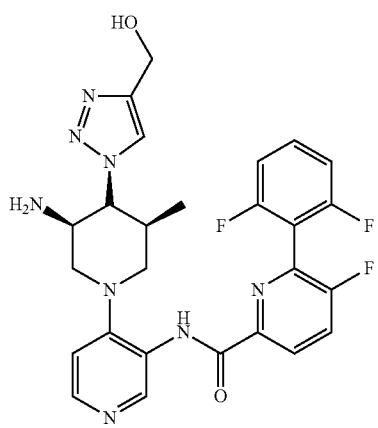

To a round-bottomed flask was added tert-butyl (3R,4S,5S)-1-(3-aminopyridin-4-yl)-4-(4-(hydroxymethyl)-1H-1,2,3-triazol-1-yl)-5-methylpiperidin-3-ylcarbamate (1.0 equiv.) and BSA (2.5 equiv.) in Acetonitrile/DMF (4/1, 0.05 M) to give a orange suspension. The mixture was stirred at room temperature for 1 hr at which time all of the solids had dissolved into solution. The mixture was taken to dryness. The crude in DMF (0.10 M) was added EDCI (2.4 equiv.), HOAT (2.4 equiv.) and 6-(2,6-difluorophenyl)-5-fluoropicolinic acid (2.4 equiv.). The mixture was stirred at rt for 16 hrs. The reaction was taken to dryness and dissolved in EtOAc and cooled to 0° C. to precipitate the urea byproduct. The mixture was filtered and the organics were washed with H$_2$O, dried over MgSO$_4$, filtered and concentrated. To a solution of the residue in EtOH (0.01 M) was added potassium carbonate (10.0 equiv.). The mixture was stirred at room temperature for 2 hrs. The reaction was diluted with DCM and quenched with NaHCO$_{300}$. The organics were separated and the aqueous solution was extracted with DCM. The combined organics were dried over MgSO$_4$, filtered, and concentrated. The crude alcohol was then dissolved in 25% TFA/DCM. The solution was stirred at room temp for 1 hr. The volatiles were removed on the rotovap. The crude product was taken up in DMSO, filtered, purified via prep-HPLC to yield N-(4-((3R,4S,5S)-3-amino-4-(4-(hydroxymethyl)-1H-1,2,3-triazol-1-yl)-5-methylpiperidin-1-yl)pyridin-3-yl)-6-(2,6-difluorophenyl)-5-fluoropicolinamide in 69% yield. LC/MS (m/z)=539.3 (MH$^+$), R$_t$=0.57 min.

Synthesis of (+/−)-tert-butyl ((1R,3S,5R)-5-(3-((tert-butoxycarbonyl)amino)pyridin-4-yl)-3-methyl-2-oxocyclohexyl)carbamate

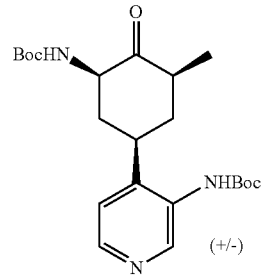

To a solution of (+/−)-tert-butyl ((1R,2R,3S,5R)-5-(3-((tert-butoxycarbonyl)amino) pyridin-4-yl)-2-hydroxy-3-methylcyclohexyl)carbamate (1.0 equiv.) DCM (0.10 M) was added Dess-Martin Periodinane (1.2 equiv.). The mixture was stirred at room temperature for 18 hrs. The volatiles were removed under reduced pressure. The residue was partitioned between EtOAc and 10% sodium thiosulfate/sat. sodium bicarbonate aqueous solution. The organic was washed with brine, dried over sodium sulfate, filtered, concentrated and purified by ISCO chromatography to afford (+/−)-tert-buty ((1R,3S,5R)-5-(3-acetamidopyridin-4-yl)-3-methyl-2-oxocyclohexyl) carbamate in 65% yield. LC/MS (m/z)=420.2 (MH$^+$), R$_t$=0.73 min. 1

Synthesis of (+/−)-benzyl ((1R,3S,5R)-5-(3-((benzoxycarbonyl)amino)pyridin-4-yl)-3-methyl-2-oxocyclohexyl)carbamate

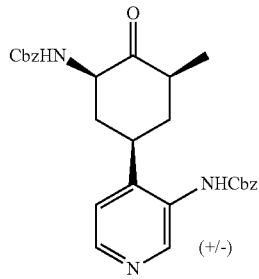 [SMILES: C[C@H]1C[C@@H](c2ccncc2NC(=O)OCc2ccccc2)C[C@@H](NC(=O)OCc2ccccc2)C1=O]

(+/−)-Tert-butyl ((1R,3S,5R)-5-(3-acetamidopyridin-4-yl)-3-methyl-2-oxocyclohexyl)carbamate (1.0 equiv.) was dissolved in 4.0 M HCl (50.0 equiv.) in p-dioxane. After stirring at room temperature for 16 hrs, the mixture was concentrated. The crude was dissolved in DCM (0.20 M) and CBZ-OSu (5.0 equiv.) was added followed by DIEA (8.0 equiv.). The reaction was stirred at room temperature for 20 hrs. The solution was diluted with EtOAc and washed with water, sat. sodium bicarbonate, and brine and dried over sodium sulfate, filtered and concentrated. The crude residue was purified by ISCO chromatography to afford (+/−)-benzyl ((1R,3S,5R)-5-(3-((benzoxycarbonyl)amino) pyridin-4-yl)-3-methyl-2-oxocyclohexyl)carbamate in 50% yield. LC/MS (m/z)=488.2 (MH$^+$), R$_t$=0.79 min.

Synthesis of (+/−)-benzyl ((6R,8R,10S)-8-(3-((benzoxycarbonyl)amino)pyridin-4-yl)-10-methyl-1,4-dioxaspiro[4.5]decan-6-yl)carbamate

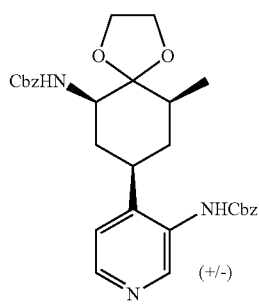 [SMILES: C[C@H]1C[C@@H](c2ccncc2NC(=O)OCc2ccccc2)C[C@@H](NC(=O)OCc2ccccc2)C12OCCO2]

(+/−)-Benzyl ((1R,3S,5R)-5-(3-((benzoxycarbonyl)amino) pyridin-4-yl)-3-methyl-2-oxocyclohexyl)carbamate (1.0 equiv.) was dissolved in dry THF (0.20 M) under nitrogen and ETHYLENE GLYCOL (8.0 equiv.) was added followed by BF$_3$.OEt$_2$ (1.4 equiv.). The solution was microwave vial and heated at 100° C. for 60 mins. The solution was diluted with EtOAc and washed with sat. sodium bicarbonate, water, brine, dried over sodium sulfate and concentrated. The crude material was purified by ISCO chromatography to afford (+/−)-benzyl ((6R,8R,10S)-8-(3-((benzoxycarbonyl)amino) pyridin-4-yl)-10-methyl-1,4-dioxaspiro[4.5]decan-6-yl)carbamate in 100% yield. LC/MS (m/z)=532.2 (MH$^+$), R$_t$=0.81 min.

Synthesis of benzyl (6S,8S,10R)-8-(3-aminopyridin-4-yl)-10-methyl-1,4-dioxaspiro[4.5]decan-6-ylcarbamate and benzyl ((6R,8R,10S)-8-(3-aminopyridin-4-yl)-10-methyl-1,4-dioxaspiro[4.5]decan-6-yl)carbamate

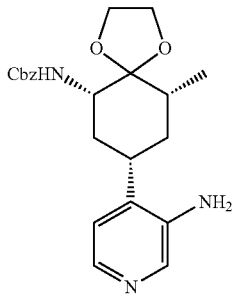 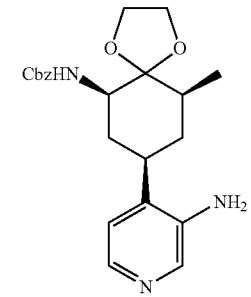

Single Enantiomer    Single Enantiomer (+/−)-Benzyl ((6R,8R,10 S)-8-(3-((benzoxycarbonyl) amino)pyridin-4-yl)-10-methyl-1,4-dioxaspiro[4.5]decan-6-yl)carbamate (1.0 equiv.) was dissolved in MeOH (0.10 M) and degassed with Argon to vacuum. Pd/C (0.05 equiv.) was added and the mixture was stirred under a H$_2$ balloon for 20 hrs. The mixture was filtered and concentrated. The crude and CBZ-OSu (0.99 equiv.) were dissolved in DCM (0.20 M). The reaction was stirred at room temperature for 2 hrs. The solution was diluted with EtOAc and washed with water, dried over sodium sulfate, filtered and concentrated. The crude residue was purified by ISCO chromatography. Purification was completed via SFC (40% EtOH, 15 mL/min, OJ column) to yield benzyl (6S,8S,10R)-8-(3-aminopyridin-4-yl)-10-methyl-1,4-dioxaspiro[4.5]decan-6-ylcarbamate (28% yield, 99% ee) and benzyl (6R,8R,10 S)-8-(3-aminopyridin-4-yl)-10-methyl-1,4-dioxaspiro[4.5]decan-6-ylcarbamate (13% yield, 99% ee). LC/MS (m/z)=398.2 (MH$^+$), R$_t$=0.64 min.

Method 7

A solution of N-Boc protected amine was treated with excess 4M HCl/dioxane for 14 hours or with 25% TFA/CH$_2$Cl$_2$ for 2 hours. Upon removal of the volatiles in vacuo, the material was purified by RP HPLC yielding after lyophilization the amide product as the TFA salt. Alternatively, the HPLC fractions could be added to EtOAc and solid Na$_2$CO$_3$, separated and washed with NaCl$_{(sat)}$ Upon drying over MgSO$_4$, filtering and removing the volatiles in vacuo the free base was obtained. Upon dissolving in MeCN/H$_2$O, adding 1 eq. of 1 N HCl and lyophilizing, the HCl salt of the amide product was obtained.

If an OBn or NCbz group was present, it was deprotected by treatment with 10% Pd/C (0.2 equiv.) under an atmosphere of hydrogen in ethyl acetate and methanol (1:2). Upon completion, the reaction was filtered through Celite, washed with methanol, and the filtrate was concentrated in vacuo.

If a CO$_2$Me group was present, it could be converted to the corresponding CO$_2$H following Method 2.

Following the procedures of Method 7, the following compounds were prepared:

TABLE 1

| Ex # | Structure | | LC/MS (MH+ on UPLC) | LC/MS (Rf on UPLC) | Chemical Name |
|---|---|---|---|---|---|
| 1 | 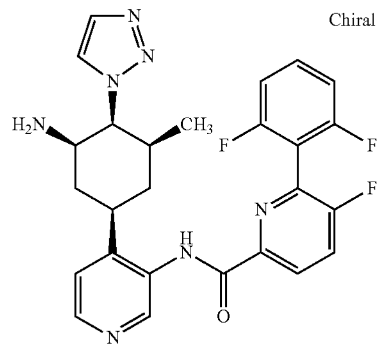 [SMILES: C[C@H]1C[C@@H](c2ccncc2NC(=O)c2ccc(F)c(-c3c(F)cccc3F)n2)C[C@@H](N)[C@H]1n1ccnn1] | Chiral | 508.2 | 0.60 | N-(4-((1R,3R,4S,5S)-3-amino-5-methyl-4-(1H-1,2,3-triazol-1-yl)cyclohexyl)pyridin-3-yl)-6-(2,6-difluorophenyl)-5-fluoropicolinamide |
| 2 | 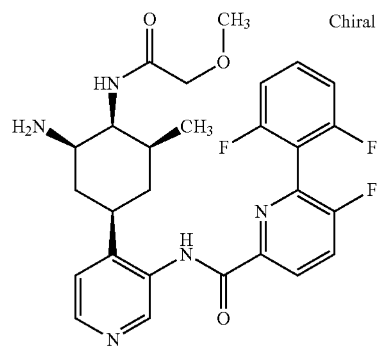 [SMILES: COCC(=O)N[C@@H]1[C@H](N)C[C@H](c2ccncc2NC(=O)c2ccc(F)c(-c3c(F)cccc3F)n2)C[C@@H]1C] | Chiral | 528.2 | 0.62 | N-(4-((1R,3R,4S,5S)-3-amino-4-(2-methoxyacetamido)-5-methylcyclohexyl)pyridin-3-yl)-6-(2,6-difluorophenyl)-5-fluoropicolinamide |
| 3 | 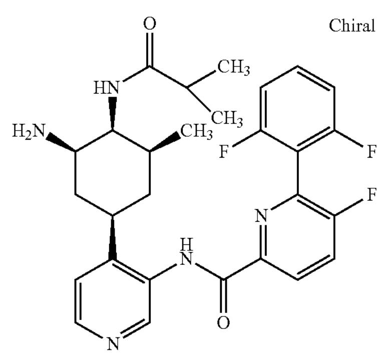 [SMILES: CC(C)C(=O)N[C@@H]1[C@H](N)C[C@H](c2ccncc2NC(=O)c2ccc(F)c(-c3c(F)cccc3F)n2)C[C@@H]1C] | Chiral | 526.3 | 0.67 | N-(4-((1R,3R,4S,5S)-3-amino-4-isobutyramido-5-methylcyclohexyl)pyridin-3-yl)-6-(2,6-difluorophenyl)-5-fluoropicolinamide |
| 4 | 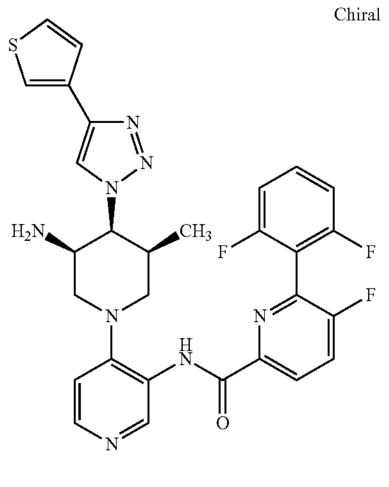 [SMILES: C[C@H]1CN(c2ccncc2NC(=O)c2ccc(F)c(-c3c(F)cccc3F)n2)C[C@@H](N)[C@H]1n1cc(-c2ccsc2)nn1] | Chiral | 591.2 | 0.72 | N-(4-((3R,4S,5S)-3-amino-5-methyl-4-(4-(thiophen-3-yl)-1H-1,2,3-triazol-1-yl)piperidin-1-yl)pyridin-3-yl)-6-(2,6-difluorophenyl)-5-fluoropicolinamide |

TABLE 1-continued

| Ex # | Structure | | LC/MS (MH+ on UPLC) | LC/MS (Rf on UPLC) | Chemical Name |
|---|---|---|---|---|---|
| 5 | 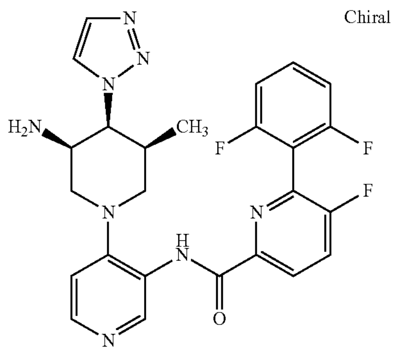 [SMILES: C[C@H]1CN(c2ccncc2NC(=O)c2ccc(F)c(-c3c(F)cccc3F)n2)C[C@@H](N)[C@H]1n1ccnn1] | Chiral | 509.2 | 0.57 | N-(4-((3R,4S,5S)-3-amino-5-methyl-4-(1H-1,2,3-triazol-1-yl)piperidin-1-yl)pyridin-3-yl)-6-(2,6-difluorophenyl)-5-fluoropicolinamide |
| 6 | 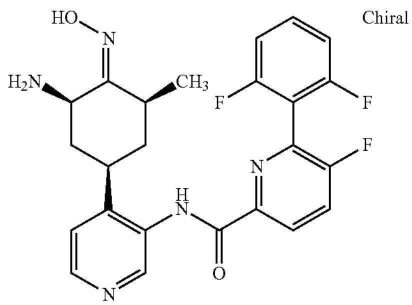 [SMILES: C[C@H]1C[C@@H](c2ccncc2NC(=O)c2ccc(F)c(-c3c(F)cccc3F)n2)C[C@@H](N)/C1=N\O] | Chiral | 470.3 | 0.61 | N-(4-((1R,3R,5S,Z)-3-amino-4-(hydroxyimino)-5-methylcyclohexyl)pyridin-3-yl)-6-(2,6-difluorophenyl)-5-fluoropicolinamide |
| 7 | 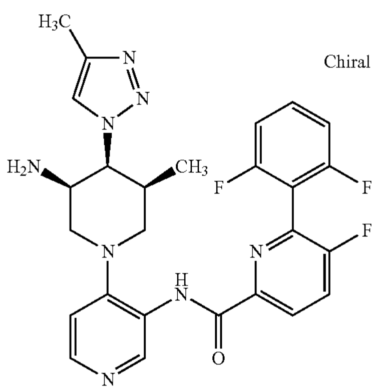 [SMILES: Cc1cn([C@@H]2[C@H](N)CN(c3ccncc3NC(=O)c3ccc(F)c(-c4c(F)cccc4F)n3)C[C@@H]2C)nn1] | Chiral | 523.1 | 0.60 | N-(4-((3R,4S,5S)-3-amino-5-methyl-4-(4-methyl-1H-1,2,3-triazol-1-yl)piperidin-1-yl)pyridin-3-yl)-6-(2,6-difluorophenyl)-5-fluoropicolinamide |
| 8 | 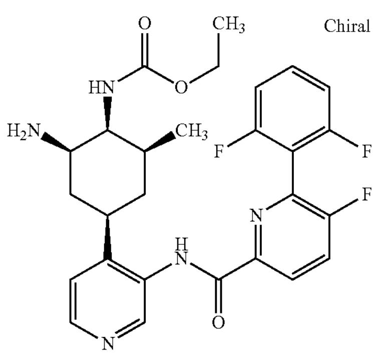 [SMILES: CCOC(=O)N[C@@H]1[C@H](N)C[C@H](c2ccncc2NC(=O)c2ccc(F)c(-c3c(F)cccc3F)n2)C[C@@H]1C] | Chiral | 528.2 | 0.65 | ethyl (1S,2R,4R,6S)-2-amino-4-(3-(6-(2,6-difluorophenyl)-5-fluoropicolinamido)pyridin-4-yl)-6-methylcyclohexylcarbamate |

TABLE 1-continued

| Ex # | Structure | LC/MS (MH+ on UPLC) | LC/MS (Rf on UPLC) | Chemical Name |
|---|---|---|---|---|
| 9 | Chiral | 542.3 | 0.68 | isopropyl (1S,2R,4R,6S)-2-amino-4-(3-(6-(2,6-difluorophenyl)-5-fluoropicolinamido)pyridin-4-yl)-6-methylcyclohexylcarbamate |
| 10 | Chiral | 512.1 | 0.62 | N-(4-((1R,3R,4S,5S)-3-amino-5-methyl-4-propionamidocyclohexyl)pyridin-3-yl)-6-(2,6-difluorophenyl)-5-fluoropicolinamide |
| 11 | Chiral | 455.1 | 0.57 | N-(4-((1R,3R,5S)-3-amino-5-methyl-4-oxocyclohexyl)pyridin-3-yl)-6-(2,6-difluorophenyl)-5-fluoropicolinamide |
| 12 | Chiral | 484.2 | 0.63 | N-(4-((1R,3R,5S,E)-3-amino-4-(methoxyimino)-5-methylcyclohexyl)pyridin-3-yl)-6-(2,6-difluorophenyl)-5-fluoropicolinamide |

TABLE 1-continued

| Ex # | Structure | LC/MS (MH+ on UPLC) | LC/MS (Rf on UPLC) | Chemical Name |
|---|---|---|---|---|
| 13 | 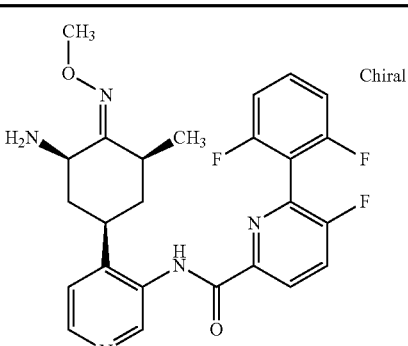 Chiral | 484.2 | 0.64 | N-(4-((1R,3R,5S,Z)-3-amino-4-(methoxyimino)-5-methylcyclohexyl)pyridin-3-yl)-6-(2,6-difluorophenyl)-5-fluoropicolinamide |
| 14 | 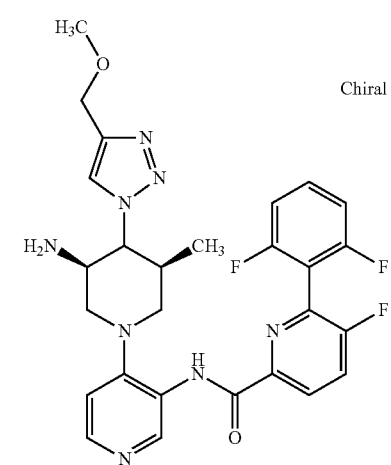 [SMILES: COCc1cn(C2[C@H](N)CN(c3ccncc3NC(=O)c3ccc(F)c(-c4c(F)cccc4F)n3)C[C@@H]2C)nn1] Chiral | 553.2 | 0.60 | N-(4-((3R,4S,5S)-3-amino-4-(4-(methoxymethyl)-1H-1,2,3-triazol-1-yl)-5-methylpiperidin-1-yl)pyridin-3-yl)-6-(2,6-difluorophenyl)-5-fluoropicolinamide |
| 15 | 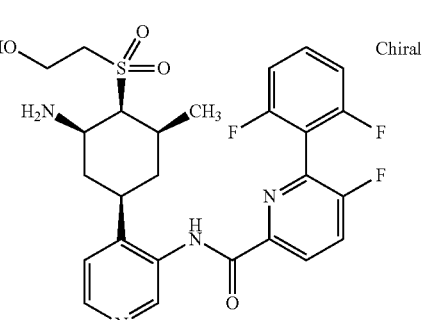 Chiral | 549.2 | 0.58 | N-(4-((1R,3R,4S,5S)-3-amino-4-(2-hydroxyethylsulfonyl)-5-methylcyclohexyl)pyridin-3-yl)-6-(2,6-difluorophenyl)-5-fluoropicolinamide |
| 16 | 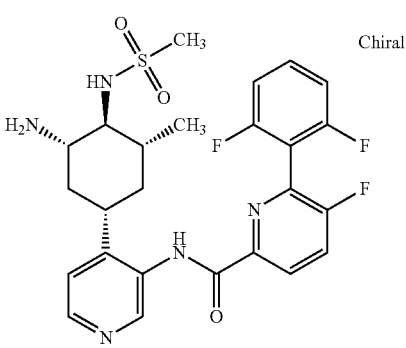 [SMILES: C[C@@H]1C[C@H](c2ccncc2NC(=O)c2ccc(F)c(-c3c(F)cccc3F)n2)C[C@H](N)[C@H]1NS(C)(=O)=O] Chiral | 534.2 | 0.57 | N-(4-((1S,3S,4S,5R)-3-amino-5-methyl-4-(methylsulfonamido)cyclohexyl)pyridin-3-yl)-6-(2,6-difluorophenyl)-5-fluoropicolinamide |

TABLE 1-continued

| Ex # | Structure | LC/MS (MH+ on UPLC) | LC/MS (Rf on UPLC) | Chemical Name |
|---|---|---|---|---|
| 17 | 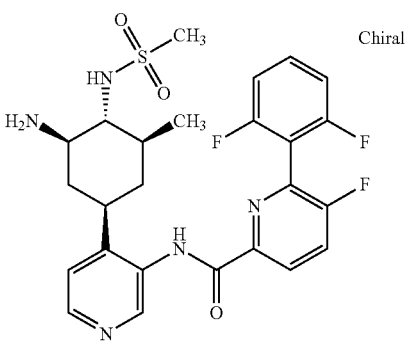 [SMILES: C[C@H]1C[C@@H](c2ccncc2NC(=O)c2ccc(F)c(-c3c(F)cccc3F)n2)C[C@@H](N)[C@@H]1NS(C)(=O)=O] Chiral | 534.2 | 0.57 | N-(4-((1R,3R,4R,5S)-3-amino-5-methyl-4-(methylsulfonamido)cylcohex-yl)pyridin-3-yl)-6-(2,6-difluorophenyl)-5-fluoropicolinamide |
| 18 | 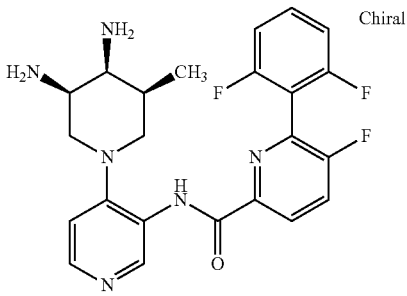 [SMILES: C[C@H]1CN(c2ccncc2NC(=O)c2ccc(F)c(-c3c(F)cccc3F)n2)C[C@@H](N)[C@H]1N] Chiral | 457.0 | 0.57 | N-(4-((3R,4S,5S)-3,4-diamino-5-methylpiperidin-1-yl)pyridin-3-yl)-6-(2,6-difluorophenyl)-5-fluoropicolinamide |
| 19 | 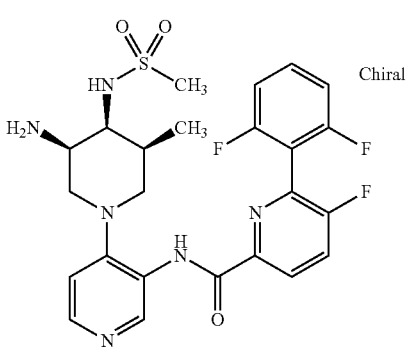 [SMILES: C[C@H]1CN(c2ccncc2NC(=O)c2ccc(F)c(-c3c(F)cccc3F)n2)C[C@@H](N)[C@H]1NS(C)(=O)=O] Chiral | 535.0 | 0.58 | N-(4-((3R,4S,5S)-3-amino-5-methyl-4-(methylsulfonamido)piperidin-1-yl)pyridin-3-yl)-6-(2,6-difluorophenyl)-5-fluoropicolinamide |
| 20 | 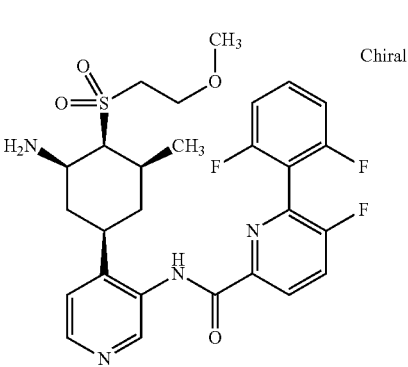 [SMILES: COCCS(=O)(=O)[C@@H]1[C@H](N)C[C@H](c2ccncc2NC(=O)c2ccc(F)c(-c3c(F)cccc3F)n2)C[C@@H]1C] Chiral | 563.3 | 0.61 | N-(4-((1R,3R,4S,5S)-3-amino-4-((2-methoxyethyl)sulfonyl)-5-methylcyclohexyl)pyridin-3-yl)-6-(2,6-difluorophenyl)-5-fluoropicolinamide |

TABLE 1-continued

| Ex # | Structure | LC/MS (MH+ on UPLC) | LC/MS (Rf on UPLC) | Chemical Name |
|---|---|---|---|---|
| 21 | 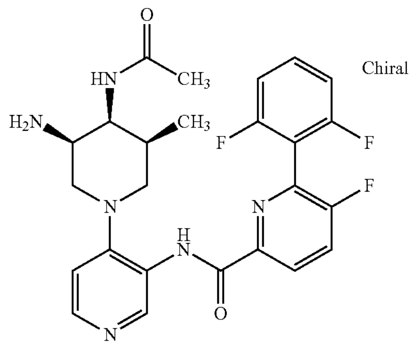 [SMILES: CC(=O)N[C@@H]1[C@H](N)CN(c2ccncc2NC(=O)c2ccc(F)c(-c3c(F)cccc3F)n2)C[C@@H]1C] | 499.1 | 0.58 | N-(4-((3R,4S,5S)-4-acetamido-3-amino-5-methylpiperidin-1-yl)pyridin-3-yl)-6-(2,6-difluorophenyl)-5-fluoropicolinamide |
| 22 | 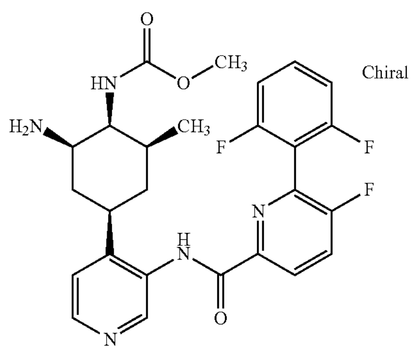 [SMILES: COC(=O)N[C@@H]1[C@H](N)C[C@H](c2ccncc2NC(=O)c2ccc(F)c(-c3c(F)cccc3F)n2)C[C@@H]1C] | 514.2 | 0.61 | methyl (1S,2R,4R,6S)-2-amino-4-(3-(6-(2,6-difluorophenyl)-5-fluoropicolinamido)pyridin-4-yl)-6-methylcyclohexylcarbamate |
| 23 | 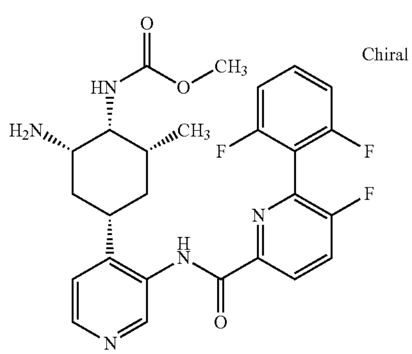 [SMILES: COC(=O)N[C@@H]1[C@H](C)C[C@H](c2ccncc2NC(=O)c2ccc(F)c(-c3c(F)cccc3F)n2)C[C@@H]1N] | 514.3 | 0.61 | methyl (1R,2S,4S,6R)-2-amino-4-(3-(6-(2,6-difluorophenyl)-5-fluoropicolinamido)pyridin-4-yl)-6-methylcyclohexylcarbamate |
| 24 | 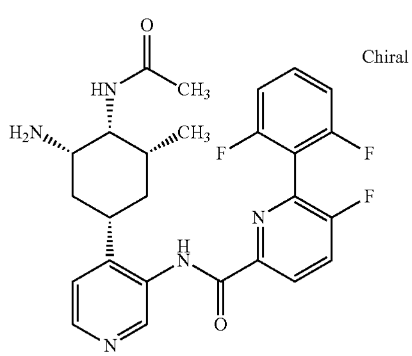 [SMILES: CC(=O)N[C@@H]1[C@H](C)C[C@H](c2ccncc2NC(=O)c2ccc(F)c(-c3c(F)cccc3F)n2)C[C@@H]1N] | 498.2 | 0.59 | N-(4-((1S,3S,4R,5R)-4-acetamido-3-amino-5-methylcyclohexyl)pyridin-3-yl)-6-(2,6-difluorophenyl)-5-fluoropicolinamide |

TABLE 1-continued

| Ex # | Structure | LC/MS (MH+ on UPLC) | LC/MS (Rf on UPLC) | Chemical Name |
|---|---|---|---|---|
| 25 | Chiral | 498.3 | 0.59 | N-(4-((1R,3R,4S,5S)-4-acetamido-3-amino-5-methylcyclohexyl)pyridin-3-yl)-6-(2,6-difluorophenyl)-5-fluoropicolinamide |
| 26 | Chiral | 534.2 | 0.58 | N-(4-((1S,3S,4R,5R)-3-amino-5-methyl-4-(methylsulfonamido)cyclohexyl)pyridin-3-yl)-6-(2,6-difluorophenyl)-5-fluoropicolinamide |
| 27 | Chiral | 534.2 | 0.58 | N-(4-((1R,3R,4S,5S)-3-amino-5-methyl-4-(methylsulfonamido)cyclohexyl)pyridin-3-yl)-6-(2,6-difluorophenyl)-5-fluoropicolinamide |
| 28 | Chiral | 482.1 | 0.64 | N-(4-((1S,3S,4R,5R)-3-amino-4-azido-5-methylcyclohexyl)pyridin-3-yl)-6-(2,6-difluorophenyl)-5-fluoropicolinamide |

TABLE 1-continued

| Ex # | Structure | | LC/MS (MH+ on UPLC) | LC/MS (Rf on UPLC) | Chemical Name |
|---|---|---|---|---|---|
| 29 | 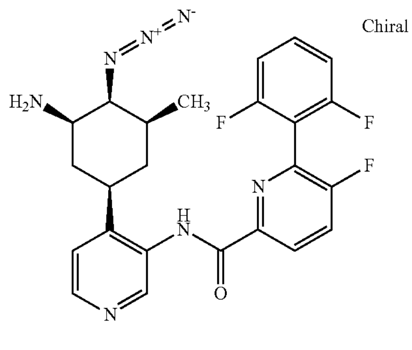 [SMILES: C[C@H]1C[C@@H](c2ccncc2NC(=O)c2ccc(F)c(-c3c(F)cccc3F)n2)C[C@@H](N)[C@H]1N=[N+]=[N-]] | Chiral | 482.2 | 0.63 | N-(4-((1R,3R,4S,5S)-3-amino-4-azido-5-methylcyclohexyl)pyridin-3-yl)-6-(2,6-difluorophenyl)-5-fluoropicolinamide |
| 30 | 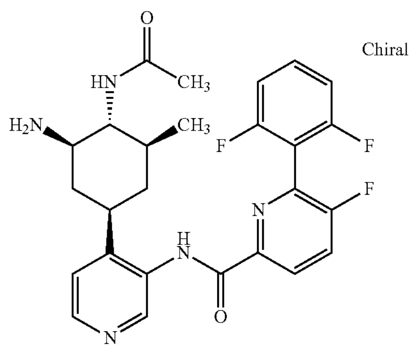 [SMILES: CC(=O)N[C@H]1[C@H](N)C[C@H](c2ccncc2NC(=O)c2ccc(F)c(-c3c(F)cccc3F)n2)C[C@@H]1C] | Chiral | 498.3 | 0.57 | N-(4-((1R,3R,4R,5S)-4-acetamido-3-amino-5-methylcyclohexyl)pyridin-3-yl)-6-(2,6-difluorophenyl)-5-fluoropicolinamide |
| 31 | 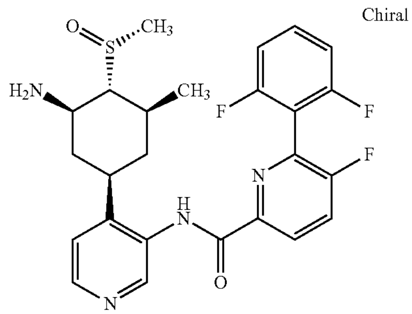 | Chiral | 503.2 | 0.59 | N-(4-((1R,3R,4R,5S)-3-amino-5-methyl-4-((R)-methylsulfinyl)cyclohexyl)pyridin-3-yl)-6-(2,6-difluorophenyl)-5-fluoropicolinamide |
| 32 | 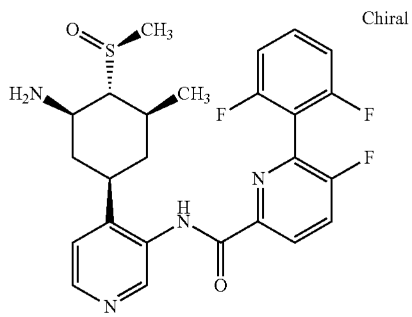 [SMILES: C[C@H]1C[C@@H](c2ccncc2NC(=O)c2ccc(F)c(-c3c(F)cccc3F)n2)C[C@@H](N)[C@@H]1[S@](C)=O] | Chiral | 503.2 | 0.57 | N-(4-((1R,3R,4R,5S)-3-amino-5-methyl-4-((S)-methylsulfinyl)cyclohexyl)pyridin-3-yl)-6-(2,6-difluorophenyl)-5-fluoropicolinamide |

TABLE 1-continued

| Ex # | Structure | | LC/MS (MH+ on UPLC) | LC/MS (Rf on UPLC) | Chemical Name |
|---|---|---|---|---|---|
| 33 | 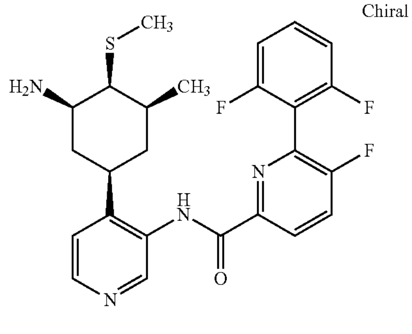 [SMILES: CS[C@@H]1[C@H](N)C[C@H](c2ccncc2NC(=O)c2ccc(F)c(-c3c(F)cccc3F)n2)C[C@@H]1C] | Chiral | 487.2 | 0.64 | N-(4-((1R,3R,4S,5S)-3-amino-5-methyl-4-(methylthio)cyclohexyl)pyridin-3-yl)-6-(2,6-difluorophenyl)-5-fluoropicolinamde |
| 34 | 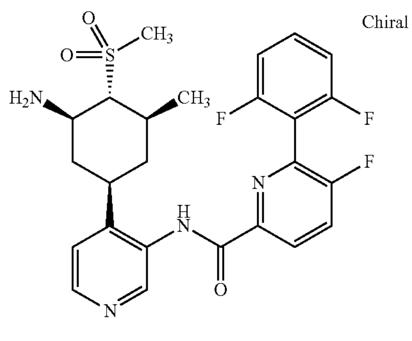 [SMILES: C[C@H]1C[C@@H](c2ccncc2NC(=O)c2ccc(F)c(-c3c(F)cccc3F)n2)C[C@@H](N)[C@@H]1S(C)(=O)=O] | Chiral | 519.2 | 0.60 | N-(4-((1R,3R,4R,5S)-3-amino-5-methyl-4-(methylsulfonyl)cylcohexyl)pyridin-3-yl)-6-(2,6-difluorophenyl)-5-fluoropicolinamide |
| 35 | 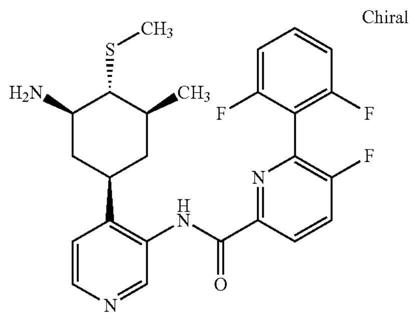 [SMILES: CS[C@H]1[C@H](N)C[C@H](c2ccncc2NC(=O)c2ccc(F)c(-c3c(F)cccc3F)n2)C[C@@H]1C] | Chiral | 487.2 | 0.65 | N-(4-((1R,3R,4R,5S)-3-amino-5-methyl-4-(methylthio)cyclohexyl)pyridin-3-yl)-6-(2,6-difluorophenyl)-5-fluoropicolinamide |
| 36 | 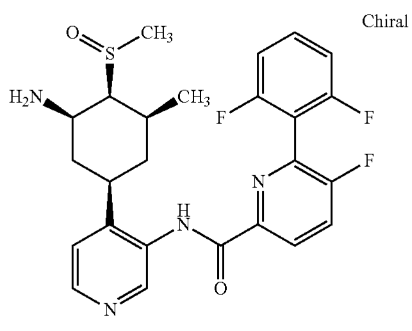 [SMILES: C[C@H]1C[C@@H](c2ccncc2NC(=O)c2ccc(F)c(-c3c(F)cccc3F)n2)C[C@@H](N)[C@H]1S(C)=O] | Chiral | 503.2 | 0.57 | N-(4-((1R,3R,4S,5S)-3-amino-5-methyl-4-((R)-methylsulfinyl)cyclohexyl)pyridin-3-yl)-6-(2,6-difluorophenyl)-5-fluoropicolinamide |

TABLE 1-continued

| Ex # | Structure | | LC/MS (MH+ on UPLC) | LC/MS (Rf on UPLC) | Chemical Name |
|---|---|---|---|---|---|
| 37 | 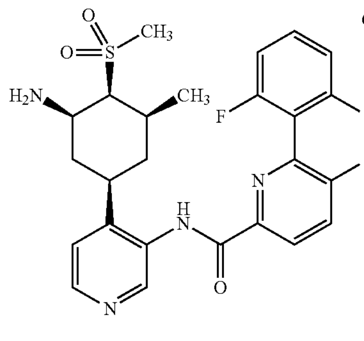 | Chiral | 519.2 | 0.58 | N-(4-((1R,3R,4S,5S)-3-amino-5-methyl-4-(methylsulfonyl)cyclohexyl)pyridin-3-yl)-6-(2,6-difluorophenyl)-5-fluoropicolinamide |
| 38 | 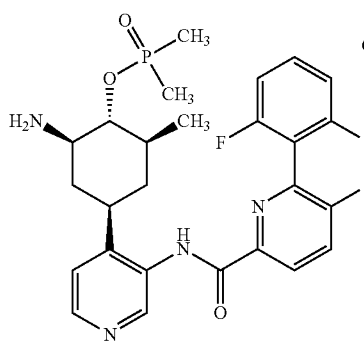 | Chiral | 533.3 | 0.60 | (1R,2R,4R,6S)-2-amino-4-(3-(6-(2,6-difluorophenyl)-5-fluoropicolinamido)pyridin-4-yl)-6-methylcyclohexyl dimethylphosphinate |
| 39 | 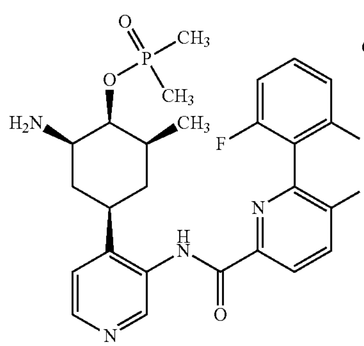 | Chiral | 533.3 | 0.59 | (1S,2R,4R,6S)-2-amino-4-(3-(6-(2,6-difluorophenyl)-5-fluoropicolinamido)pyridin-4-yl)-6-methylcyclohexyl dimethylphosphinate |
| 40 | 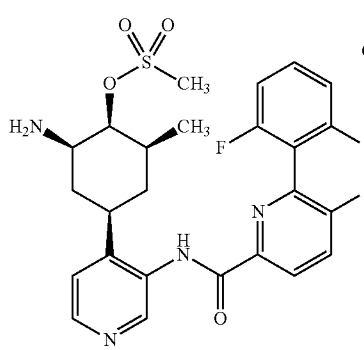 | Chiral | 535.2 | 0.60 | (1S,2R,4R,6S)-2-amino-4-(3-(6-(2,6-difluorophenyl)-5-fluoropicolinamido)pyridin-4-yl)-6-methylcyclohexyl methanesulfonate |

TABLE 1-continued

| Ex # | Structure | LC/MS (MH+ on UPLC) | LC/MS (Rf on UPLC) | Chemical Name |
|---|---|---|---|---|
| 41 | 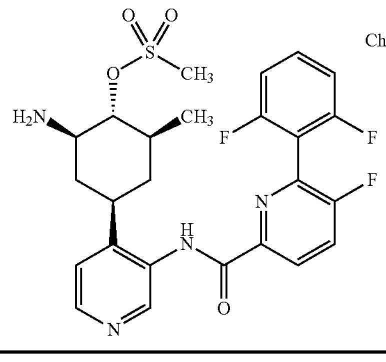 | 535.2 | 0.61 | (1R,2R,4R,6S)-2-amino-4-(3-(6-(2,6-difluorophenyl)-5-fluoropicolinamido)pyridin-4-yl)-6-methylcyclohexyl methanesulfonate |

Method 8

A homogeneous solution of 1 eq each of amine, carboxylic acid, HOAT and EDC in DMF, at a concentration of 0.5 M, was left standing for 24 hours at which time water and ethyl acetate were added. The organic phase was dried with sodium sulfate and purified via silica gel column chromatography eluting with ethyl acetate and hexanes to give the desired protected amide product. Alternatively the crude reaction mixture was directly purified by HPLC. Upon lyophilization, the TFA salt of the protected amide product was obtained. Alternatively, the HPLC fractions could be added to EtOAc and solid $Na_2CO_3$, separated and washed with $NaCl_{(sat)}$ Upon drying over $MgSO_4$, filtering and removing the volatiles in vacuo, the protected amide product was obtained as a free base. Alternatively, the crude reaction mixture was used for the deprotection step without further purification.

If an N-Boc protected amine was present, it was removed by treating with excess 4M HCl/dioxane for 14 hours or by treating with 25% $TFA/CH_2Cl_2$ for 2 hours. Upon removal of the volatiles in vacuo, the material was purified by RP HPLC yielding after lyophilization the amide product as the TFA salt. Alternatively, the HPLC fractions could be added to EtOAc and solid $Na_2CO_3$, separated and washed with $NaCl_{(sat)}$ Upon drying over $MgSO_4$, filtering and removing the volatiles in vacuo the free base was obtained. Upon dissolving in $MeCN/H_2O$, adding 1 eq. of 1 N HCl and lyophilizing, the HCl salt of the amide product was obtained.

If an N-Boc, OAc group were present, prior to Boc deprotection, the acetate group could be cleaved by treating with $K_2CO_3$ (2.0 equiv.) in ethanol at a concentration of 0.1 M for 24 hours.

If a TBDMS ether was present, it was deprotected prior to Boc removal by treating with 6N HCl, THF, methanol (1:2:1) at room temperature for 12 h. After removal of volatiles in vacuo, the Boc amino group was deprotected as described above. Alternatively, the TBDMS ether and Boc group could be both deprotected with 6N HCl, THF, methanol (1:2:1) if left at rt for 24 hours, or heated at 60° C. for 3 hours.

If a OBn or Cbz protecting group was present, it was deprotected by treatment with 10% Pd/C (0.2 equiv.) under an atmosphere of hydrogen in ethyl acetate and methanol (1:2). Upon completion, the reaction was filtered through Celite, washed with methanol, and the filtrate was concentrated in vacuo.

If a $CO_2Me$ group was present, it could be converted to the corresponding $CO_2H$ following Method 2.

Following the procedures of Method 8, the following compounds were prepared:

TABLE 2

| Ex# | Structure | LC/MS (MH+ on UPLC) | LC/MS (Rf on UPLC) | Chemical Name |
|---|---|---|---|---|
| 42 | 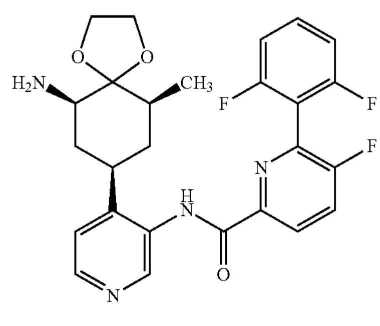 | 499.2 | 0.64 | N-(4-((6R,8R,10S)-6-amino-10-methyl-1,4-dioxaspiro[4.5]decan-8-yl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 43 | 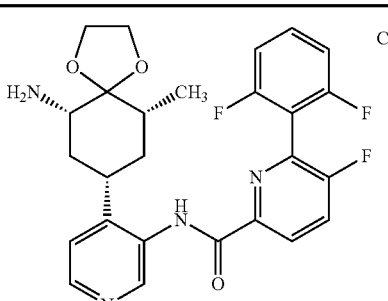 Chiral | 499.2 | 0.64 | N-(4-((6S,8S,10R)-6-amino-10-methyl-1,4-dioxaspiro[4.5]decan-8-yl)pyridin-3-yl)-6-(2,6-difluorophenyl)-5-fluoropicolinamide |
| 44 | 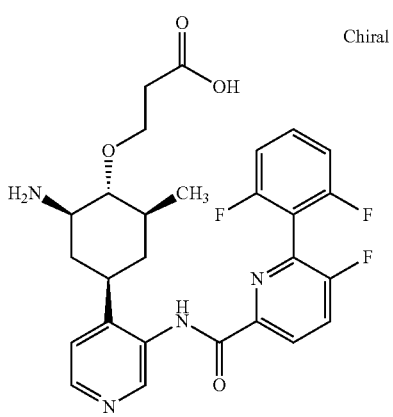 [SMILES: C[C@H]1C[C@@H](c2ccncc2NC(=O)c2ccc(F)c(-c3c(F)cccc3F)n2)C[C@@H](N)[C@@H]1OCCC(=O)O] Chiral | 529.3 | 0.63 | 3-((1R,2R,4R,6S)-2-amino-4-(3-(6-(2,6-difluorophenyl)-5-fluoropicolinamido)pyridin-4-yl)-6-methylcyclohexyloxy)propanoic acid |
| 45 | 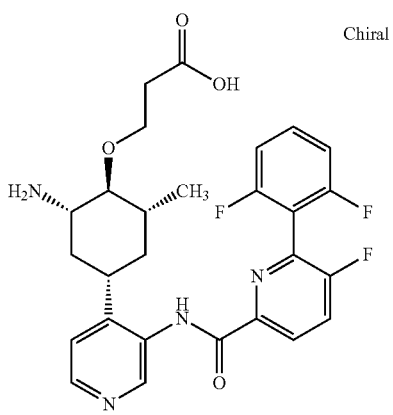 [SMILES: C[C@@H]1C[C@H](c2ccncc2NC(=O)c2ccc(F)c(-c3c(F)cccc3F)n2)C[C@H](N)[C@H]1OCCC(=O)O] Chiral | 529.3 | 0.62 | 3-((1S,2S,4S,6R)-2-amino-4-(3-(6-(2,6-difluorophenyl)-5-fluoropicolinamido)pyridin-4-yl)-6-methylcyclohexyloxy)propanoic acid |
| 46 | 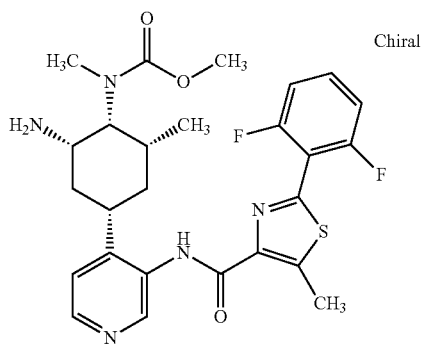 [SMILES: COC(=O)N(C)[C@@H]1[C@H](C)C[C@H](c2ccncc2NC(=O)c2nc(-c3c(F)cccc3F)sc2C)C[C@@H]1N] Chiral | 531.3 | 0.59 | methyl (1R,2S,4S,6R)-2-amino-4-(3-(5-amino-2-(2,6-difluorophenyl)thiazole-4-carboxamido)pyridin-4-yl)-6-methylcyclohexyl(methyl)carbamate |

TABLE 2-continued

| Ex# | Structure | LC/MS (MH+ on UPLC) | LC/MS (Rf on UPLC) | Chemical Name |
|---|---|---|---|---|
| 47 | Chiral | 531.3 | 0.58 | methyl (1S,2R,4R,6S)-2-amino-4-(3-(5-amino-2-(2,6-difluorophenyl)thiazole-4-carboxamido)pyridin-4-yl)-6-methylcyclohexyl(methyl)carbamate |
| 48 | Chiral | 508.3 | 0.59 | N-(4-((1S,3S,4R,5R)-3-amino-5-methyl-4-(1H-1,2,4-triazol-1-yl)cyclohexyl)pyridin-3-yl)-6-(2,6-difluorophenyl)-5-fluoropicolinamide |
| 49 | Chiral | 508.3 | 0.59 | N-(4-((1R,3R,4S,5S)-3-amino-5-methyl-4-(1H-1,2,4-triazol-1-yl)cyclohexyl)pyridin-3-yl)-6-(2,6-difluorophenyl)-5-fluoropicolinamide |
| 50 | Chiral | 459.2 | 0.58 | N-(4-((1R,3R,4S,5S)-3-amino-4-methoxy-5-methylcyclohexyl)pyridin-3-yl)-2-(2,6-difluorophenyl)thiazole-4-carboxamide |

TABLE 2-continued

| Ex# | Structure | LC/MS (MH+ on UPLC) | LC/MS (Rf on UPLC) | Chemical Name |
|---|---|---|---|---|
| 51 | Chiral | 454.3 | 0.54 | N-(4-((1R,3R,4S,5S)-3-amino-4-methoxy-5-methylcyclohexyl)pyridin-3-yl)-2-(2,6-difluorophenyl)pyrimidine-4-carboxamide |
| 52 | Chiral | 542.2 | 0.68 | methyl (1R,2S,4S,6R)-2-amino-4-(3-(6-(2,6-difluoro-4-methylphenyl)-5-fluoropicolinamido)pyridin-4-yl)-6-methylcyclohexyl(methyl)carbamate |
| 53 | Chiral | 542.2 | 0.67 | methyl (1S,2R,4R,6S)-2-amino-4-(3-(6-(2,6-difluoro-4-methylphenyl)-5-fluoropicolinamido)pyridin-4-yl)-6-methylcyclohexyl(methyl)carbamate |
| 54 | Chiral | 470.0 | 0.57 | 5-amino-N-(4-((3S,4S,5R)-3-amino-4-cyano-5-methylpiperidin-1-yl)pyridin-3-yl)-2-(2,6-difluorophenyl)thiazole-4-carboxamide |

TABLE 2-continued

| Ex# | Structure | LC/MS (MH+ on UPLC) | LC/MS (Rf on UPLC) | Chemical Name |
|---|---|---|---|---|
| 55 | Chiral | 481.1 | 0.66 | N-(4-((3S,4S,5R)-3-amino-4-cayno-5-methylpiperidin-1-yl)pyridin-3-yl)-6-(2,6-difluoro-4-methylphenyl)-5-fluoropicolinamide |
| 56 | Chiral | 509.2 | 0.57 | N-(4-((3R,4S,5S)-3-amino-5-methyl-4-(1H-1,2,4-triazol-1-yl)piperidin-1-yl)pyridin-3-yl)-6-(2,6-difluorophenyl)-5-fluoropicolinamide |
| 57 | Chiral | 467.0 | 0.60 | N-(4-((3S,4S,5R)-3-amino-4-cyano-5-methylpiperidin-1-yl)pyridin-3-yl)-6-(2,6-difluorophenyl)-5-fluoropicolinamide |
| 58 | Chiral | 543.2 | 0.67 | methyl (3R,4S,5S)-3-amino-1-(3-(6-(2,6-difluoro-4-methylphenyl)-5-fluoropicolinamido)pyridin-4-yl)-5-methylpiperidin-4-yl(methyl)carbamate |

TABLE 2-continued

| Ex# | Structure | | LC/MS (MH+ on UPLC) | LC/MS (Rf on UPLC) | Chemical Name |
|---|---|---|---|---|---|
| 59 | 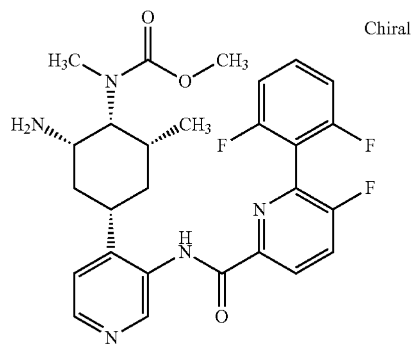 [SMILES: COC(=O)N(C)[C@@H]1[C@H](C)C[C@H](c2ccncc2NC(=O)c2ccc(F)c(-c3c(F)cccc3F)n2)C[C@@H]1N] | Chiral | 528.1 | 0.64 | methyl (1R,2S,4S,6R)-2-amino-4-(3-(6-(2,6-difluorophenyl)-5-fluoropicolinamido)pyridin-4-yl)-6-methylcyclohexyl(methyl)carbamate |
| 60 | 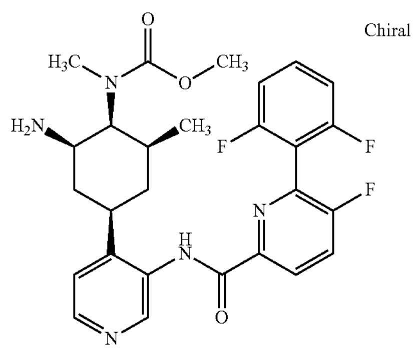 [SMILES: COC(=O)N(C)[C@@H]1[C@H](N)C[C@H](c2ccncc2NC(=O)c2ccc(F)c(-c3c(F)cccc3F)n2)C[C@@H]1C] | Chiral | 528.2 | 0.63 | methyl (1S,2R,4R,6S)-2-amino-4-(3-(6-(2,6-difluorophenyl)-5-fluoropicolinamido)pyridin-4-yl)-6-methylcyclohexyl(methyl)carbamate |
| 61 | 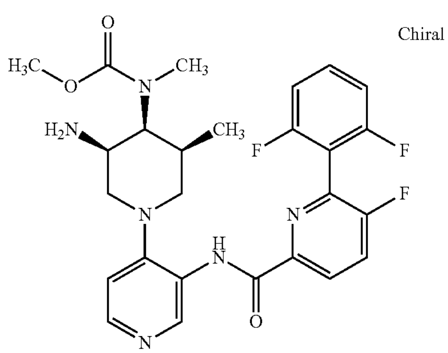 [SMILES: COC(=O)N(C)[C@@H]1[C@H](N)CN(c2ccncc2NC(=O)c2ccc(F)c(-c3c(F)cccc3F)n2)C[C@@H]1C] | Chiral | 529.2 | 0.63 | methyl (3R,4S,5S)-3-amino-1-(3-(6-(2,6-difluorophenyl)-5-fluoropicolinamido)pyridin-4-yl)-5-methylpiperidin-4-yl(methyl)carbamate |
| 62 | 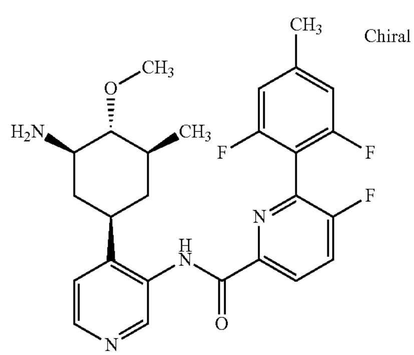 [SMILES: CO[C@H]1[C@H](N)C[C@H](c2ccncc2NC(=O)c2ccc(F)c(-c3c(F)cc(C)cc3F)n2)C[C@@H]1C] | Chiral | 485.1 | 0.69 | N-(4-((1R,3R,4R,5S)-3-amino-4-methoxy-5-methylcyclohexyl)pyridin-3-yl)-6-(2,6-difluoro-4-methylphenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 63 | Chiral | 513.2 | 0.61 | 5-amino-N-(4-((1S,3S,4R,5R)-3-amino-4-(2-cyanoethoxy)-5-methylcyclohexyl)pyridin-3-yl)-2-(2,6-difluorophenyl)thiazole-4-carboxamide |
| 64 | Chiral | 513.2 | 0.61 | 5-amino-N-(4-((1R,3R,4S,5S)-3-amino-4-(2-cyanoethoxy)-5-methylcyclohexyl)pyridin-3-yl)-2-(2,6-difluorophenyl)thiazole-4-carboxamide |
| 65 | Chiral | 513.2 | 0.53 | N-(4-((3R,4S,5S)-3-amino-5-methyl-4-(N-methylacetamido)piperidin-1-yl)pyridin-3-yl)-6-(2,6-difluorophenyl)-5-fluoropicolinamide |
| 66 | Chiral | 539.3 | 0.57 | N-(4-((3R,4S,5S)-3-amino-4-(4-(hydroxymethyl)-1H-1,2,3-triazol-1-yl)-5-methylpiperidin-1-yl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 67 | Chiral | 466.1 | 0.61 | N-(4-((1S,3S,4R,5R)-3-amino-4-cyano-5-methylcyclohexyl)pyridin-3-yl)-6-(2,6-difluorophenyl)-5-fluoropicolinamide |
| 68 | Chiral | 466.1 | 0.61 | N-(4-((1R,3R,4S,5S)-3-amino-4-cyano-5-methylcyclohexyl)pyridin-3-yl)-6-(2,6-difluorophenyl)-5-fluoropicolinamide |
| 69 | Chiral | 474.1 | 0.58 | 5-amino-N-(4-((1R,3R,4R,5S)-3-amino-4-methoxy-5-methylcyclohexyl)pyridin-3-yl)-2-(2,6-difluorophenyl)thiazole-4-carboxamide |
| 70 | Chiral | 469.1 | 0.54 | 5-amino-N-(4-((1R,3R,4R,5S)-3-amino-4-methoxy-5-methylcyclohexyl)pyridin-3-yl)-2-(2,6-difluorophenyl)pyrimidine-4-carboxamide |

TABLE 2-continued

| Ex# | Structure | LC/MS (MH+ on UPLC) | LC/MS (Rf on UPLC) | Chemical Name |
|---|---|---|---|---|
| 71 | Chiral | 488.2 | 0.68 | 5-amino-N-(4-((1R,3R,4S,5S)-3-amino-4-ethoxy-5-methylcyclohexyl)pyridin-3-yl)-2-(2,6-difluorophenyl)thiazole-4-carboxamide |
| 72 | Chiral | 518.1 | 0.60 | methyl ((3R,4S,5S)-3-amino-1-(2-(5-amino-2-(2,6-difluorophenyl)thiazole-4-carboxamido)phenyl)-5-methylpiperidin-4-yl)carbamate |
| 73 | Chiral | 577.2 | 0.65 | N-(4-((1R,3R,4S,5S)-3-amino-5-methyl-4-(2-(methylsulfonyl)ethoxy)cyclohexyl)pyridin-3-yl)-6-(2,6-difluoro-4-methylphenyl)-5-fluoropicolinamide |
| 74 | Chiral | 577.2 | 0.65 | N-(4-((1S,3S,4R,5R)-3-amino-5-methyl-4-(2-(methylsulfonyl)ethoxy)cyclohexyl)pyridin-3-yl)-6-(2,6-difluoro-4-methylphenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 75 | 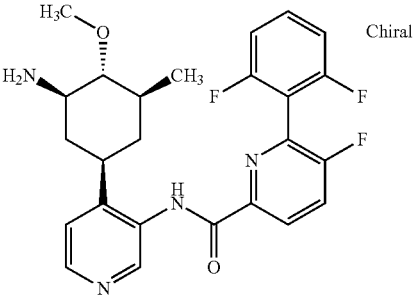 [SMILES: CO[C@H]1[C@H](N)C[C@H](c2ccncc2NC(=O)c2ccc(F)c(-c3c(F)cccc3F)n2)C[C@@H]1C] | 471.1 | 0.66 | N-(4-((1R,3R,4R,5S)-3-amino-4-methoxy-5-methylcyclohexyl)pyridin-3-yl)-6-(2,6-difluorophenyl)-5-fluoropicolinamide |
| 76 | 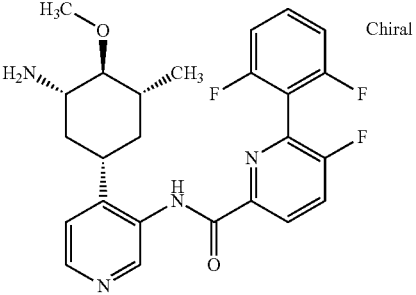 [SMILES: CO[C@H]1[C@H](C)C[C@H](c2ccncc2NC(=O)c2ccc(F)c(-c3c(F)cccc3F)n2)C[C@@H]1N] | 471.1 | 0.67 | N-(4-((1S,3S,4S,5R)-3-amino-4-methoxy-5-methylcyclohexyl)pyridin-3-yl)-6-(2,6-difluorophenyl)-5-fluoropicolinamide |
| 77 | 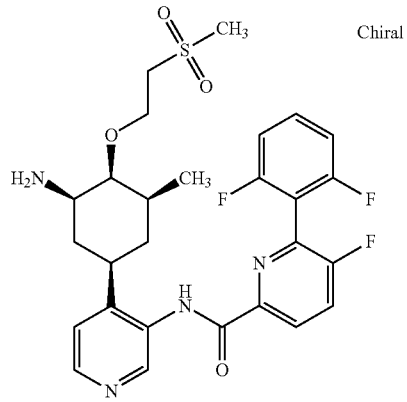 [SMILES: C[C@H]1C[C@@H](c2ccncc2NC(=O)c2ccc(F)c(-c3c(F)cccc3F)n2)C[C@@H](N)[C@H]1OCCS(C)(=O)=O] | 563.3 | 0.61 | N-(4-((1R,3R,4S,5S)-3-amino-5-methyl-4-(2-(methylsulfonyl)ethoxy)cyclohexyl)pyridin-3-yl)-6-(2,6-difluorophenyl)-5-fluoropicolinamide |
| 78 | 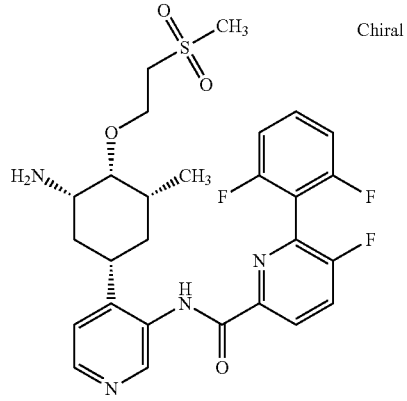 [SMILES: C[C@@H]1C[C@H](c2ccncc2NC(=O)c2ccc(F)c(-c3c(F)cccc3F)n2)C[C@H](N)[C@@H]1OCCS(C)(=O)=O] | 563.3 | 0.61 | N-(4-((1S,3S,4R,5R)-3-amino-5-methyl-4-(2-(methylsulfonyl)ethoxy)cyclohexyl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 79 | Chiral | 469.3 | 0.53 | 5-amino-N-(4-((1R,3R,4S,5S)-3-amino-4-methoxy-5-methylcyclohexyl)pyridin-3-yl)-2-(2,6-difluorophenyl)pyrimidine-4-carboxamide |
| 80 | Chiral | 529.1 | 0.69 | methyl ((3R,4S,5S)-3-amino-1-(3-(6-(2,6-difluro-4-methylphneyl)-5-fluoropicolinamido)pyridin-4-yl)-5-methylpiperidin-4-yl)carbamate |
| 81 | Chiral | 515.1 | 0.64 | methyl ((3R,4S,5S)-3-amino-1-(3-(6-(2,6-difluorophenyl)-5-fluoropicolinamido)pyridin-4-yl)-5-methylpiperidin-4-yl)carbamate |
| 82 | Chiral | 474.2 | 0.59 | 5-amino-N-(4-((1R,3R,4S,5S)-3-amino-4-methoxy-5-methylcyclohexyl)pyridin-3-yl)-2-(2,6-difluorophenyl)thiazole-4-carboxamide |

TABLE 2-continued

| Ex# | Structure | LC/MS (MH+ on UPLC) | LC/MS (Rf on UPLC) | Chemical Name |
|---|---|---|---|---|
| 83 | Chiral | 524.3 | 0.67 | N-(4-((1R,3R,4S,5S)-3-amino-4-(2-cyanoethoxy)-5-methylcyclohexyl)pyridin-3-yl)-6-(2,6-difluoro-4-methylphenyl)-5-fluoropicolinamide |
| 84 | Chiral | 524.3 | 0.67 | N-(4-((1S,3S,4R,5R)-3-amino-4-(2-cyanoethoxy)-5-methylcyclohexyl)pyridin-3-yl)-6-(2,6-difluoro-4-methylphenyl)-5-fluoropicolinamide |
| 85 | Chiral | 510.3 | 0.62 | N-(4-((1R,3R,4S,5S)-3-amino-4-(2-cyanoethoxy)-5-methylcyclohexyl)pyridin-3-yl)-6-(2,6-difluorophenyl)-5-fluoropicolinamide |
| 86 | Chiral | 510.3 | 0.62 | N-(4-((1S,3S,4R,5R)-3-amino-4-(2-cyanoethoxy)-5-methylcyclohexyl)pyridin-3-yl)-6-(2,6-difluorophenyl)-5-fluoropicolinamide |

TABLE 2-continued

| Ex# | Structure | | LC/MS (MH+ on UPLC) | LC/MS (Rf on UPLC) | Chemical Name |
|---|---|---|---|---|---|
| 87 | 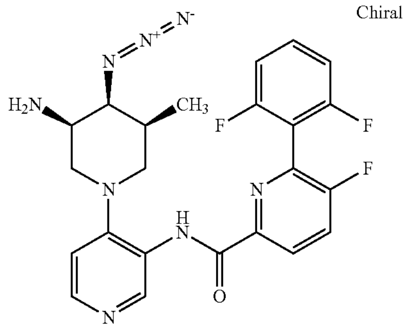 [SMILES: C[C@H]1CN(c2ccncc2NC(=O)c2ccc(F)c(-c3c(F)cccc3F)n2)C[C@@H](N)[C@H]1N=[N+]=[N-]] | Chiral | 483.1 | 0.62 | N-(4-((3R,4S,5S)-3-amino-4-azido-5-methylpiperidin-1-yl)pyridin-3-yl)-6-(2,6-difluorophenyl)-5-fluoropicolinamide |
| 88 | 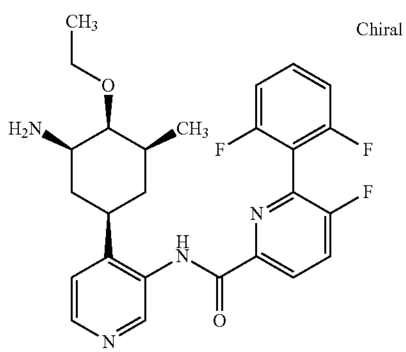 [SMILES: CCO[C@@H]1[C@H](N)C[C@H](c2ccncc2NC(=O)c2ccc(F)c(-c3c(F)cccc3F)n2)C[C@@H]1C] | Chiral | 499.2 | 0.73 | N-(4-((1R,3R,4S,5S)-3-amino-4-ethoxy-5-methylcyclohexyl)pyridin-3-yl)-6-(2,6-difluorophenyl)-5-fluoropicolinamide |
| 89 | 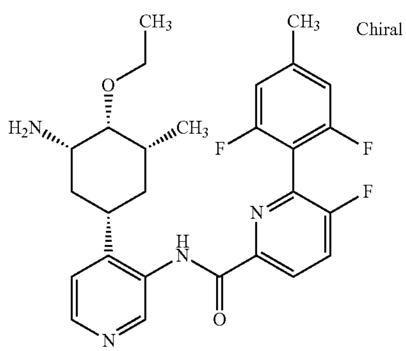 [SMILES: CCO[C@@H]1[C@H](C)C[C@H](c2ccncc2NC(=O)c2ccc(F)c(-c3c(F)cc(C)cc3F)n2)C[C@@H]1N] | Chiral | 499.2 | 0.73 | N-(4-((1S,3S,4R,5R)-3-amino-4-ethoxy-5-methylcyclohexyl)pyridin-3-yl)-6-(2,6-difluoro-4-methylphenyl)-5-fluoropicolinamide |
| 90 | 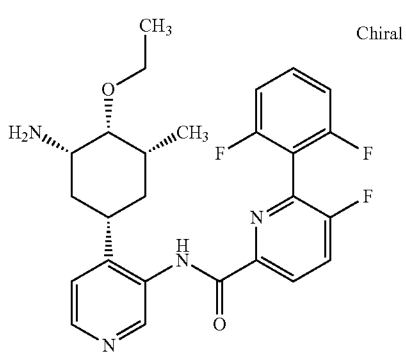 [SMILES: CCO[C@@H]1[C@H](C)C[C@H](c2ccncc2NC(=O)c2ccc(F)c(-c3c(F)cccc3F)n2)C[C@@H]1N] | Chiral | 485.2 | 0.68 | N-(4-((1S,3S,4R,5R)-3-amino-4-ethoxy-5-methylcyclohexyl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 91 | 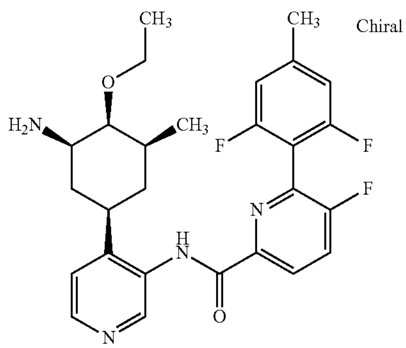 [SMILES: CCO[C@@H]1[C@H](N)C[C@H](c2ccncc2NC(=O)c2ccc(F)c(-c3c(F)cc(C)cc3F)n2)C[C@@H]1C] | 485.2 | 0.68 | N-(4-((1R,3R,4S,5S)-3-amino-4-ethoxy-5-methylcyclohexyl)pyridin-3-yl)-6-(2,6-difluoro-4-methylphenyl)-5-fluoropicolinamide |
| 92 | 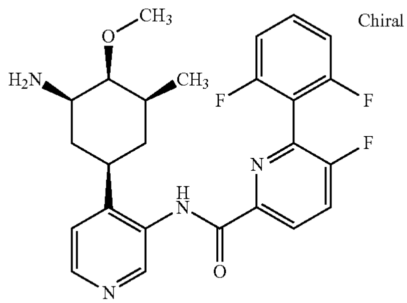 [SMILES: CO[C@@H]1[C@H](N)C[C@H](c2ccncc2NC(=O)c2ccc(F)c(-c3c(F)cccc3F)n2)C[C@@H]1C] | 471.1 | 0.64 | N-(4-((1R,3R,4S,5S)-3-amino-4-methoxy-5-methylcyclohexyl)pyridin-3-yl)-6-(2,6-difluorophenyl)-5-fluoropicolinamide |
| 93 | 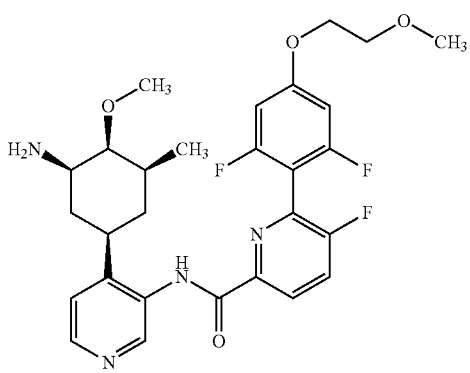 | 545.3 | 0.64 | N-(4-((1R,3R,4S,5S)-3-amino-4-methoxy-5-methylcyclohexyl)pyridin-3-yl)-6-(2,6-difluoro-4-(2-methoxyethoxy)phenyl)-5-fluoropicolinamide |
| 94 | 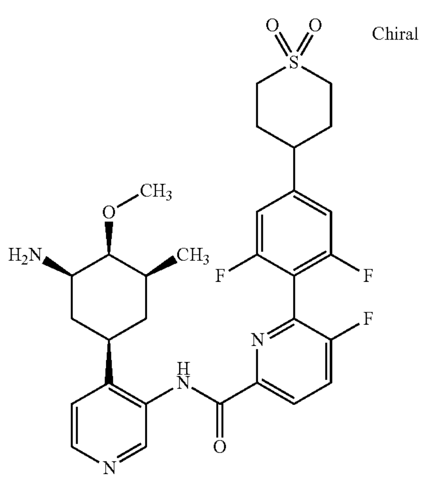 [SMILES: CO[C@@H]1[C@H](N)C[C@H](c2ccncc2NC(=O)c2ccc(F)c(-c3c(F)cc(C4CCS(=O)(=O)CC4)cc3F)n2)C[C@@H]1C] | 603.3 | 0.63 | N-(4-((1R,3R,4S,5S)-3-amino-4-methoxy-5-methylcyclohexyl)pyridin-3-yl)-6-(4-(1,1-dioxidotetrahydro-2H-thiopyran-4-yl)-2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 95 | 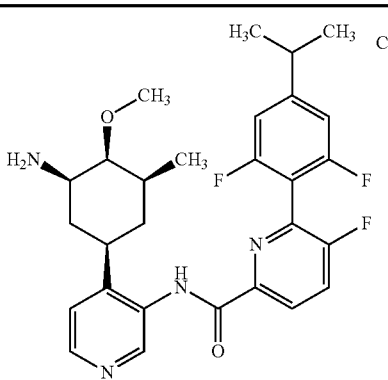 | 513.2 | 0.79 | N-(4-((1R,3R,4S,5S)-3-amino-4-methoxy-5-methylcyclohexyl)pyridin-3-yl)-6-(2,6-difluoro-4-isopropylphenyl)-5-fluoropicolinamide |
| 96 | 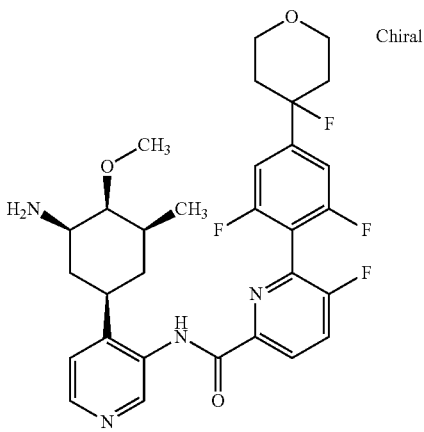 [SMILES: CO[C@@H]1[C@H](N)C[C@H](c2ccncc2NC(=O)c2ccc(F)c(-c3c(F)cc(C4(F)CCOCC4)cc3F)n2)C[C@@H]1C] | 573.3 | 0.76 | N-(4-((1R,3R,4S,5S)-3-amino-4-methoxy-5-methylcyclohexyl)pyridin-3-yl)-6-(2,6-difluoro-4-(4-fluorotetrahydro-2H-pyran-4-yl)phenyl)-5-fluoropicolinamide |
| 97 | 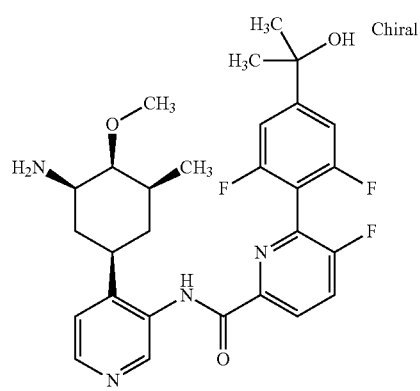 [SMILES: CO[C@@H]1[C@H](N)C[C@H](c2ccncc2NC(=O)c2ccc(F)c(-c3c(F)cc(C(C)(C)O)cc3F)n2)C[C@@H]1C] | 529.3 | 0.68 | N-(4-((1R,3R,4S,5S)-3-amino-4-methoxy-5-methylcyclohexyl)pyridin-3-yl)-6-(2,6-difluoro-4-(2-hydroxypropan-2-yl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 98 | Chiral | 541.3 | 0.75 | N-(4-((1R,3R,4S,5S)-3-amino-4-methoxy-5-methylcyclohexyl)pyridin-3-yl)-6-(2,6-difluoro-4-(1-hydroxycyclobutyl)phenyl)-5-fluoropicolinamide |
| 99 | Chiral | 555.3 | 0.66 | N-(4-((1R,3R,4S,5S)-3-amino-4-methoxy-5-methylcyclohexyl)pyridin-3-yl)-6-(2,6-difluoro-4-tetrahydro-2H-pyran-4-yl)phenyl)-5-fluoropicolinamide |
| 100 | Chiral | 529.3 | 0.80 | N-(4-((1R,3R,4S,5S)-3-amino-4-methoxy-5-methylcyclohexyl)pyridin-3-yl)-6-(4-(ethoxymethyl)-2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 101 | 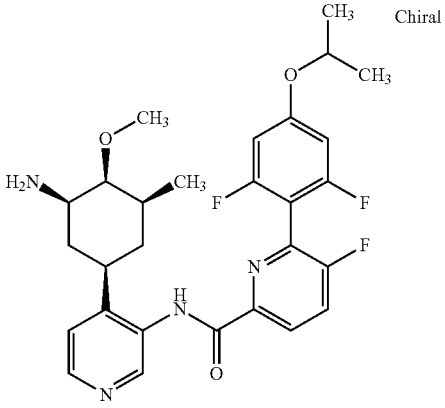 [SMILES: CO[C@@H]1[C@H](N)C[C@H](c2ccncc2NC(=O)c2ccc(F)c(-c3c(F)cc(OC(C)C)cc3F)n2)C[C@@H]1C] | 529.3 | 0.86 | N-(4-((1R,3R,4S,5S)-3-amino-4-methoxy-5-methylcyclohexyl)pyridin-3-yl)-6-(2,6-difluoro-4-isopropoxyphenyl)-5-fluoropicolinamide |
| 102 | 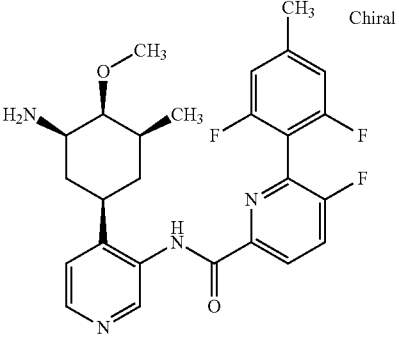 [SMILES: CO[C@@H]1[C@H](N)C[C@H](c2ccncc2NC(=O)c2ccc(F)c(-c3c(F)cc(C)cc3F)n2)C[C@@H]1C] | 485.2 | 0.73 | N-(4-((1R,3R,4S,5S)-3-amino-4-methoxy-5-methylcyclohexyl)pyridin-3-yl)-6-(2,6-difluoro-4-methylphenyl)-5-fluoropicolinamide |
| 103 | 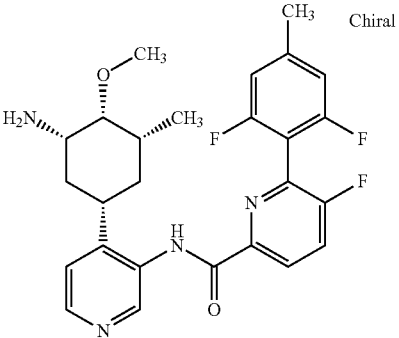 [SMILES: CO[C@@H]1[C@H](C)C[C@H](c2ccncc2NC(=O)c2ccc(F)c(-c3c(F)cc(C)cc3F)n2)C[C@@H]1N] | 485.4 | 0.68 | N-(4-((1S,3S,4R,5R)-3-amino-4-methoxy-5-methylcyclohexyl)pyridin-3-yl)-6-(2,6-difluoro-4-methylphenyl)-5-fluoropicolinamide |
| 104 | 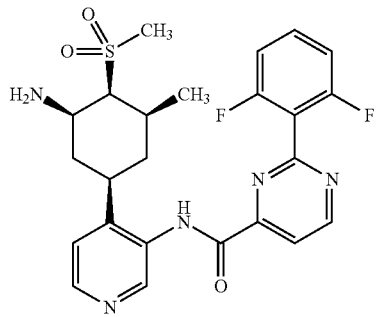 [SMILES: C[C@H]1C[C@@H](c2ccncc2NC(=O)c2ccnc(-c3c(F)cccc3F)n2)C[C@@H](N)[C@H]1S(C)(=O)=O] | 502.3 | 0.50 | N-(4-((1R,3R,4S,5S)-3-amino-5-methyl-4-(methylsulfonyl)cyclohexyl)pyridin-3-yl)-2-(2,6-difluorophenyl)pyrimidine-4-carboxamide |

TABLE 2-continued

| Ex# | Structure | LC/MS (MH+ on UPLC) | LC/MS (Rf on UPLC) | Chemical Name |
|---|---|---|---|---|
| 105 | 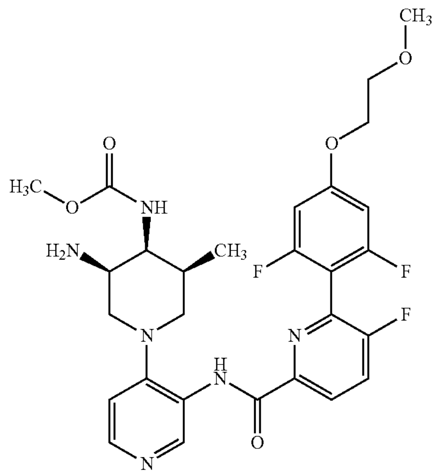 | 589.4 | 0.62 | methyl ((3R,4S,5S)-3-amino-1-(3-(6-(2,6-difluoro-4-(2-methoxyethoxy)phenyl)-5-fluoropicolinamido)pyridin-4-yl)-5-methylpiperidin-4-yl)carbamate |
| 106 | 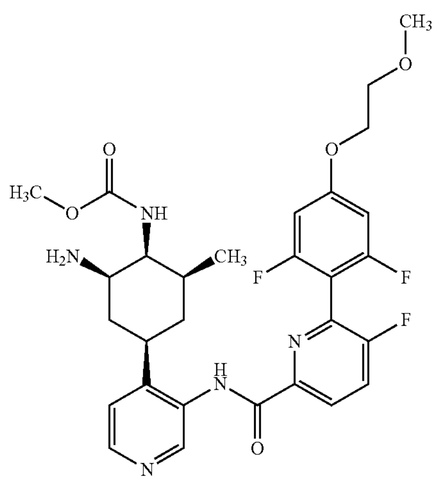 | 588.4 | 0.63 | methyl ((1S,2R,4R,6S)-2-amino-4-(3-(6-(2,6-difluoro-4-(2-methoxyethoxy)phenyl)-5-fluoropicolinamido)pyridin-4-yl)-6-methylcyclohexyl)carbamate |
| 107 | 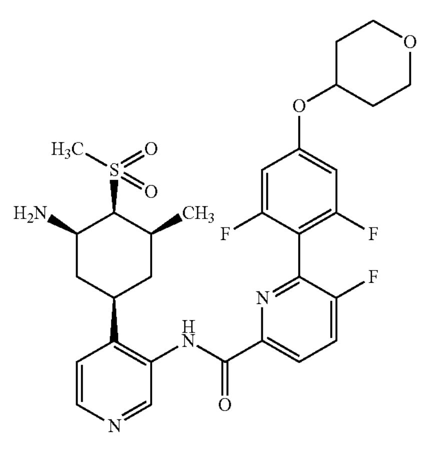 [SMILES: C[C@H]1C[C@@H](c2ccncc2NC(=O)c2ccc(F)c(-c3c(F)cc(OC4CCOCC4)cc3F)n2)C[C@@H](N)[C@H]1S(C)(=O)=O] | 619.4 | 0.65 | N-(4-((1R,3R,4S,5S)-3-amino-5-methyl-4-(methylsulfonyl)cyclohexyl)pyridin-3-yl)-6-(2,6-difluoro-4-((tetrahydro-2H-pyran-4-yl)oxy)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 108 | 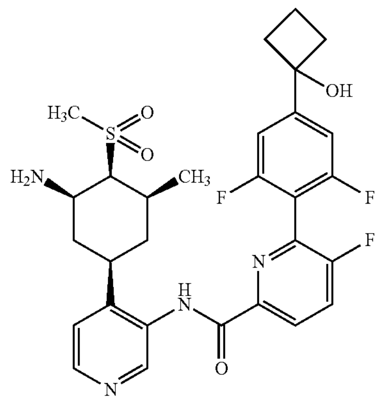 [SMILES: C[C@H]1C[C@@H](c2ccncc2NC(=O)c2ccc(F)c(-c3c(F)cc(C4(O)CCC4)cc3F)n2)C[C@@H](N)[C@H]1S(C)(=O)=O] | 589.4 | 0.62 | N-(4-((1R,3R,4S,5S)-3-amino-5-methyl-4-(methylsulfonyl)cyclohexyl)pyridin-3-yl)-6-(2,6-difluoro-4-(1-hydroxycyclobutyl)phenyl)-5-fluoropicolinamide |
| 109 | 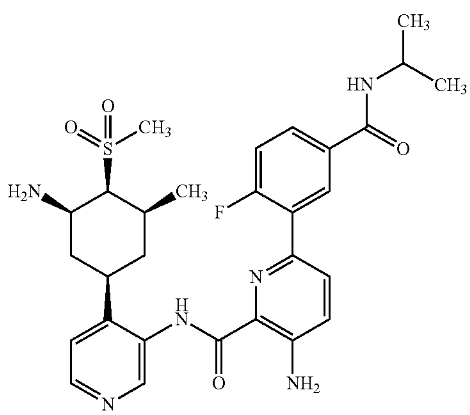 [SMILES: CC(C)NC(=O)c1ccc(F)c(-c2ccc(N)c(C(=O)Nc3cnccc3[C@H]3C[C@@H](N)[C@@H](S(C)(=O)=O)[C@@H](C)C3)n2)c1] | 583.4 | 0.58 | 3-amino-N-(4-((1R,3R,4S,5S)-3-amino-5-methyl-4-(methylsulfonyl)cyclohexyl)pyridin-3-yl)-6-(2-fluoro-5-(isopropylcarbamoyl)phenyl)picolinamide |
| 110 | 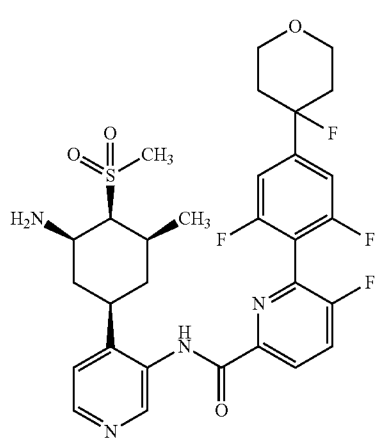 [SMILES: C[C@H]1C[C@@H](c2ccncc2NC(=O)c2ccc(F)c(-c3c(F)cc(C4(F)CCOCC4)cc3F)n2)C[C@@H](N)[C@H]1S(C)(=O)=O] | 621.4 | 0.66 | N-(4-((1R,3R,4S,5S)-3-amino-5-methyl-4-(methylsulfonyl)cyclohexyl)pyridin-3-yl)-6-(2,6-difluoro-4-(4-fluorotetrahydro-2H-pyran-4-yl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 111 | 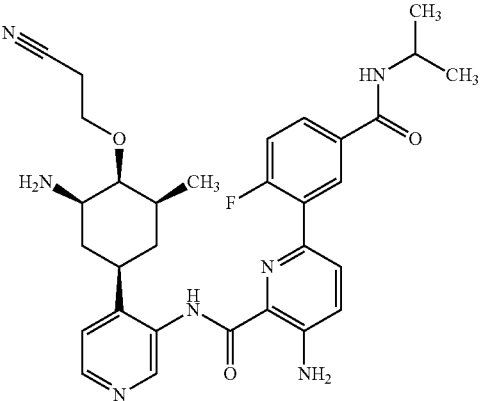 [SMILES: CC(C)NC(=O)c1ccc(F)c(-c2ccc(N)c(C(=O)Nc3cnccc3[C@H]3C[C@@H](N)[C@@H](OCCC#N)[C@@H](C)C3)n2)c1] | 574.4 | 0.59 | 3-amino-N-(4-((1R,3R,4S,5S)-3-amino-4-(2-cyanoethoxy)-5-methylcyclohexyl)pyridin-3-yl)-6-(2-fluoro-5-(isopropylcarbamoyl)phenyl)picolinamide |
| 112 | 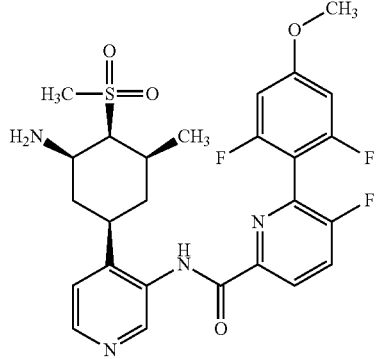 [SMILES: COc1cc(F)c(-c2nc(C(=O)Nc3cnccc3[C@H]3C[C@@H](N)[C@@H](S(C)(=O)=O)[C@@H](C)C3)ccc2F)c(F)c1] | 549.3 | 0.63 | N-(4-((1R,3R,4S,5S)-3-amino-5-methyl-4-(methylsulfonyl)cyclohexyl)pyridin-3-yl)-6-(2,6-difluoro-4-methoxyphenyl)-5-fluoropicolinamde |
| 113 | 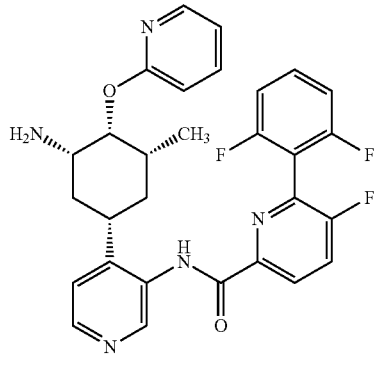 [SMILES: C[C@@H]1C[C@H](c2ccncc2NC(=O)c2ccc(F)c(-c3c(F)cccc3F)n2)C[C@H](N)[C@@H]1Oc1ccccn1] | 534.2 | 0.69 | N-(4-((1S,3S,4R,5R)-3-amino-5-methyl-4-(pyridin-2-yloxy)cyclohexyl)pyridin-3-yl)-6-(2,6-difluorophenyl)-5-fluoropicolinamide |
| 114 | 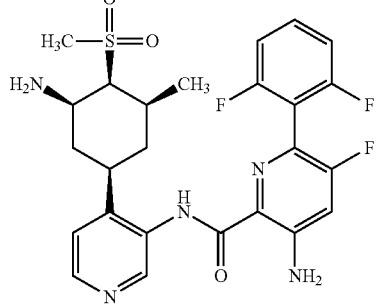 | 534.3 | 0.61 | 3-amino-N-(4-((1R,3R,4S,5S)-3-amino-5-methyl-4-(methylsulfonyl)cyclohexyl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 115 | 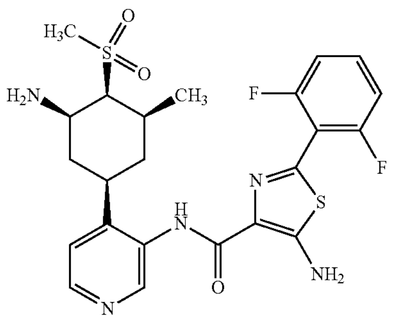 [SMILES: C[C@H]1C[C@@H](c2ccncc2NC(=O)c2nc(-c3c(F)cccc3F)sc2N)C[C@@H](N)[C@H]1S(C)(=O)=O] | 522.2 | 0.57 | 5-amino-N-(4-((1R,3R,4S,5S)-3-amino-5-methyl-4-(methylsulfonyl)cyclohexyl)pyridin-3-yl)-2-(2,6-difluorophenyl)thiazole-4-carboxamide |
| 116 | AND Enantiomer | 577.3 | 0.66 | N-(4-((1R,3R,4S,5S)-3-amino-5-methyl-4-(methylsulfonyl)cyclohexyl)pyridin-3-yl)-6-(4-(ethoxymethyl)-2,6-difluorophenyl)-5-fluoropicolinamide |
| 117 | 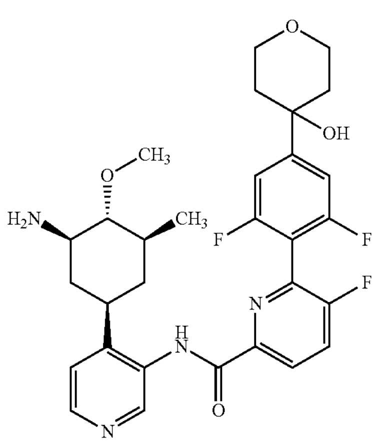 [SMILES: CO[C@H]1[C@H](N)C[C@H](c2ccncc2NC(=O)c2ccc(F)c(-c3c(F)cc(C4(O)CCOCC4)cc3F)n2)C[C@@H]1C] | 571.4 | 0.59 | N-(4-((1R,3R,4R,5S)-3-amino-4-methoxy-5-methylcyclohexyl)pyridin-3-yl)-5-(2,6-difluoro-4-(4-hydroxytetrahydro-2H-pyran-4-yl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 118 | 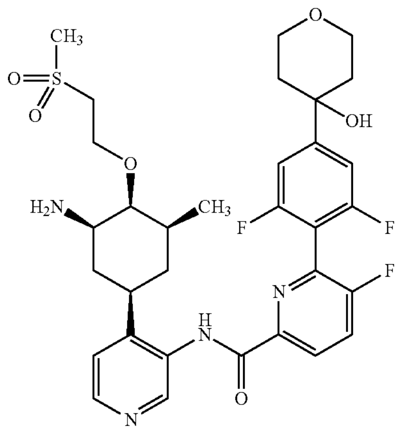 [SMILES: C[C@H]1C[C@@H](c2ccncc2NC(=O)c2ccc(F)c(-c3c(F)cc(C4(O)CCOCC4)cc3F)n2)C[C@@H](N)[C@H]1OCCS(C)(=O)=O] | 663.5 | 0.58 | N-(4-((1R,3R,4S,5S)-3-amino-5-methyl-4-(2-(methylsulfonyl)ethoxy)cyclohexyl)pyridin-3-yl)-6-(2,6-difluoro-4-(4-hydroxytetrahydro-2H-pyran-4-yl)phenyl)-5-fluoropicolinamide |
| 119 | 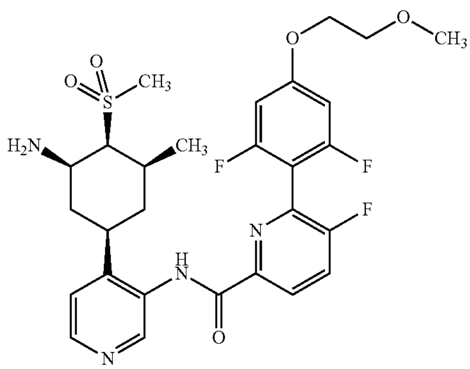 [SMILES: COCCOc1cc(F)c(-c2nc(C(=O)Nc3cnccc3[C@H]3C[C@@H](N)[C@@H](S(C)(=O)=O)[C@@H](C)C3)ccc2F)c(F)c1] | 593.3 | 0.62 | N-(4-((1R,3R,4S,5S)-3-amino-5-methyl-4-(methylsulfonyl)cyclohexyl)pyridin-3-yl)-6-(2,6-difluoro-4-(2-methoxyethoxy)phenyl)-5-fluoropicolinamide |
| 120 | 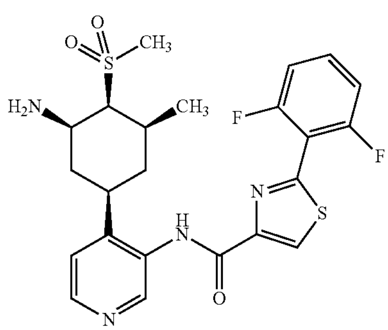 [SMILES: C[C@H]1C[C@@H](c2ccncc2NC(=O)c2csc(-c3c(F)cccc3F)n2)C[C@@H](N)[C@H]1S(C)(=O)=O] | 507.2 | 0.55 | N-(4-((1R,3R,4S,5S)-3-amino-5-methyl-4-(methylsulfonyl)cyclohexyl)pyridin-3-yl)-2-(2,6-difluorophenyl)thiazole-4-carboxamide |
| 121 | 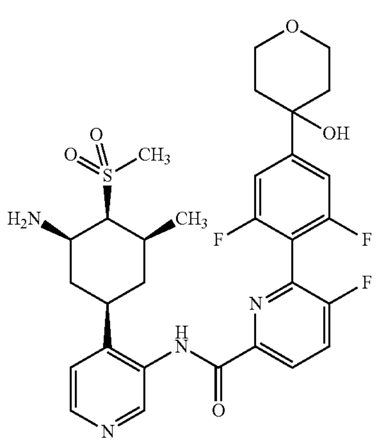 [SMILES: C[C@H]1C[C@@H](c2ccncc2NC(=O)c2ccc(F)c(-c3c(F)cc(C4(O)CCOCC4)cc3F)n2)C[C@@H](N)[C@H]1S(C)(=O)=O] | 619.4 | 0.56 | N-(4-((1R,3R,4S,5S)-3-amino-5-methyl-4-(methylsulfonyl)cyclohexyl)pyridin-3-yl)-6-(2,6-difluoro-4-(4-hydroxytetrahydro-2H-pyran-4-yl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 122 | 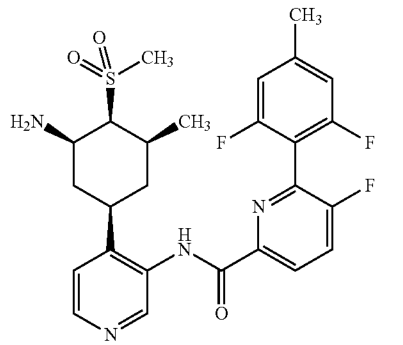 [SMILES: Cc1cc(F)c(-c2nc(C(=O)Nc3cnccc3[C@H]3C[C@@H](N)[C@@H](S(C)(=O)=O)[C@@H](C)C3)ccc2F)c(F)c1] | 533.4 | 0.63 | N-(4-((1R,3R,4S,5S)-3-amino-5-methyl-4-(methylsulfonyl)cyclohexyl)pyridin-3-yl)-6-(2,6-difluoro-4-methylphenyl)-5-fluoropicolinamide |
| 123 | Chiral | 534.4 | 0.69 | N-(4-((1R,3R,4S,5S)-3-amino-5-methyl-4-(pyridin-2-yloxy)cyclohexyl)pyridin-3-yl)-6-(2,6-difluorophenyl)-5-fluoropicolinamide |
| 124 | Chiral | 545.3 | 0.67 | N-(4-((1R,3R,4R,5S)-3-amino-4-methoxy-5-methylcyclohexyl)pyridin-3-yl)-6-(2,6-difluoro-4-(2-methoxyethoxy)phenyl)-5-fluoropicolinamide |
| 125 | Chiral | 621.3 | 0.72 | N-(4-((1R,3R,4S,5S)-3-amino-5-methyl-4-(2-(methylsulfonyl)ethoxy)cyclohexyl)pyridin-3-yl)-6-(4-(ethoxymethyl)-2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 126 | 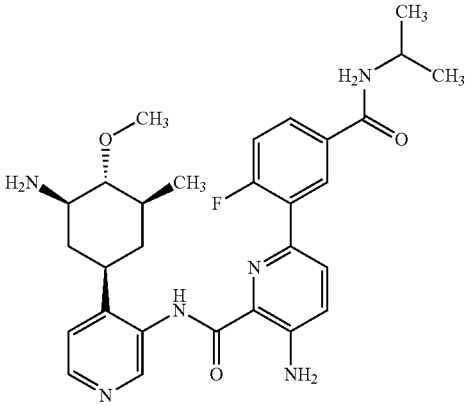 | 535.4 | 0.61 | 3-amino-N-(4-((1R,3R,4R,5S)-3-amino-4-methoxy-5-methylcyclohexyl)pyridin-3-yl)-6-(2-fluoro-5-(isopropylcarbamoyl)phenyl)picolinamide |
| 127 | 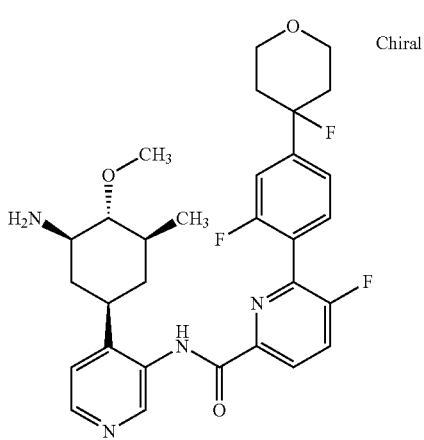 [SMILES: CO[C@H]1[C@H](N)C[C@H](c2ccncc2NC(=O)c2ccc(F)c(-c3ccc(C4(F)CCOCC4)cc3F)n2)C[C@@H]1C] | 573.3 | 0.70 | N-(4-((1R,3R,4R,5S)-3-amino-4-methoxy-5-methylcyclohexyl)pyridin-3-yl)-6-(2,6-difluoro-4-(4-fluorotetrahydro-2H-pyran-4-yl)phenyl)-5-fluoropicolinamide |
| 128 | 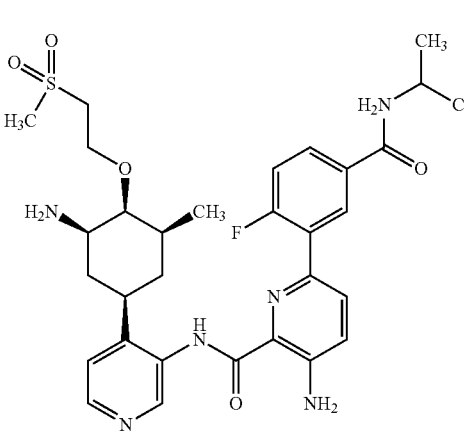 | 627.4 | 0.59 | 3-amino-N-(4-((1R,3R,4S,5S)-3-amino-5-methyl-4-(2-(methylsulfonyl)ethoxy)cyclohexyl)pyridin-3-yl)-6-(2-fluoro-5-(isopropylcarbamoyl)phenyl)picolinamide |

TABLE 2-continued

| Ex# | Structure | LC/MS (MH+ on UPLC) | LC/MS (Rf on UPLC) | Chemical Name |
|---|---|---|---|---|
| 129 | Chiral | 665.4 | 0.68 | N-(4-((1R,3R,4S,5S)-3-amino-5-methyl-4-(2-(methylsulfonyl)ethoxy)cyclohexyl)pyridin-3-yl)-6-(2,6-difluoro-4-(4-fluorotetrahydro-2H-pyran-4-yl)phenyl)-5-fluoropicolinamide |
| 130 | Chiral | 637.4 | 0.68 | N-(4-((1R,3R,4S,5S)-3-amino-5-methyl-4-(2-(methylsulfonyl)ethoxy)cyclohexyl)pyridin-3-yl)-6-(2,6-difluoro-4-(2-methoxyethoxy)phenyl)-5-fluoropicolinamide |
| 131 | Chiral | 497.2 | 0.62 | N-(4-((3R,4S,5S)-3-amino-5-methyl-4-(1H-1,2,3-triazol-1-yl)piperidin-1-yl)pyridin-3-yl)-2-(2,6-difluorophenyl)thiazole-4-carboxamide |

TABLE 2-continued

| Ex# | Structure | LC/MS (MH+ on UPLC) | LC/MS (Rf on UPLC) | Chemical Name |
|---|---|---|---|---|
| 132 | Chiral | 583.3 | 0.68 | N-(4-((3R,4S,5S)-3-amino-5-methyl-4-(1H-1,2,3-triazol-1-yl)piperidin-1-yl)pyridin-3-yl)-6-(2,6-difluoro-4-(2-methoxyethoxy)phenyl)-5-fluoropicolinamide |
| 133 | Chiral | 551.1 | 0.61 | N-(4-((1R,3R,4S,5S)-3-amino-5-methyl-4-(2-(methylsulfonyl)ethoxy)cyclohexyl)pyridin-3-yl)-2-(2,6-difluorophenyl)thiazole-4-carboxamide |
| 134 | 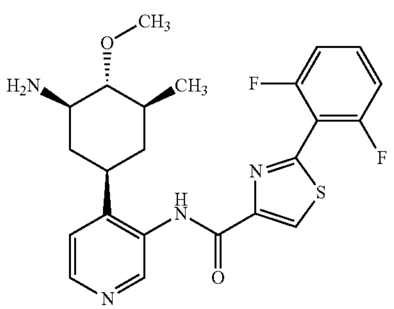 [SMILES: CO[C@H]1[C@H](N)C[C@H](c2ccncc2NC(=O)c2csc(-c3c(F)cccc3F)n2)C[C@@H]1C] | 459.3 | 0.69 | N-(4-((1R,3R,4R,5S)-3-amino-4-methoxy-5-methylcyclohexyl)pyridin-3-yl)-2-(2,6-difluorophenyl)thiazole-4-carboxamide |
| 135 | Chiral | 566.2 | 0.63 | 5-amino-N-(4-((1R,3R,4S,5S)-3-amino-5-methyl-4-(2-methylsulfonyl)ethoxy)cyclohexyl)pyridin-3-yl)-2-(2,6-difluorophenyl)thiazole-4-carboxamide |

TABLE 2-continued

| Ex# | Structure | | LC/MS (MH+ on UPLC) | LC/MS (Rf on UPLC) | Chemical Name |
|---|---|---|---|---|---|
| 136 | 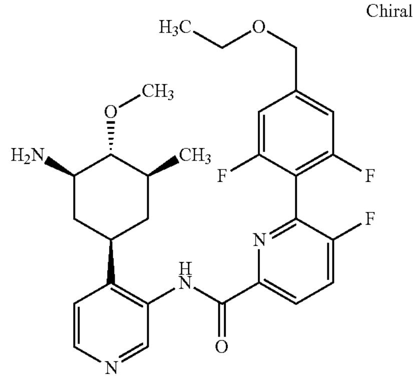 [SMILES: CCOCc1cc(F)c(-c2nc(C(=O)Nc3cnccc3[C@H]3C[C@@H](N)[C@H](OC)[C@@H](C)C3)ccc2F)c(F)c1] | Chiral | 529.3 | 0.74 | N-(4-((1R,3R,4R,5S)-3-amino-4-methoxy-5-methylcyclohexyl)pyridin-3-yl)-6-(4-(ethoxymethyl)-2,6-difluorophenyl)-5-fluoropicolinamide |
| 137 | 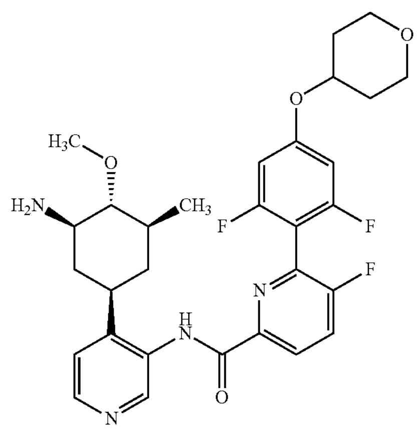 | Chiral | 571.4 | 0.67 | N-(4-((1R,3R,4R,5S)-3-amino-4-methoxy-5-methylcyclohexyl)pyridin-3-yl)-6-(2,6-difluoro-4-((tetrahydro-2H-pyran-4-yl)oxy)phenyl)-5-fluoropicolinamide |
| 138 | 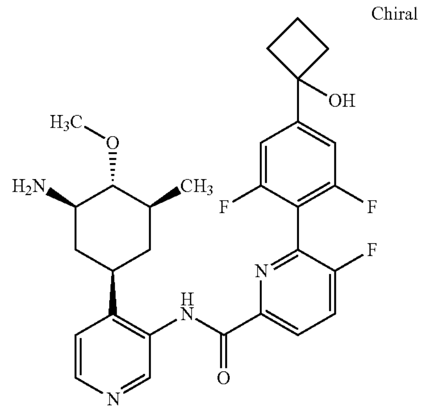 [SMILES: CO[C@H]1[C@H](N)C[C@H](c2ccncc2NC(=O)c2ccc(F)c(-c3c(F)cc(C4(O)CCC4)cc3F)n2)C[C@@H]1C] | Chiral | 541.3 | 0.64 | N-(4-((1R,3R,4R,5S)-3-amino-4-methoxy-5-methylcyclohexyl)pyridin-3-yl)-6-(2,6-difluoro-4-(1-hydroxycyclobutyl)phenyl)-5-fluoropicolinamide |

TABLE 2-continued

| Ex# | Structure | | LC/MS (MH+ on UPLC) | LC/MS (Rf on UPLC) | Chemical Name |
|---|---|---|---|---|---|
| 139 | 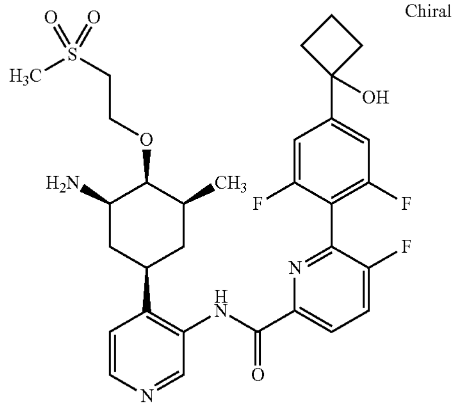 [SMILES: C[C@H]1C[C@@H](c2ccncc2NC(=O)c2ccc(F)c(-c3c(F)cc(C4(O)CCC4)cc3F)n2)C[C@@H](N)[C@H]1OCCS(C)(=O)=O] | Chiral | 633.4 | 0.63 | N-(4-((1R,3R,4S,5S)-3-amino-5-methyl-4-(2-(methylsulfonyl)ethoxy)cyclo-hexyl)pyridin-3-yl)-6-(2,6-difluoro-4-(1-hydroxycyclobutyl)phenyl)-5-fluoropicolinamide |
| 140 | 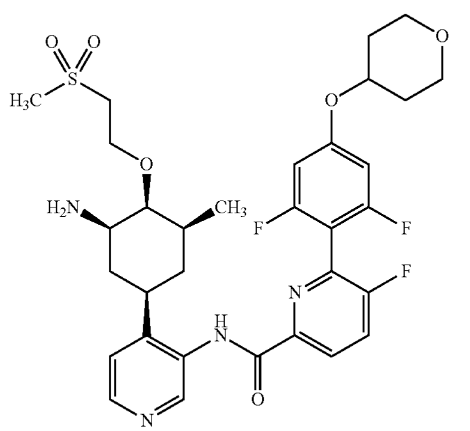 | Chiral | 663.4 | 0.66 | N-(4-((1R,3R,4S,5S)-3-amino-5-methyl-4-(2-(methylsulfonyl)ethoxy)cyclo-hexyl)pyridin-3-yl)-6-(2,6-difluoro-4-((tetrahydro-2H-pyran-4-yl)oxy)phenyl)-5-fluoropicolinamide |
| 141 | 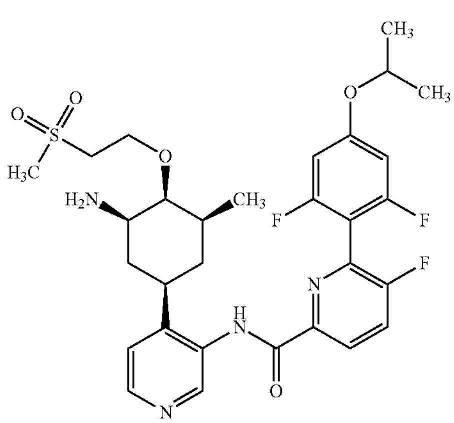 | Chiral | 621.4 | 0.81 | N-(4-((1R,3R,4S,5S)-3-amino-5-methyl-4-(2-(methylsulfonyl)ethoxy)cyclo-hexyl)pyridin-3-yl)-6-(2,6-difluoro-4-isopropoxyphenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 142 | 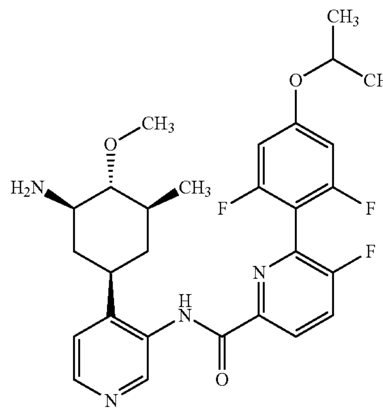 | 529.3 | 0.82 | N-(4-((1R,3R,4R,5S)-3-amino-4-methoxy-5-methylcyclohexyl)pyridin-3-yl)-6-(2,6-difluoro-4-isopropoxyphenyl)-5-fluoropicolinamide |
| 143 | 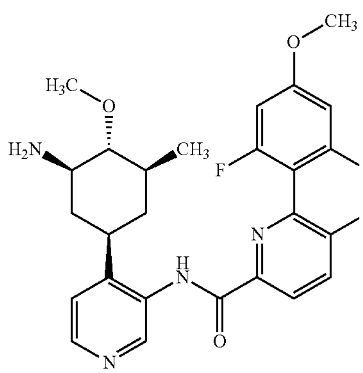 | 501.1 | 0.70 | N-(4-((1R,3R,4R,5S)-3-amino-4-methoxy-5-methylcyclohexyl)pyridin-3-yl)-6-(2,6-difluoro-4-methoxyphenyl)-5-fluoropicolinamide |
| 144 | 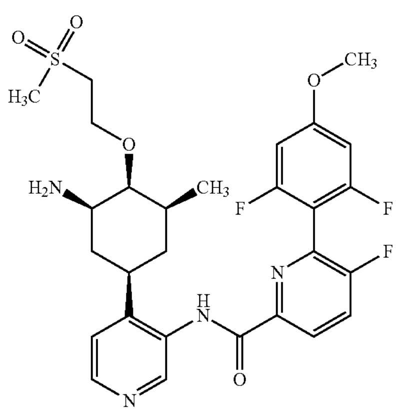 | 593.3 | 0.68 | N-(4-((1R,3R,4S,5S)-3-amino-5-methyl-4-(2-(methylsulfonyl)ethoxy)cyclohexyl)pyridin-3-yl)-6-(2,6-difluoro-4-methoxyphenyl)-5-fluoropicolinamide |
| 145 | 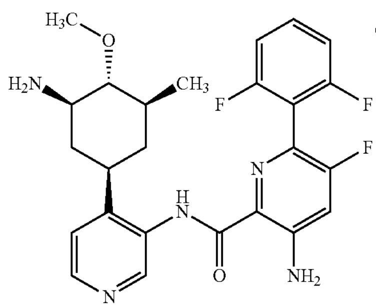 | 486.1 | 0.69 | 3-amino-N-(4-((1R,3R,4R,5S)-3-amino-4-methoxy-5-methylcyclohexyl)pyridin-3-yl)-6-(2,6-difluorophenyl)-5-fluoropicolinamide |

| Ex# | Structure | LC/MS (MH+ on UPLC) | LC/MS (Rf on UPLC) | Chemical Name |
|---|---|---|---|---|
| 146 | Chiral | 578.2 | 0.66 | 3-amino-N-(4-((1R,3R,4S,5S)-3-amino-5-methyl-4-(2-(methylsuflonyl)ethoxy)cyclohexyl)pyridin-3-yl)-6-(2,6-difluorophenyl)-5-fluoropicolinamide |
| 147 | Chiral | 567.3 | 0.72 | N-(4-((3R,4S,5S)-3-amino-5-methyl-4-(1H-1,2,3-triazol-1-yl)piperidin-1-yl)pyridin-3-yl)-6-(2,6-difluoro-4-isopropoxyphenyl)-5-fluoropicolinamide |
| 148 | Chiral | 573.3 | 0.72 | methyl (3R,4S,5S)-3-amino-1-(3-(6-(2,6-difluoro-4-isopropoxyphenyl)-5-fluoropicolinamido)pyridin-4-yl)-5-methylpiperidin-4-ylcarbamate |

TABLE 2-continued

| Ex# | Structure | LC/MS (MH+ on UPLC) | LC/MS (Rf on UPLC) | Chemical Name |
|---|---|---|---|---|
| 149 | 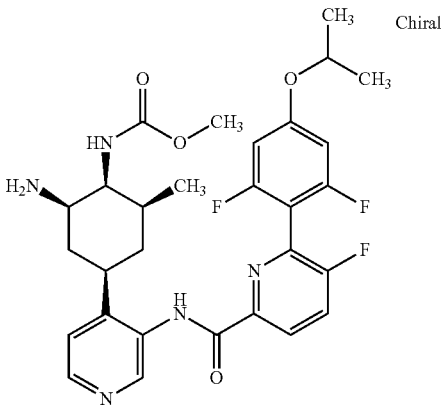 [SMILES: COC(=O)N[C@@H]1[C@H](N)C[C@H](c2ccncc2NC(=O)c2ccc(F)c(-c3c(F)cc(OC(C)C)cc3F)n2)C[C@@H]1C] Chiral | 572.3 | 0.74 | methyl (1S,2R,4R,6S)-2-amino-4-(3-(6-(2,6-difluoro-4-isopropoxyphenyl)-5-fluoropicolinamido)pyridin-4-yl)-6-methylcyclohexylcarbamate |
| 150 | 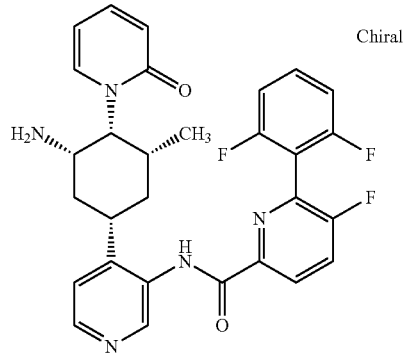 [SMILES: C[C@@H]1C[C@H](c2ccncc2NC(=O)c2ccc(F)c(-c3c(F)cccc3F)n2)C[C@H](N)[C@@H]1n1ccccc1=O] Chiral | 534.4 | 0.60 | N-(4-((1S,3S,4R,5R)-3-amino-5-methyl-4-(2-oxopyridin-1(2H)-yl)cyclohexyl)pyridin-3-yl)-6-(2,6-difluorophenyl)-5-fluoropicolinamide |
| 151 | 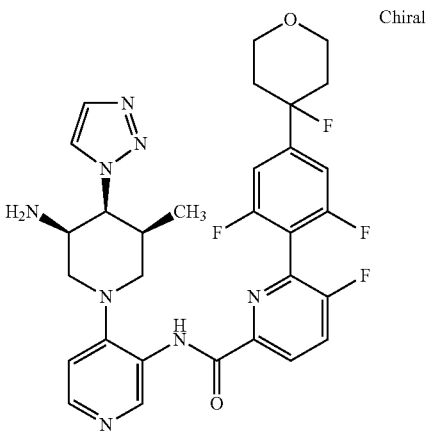 [SMILES: C[C@H]1CN(c2ccncc2NC(=O)c2ccc(F)c(-c3c(F)cc(C4(F)CCOCC4)cc3F)n2)C[C@@H](N)[C@H]1n1ccnn1] Chiral | 611.4 | 0.67 | N-(4-((3R,4S,5S)-3-amino-5-methyl-4-(1H-1,2,3-triazol-1-yl)piperidin-1-yl)pyridin-3-yl)-6-(2,6-difluoro-4-(4-fluorotetrahydro-2H-pyran-4-yl)phenyl)-5-fluoropicolinamide |

TABLE 2-continued

| Ex# | Structure | | LC/MS (MH+ on UPLC) | LC/MS (Rf on UPLC) | Chemical Name |
|---|---|---|---|---|---|
| 152 | 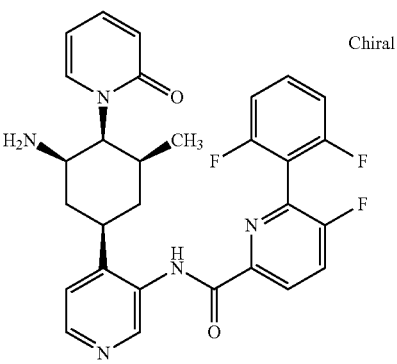 [SMILES: C[C@H]1C[C@@H](c2ccncc2NC(=O)c2ccc(F)c(-c3c(F)cccc3F)n2)C[C@@H](N)[C@H]1n1ccccc1=O] | Chiral | 534.4 | 0.60 | N-(4-((1R,3R,4S,5S)-3-amino-5-methyl-4-(2-oxopyridin-1(2H)-yl)cyclohexyl)pyridin-3-yl)-6-(2,6-difluorophenyl)-5-fluoropicolinamide |
| 153 | 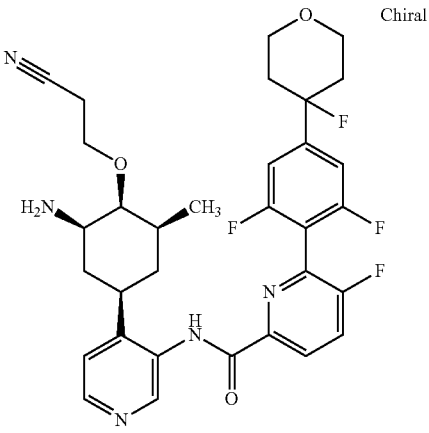 [SMILES: C[C@H]1C[C@@H](c2ccncc2NC(=O)c2ccc(F)c(-c3c(F)cc(C4(F)CCOCC4)cc3F)n2)C[C@@H](N)[C@H]1OCCC#N] | Chiral | 612.4 | 0.70 | N-(4-((1R,3R,4S,5S)-3-amino-4-(2-cyanoethoxy)-5-methylcyclohexyl)pyridin-3-yl)-6-(2,6-difluoro-4-(4-fluorotetrahydro-2H-pyran-4-yl)phenyl)-5-fluoropicolinamide |
| 154 | 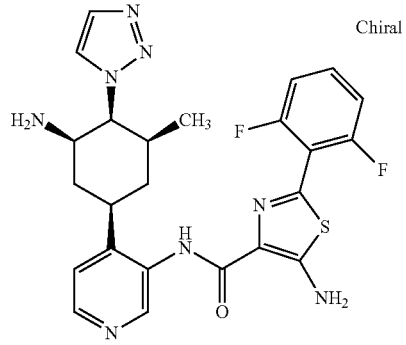 [SMILES: C[C@H]1C[C@@H](c2ccncc2NC(=O)c2nc(-c3c(F)cccc3F)sc2N)C[C@@H](N)[C@H]1n1ccnn1] | Chiral | 511.2 | 0.58 | 5-amino-N-(4-((1R,3R,4S,5S)-3-amino-5-methyl-4-(1H-1,2,3-triazol-1-yl)cyclohexyl)pyridin-3-yl)-2-(2,6-difluorophenyl)thiazole-4-carboxamide |
| 155 | 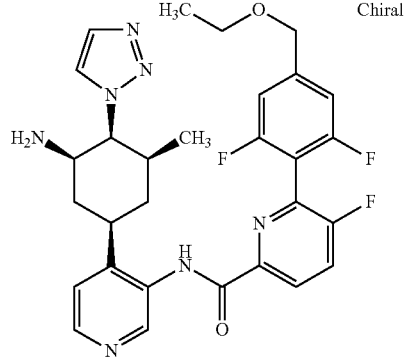 [SMILES: CCOCc1cc(F)c(-c2nc(C(=O)Nc3cnccc3[C@H]3C[C@@H](N)[C@@H](n4ccnn4)[C@@H](C)C3)ccc2F)c(F)c1] | Chiral | 566.3 | 0.68 | N-(4-((1S,3R,4S,5S)-3-amino-5-methyl-4-(1H-1,2,3-triazol-1-yl)cyclohexyl)pyridin-3-yl)-6-(4-(ethoxymethyl)-2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 156 | Chiral | 512.2 | 0.56 | 5-amino-N-(4-((3R,4S,5S)-3-amino-5-methyl-4-(1H-1,2,3-triazol-1-yl)piperidin-1-yl)pyridin-3-yl)-2-(2,6-difluorophenyl)thiazole-4-carboxamide |
| 157 | Chiral | 567.3 | 0.67 | N-(4-((3R,4S,5S)-3-amino-5-methyl-4-(1H-1,2,3-triazol-1-yl)piperidin-1-yl)pyridin-3-yl)-6-(4-(ethoxymethyl)-2,6-difluorophenyl)-5-fluoropicolinamide |
| 158 | Chiral | 585.4 | 0.62 | methyl (3R,4S,5S)-3-amino-1-(3-(6-(2,6-difluoro-4-(1-hydroxycyclobutyl)phenyl)-5-fluoropicolinamido)pyridin-4-yl)-5-methylpiperidin-4-ylcarbamate |
| 159 | Chiral | 615.4 | 0.64 | methyl (3R,4S,5S)-3-amino-1-(3-(6-(2,6-difluoro-4-(tetrahydro-2H-pyran-4-yloxy)phenyl)-5-fluoropicolinamido)pyridin-4-yl)-5-methylpiperidin-4-ylcarbamate |

TABLE 2-continued

| Ex# | Structure | LC/MS (MH+ on UPLC) | LC/MS (Rf on UPLC) | Chemical Name |
|---|---|---|---|---|
| 160 | 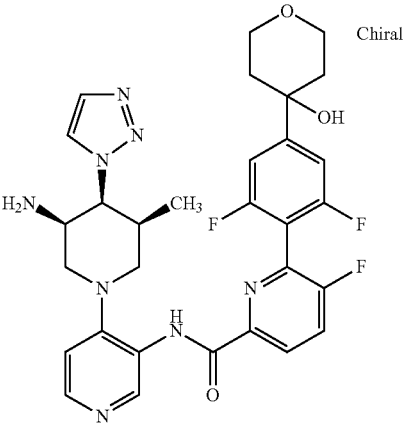 [SMILES: C[C@H]1CN(c2ccncc2NC(=O)c2ccc(F)c(-c3c(F)cc(C4(O)CCOCC4)cc3F)n2)C[C@@H](N)[C@H]1n1ccnn1] | 609.4 | 0.59 | N-(4-((3R,4S,5S)-3-amino-5-methyl-4-(1H-1,2,3-triazol-1-yl)piperidin-1-yl)pyridin-3-yl)-6-(2,6-difluoro-4-(4-hydroxytetrahydro-2H-pyran-4-yl)phenyl)-5-fluoropicolinamide |
| 161 | 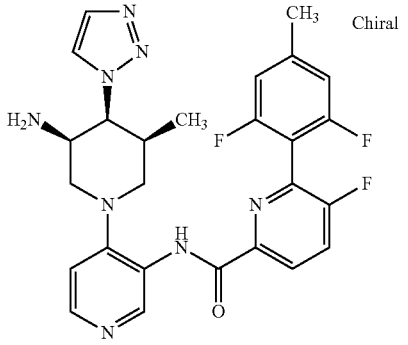 [SMILES: Cc1cc(F)c(-c2nc(C(=O)Nc3cnccc3N3C[C@@H](N)[C@@H](n4ccnn4)[C@@H](C)C3)ccc2F)c(F)c1] | 523.3 | 0.65 | N-(4-((3R,4S,5S)-3-amino-5-methyl-4-(1H-1,2,3-triazol-1-yl)piperidin-1-yl)pyridin-3-yl)-6-(2,6-difluoro-4-methylphenyl)-5-fluoropicolinamide |
| 162 | 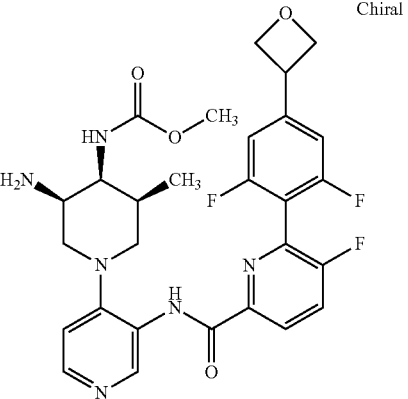 [SMILES: COC(=O)N[C@@H]1[C@H](N)CN(c2ccncc2NC(=O)c2ccc(F)c(-c3c(F)cc(C4COC4)cc3F)n2)C[C@@H]1C] | 571.3 | 0.58 | methyl (3R,4S,5S)-3-amino-1-(3-(6-(2,6-difluoro-4-(oxetan-3-yl)phenyl)-5-fluoropicolinamido)pyridin-4-yl)-5-methylpiperidin-4-ylcarbamate |

TABLE 2-continued

| Ex# | Structure | LC/MS (MH+ on UPLC) | LC/MS (Rf on UPLC) | Chemical Name |
|---|---|---|---|---|
| 163 | Chiral | 566.3 | 0.61 | N-(4-((1R,3R,4S,5S)-3-amino-4-(2-cyanoethoxy)-5-methylcyclohexyl)pyridin-3-yl)-6-(2,6-difluoro-4-(oxetan-3-yl)phenyl)-5-fluoropicolinamide |
| 164 | Chiral | 565.3 | 0.48 | N-(4-((3R,4S,5S)-3-amino-5-methyl-4-(1H-1,2,3-triazol-1-yl)piperidin-1-yl)pyridin-3-yl)-6-(2,6-difluoro-4-(oxetan-3-yl)phenyl)-5-fluoropicolinamide |
| 165 | Chiral | 540.1 | 0.67 | N-(4-((1R,3R,4S,5S)-3-amino-4-(2-cyanoethoxy)-5-methylcyclohexyl)pyridin-3-yl)-6-(2,6-difluoro-4-methoxyphenyl)-5-fluoropicolinamide |

| Ex# | Structure | | LC/MS (MH+ on UPLC) | LC/MS (Rf on UPLC) | Chemical Name |
|---|---|---|---|---|---|
| 166 | 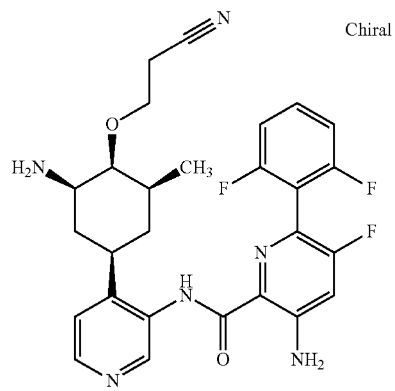 [SMILES: C[C@H]1C[C@@H](c2ccncc2NC(=O)c2nc(-c3c(F)cccc3F)c(F)cc2N)C[C@@H](N)[C@H]1OCCC#N] | Chiral | 525.1 | 0.66 | 3-amino-N-(4-((1R,3R,4S,5S)-3-amino-4-(2-cyanoethoxy)-5-methylcyclohexyl)pyridin-3-yl)-6-(2,6-difluorophenyl)-5-fluoropicolinamide |
| 167 | 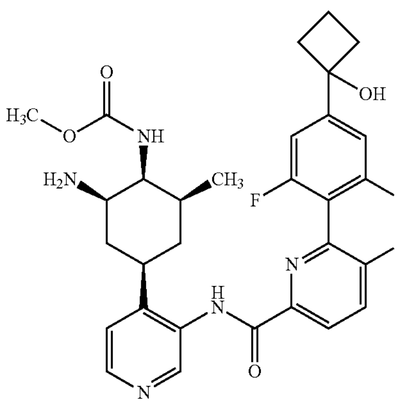 | Chiral | 584.4 | 0.63 | methyl (1S,2R,4R,6S)-2-amino-4-(3-(6-(2,6-difluoro-4-(1-hydroxycyclobutyl)phenyl)-5-fluoropicolinamido)pyridin-4-yl)-6-methylcyclohexylcarbamate |
| 168 | 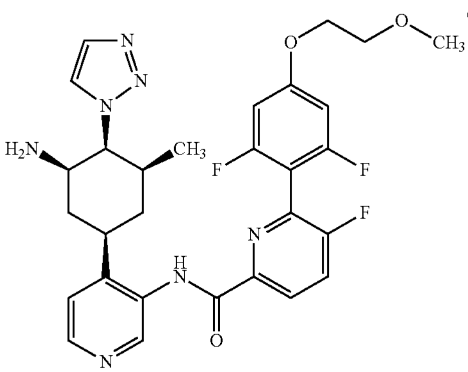 | Chiral | 582.3 | 0.64 | N-(4-((1R,3R,4S,5S)-3-amino-5-methyl-4-(1H-1,2,3-triazol-1-yl)cyclohexyl)pyridin-3-yl)-6-(2,6-difluoro-4-(2-methoxyethoxy)phenyl)-5-fluoropicolinamide |
| 169 | 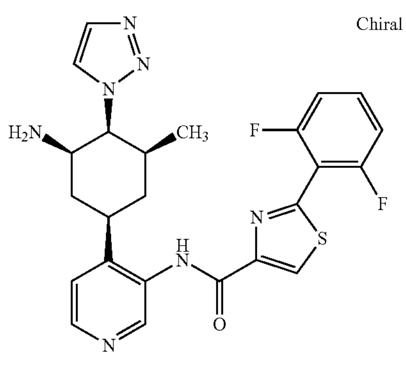 [SMILES: C[C@H]1C[C@@H](c2ccncc2NC(=O)c2csc(-c3c(F)cccc3F)n2)C[C@@H](N)[C@H]1n1ccnn1] | Chiral | 496.2 | 0.57 | N-(4-((1R,3R,4S,5S)-3-amino-5-methyl-4-(1H-1,2,3-triazol-1-yl)cyclohexyl)pyridin-3-yl)-2-(2,6-difluorophenyl)thiazole-4-carboxamide |

TABLE 2-continued

| Ex# | Structure | LC/MS (MH+ on UPLC) | LC/MS (Rf on UPLC) | Chemical Name |
|---|---|---|---|---|
| 170 | 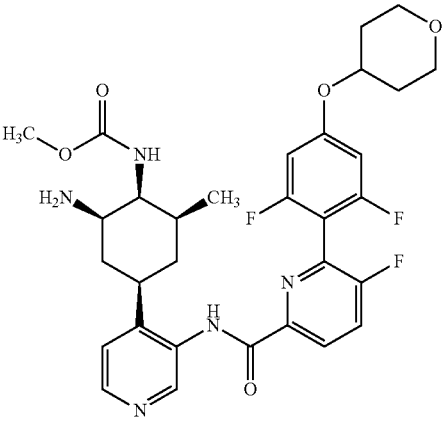 | 614.4 | 0.66 | methyl (1S,2R,4R,6S)-2-amino-4-(3-(6-(2,6-difluoro-4-(tetrahydro-2H-pyran-4-yloxy)phenyl)-5-fluoropicolinamido)pyridin-4-yl)-6-methylcyclohexylcarbamate |
| 171 | 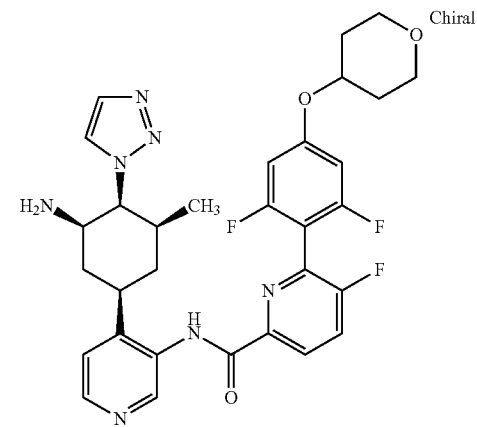 [SMILES: C[C@H]1C[C@@H](c2ccncc2NC(=O)c2ccc(F)c(-c3c(F)cc(OC4CCOCC4)cc3F)n2)C[C@@H](N)[C@H]1n1ccnn1] | 608.4 | 0.65 | N-(4-((1R,3R,4S,5S)-3-amino-5-methyl-4-(1H-1,2,3-triazol-1-yl)cyclohexyl)pyridin-3-yl)-6-(2,6-difluoro-4-(tetrahydro-2H-pyran-4-yloxy)phenyl)-5-fluoropicolinamide |
| 172 | 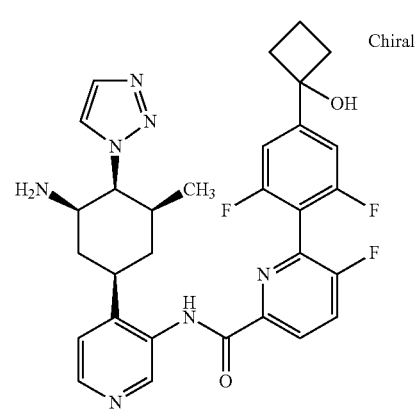 [SMILES: C[C@H]1C[C@@H](c2ccncc2NC(=O)c2ccc(F)c(-c3c(F)cc(C4(O)CCC4)cc3F)n2)C[C@@H](N)[C@H]1n1ccnn1] | 578.4 | 0.62 | N-(4-((1R,3R,4S,5S)-3-amino-5-methyl-4-(1H-1,2,3-triazol-1-yl)cyclohexyl)pyridin-3-yl)-6-(2,6-difluoro-4-(1-hydroxycyclobutyl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 173 | 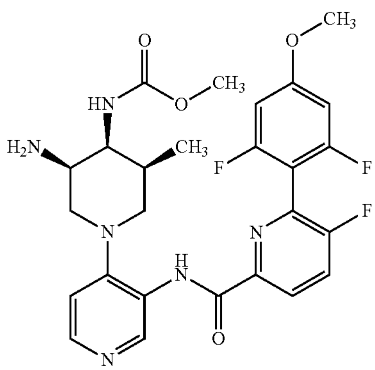 | 545.3 | 0.64 | methyl ((3R,4S,5S)-3-amino-1-(3-(6-(2,6-difluoro-4-methoxyphenyl)-5-fluoropicolinamido)pyridin-4-yl)-5-methylpiperidin-4-yl)carbamate |
| 174 | 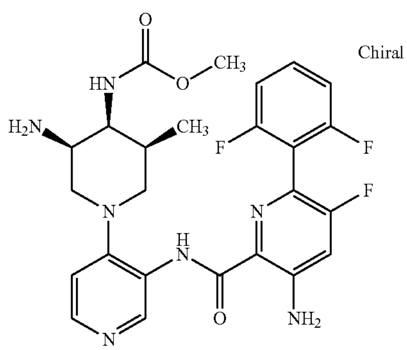 [SMILES: COC(=O)N[C@@H]1[C@H](N)CN(c2ccncc2NC(=O)c2nc(-c3c(F)cccc3F)c(F)cc2N)C[C@@H]1C] | 530.3 | 0.62 | methyl ((3R,4S,5S)-3-amino-1-(3-(3-amino-6-(2,6-difluorophenyl)-5-fluoropicolinamido)pyridin-4-yl)-5-methylpiperidin-4-yl)carbamate |
| 175 | 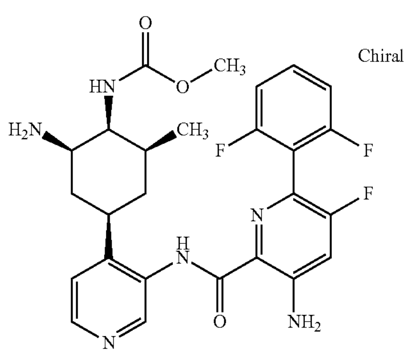 [SMILES: COC(=O)N[C@@H]1[C@H](N)C[C@H](c2ccncc2NC(=O)c2nc(-c3c(F)cccc3F)c(F)cc2N)C[C@@H]1C] | 529.3 | 0.65 | methyl (1S,2R,4R,6)S-2-amino-4-(3-(3-amino-6-(2,6-difluorophenyl)-5-fluoropicolinamido)pyridin-4-yl)-6-methylcyclohexylcarbamate |
| 176 | 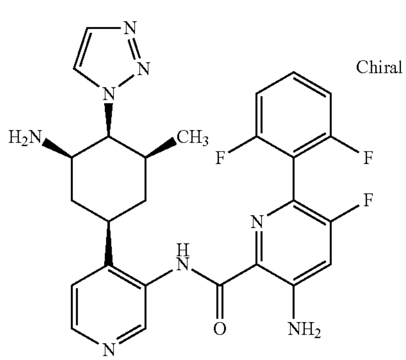 [SMILES: C[C@H]1C[C@@H](c2ccncc2NC(=O)c2nc(-c3c(F)cccc3F)c(F)cc2N)C[C@@H](N)[C@H]1n1ccnn1] | 523.3 | 0.63 | 3-amino-N-(4-((1R,3R,4S,5S)-3-amino-5-methyl-4-(1H-1,2,3-triazol-1-yl)cyclohexyl)pyridin-3-yl)-6-(2,6-difluorophenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 177 | 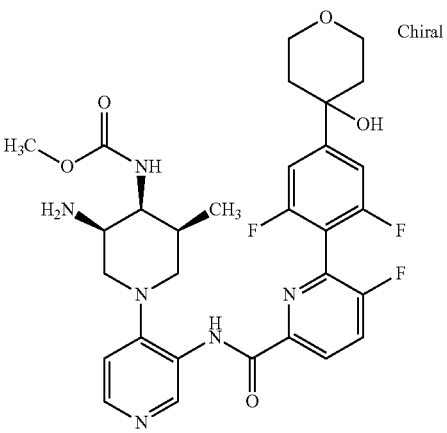 [SMILES: COC(=O)N[C@@H]1[C@H](N)CN(c2ccncc2NC(=O)c2ccc(F)c(-c3c(F)cc(C4(O)CCOCC4)cc3F)n2)C[C@@H]1C] Chiral | 615.3 | 0.59 | methyl (3R,4S,5S)-3-amino-1-(3-(6-(2,6-difluoro-4-(4-hydroxytetrahydro-2H-pyran-4-yl)phenyl)-5-fluoropicolinamido)pyridin-4-yl)-5-methylpiperidin-4-ylcarbamate |
| 178 | 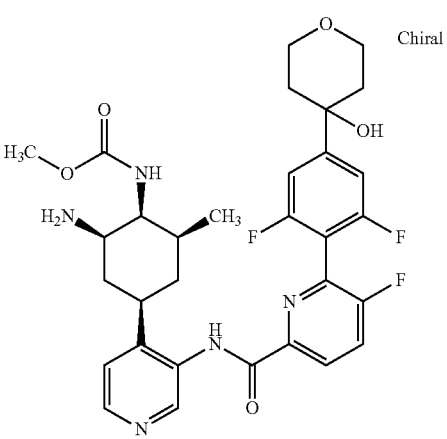 [SMILES: COC(=O)N[C@@H]1[C@H](N)C[C@H](c2ccncc2NC(=O)c2ccc(F)c(-c3c(F)cc(C4(O)CCOCC4)cc3F)n2)C[C@@H]1C] Chiral | 614.3 | 0.59 | methyl (1S,2R,4R,6S)-2-amino-4-(3-(6-(2,6-difluoro-4-(4-hydroxytetrahydro-2H-pyran-4-yl)phenyl)-5-fluoropicolinamido)pyridin-4-yl)-6-methylcyclohexylcarbamate |
| 179 | 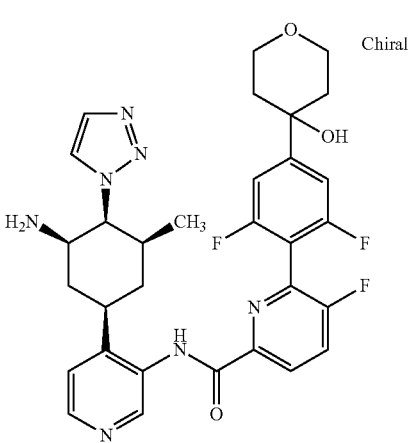 [SMILES: C[C@H]1C[C@@H](c2ccncc2NC(=O)c2ccc(F)c(-c3c(F)cc(C4(O)CCOCC4)cc3F)n2)C[C@@H](N)[C@H]1n1ccnn1] Chiral | 608.3 | 0.58 | N-(4-((1R,3R,4S,5S)-3-amino-5-methyl-4-(1H-1,2,3-triazol-1-yl)cyclohexyl)pyridin-3-yl)-6-(2,6-difluoro-4-(4-hydroxytetrahydro-2H-pyran-4-yl)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 180 | 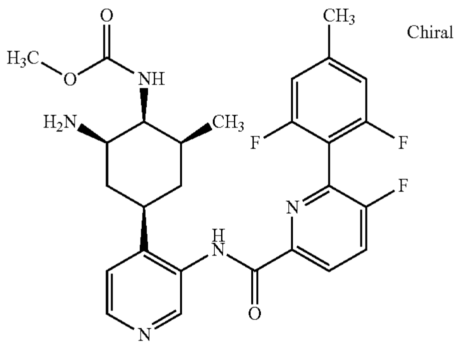 [SMILES: COC(=O)N[C@@H]1[C@H](N)C[C@H](c2ccncc2NC(=O)c2ccc(F)c(-c3c(F)cc(C)cc3F)n2)C[C@@H]1C] | 528.2 | 0.66 | methyl (1S,2R,4R,6S)-2-amino-4-(3-(6-(2,6-difluoro-4-methylphenyl)-5-fluoropicolinamido)pyridin-4yl)-6-methylcyclohexylcarbamate |
| 181 | 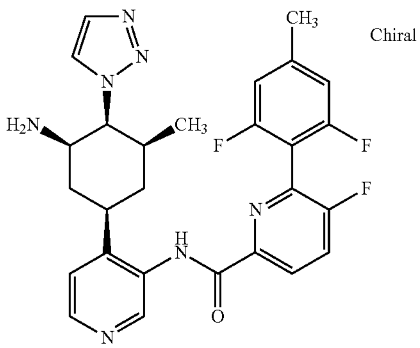 [SMILES: Cc1cc(F)c(-c2nc(C(=O)Nc3cnccc3[C@H]3C[C@@H](N)[C@@H](n4ccnn4)[C@@H](C)C3)ccc2F)c(F)c1] | 522.2 | 0.65 | N-(4-((1R,3R,4S,5S)-3-amino-5-methyl-4-(1H-1,2,3-triazol-1-yl)cyclohexyl)pyridin-3-yl)-6-(2,6-difluoro-4-methylphenyl)-5-fluoropicolinamide |
| 182 | 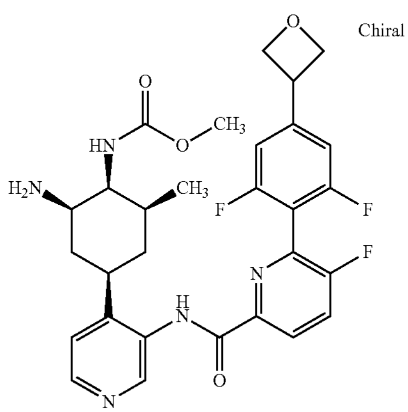 [SMILES: COC(=O)N[C@@H]1[C@H](N)C[C@H](c2ccncc2NC(=O)c2ccc(F)c(-c3c(F)cc(C4COC4)cc3F)n2)C[C@@H]1C] | 570.3 | 0.61 | methyl (1S,2R,4R,6S)-2-amino-4-(3-(6-(2,6-difluoro-4-(oxetan-3-yl)phenyl)-5-fluoropicolinamido)pyridin-4-yl)-6-methylcyclohexylcarbamate |
| 183 | 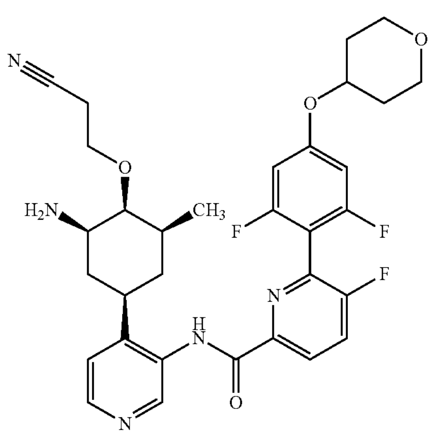 | 610.4 | 0.70 | N-(4-((1R,3R,4S,5S)-3-amino-4-(2-cyanoethoxy)-5-methylcyclohexyl)pyridin-3-yl)-6-(2,6-difluoro-4-((tetrahydro-2H-pyran-4-yl)oxy)phenyl)-5-fluoropicolinamide |

TABLE 2-continued

| Ex# | Structure | LC/MS (MH+ on UPLC) | LC/MS (Rf on UPLC) | Chemical Name |
|---|---|---|---|---|
| 184 | 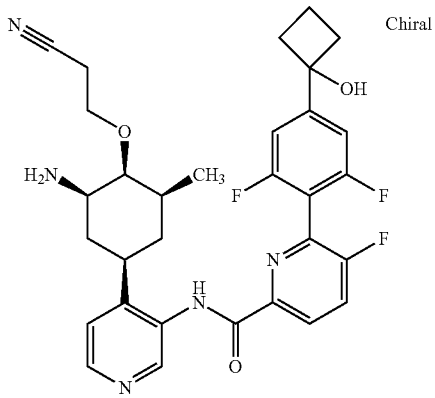 [SMILES: C[C@H]1C[C@@H](c2ccncc2NC(=O)c2ccc(F)c(-c3c(F)cc(C4(O)CCC4)cc3F)n2)C[C@@H](N)[C@H]1OCCC#N] | 580.4 | 0.66 | N-(4-((1R,3R,4S,5S)-3-amino-4-(2-cyanoethoxy)-5-methylcyclohexyl)pyridin-3-yl)-6-(2,6-difluoro-4-(1-hydroxycyclobutyl)phenyl)-5-fluoropicolinamide |
| 185 | 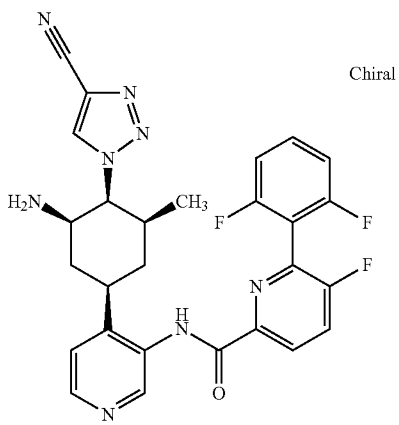 [SMILES: C[C@H]1C[C@@H](c2ccncc2NC(=O)c2ccc(F)c(-c3c(F)cccc3F)n2)C[C@@H](N)[C@H]1n1cc(C#N)nn1] | 533.3 | 0.66 | N-(4-((1R,3R,4S,5S)-3-amino-4-(4-cyano-1H-1,2,3-triazol-1-yl)-5-methylcyclohexyl)pyridin-3-yl)-6-(2,6-difluorophenyl)-5-fluoropicolinamide |
| 186 | 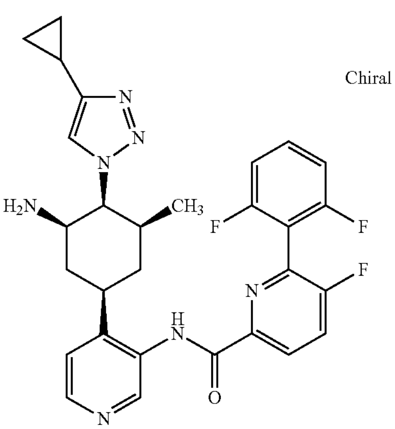 [SMILES: C[C@H]1C[C@@H](c2ccncc2NC(=O)c2ccc(F)c(-c3c(F)cccc3F)n2)C[C@@H](N)[C@H]1n1cc(C2CC2)nn1] | 548.4 | 0.67 | N-(4-((1R,3R,4S,5S)-3-amino-4-(4-cyclopropyl-1H-1,2,3-triazol-1-yl)-5-methylcyclohexyl)pyridin-3-yl)-6-(2,6-difluorophenyl)-5-fluoropicolinamide |

TABLE 2-continued

| Ex# | Structure | | LC/MS (MH+ on UPLC) | LC/MS (Rf on UPLC) | Chemical Name |
|---|---|---|---|---|---|
| 187 | 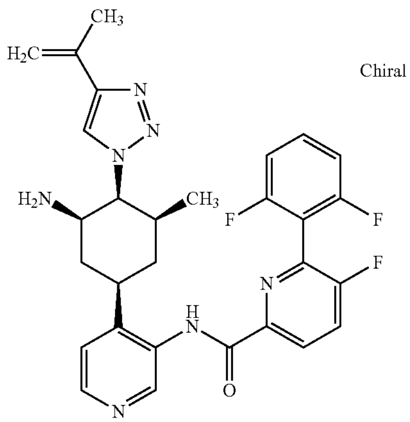 [SMILES: C=C(C)c1cn([C@@H]2[C@H](N)C[C@H](c3ccncc3NC(=O)c3ccc(F)c(-c4c(F)cccc4F)n3)C[C@@H]2C)nn1] | Chiral | 548.3 | 0.69 | N-(4-((1R,3R,4S,5S)-3-amino-5-methyl-4-(4-(prop-1-en-2-yl)-1H-1,2,3-triazol-1-yl)cyclohexyl)pyridin-3-yl)-6-(2,6-difluorophenyl)-5-fluoropicolinamide |
| 188 | 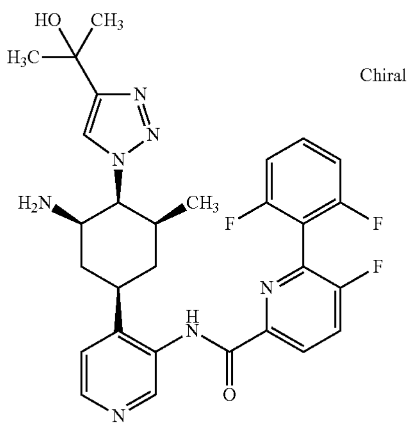 [SMILES: C[C@H]1C[C@@H](c2ccncc2NC(=O)c2ccc(F)c(-c3c(F)cccc3F)n2)C[C@@H](N)[C@H]1n1cc(C(C)(C)O)nn1] | Chiral | 566.4 | 0.62 | N-(4-((1R,3R,4S,5S)-3-amino-4-(4-(2-hydroxypropan-2-yl)-1H-1,2,3-triazol-1-yl)-5-methylcyclohexyl)pyridin-3-yl)-6-(2,6-difluorophenyl)-5-fluoropicolinamide |
| 189 | 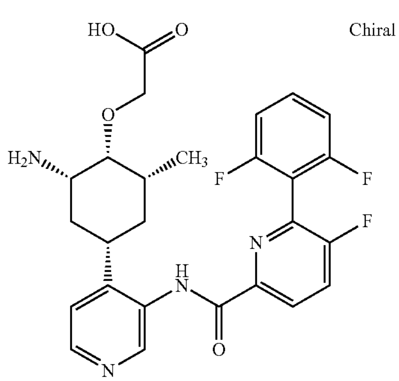 [SMILES: C[C@@H]1C[C@H](c2ccncc2NC(=O)c2ccc(F)c(-c3c(F)cccc3F)n2)C[C@H](N)[C@@H]1OCC(=O)O] | Chiral | 515.3 | 0.62 | 2-((1R,2S,4S,6R)-2-amino-4-(3-(6-(2,6-difluorophenyl)-5-fluoropicolinamido)pyridin-4-yl)-6-methylcyclohexyloxy)acetic acid |

TABLE 2-continued

| Ex# | Structure | | LC/MS (MH+ on UPLC) | LC/MS (Rf on UPLC) | Chemical Name |
|---|---|---|---|---|---|
| 190 | 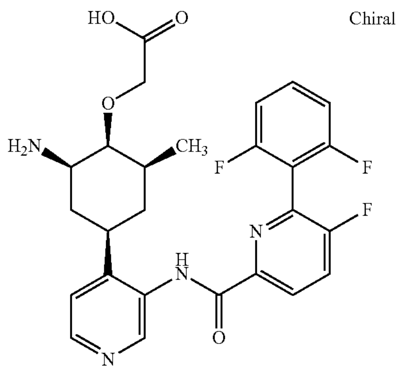 [SMILES: C[C@H]1C[C@@H](c2ccncc2NC(=O)c2ccc(F)c(-c3c(F)cccc3F)n2)C[C@@H](N)[C@H]1OCC(=O)O] | Chiral | 515.3 | 0.62 | 2-((1S,2R,4R,6S)-2-amino-4-(3-(6-(2,6-difluorophenyl)-5-fluoropicolinamido)pyridin-4-yl)-6-methylcyclohexyloxy)acetic acid |
| 191 | 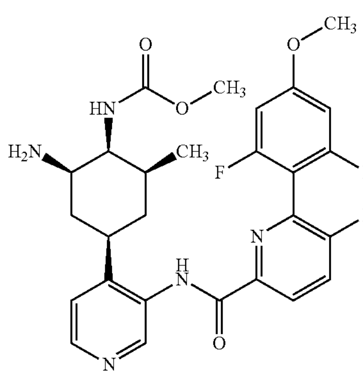 | Chiral | 544.3 | 0.66 | methyl (1S,2R,4R,6S)-2-amino-4-(3-(6-(2,6-difluoro-4-methoxyphenyl)-5-fluoropicolinamido)pyridin-4-yl)-6-methylcyclohexylcarbamate |
| 192 | 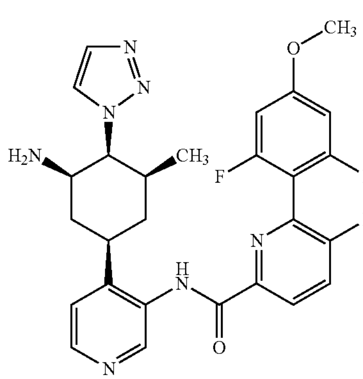 | Chiral | 538.3 | 0.65 | N-(4-((1R,3R,4S,5S)-3-amino-5-methyl-4-(1H-1,2,3-triazol-1-yl)cyclohexyl)pyridin-3-yl)-6-(2,6-difluoro-4-methoxyphenyl)-5-fluoropicolinamide |
| 193 | 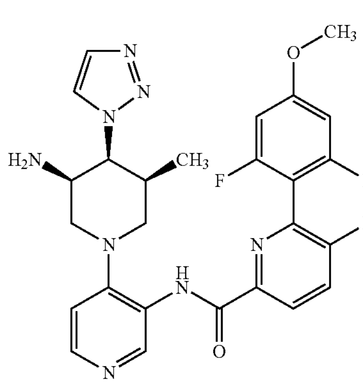 | Chiral | 539.3 | 0.64 | N-(4-((3R,4S,5S)-3-amino-5-methyl-4-(1H-1,2,3-triazol-1-yl)piperidin-1-yl)pyridin-3-yl)-6-(2,6-difluoro-4-methoxyphenyl)-5-fluoropicolinamide |

TABLE 2-continued

| Ex# | Structure | LC/MS (MH+ on UPLC) | LC/MS (Rf on UPLC) | Chemical Name |
| --- | --- | --- | --- | --- |
| 194 | Chiral | 524.3 | 0.62 | 3-amino-N-(4-((3R,4S,5S)-3-amino-5-methyl-4-(1H-1,2,3-triazol-1-yl)piperidin-1-yL)pyridin-3-yl)-6-(2,6-difluorophenyl)-5-fluoropicolinamide |
| 195 | 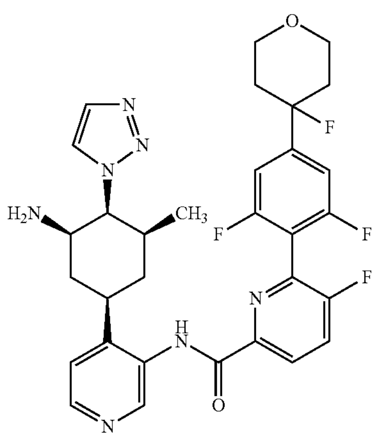 [SMILES: C[C@H]1C[C@@H](c2ccncc2NC(=O)c2ccc(F)c(-c3c(F)cc(C4(F)CCOCC4)cc3F)n2)C[C@@H](N)[C@H]1n1ccnn1] | 610.4 | 0.67 | N-(4-((1R,3R,4S,5S)-3-amino-5-methyl-4-(1H-1,2,3-triazol-1-yl)cyclohexyl)pyridin-3-yl)-6-(2,6-difluoro-4-(4-fluorotetrahydro-2H-pyran-4-yl)phenyl)-5-fluoropicolinamide |
| 196 | 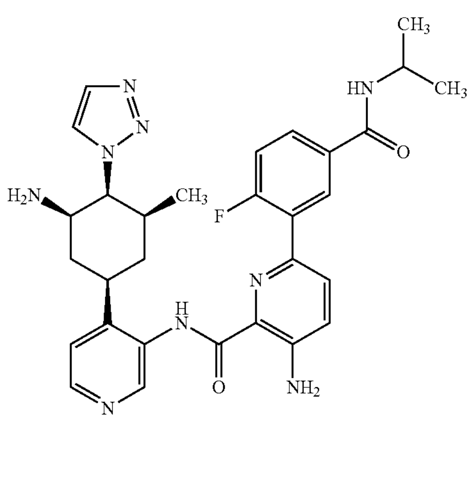 [SMILES: CC(C)NC(=O)c1ccc(F)c(-c2ccc(N)c(C(=O)Nc3cnccc3[C@H]3C[C@@H](N)[C@@H](n4ccnn4)[C@@H](C)C3)n2)c1] | 572.4 | 0.59 | 3-amino-N-(4-((1R,3R,4S,5S)-3-amino-5-methyl-4-(1H-1,2,3-triazol-1-yl)cyclohexyl)pyridin-3-yl)-6-(2-fluoro-5-(isopropylcarbamoyl)phenyl)picolinamide |

TABLE 2-continued

| Ex# | Structure | LC/MS (MH+ on UPLC) | LC/MS (Rf on UPLC) | Chemical Name |
|---|---|---|---|---|
| 197 | 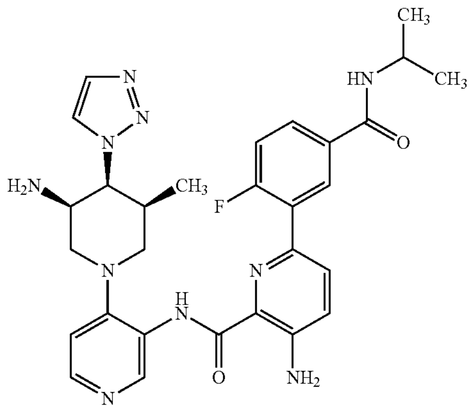 [SMILES: CC(C)NC(=O)c1ccc(F)c(-c2ccc(N)c(C(=O)Nc3cnccc3N3C[C@@H](N)[C@@H](n4ccnn4)[C@@H](C)C3)n2)c1] | 573.4 | 0.58 | 3-amino-N-(4-((3R,4S,5S)-3-amino-5-methyl-4-(1H-1,2,3-triazol-1-yl)piperidin-1-yl)pyridin-3-yl)-6-(2-fluoro-5-(isopropylcarbamoyl)phenyl)picolinamide |
| 198 | 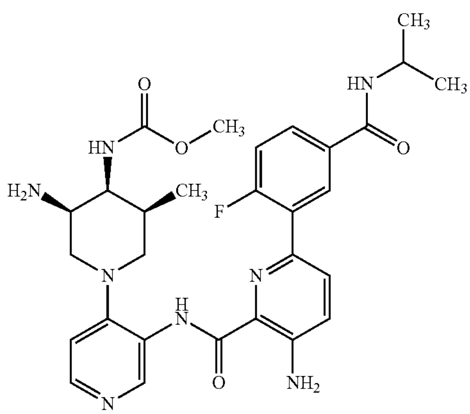 [SMILES: COC(=O)N[C@@H]1[C@H](N)CN(c2ccncc2NC(=O)c2nc(-c3cc(C(=O)NC(C)C)ccc3F)ccc2N)C[C@@H]1C] | 579.3 | 0.60 | methyl (3R,4S,5S)-3-amino-1-(3-(3-amino-6-(2-fluoro-5-(isopropylcarbamoyl)phenyl)picolinamido)pyridin-4-yl)-5-methylpiperidin-4-ylcarbamate |
| 199 | 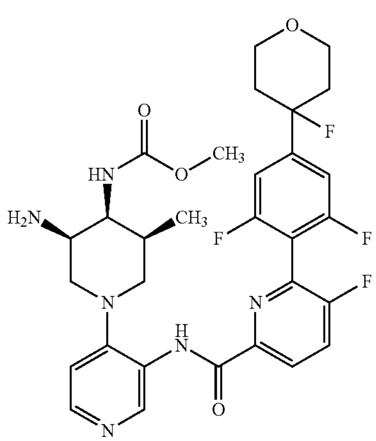 [SMILES: COC(=O)N[C@@H]1[C@H](N)CN(c2ccncc2NC(=O)c2ccc(F)c(-c3c(F)cc(C4(F)CCOCC4)cc3F)n2)C[C@@H]1C] | 617.4 | 0.68 | methyl (3R,4S,5S)-3-amino-1-(3-(6-(2,6-difluoro-4-(4-fluorotetrahydro-2H-pyran-4-yl)phenyl)-5-fluoropicolinamido)pyridin-4-yl)-5-methylpiperidin-4-ylcarbamate |

TABLE 2-continued

| Ex# | Structure | LC/MS (MH+ on UPLC) | LC/MS (Rf on UPLC) | Chemical Name |
|---|---|---|---|---|
| 200 | 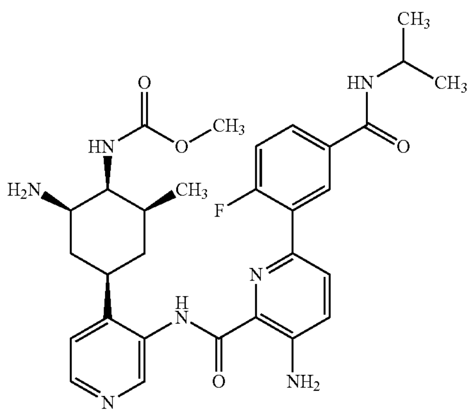 [SMILES: COC(=O)N[C@@H]1[C@H](N)C[C@H](c2ccncc2NC(=O)c2nc(-c3cc(C(=O)NC(C)C)ccc3F)ccc2N)C[C@@H]1C] | 578.4 | 0.60 | methyl (1S,2R,4R,6S)-2-amino-4-(3-(3-amino-6-(2-fluoro-5-(isopropylcarbamoyl)phenyl)picolinamido)pyridin-4-yl)-6-methylcyclohexylcarbamate |
| 201 | 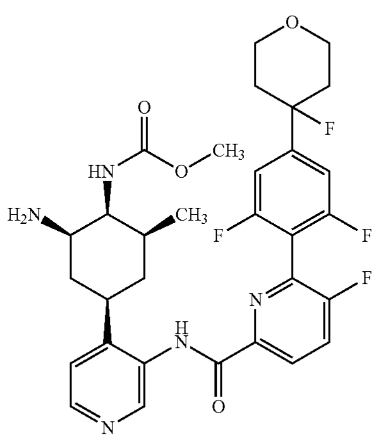 [SMILES: COC(=O)N[C@@H]1[C@H](N)C[C@H](c2ccncc2NC(=O)c2ccc(F)c(-c3c(F)cc(C4(F)CCOCC4)cc3F)n2)C[C@@H]1C] | 616.4 | 0.68 | methyl (1S,2R,4R,6S)-2-amino-4-(3-(6-(2,6-difluoro-4-(4-fluorotetrahydro-2H-pyran-4-yl)phenyl)-5-fluoropicolinamido)pyridin-4-yl)-6-methylcyclohexylcarbamate |
| 202 | 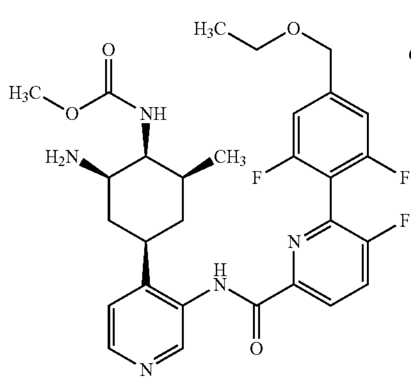 | 572.2 | 0.67 | methyl (1S,2R,4R,6S)-2-amino-4-(3-(6-(4-(ethoxymethyl)-2,6-difluorophenyl)-5-fluoropicolinamido)pyridin-4-yl)-6-methylcyclohexylcarbamate |

TABLE 2-continued

| Ex# | Structure | LC/MS (MH+ on UPLC) | LC/MS (Rf on UPLC) | Chemical Name |
|---|---|---|---|---|
| 203 | 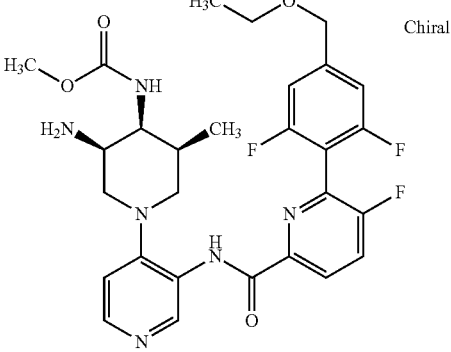 Chiral | 573.2 | 0.66 | methyl (3R,4S,5S)-3-amino-1-(3-(6-(4-(ethoxymethyl)-2,6-difluorophenyl)-5-fluoropicolinamido)pyridin-4-yl)-5-methylpiperidin-4-ylcarbamate |

In addition to LC/MS and LC characterization, representative compounds were analyzed by $^1$H-NMR. The following data in Table 3 are typical spectra of the compounds of the invention.

TABLE 3

| Ex # | $^1$H-NMR data |
|---|---|
| 1 | $^1$H NMR (400 MHz, Methanol-d) δ ppm 0.65 (d, J = 6.70 Hz, 1 H) 1.81 (d, J = 13.11 Hz, 1 H) 2.00-2.20 (m, 1 H) 2.22-2.37 (m, 1 H) 2.61-2.79 (m, 1 H) 3.34-3.45 (m, 1 H) 3.89 (dt, J = 12.76, 4.30 Hz, 1 H) 4.86 (s, 5 H) 5.00 (br. s., 1 H) 7.22 (t, J = 8.31 Hz, 1 H) 7.64 (tt, J = 8.48, 6.46 Hz, 1 H) 7.83-7.92 (m, 1 H) 8.04 (t, J = 8.73 Hz, 1 H) 8.08 (s, 1 H) 8.42 (dd, J = 8.63, 3.94 Hz, 1 H) 8.60 (br. s., 1 H) 8.90 (br. s., 1 H) |
| 4 | $^1$H NMR (400 MHz, METHANOL-d4) δ ppm 0.48 (d, J = 6.90 Hz, 3 H) 2.40-2.55 (m, 1 H) 2.64 (s, 1 H) 3.49-3.61 (m, 1 H) 3.67-3.79 (m, 1 H) 3.90 (dd, J = 11.40, 4.30 Hz, 1 H) 3.97-4.08 (m, 1 H) 4.14-4.28 (m, 1 H) 4.96 (t, J = 4.38 Hz, 1 H) 7.26 (t, J = 8.39 Hz, 2 H) 7.49-7.57 (m, 3 H) 7.61-7.72 (m, 1 H) 7.82 (dd, J = 2.64, 1.52 Hz, 1 H) 8.05 (t, J = 8.71 Hz, 1 H) 8.33 (s, 1 H) 8.39 (dd, J = 6.58, 0.90 Hz, 1 H) 8.46 (dd, J = 8.68, 3.94 Hz, 1 H) 9.15 (s, 1 H) |
| 5 | $^1$H NMR (400 MHz, METHANOL-d4) δ ppm 0.41 (d, J = 6.85 Hz, 3 H) 2.50 (td, J = 11.57, 4.55 Hz, 1 H) 3.59 (t, J = 12.94 Hz, 1 H) 3.81 (dd, J = 13.60, 3.81 Hz, 1 H) 3.94-4.15 (m, 2 H) 4.18-4.33 (m, 1 H) 5.11 (t, J = 4.16 Hz, 1 H) 7.29 (t, J = 8.49 Hz, 2 H) 7.62 (d, J = 6.75 Hz, 1 H) 7.70 (tt, J = 8.49, 6.50 Hz, 1 H) 7.90 (d, J = 0.93 Hz, 1 H) 8.07 (t, J = 8.68 Hz, 1 H) 8.17 (d, J = 0.68 Hz, 1 H) 8.42 (d, J = 6.65 Hz, 1 H) 8.48 (dd, J = 8.66, 3.96 Hz, 1 H) 9.13 (s, 1 H) |
| 6 | $^1$H NMR in DMSOd6: δ 10.94 (s, 1H), 10.49 (s, 1H), 8.60 (s, 1H), 8.48 (d, J = 4.0, 1H), 8.35 (dd, J = 8.0, 4.0, 1H), 8.20 (t, J = 8.0, 1 H), 8.02 (broad doublet, J = 4.0, 2H), 7.67-7.74 (m, 1H), 7.42 (d, J = 4.0, 1H), 7.36 (t, J = 8.0, 2H), 4.24 (m, 1H), 3.82-3.86 (m, 1H), 3.21-3.27 (m, 1H), 2.50-2.55 (m, 1H), 2.24 (d, J = 12.0, 1H), 1.86 (d, J = 16.0, 1H), 1.68 (q, J = 12.0, 1H), 1.59 (q, J = 12.0, 1H), 1.40 (d, J = 8.0, 3H). |
| 7 | $^1$H NMR (400 MHz, METHANOL-d4) δ ppm 0.42 (d, J = 6.85 Hz, 3 H) 2.37 (s, 3 H) 2.46 (dd, J = 11.71, 7.02 Hz, 1 H) 3.55 (t, J = 12.84 Hz, 1 H) 3.77 (dd, J = 13.62, 3.99 Hz, 1 H) 3.89-4.09 (m, 2 H) 4.12-4.30 (m, 1 H) 4.93 (t, J = 4.40 Hz, 1 H) 7.27 (t, J = 8.41 Hz, 2 H) 7.56 (d, J = 6.75 Hz, 1 H) 7.68 (tt, J = 8.49, 6.48 Hz, 1 H) 7.83 (d, J = 0.59 Hz, 1 H) 8.06 (t, J = 8.71 Hz, 1 H) 8.36-8.42 (m, 1 H) 8.47 (dd, J = 8.68, 3.94 Hz, 1 H) 9.14 (s, 1 H) |
| 11 | $^1$H NMR in DMSO$_{d6}$: δ 10.55 (s, 1H), 8.55 (s, 1H), 8.47 (d, J = 4.0, 1H), 8.37 (dd, J = 8.0, 4.0, 1H), 8.21 (t, J = 8.0, 1H), 8.16 (broad doublet, J = 4.0, 2H), 7.67-7.74 (m, 1H), 7.40 (d, J = 8.0, 1H), 7.36 (t, J = 8.0, 2H), 4.20-4.26 (m, 1H), 3.50-3.70 (m, 2H), 2.76-2.82 (m, 1H), 2.49-2.54 (m, 1H), 2.32-2.36 (m, 1H), 2.16-2.18 (m, 1 H), 1.91(q, J = 12, 1H), 1.65(q, J = 12, 1H), 0.97 (d, J = 8.0, 3H). |
| 12 | $^1$H NMR in DMSO$_{d6}$: δ 10.49 (s, 1H), 8.57 (s, 1H), 8.47(d, J = 4.0, 1H), 8.35 (dd, J = 8.0, 4.0, 1H), 8.25 (broad doublet, J = 4.0, 2H), 8.20 (t, J = 8.0, 1H), 7.67-7.74 (m, 1H), 7.42 (d, J = 8.0, 1H), 7.36 (t, J = 8.0, 2H), 4.04-4.08 (m, 1H), 3.79 (s, 3H), 3.23-3.29 (m, 1H), 2.39-2.45 (m, 1H), 2.11 (d, J = 8.0, 1H), 2.10 (d, J = 8.0, 1H), 1.90 (q, J = 12, 1H), 1.40 (q, J = 12, 1H), 1.01 (d, J = 4.0, 3H). |
| 13 | $^1$H NMR in DMSO$_{d6}$: δ 10.48 (s, 1H), 8.57 (s, 1H), 8.47(d, J = 4.0, 1H), 8.35 (dd, J = 8.0, 4.0, 1H), 8.20 (t, J = 8.0, 1H), 8.08 (broad singlet, 2H), 7.67-7.74 (m, 1H), 7.42 (d, J = 8.0, 1H), 7.36 (t, J = 8.0, 2H), 3.88-3.92 (m, 1H), 3.80 (s, 3H), 3.22-3.28 (m, 1H), 2.51-2.58 (m, 1H), 2.25 (d, J = 12.0, 1H), 1.86 (d, J = 12.0, 1H), 1.70 (q, J = 12, 1H), 1.62 (q, J = 12, 1H), 1.34 (d, J = 4.0, 3H). |

TABLE 3-continued

| Ex # | $^1$H-NMR data |
|---|---|
| 14 | $^1$H NMR (400 MHz, METHANOL-d4) δ ppm 0.43 (d, J = 6.85 Hz, 3 H) 2.36-2.53 (m, 1 H) 3.43 (s, 3 H) 3.46-3.58 (m, 1 H) 3.69 (dd, J = 13.57, 3.79 Hz, 1 H) 3.88 (dd, J = 12.30, 4.52 Hz, 1 H) 4.02 (dt, J = 11.63, 4.68 Hz, 1 H) 4.12-4.26 (m, 1 H) 4.60 (s, 2 H) 4.95 (t, J = 4.38 Hz, 2 H) 7.28 (t, J = 8.39 Hz, 2 H) 7.54 (d, J = 6.55 Hz, 1 H) 7.69 (tt, J = 8.50, 6.47 Hz, 1 H) 8.00-8.12 (m, 2 H) 8.39 (dd, J = 6.55, 0.88 Hz, 1 H) 8.47 (dd, J = 8.66, 3.96 Hz, 1 H) 9.18 (s, 1 H) |
| 15 | $^1$H NMR in DMSO$_{d6}$: δ 10.51 (s, 1H), 8.53 (s, 1H), 8.51 (d, J = 4.0, 1H), 8.33 (dd, J = 8.0, 4.0, 1H), 8.20 (t, J = 8.0, 1H), 8.09 (broad doublet, J = 4.0, 2H), 7.65-7.75 (m, 1H), 7.36 (t, J = 8.0, 2H), 7.30 (d, J = 8.0, 1H), 3.84-4.02 (m, 3H), 3.58-3.68 (m, 1H), 3.43-3.53 (m, 1H), 3.28-3.36 (m, 1H), 3.04-3.14 (m, 1H), 1.92-2.18 (m, 4 H), 1.56-1.63 (m, 1H), 1.24 (d, J = 8.0, 3H). |
| 30 | ($^1$H NMR, DMSO$_{d-6}$) δ 10.48 (s, 1H), 8.57 (s, 1H), 8.48 (d, J = 8.0, 1H), 8.33 (dd, J = 8.0, 4.0, 1H), 8.20 (t, J = 8.0, 1H), 7.80 (bs, 2H), 7.71 (quintet, J = 8.0, 2H), 7.43 (d, J = 4.0, 1H), 7.37 (t, J = 8.0, 2H), 3.43-3.50 (m, 2H), 2.88-2.96 (m, 1H), 2.04 (d, J = 8.0, 1H), 1.90 (s, 3H), 1.82 (d, J = 12.0, 1H), 1.64 (q, J = 12.0, 1H), 1.46-1.55 (m, 1H), 1.32 (q, J = 12.0, 1H), 0.85 (d, J = 4.0, 3H). |
| 33 | $^1$H NMR, 400 MHz DMSOd6, δ 10.44 (s, 1H), 8.58 (d, J = 4.0, 1H), 8.47 (d, J = 4.0, 1H), 8.34 (dd, J = 8.0, 4.0, 1H), 8.20 (dd, J = 8.0, 8.0, 1H), 8.20 (dd, J = 16.0, 4.0, 1H), 7.67-7.74 (m, 1H), 7.36 (dd, J = 8.0, 8.0, 2H), 7.26 (d, J = 4.0, 1H), 2.85-2.95 (m, 2H), 2.18 (s, 3H), 1.88-1.98 (m, 1H), 1.74-1.84 (m, 1H), 1.48-1.56 (m, 1H), 1.38-1.48 (m, 1H), 1.18-1.28 (m, 1H), 1.02 (d, J = 8.0, 3H) |
| 34 | $^1$H NMR, 400 MHz DMSOd6, δ 10.44 (s, 1H), 8.60 (d, J = 8.0, 1H), 8.48 (d, J = 4.0, 1H), 8.34 (dd, J = 8.0, 4.0, 1H), 8.20 (dd, J = 8.0, 8.0, 1H), 8.00 (dd, J = 16.0, 4.0, 1H), 7.67-7.74 (m, 1H), 7.34-7.38 (m, 3H), 3.14 (s, 3H), 3.02-3.12 (m, 2H), 2.18-2.24 (m, 1H), 1.84-1.96 (m, 3H), 1.62-1.72 (m, 1H), 1.38-1.48 (m, 1H), 1.18 (d, J = 4.0, 3H). |
| 36 | $^1$H NMR, 400 MHz DMSOd6, δ 10.48 (s, 1H), 8.58 (d, J = 4.0, 1H), 8.50 (d, J = 4.0, 1H), 8.34 (dd, J = 8.0, 4.0, 1H), 8.20 (dd, J = 8.0, 8.0, 1H), 8.20 (dd, J = 16.0, 4.0, 1H), 7.67-7.74 (m, 1H), 7.42 (d, J = 4.0, 1H), 7.36 (dd, J = 8.0, 8.0, 2H), 3.40-3.42 (m, 1H), 3.06-3.20 (m, 1H), 2.92 (s, 3H), 2.06-2.20 (m, 1H), 1.95-2.04 (m, 2H), 1.70-1.80 (m, 1H), 1.56-1.70 (m, 1H), 0.86 (d, J = 8.0, 3H). |
| 37 | $^1$H NMR, 400 MHz DMSOd6, δ 10.52 (s, 1H), 8.51-8.54 (m, 2H), 8.34 (dd, J = 8.0, 4.0, 1H), 8.20 (dd, J = 8.0, 8.0, 1H), 8.15 (dd, J = 16.0, 4.0, 1H), 7.67-7.74 (m, 1H), 7.36 (dd, J = 8.0, 8.0, 2H), 7.28 (d, J = 4.0, 1H), 3.77-3.79 (m, 1H), 3.18 (s, 3H), 3.02-3.20 (m, 1H), 1.94-2.40 (m, 4H), 1.57-1.62 (m, 1H), 1.24 (d, J = 8.0, 3H). |
| 56 | $^1$H NMR, (400, DMSOd6) δ 10.45 (s, 1H), 8.92 (s, 1H), 8.56 (s, 1H), 8.43 (d, J = 4.0, 1H), 8.40 (dd, J = 8.0, 4.0, 1H), 8.24 (t, J = 8.0, 1H), 8.17-8.24 (m, 2H), 8.17 (s, 1H), 7.70-7.80 (m, 1H), 7.35-7.43 (m, 3H), 4.780-4.82 (m, 1H), 3.96 (t, J = 12.0, 1H), 3.60-3.90 (m, 3H), 3.50 (t, J = 12.0, 1H), 2.25-2.35 (m, 1H), 0.31 (d, J = 8.0, 3H). |
| 64 | $^1$H NMR, (400 MHz, METHANOL-d4) δ ppm 1.19 (d, J = 6.90 Hz, 3 H) 1.42 (d, J = 12.76 Hz, 1 H) 1.63-1.77 (m, 2 H) 1.84-2.04 (m, 3 H) 2.71-2.91 (m, 2 H) 3.13-3.24 (m, 2 H) 3.40-3.52 (m, 1 H) 3.73 (s, 1 H) 3.76-3.87 (m, 1 H) 3.93 (td, J = 8.68, 5.14 Hz, 1 H) 7.14 (t, J = 8.75 Hz, 2 H) 7.47 (tt, J = 8.44, 6.25 Hz, 1 H) 7.68 (d, J = 5.62 Hz, 1 H) 8.46 (d, J = 5.62 Hz, 1 H) 9.18 (s, 1 H) |
| 66 | $^1$H NMR, (400 MHz, METHANOL-d4) δ ppm 0.43 (d, J = 6.80 Hz, 3 H) 2.37-2.60 (m, 1 H) 3.60 (t, J = 12.94 Hz, 1 H) 3.83 (dd, J = 13.64, 4.11 Hz, 1 H) 3.95-4.14 (m, 2 H) 4.17-4.32 (m, 1 H) 4.75 (s, 2 H) 5.03 (t, J = 4.01 Hz, 2 H) 7.27 (t, J = 8.46 Hz, 2 H) 7.59 (d, J = 6.85 Hz, 1 H) 7.62-7.75 (m, 1 H) 7.97-8.12 (m, 2 H) 8.40 (dd, J = 6.80, 0.93 Hz, 1 H) 8.47 (dd, J = 8.66, 3.91 Hz, 1 H) 9.12 (d, J = 0.83 Hz, 1 H). |
| 74 | $^1$H NMR, (400 MHz, DMSO-d6) δ ppm 0.96 (d, J = 6.85 Hz, 3 H) 1.16-1.36 (m, 1 H) 1.46 (d, J = 12.81 Hz, 1 H) 1.50-1.78 (m, 3 H) 2.41 (s, 3 H) 2.89 (t, J = 12.06 Hz, 1 H) 3.07 (s, 3 H) 3.24 (br. s., 2 H) 3.86 (dt, J = 10.20, 5.12 Hz, 2 H) 3.99 (td, J = 9.29, 4.30 Hz, 1 H) 7.17 (d, J = 9.29 Hz, 2 H) 7.22 (d, J = 5.23 Hz, 1 H) 7.86 (br. s., 3 H) 8.08-8.20 (m, 1 H) 8.28 (dd, J = 8.66, 4.06 Hz, 1 H) 8.43 (d, J = 5.18 Hz, 1 H) 8.58 (s, 1 H) 10.38 (s, 1 H). |
| 77 | $^1$H NMR, (400 MHz, DMSO-d6) δ ppm 1.00 (d, J = 6.80 Hz, 3 H) 1.42-1.81 (m, 3 H) 2.92 (t, J = 12.32 Hz, 1 H) 3.10 (s, 2 H) 3.28 (br. s., 1 H) 3.33-3.44 (m, 1 H) 3.54 (br. s., 1 H) 3.59-3.72 (m, 1 H) 3.89 (dt, J = 10.17, 5.09 Hz, 1 H) 4.02 (td, J = 9.26, 4.23 Hz, 1 H) 7.23 (d, J = 5.23 Hz, 1 H) 7.36 (t, J = 8.31 Hz, 2 H) 7.63-7.77 (m, 1 H) 7.89 (br. s., 2 H) 8.13-8.27 (m, 1 H) 8.33 (dd, J = 8.68, 4.08 Hz, 1 H) 8.46 (d, J = 5.13 Hz, 1 H) 8.60 (s, 1 H) 10.43 (s, 1 H). |
| 86 | $^1$H NMR, (400 MHz, METHANOL-d4) δ ppm 1.13 (d, J = 6.80 Hz, 3 H) 1.46-1.86 (m, 3 H) 1.88-2.06 (m, 2 H) 2.72-2.93 (m, 2 H) 3.08-3.21 (m, 1 H) 3.34-3.42 (m, 1 H) 3.70 (s, 1 H) 3.76-3.88 (m, 1 H) 3.93 (td, J = 8.69, 5.01 Hz, 1 H) 7.22 (t, J = 8.27 Hz, 2 H) 7.55-7.77 (m, 2 H) 8.04 (t, J = 8.71 Hz, 1 H) 8.42 (dd, J = 8.66, 3.96 Hz, 1 H) 8.55 (d, J = 5.62 Hz, 1 H) 9.03 (s, 1 H) |
| 90 | $^1$H NMR, (400 MHz, <cd3od>) δ ppm 8.95 (s, 1 H), 8.50 (d, J = 5.48 Hz, 1 H), 8.39 (dd, J = 8.61, 3.91 Hz, 1 H), 8.00 (t, J = 8.80 Hz, 1 H), 7.60 (d, J = 5.48 Hz, 1 H), 7.05 (d, J = 9.39 Hz, 2 H), 3.72 (quin, J = 7.24 Hz, 2 H), 3.57 (br. s., 1 H), 3.08 (t, J = 11.74 Hz, 1 H), 2.47 (s, 3 H), 1.84-2.00 (m, 2 H), 1.72 (d, J = 5.48 Hz, 1 H), 1.54-1.65 (m, 2 H), 1.28 (t, J = 7.04 Hz, 3 H), 1.06 (d, J = 6.65 Hz, 3 H) |

TABLE 3-continued

| Ex # | $^1$H-NMR data |
|---|---|
| 91 | $^1$H NMR, (400 MHz, <cd3od>) δ ppm 8.96 (s, 1 H), 8.50 (d, J = 5.48 Hz, 1 H), 8.41 (dd, J = 8.61, 3.91 Hz, 1 H), 8.03 (t, J = 8.80 Hz, 1 H), 7.58-7.68 (m, 2 H), 7.21 (t, J = 8.41 Hz, 2 H), 3.72 (quin, J = 7.24 Hz, 2 H), 3.57 (br. s., 1 H), 3.03-3.15 (m, 1 H), 1.84-2.00 (m, 2 H), 1.72 (br. s., 1 H), 1.51-1.66 (m, 2 H), 1.28 (t, J = 7.04 Hz, 3 H), 1.06 (d, J = 6.65 Hz, 3 H) |
| 92 | $^1$H NMR, (300 MHz, <cd3od>) δ ppm 8.93-9.05 (m, 1 H), 8.46-8.57 (m, 1 H), 8.35-8.46 (m, 1 H), 7.97-8.09 (m, 1 H), 7.55-7.73 (m, 2 H), 7.15-7.30 (m, 2 H), 3.58 (s, 3 H), 3.42-3.51 (m, 1 H), 3.00-3.18 (m, 1 H), 1.83-2.00 (m, 2 H), 1.45-1.81 (m, 3 H), 1.07 (d, J = 6.74 Hz, 3 H) |
| 94 | $^1$H NMR, (400 MHz, METHANOL-d4) δ ppm 8.82 (s, 1 H), 8.48 (d, J = 5.48 Hz, 1 H), 8.39 (dd, J = 8.61, 3.91 Hz, 1 H), 8.01 (t, J = 8.61 Hz, 1 H), 7.54 (d, J = 5.09 Hz, 1 H), 7.19 (d, J = 9.39 Hz, 2 H), 3.58 (s, 3 H), 3.46 (s, 1 H), 3.00-3.21 (m, 5 H), 2.23-2.40 (m, 4 H), 1.85-1.95 (m, 2 H), 1.75 (br. s., 1 H), 1.50-1.67 (m, 2 H), 1.08 (d, J = 6.65 Hz, 3 H) |
| 95 | $^1$H NMR, (400 MHz, METHANOL-d4) δ ppm 8.92 (s, 1 H), 8.47 (d, J = 5.48 Hz, 1 H), 8.36 (dd, J = 8.63, 3.94 Hz, 1 H), 7.98 (t, J = 8.71 Hz, 1 H), 7.56 (d, J = 5.48 Hz, 1 H), 7.08 (d, J = 9.44 Hz, 2 H), 3.56 (s, 3 H), 3.44 (s, 1 H), 2.95-3.10 (m, 2 H), 1.81-1.97 (m, 2 H), 1.71 (d, J = 5.97 Hz, 1 H), 1.46-1.66 (m, 2 H) 1.30 (d, J = 6.94 Hz, 6 H), 1.05 (d, J = 6.80 Hz, 3 H) |
| 96 | $^1$H NMR, (400 MHz, METHANOL-d4) δ ppm 8.92 (s, 1 H), 8.49 (d, J = 5.53 Hz, 1 H), 8.39 (dd, J = 8.68, 3.94 Hz, 1 H), 8.01 (t, J = 8.73 Hz, 1 H), 7.60 (d, J = 5.58 Hz, 1 H), 7.30 (d, J = 9.24 Hz, 2 H), 3.90-4.01 (m, 2 H), 3.84 (td, J = 11.91, 1.61 Hz, 2 H), 3.44 (s, 1 H), 2.99-3.15 (m, 1 H), 2.30 (td, J = 13.14, 5.45 Hz, 1 H), 2.20 (td, J = 13.14, 5.40 Hz, 1 H), 1.81-1.98 (m, 4 H), 1.66-1.79 (m, 1 H), 1.44-1.65 (m, 2 H), 1.05 (d, J = 6.85 Hz, 3 H) |
| 97 | $^1$H NMR, (400 MHz, METHANOL-d4) δ ppm 8.93 (s, 1 H), 8.46 (d, J = 5.43 Hz, 1 H), 8.37 (dd, J = 8.63, 3.94 Hz, 1 H), 7.99 (t, J = 8.73 Hz, 1 H), 7.55 (d, J = 5.48 Hz, 1 H), 7.29 (d, J = 9.68 Hz, 2 H), 3.56 (s, 3 H), 3.42-3.45 (m, 1 H), 3.05 (ddd, J = 15.75, 11.59, 3.91 Hz, 1 H), 1.80-1.98 (m, 2 H), 1.66-1.78 (m, 1 H), 1.45-1.65 (m, 8 H), 1.05 (d, J = 6.85 Hz, 3 H) |
| 98 | $^1$H NMR, (300 MHz, <cd3od>) δ ppm 8.98 (s, 1 H), 8.49 (d, J = 5.57 Hz, 1 H), 8.40 (dd, J = 8.64, 3.96 Hz, 1 H), 8.02 (t, J = 8.64 Hz, 1 H), 7.60 (d, J = 5.57 Hz, 1 H), 7.35 (d, J = 9.67 Hz, 2 H), 3.58 (s, 3 H), 3.46 (s, 1 H), 3.00-3.15 (m, 1 H), 2.35-2.62 (m, 4 H), 2.02-2.21 (m, 1 H), 1.78-1.99 (m, 3 H), 1.45-1.68 (m, 1 H), 1.07 (d, J = 6.74 Hz, 3 H) |
| 99 | $^1$H NMR, (400 MHz, <cd3od>) δ ppm 0.97 (d, J = 6.80 Hz, 3 H) 1.36-1.52 (m, 1 H) 1.63-1.73 (m, 1 H) 1.75-1.91 (m, 7 H) 2.83-3.02 (m, 1 H) 3.25 (s, 2 H) 3.51-3.54 (m, 3 H) 3.56-3.63 (m, 1 H) 4.06 (dt, J = 11.21, 2.95 Hz, 4 H) 7.12 (d, J = 9.19 Hz, 2 H) 7.38 (d, J = 5.33 Hz, 1 H) 7.97 (t, J = 8.73 Hz, 1 H) 8.29-8.41 (m, 2 H) 8.95 (s, 1 H) |
| 100 | $^1$H NMR, (300 MHz, <cd3od>) δ ppm 8.97 (s, 1 H), 8.50 (d, J = 5.57 Hz, 1 H), 8.40 (dd, J = 8.64, 3.96 Hz, 1 H), 8.02 (t, J = 8.79 Hz, 1 H), 7.62 (d, J = 5.57 Hz, 1 H), 7.19 (d, J = 9.08 Hz, 2 H), 4.61 (s, 2 H), 3.63 (q, J = 7.03 Hz, 2 H), 3.58 (s, 3 H), 3.43-3.50 (m, 1 H), 3.01-3.16 (m, 1 H), 1.83-1.99 (m, 2 H), 1.68-1.82 (m, 1 H), 1.48-1.67 (m, 2 H), 1.28 (t, J = 7.03 Hz, 3 H), 1.07 (d, J = 6.74 Hz, 3 H) |
| 101 | $^1$H NMR, (300 MHz, <cd3od>) δ ppm 8.97-9.13 (m, 1 H), 8.48-8.60 (m, 1 H), 8.33-8.45 (m, 1 H), 7.94-8.08 (m, 1 H), 7.60-7.72 (m, 1 H), 6.71-6.87 (m, 2 H), 4.92-5.04 (m, 1 H), 4.65-4.79 (m, 1 H), 3.47-3.53 (m, 1 H) 3.60 (s, 3 H), 3.02-3.20 (m, 1 H), 1.86-2.06 (m, 2 H), 1.71-1.85 (m, 1 H), 1.48-1.70 (m, 2 H), 1.39 (d, J = 6.15 Hz, 6 H), 1.10 (d, J = 6.74 Hz, 3 H) |
| 104 | $^1$H NMR, (400 MHz, <cd3od>) δ ppm 9.26 (d, J = 5.1 Hz, 1 H), 8.74 (s, 1 H), 8.55 (d, J = 5.5 Hz, 1 H), 8.21 (d, J = 5.1 Hz, 1 H), 7.51-7.70 (m, 2 H), 7.10-7.27 (m, 2 H), 3.80 (br. s., 1 H), 3.60-3.74 (m, 1 H), 3.20-3.28 (m, 1 H), 3.16 (s, 3 H), 2.32 (quin, J = 12.7 Hz, 2 H), 2.04-2.24 (m, 2 H), 1.65-1.84 (m, 1 H), 1.37 (d, J = 7.0 Hz, 3 H) |
| 107 | $^1$H NMR, (400 MHz, <cd3od>) δ ppm 1.36 (d, J = 7.04 Hz, 3 H) 1.75 (dtd, J = 12.98, 8.61, 8.61, 3.99 Hz, 3 H) 2.01-2.23 (m, 4 H) 2.24-2.39 (m, 2 H) 3.16 (s, 3 H) 3.19-3.28 (m, 1 H) 3.54-3.73 (m, 3 H) 3.79 (br. s., 1 H) 3.89-4.04 (m, 2 H) 4.64-4.75 (m, 1 H) 6.83 (d, J = 9.98 Hz, 2 H) 7.61 (d, J = 5.53 Hz, 1 H) 7.96 (t, J = 8.68 Hz, 1 H) 8.34 (dd, J = 8.61, 3.91 Hz, 1 H) 8.53 (d, J = 5.48 Hz, 1 H) 8.72 (s, 1 H) |
| 108 | $^1$H NMR, (400 MHz, <cd3od>) δ ppm 1.36 (d, J = 6.99 Hz, 3 H) 1.75 (d, J = 13.50 Hz, 1 H) 1.80-1.91 (m, 1 H) 2.03-2.23 (m, 3 H) 2.23-2.37 (m, 2 H) 2.38-2.62 (m, 4 H) 3.17 (s, 3 H) 3.61-3.73 (m, 1 H) 3.78 (br. s., 1 H) 7.34 (d, J = 9.59 Hz, 2 H) 7.59 (d, J = 5.48 Hz, 1 H) 8.01 (t, J = 8.66 Hz, 1 H) 8.38 (dd, J = 8.61, 3.91 Hz, 1 H) 8.52 (d, J = 5.43 Hz, 1 H) 8.73 (s, 1 H) |
| 109 | $^1$H NMR (400 MHz, <dmso-$_{d6}$>) δ ppm 1.15 (dd, J = 6.46, 1.76 Hz, 7 H) 1.22 (d, J = 6.65 Hz, 4 H) 1.60 (d, J = 12.91 Hz, 1 H) 1.86-2.06 (m, 2 H) 2.08-2.35 (m, 3 H) 4.10 (dd, J = 13.89, 6.85 Hz, 4 H) 7.26-7.47 (m, 4 H) 7.77 (dd, J = 8.61, 2.35 Hz, 1 H) 7.88 (ddd, J = 8.31, 4.60, 2.35 Hz, 1 H) 8.15 (d, J = 3.13 Hz, 1 H) 8.35 (d, J = 7.83 Hz, 1 H) 8.40-8.54 (m, 2 H) 8.76 (s, 1 H) 10.36 (s, 1 H) |
| 110 | $^1$H NMR (400 MHz, <dmso-$_{d6}$>) δ ppm 1.23 (d, J = 6.65 Hz, 5 H) 1.59 (br. s., 2 H) 1.78-2.37 (m, 14 H) 3.00-3.13 (m, 2 H) 3.51-3.73 (m, 6 H) 3.77 (br. s., 2 H) 3.89 (dd, J = 11.35, 5.09 Hz, 4 H) 7.29 (d, J = 5.48 Hz, 2 H) 7.39-7.55 (m, 4 H) 8.04-8.24 (m, 7 H) 8.32 (dd, J = 8.61, 4.30 Hz, 2 H) 8.44-8.57 (m, 3 H) 10.48-10.57 (m, 2 H) |

TABLE 3-continued

| Ex # | ¹H-NMR data |
|---|---|
| 111 | ¹H NMR (400 MHz, <dmso-$_{d6}$>) δ ppm 0.95 (d, J = 6.65 Hz, 2 H) 1.15 (d, J = 6.26 Hz, 4 H) 1.48 (br. s., 3 H) 2.75-2.86 (m, 1 H) 3.02 (br. s., 1 H) 3.64-3.81 (m, 2 H) 4.00-4.18 (m, 1 H) 7.24-7.50 (m, 2 H) 7.78 (dd, J = 8.61, 2.35 Hz, 1 H) 7.83-8.01 (m, 3 H) 8.35 (d, J = 7.43 Hz, 1 H) 8.39-8.49 (m, 1 H) 8.88 (s, 1 H) 10.34 (s, 1 H) |
| 112 | ¹H NMR, (400 MHz, <cd3od>) δ ppm 1.36 (d, J = 7.04 Hz, 3 H) 1.71-1.83 (m, 1 H) 2.05-2.25 (m, 2 H) 2.25-2.41 (m, 2 H) 3.13-3.21 (m, 3 H) 3.23-3.29 (m, 1 H) 3.63-3.73 (m, 1 H) 3.80-3.86 (m, 1 H) 3.89 (s, 3 H) 6.80 (d, J = 9.78 Hz, 2 H) 7.59-7.71 (m, 1 H) 7.97 (s, 1 H) 8.31-8.40 (m, 1 H) 8.51-8.59 (m, 1 H) 8.83 (s, 1 H) |
| 114 | ¹H NMR (400 MHz, <cd3od>) δ ppm 1.32 (d, J = 6.65 Hz, 3 H) 1.69-1.84 (m, 1 H) 2.04-2.19 (m, 2 H) 2.20-2.45 (m, 2 H) 3.13-3.22 (m, 3 H) 3.24-3.29 (m, 1 H) 3.57-3.73 (m, 1 H) 3.89 (br. s., 1 H) 7.05-7.19 (m, 3 H) 7.47-7.59 (m, 1 H) 7.76 (d, J = 5.48 Hz, 1 H) 8.45-8.59 (m, 1 H) 9.16 (s, 1 H) |
| 115 | ¹H NMR, (400 MHz, <cd3od>) δ ppm 1.26 (d, J = 6.65 Hz, 3 H) 1.54-1.67 (m, 1 H) 1.89-2.02 (m, 2 H) 2.08 (q, J = 12.52 Hz, 1 H) 2.94-3.15 (m, 1H) 3.16-3.24 (m, 3 H) 3.65 (br. s., 1 H) 3.81 (br. s., 1 H) 7.10-7.34 (m, 3 H) 7.44-7.68 (m, 3 H) 8.15 (d, J = 3.91 Hz, 3 H) 8.46 (d, J = 5.48 Hz, 1 H) 8.62 (s, 1 H) 9.59 (s, 1 H) |
| 116 | ¹H NMR (400 MHz, <dmso-$_{d6}$>) δ ppm 1.03-1.31 (m, 6 H) 1.57 (d, J = 12.91 Hz, 1 H) 1.81-2.08 (m, 3 H) 2.09-2.20 (m, 1 H) 2.92-3.11 (m, 1 H) 3.17 (s, 3 H) 3.53 (q, J = 7.04 Hz, 2 H) 3.60 (d, J = 5.87 Hz, 1 H) 3.79 (br. s., 1 H) 4.48-4.67 (m, 2 H) 7.15-7.37 (m, 3 H) 8.01-8.22 (m, 4 H) 8.31 (dd, J = 8.61, 3.91 Hz, 1 H) 8.44-8.59 (m, 2 H) 10.32-10.60 (m, 1 H) |
| 117 | ¹H NMR, (400 MHz, <cd3od>) δ ppm 9.03 (s, 1 H), 8.45 (d, J = 5.1 Hz, 1 H), 8.40 (dd, J = 8.6, 3.9 Hz, 1 H), 8.02 (t, J = 8.6 Hz, 1 H), 7.53 (d, J = 5.5 Hz, 1 H), 7.35 (d, J = 10.2 Hz, 2 H), 3.91-4.03 (m, 2 H), 3.79-3.90 (m, 2 H), 3.53 (s, 3 H), 3.05-3.21 (m, 2 H), 2.93 (t, J = 10.2 Hz, 1 H), 2.09-2.26 (m, 3 H), 1.93 (dd, J = 13.5, 2.5 Hz, 1 H), 1.78 (q, J = 12.1 Hz, 1 H), 1.67 (d, J = 13.7 Hz, 2 H), 1.21-1.51 (m, 2 H), 1.07 (d, J = 6.3 Hz, 3 H) |
| 118 | ¹H NMR, (400 MHz, <cd3od>) δ ppm 8.95 (s, 1 H), 8.51 (d, J = 5.5 Hz, 1 H), 8.40 (dd, J = 8.6, 3.9 Hz, 1 H), 8.02 (t, J = 8.6 Hz, 1 H), 7.63 (d, J = 5.5 Hz, 1 H), 7.35 (d, J = 9.8 Hz, 2 H), 4.26 (dt, J = 10.7, 5.0 Hz, 1 H), 4.00-4.12 (m, 1 H), 3.91-4.00 (m, 2 H), 3.79-3.90 (m, 2 H), 3.69 (s, 1 H), 3.55 (t, J = 5.3 Hz, 2 H), 3.35-3.46 (m, 1 H), 3.03-3.20 (m, 4 H), 2.16 (td, J = 13.0, 4.9 Hz, 2 H), 1.88-2.01 (m, 2 H), 1.78 (d, J = 6.3 Hz, 1 H), 1.49-1.72 (m, 4 H), 1.11 (d, J = 6.7 Hz, 3 H) |
| 119 | ¹H NMR, (400 MHz, <cd3od>) δ ppm 8.76 (s, 1 H), 8.52 (d, J = 5.5 Hz, 1 H), 8.34 (dd, J = 8.6, 3.9 Hz, 1 H), 7.97 (t, J = 8.8 Hz, 1 H), 7.61 (d, J = 5.5 Hz, 1 H), 6.82 (d, J = 10.2 Hz, 2 H), 4.21 (dd, J = 5.1, 3.5 Hz, 2 H), 3.73-3.87 (m, 3 H), 3.63-3.72 (m, 1 H), 3.43 (s, 3 H), 3.19-3.28 (m, 1 H), 3.17 (s, 3 H), 2.32 (qd, J = 12.7, 6.1 Hz, 2 H), 2.05-2.24 (m, 2 H), 1.75 (d, J = 13.3 Hz, 1 H), 1.36 (d, J = 7.0 Hz, 3 H) |
| 120 | ¹H NMR, (300 MHz, <cd3od>) δ ppm 8.77 (s, 1 H), 8.62 (s, 1 H), 8.54 (d, J = 5.5 Hz, 1 H), 7.55-7.69 (m, 2 H), 7.23 (t, J = 8.6 Hz, 2 H), 3.81 (br. s., 1 H), 3.67-3.78 (m, 1 H), 3.17 (s, 3 H), 2.20-2.46 (m, 3 H), 2.08-2.19 (m, 1 H), 1.78 (d, J = 13.3 Hz, 1 H), 1.40 (d, J = 7.0 Hz, 3 H) |
| 121 | ¹H NMR, (400 MHz, <cd3od>) δ ppm 8.72 (s, 1 H), 8.53 (d, J = 5.5 Hz, 1 H), 8.38 (dd, J = 8.6, 3.9 Hz, 1 H), 8.00 (t, J = 8.6 Hz, 1 H), 7.62 (d, J = 5.5 Hz, 1 H), 7.34 (d, J = 9.8 Hz, 2 H), 3.82-4.01 (m, 4 H), 3.79 (br. s., 1 H), 3.63-3.73 (m, 1 H), 3.20-3.28 (m, 1 H), 3.17 (s, 3 H), 2.31 (qd, J = 12.7, 8.4 Hz, 2 H), 2.06-2.24 (m, 4 H), 1.75 (d, J = 13.3 Hz, 1 H), 1.65 (d, J = 13.3 Hz, 2 H), 1.36 (d, J = 7.0 Hz, 3 H) |
| 122 | ¹H NMR, (400 MHz, <cd3od>) δ ppm 8.77 (s, 1 H), 8.54 (d, J = 5.5 Hz, 1 H), 8.36 (dd, J = 8.8, 4.1 Hz, 1 H), 7.99 (t, J = 8.6 Hz, 1 H), 7.63 (d, J = 5.5 Hz, 1 H), 7.03 (d, J = 9.4 Hz, 2 H), 3.80 (br. s., 1 H), 3.62-3.73 (m, 1 H), 3.20-3.29 (m, 1 H), 3.17 (s, 3 H), 2.46 (s, 3 H), 2.25-2.40 (m, 2 H), 2.06-2.24 (m, 2 H), 1.68-1.82 (m, 1 H), 1.36 (d, J = 7.0 Hz, 3 H) |
| 123 | ¹H NMR, (400 MHz, <cd3od>) δ ppm 0.90 (d, J = 6.65 Hz, 3 H) 1.72-1.81 (m, 2 H) 1.88-2.07 (m, 2 H) 2.07-2.21 (m, 1 H) 3.24-3.28 (m, 1 H) 3.53-3.63 (m, 1 H) 4.87-4.97 (m, 1 H) 5.59-5.69 (m, 1 H) 6.94-7.08 (m, 2 H) 7.23 (s, 2 H) 7.58-7.70 (m, 1 H) 7.72-7.84 (m, 2 H) 8.01-8.09 (m, 1 H) 8.15-8.22 (m, 1 H) 8.39-8.48 (m, 1 H) 8.55-8.62 (m, 1 H) 9.08 (s, 1 H) |
| 124 | ¹H NMR, (400 MHz, <cd3od>) δ ppm 1.08 (d, J = 6.26 Hz, 3 H) 1.43 (q, J = 12.52 Hz, 1 H) 1.59-1.75 (m, 1 H) 1.81 (q, J = 12.39 Hz, 1 H) 1.94 (dd, J = 13.30, 2.74 Hz, 1 H) 2.15-2.30 (m, 1 H) 2.96 (t, J = 9.98 Hz, 1 H) 3.08-3.22 (m, 2 H) 3.44 (s, 3 H) 3.53 (s, 3 H) 3.73-3.83 (m, 2 H) 4.11-4.28 (m, 2 H) 6.83 (d, J = 10.17 Hz, 2 H) 7.69 (d, J = 5.48 Hz, 1 H) 8.00 (t, J = 8.80 Hz, 1 H) 8.38 (dd, J = 8.61, 3.52 Hz, 1 H) 8.51 (d, J = 5.48 Hz, 1 H) 9.20 (s, 1 H) |
| 125 | ¹H NMR (400 MHz, <dmso-$_{d6}$>) δ ppm 1.03 (d, J = 6.65 Hz, 3 H) 1.33 (q, J = 12.52 Hz, 1 H) 1.45-1.68 (m, 2 H) 1.70-1.88 (m, 2 H) 2.86-3.04 (m, 1 H) 3.04-3.15 (m, 3 H) 3.22-3.43 (m, 3 H) 3.58 (br. s., 2 H) 3.61-3.72 (m, 2 H) 3.89 (dt, J = 10.08, 4.94 Hz, 6 H) 4.02 (td, J = 9.20, 4.30 Hz, 5 H) 7.15-7.34 (m, 3 H) 7.45-7.69 (m, 3 H) 7.95 (br. s., 3 H) 8.42 (d, J = 5.48 Hz, 1 H) 8.78 (s, 1 H) 9.48 (s, 1 H) |

TABLE 3-continued

| Ex # | ¹H-NMR data |
|---|---|
| 126 | ¹H NMR (400 MHz, <dmso-$_{d6}$>) δ ppm 0.93 (d, J = 6.26 Hz, 7 H) 1.15 (d, J = 6.65 Hz, 14 H) 1.32-1.46 (m, 2 H) 1.49-1.70 (m, 5 H) 1.72-1.85 (m, 2 H) 2.09 (d, J = 10.17 Hz, 2 H) 2.88 (t, J = 9.98 Hz, 2 H) 2.98-3.14 (m, 5 H) 3.30 (s, 7 H) 4.00-4.17 (m, 2 H) 7.31-7.41 (m, 4 H) 7.45 (d, J = 5.09 Hz, 2 H) 7.79 (dd, J = 9.00, 1.96 Hz, 2 H) 7.85-8.00 (m, 8 H) 8.33 (d, J = 7.83 Hz, 2 H) 8.46 (d, J = 5.09 Hz, 4 H) 8.89 (s, 2 H) 10.36 (s, 2 H) |
| 127 | ¹H NMR (400 MHz, <dmso-$_{d6}$>) δ ppm 0.95 (d, J = 6.26 Hz, 3 H) 1.19-1.39 (m, 1 H) 1.47-1.67 (m, 2 H) 1.74 (d, J = 11.35 Hz, 1 H) 1.87 (t, J = 11.93 Hz, 2 H) 2.00 (br. s., 1 H) 2.11-2.37 (m, 2 H) 2.82-3.13 (m, 3 H) 3.37 (s, 3 H) 3.69 (t, J = 11.35 Hz, 2 H) 3.89 (dd, J = 11.35, 5.09 Hz, 2 H) 7.37 (d, J = 5.48 Hz, 1 H) 7.44 (d, J = 9.39 Hz, 2 H) 7.91 (br. s., 3 H) 8.15-8.25 (m, 1 H) 8.33 (dd, J = 8.80, 4.11 Hz, 1 H) 8.44 (d, J = 5.09 Hz, 1 H) 8.62-8.70 (m, 1 H) 10.39 (s, 1 H) |
| 128 | ¹H NMR (400 MHz, <dmso-$_{d6}$>) δ ppm 0.96 (d, J = 6.65 Hz, 3 H) 1.16 (d, J = 6.65 Hz, 6 H) 1.29-1.64 (m, 3 H) 1.70-1.88 (m, 2 H) 2.97-3.14 (m, 4 H) 3.30-3.44 (m, 2 H) 3.53 (br. s., 1 H) 3.57-3.69 (m, 1 H) 3.88 (dt, J = 10.17, 5.09 Hz, 1 H) 4.00 (td, J = 9.19, 4.30 Hz, 1 H) 4.11 (dq, J = 13.60, 6.68 Hz, 1 H) 7.25-7.47 (m, 3 H) 7.78 (dd, J = 8.80, 2.15 Hz, 1 H) 7.84-8.01 (m, 4 H) 8.28-8.50 (m, 3 H) 8.90 (s, 1 H) 10.35 (s, 1 H) |
| 129 | ¹H NMR (400 MHz, <dmso-$_{d6}$>) δ ppm 0.98 (d, J = 7.04 Hz, 3 H) 1.30 (q, J = 12.52 Hz, 1 H) 1.47 (d, J = 12.52 Hz, 1 H) 1.53-1.79 (m, 3 H) 1.87 (t, J = 11.93 Hz, 2 H) 2.10-2.38 (m, 2 H) 2.91 (t, J = 12.33 Hz, 1 H) 3.09 (s, 3 H) 3.26 (br. s., 1 H) 3.32-3.44 (m, 1 H) 3.52 (br. s., 1 H) 3.58-3.77 (m, 3 H) 3.79-3.95 (m, 3 H) 4.01 (td, J = 9.19, 4.30 Hz, 1 H) 7.23 (d, J = 5.09 Hz, 1 H) 7.38-7.53 (m, 2 H) 7.87 (br. s., 3 H) 8.19 (t, J = 8.80 Hz, 1 H) 8.32 (dd, J = 8.61, 3.91 Hz, 1 H) 8.45 (d, J = 5.09 Hz, 1 H) 8.53-8.63 (m, 1 H) 10.37-10.49 (m, 1 H) |
| 130 | ¹H NMR, (400 MHz, <cd3od>) δ ppm 1.13 (d, J = 6.65 Hz, 3 H) 1.46-1.72 (m, 2 H) 1.79 (d, J = 5.87 Hz, 1 H) 1.88-2.05 (m, 2 H) 3.10 (s, 4 H) 3.35-3.47 (m, 4 H) 3.50-3.63 (m, 2 H) 3.71 (s, 1 H) 3.76-3.81 (m, 2 H) 4.05 (ddd, J = 10.86, 6.95, 4.11 Hz, 1 H) 4.17-4.33 (m, 3 H) 6.83 (d, J = 10.17 Hz, 2 H) 7.71 (d, J = 5.48 Hz, 1 H) 7.99 (t, J = 8.61 Hz, 1 H) 8.37 (dd, J = 8.80, 3.72 Hz, 1 H) 8.54 (d, J = 5.87 Hz, 1 H) 9.09 (s, 1 H) |
| 131 | ¹H NMR, (400 MHz, <cd3od>) δ ppm 0.53 (d, J = 7.04 Hz, 3 H) 2.57-2.82 (m, 1 H) 3.56-3.72 (m, 1 H) 3.83 (dd, J = 13.30, 3.91 Hz, 1 H) 4.04 (d, J = 10.17 Hz, 1 H) 4.12-4.36 (m, 2 H) 5.20 (t, J = 3.91 Hz, 1 H) 7.16-7.36 (m, 2 H) 7.50-7.71 (m, 2 H) 7.89 (d, J = 0.78 Hz, 1 H) 8.12 (d, J = 0.78 Hz, 1 H) 8.34-8.48 (m, 1 H) 8.73 (s, 1 H) 9.08 (s, 1 H) |
| 132 | ¹H NMR, (400 MHz, <cd3od>) δ ppm 0.34 (d, J = 6.65 Hz, 3 H) 2.22-2.53 (m, 1 H) 3.36 (s, 3 H) 3.39-3.56 (m, 1 H) 3.60-3.76 (m, 3 H) 3.85 (d, J = 6.65 Hz, 1 H) 3.93-4.03 (m, 1 H) 4.10-4.25 (m, 3 H) 4.94 (br. s., 1 H) 6.80 (d, J = 10.17 Hz, 2 H) 7.46 (d, J = 7.04 Hz, 1 H) 7.81 (s, 1 H) 7.92 (t, J = 8.61 Hz, 1 H) 8.00 (d, J = 0.78 Hz, 1 H) 8.26-8.45 (m, 2 H) 9.08 (s, 1 H) |
| 133 | ¹H NMR, (400 MHz, <cd3od>) δ ppm 1.19 (d, J = 6.65 Hz, 3 H) 1.56-1.77 (m, 2 H) 1.84-2.05 (m, 3 H) 3.11 (s, 3 H) 3.17-3.27 (m, 1 H) 3.47 (ddd, J = 11.64, 4.40, 2.74 Hz, 1 H) 3.53-3.63 (m, 2 H) 3.73 (s, 1 H) 4.06 (ddd, J = 10.76, 6.46, 4.70 Hz, 1 H) 4.23-4.37 (m, 1 H) 7.24 (t, J = 8.61 Hz, 2 H) 7.62 (tt, J = 8.61, 6.26 Hz, 1 H) 7.73 (d, J = 5.87 Hz, 1 H) 8.55 (d, J = 5.48 Hz, 1 H) 8.66 (s, 1 H) 9.02 (s, 1 H) |
| 134 | ¹H NMR, (400 MHz, <cd3od>) δ ppm 1.15 (d, J = 6.26 Hz, 3 H) 1.43-1.58 (m, 1 H) 1.69-1.92 (m, 2 H) 1.93-2.08 (m, 1 H) 2.20-2.35 (m, 1 H) 3.00 (t, J = 10.17 Hz, 1 H) 3.17-3.29 (m, 2 H) 3.54 (s, 3 H) 7.25 (t, J = 8.61 Hz, 2 H) 7.62 (tt, J = 8.56, 6.31 Hz, 1 H) 7.76 (d, J = 5.87 Hz, 1 H) 8.55 (d, J = 5.48 Hz, 1 H) 8.67 (s, 1 H) 9.11 (s, 1 H) |
| 135 | ¹H NMR (400 MHz, <dmso-$_{d6}$>) δ ppm 1.03 (d, J = 6.65 Hz, 3 H) 1.33 (q, J = 12.52 Hz, 1 H) 1.45-1.68 (m, 2 H) 1.70-1.88 (m, 2 H) 2.86-3.04 (m, 1 H) 3.04-3.15 (m, 3 H) 3.22-3.43 (m, 3 H) 3.58 (br. s., 2 H) 3.61-3.72 (m, 2 H) 3.89 (dt, J = 10.08, 4.94 Hz, 6 H) 4.02 (td, J = 9.20, 4.30 Hz, 5 H) 7.15-7.34 (m, 3 H) 7.45-7.69 (m, 3 H) 7.95 (br. s., 3 H) 8.42 (d, J = 5.48 Hz, 1 H) 8.78 (s, 1 H) 9.48 (s, 1 H) |
| 136 | 1H NMR, (400 MHz, <dmso>) d ppm 0.83-1.01 (m, 3 H) 1.09-1.22 (m, 3 H) 1.30 (q, J = 12.52 Hz, 1 H) 1.45-1.68 (m, 2 H) 1.74 (d, J = 10.96 Hz, 1H) 2.02 (d, J = 9.78 Hz, 1 H) 2.82-2.95 (m, 1 H) 2.95-3.12 (m, 2 H) 3.37 (s, 3 H) 3.54 (q, J = 7.04 Hz, 2 H) 4.57 (s, 2 H) 7.09-7.32 (m, 2 H) 7.43 (d, J = 5.09 Hz, 1 H) 7.99 (br. s., 3 H) 8.10-8.23 (m, 1 H) 8.32 (dd, J = 8.61, 4.30 Hz, 1 H) 8.47 (d, J = 5.09 Hz, 1 H) 8.71 (s, 1 H) 10.41 (s, 1 H) |
| 137 | ¹H NMR, (400 MHz, <cd3od>) δ ppm 1.09 (d, J = 6.46 Hz, 3 H) 1.36-1.50 (m, 1 H) 1.63-1.87 (m, 4 H) 1.95 (dd, J = 13.55, 2.59 Hz, 1 H) 2.05-2.14 (m, 2 H) 2.17-2.29 (m, 1 H) 2.91-3.01 (m, 1 H) 3.10-3.23 (m, 2 H) 3.54 (s, 3 H) 3.64 (ddd, J = 11.73, 8.74, 3.01 Hz, 2 H) 3.93-4.02 (m, 2 H) 4.66-4.75 (m, 1 H) 6.85 (d, J = 10.12 Hz, 2 H) 7.64 (d, J = 5.53 Hz, 1 H) 8.00 (t, J = 8.71 Hz, 1 H) 8.38 (dd, J = 8.63, 3.89 Hz, 1 H) 8.50 (d, J = 5.48 Hz, 1 H) 9.12 (s, 1 H) |
| 138 | ¹H NMR, (400 MHz, <cd3od>) δ ppm 1.09 (d, J = 6.50 Hz, 3 H) 1.36-1.51 (m, 1 H) 1.64-2.00 (m, 4 H) 2.04-2.27 (m, 2 H) 2.38-2.50 (m, 2 H) 2.51-2.63 (m, 2 H) 2.85-3.03 (m, 2 H) 3.11-3.24 (m, 2 H) 3.54 (s, 3 H) 7.36 (d, J = 9.49 Hz, 2 H) 7.64 (d, J = 5.58 Hz, 1 H) 8.04 (t, J = 8.71 Hz, 1 H) 8.42 (dd, J = 8.66, 3.91 Hz, 1 H) 8.50 (d, J = 5.58 Hz, 1 H) 9.15 (s, 1 H) |

TABLE 3-continued

| Ex # | ¹H-NMR data |
|---|---|
| 139 | ¹H NMR, (400 MHz, <cd3od>) δ ppm 1.12 (d, J = 6.85 Hz, 3 H) 1.52-1.71 (m, 2 H) 1.72-1.98 (m, 4 H) 2.05-2.18 (m, 1 H) 2.35-2.60 (m, 4 H) 3.06-3.17 (m, 4 H) 3.55 (t, J = 5.31 Hz, 2 H) 3.68 (s, 1 H) 3.97-4.11 (m, 1 H) 4.19-4.34 (m, 1 H) 7.35 (d, J = 9.44 Hz, 2 H) 7.58 (br. s., 1 H) 8.02 (t, J = 8.71 Hz, 1 H) 8.40 (dd, J = 8.73, 3.94 Hz, 1 H) 8.49 (d, J = 5.38 Hz, 1 H) 8.91 (br. s., 1 H) |
| 140 | ¹H NMR, (400 MHz, <cd3od>) δ ppm 1.14 (d, J = 6.94 Hz, 3 H) 1.55-1.83 (m, 5 H) 1.87-2.01 (m, 2 H) 2.03-2.18 (m, 2 H) 3.12 (s, 3 H) 3.14 (dd, J = 3.28, 1.66 Hz, 1 H) 3.52-3.73 (m, 5 H) 3.91-4.11 (m, 3 H) 4.22-4.35 (m, 1 H) 4.72 (tt, J = 8.08, 4.13 Hz, 1 H) 6.86 (d, J = 10.08 Hz, 2 H) 7.64 (d, J = 5.53 Hz, 1 H) 7.99 (t, J = 8.71 Hz, 1 H) 8.37 (dd, J = 8.63, 3.94 Hz, 1 H) 8.52 (d, J = 5.53 Hz, 1 H) 8.95 (s, 1 H) |
| 141 | ¹H NMR, (400 MHz, <cd3od>) δ ppm 1.08 (d, J = 6.50 Hz, 3 H) 1.34-1.49 (m, 7 H) 1.63-1.76 (m, 1 H) 1.81-1.99 (m, 2 H) 2.18-2.28 (m, 1 H) 2.99 (t, J = 10.00 Hz, 1 H) 3.12-3.25 (m, 2 H) 3.54 (s, 3 H) 4.72 (dt, J = 12.07, 6.02 Hz, 1 H) 6.76 (d, J = 10.22 Hz, 2 H) 7.75 (d, J = 5.62 Hz, 1 H) 7.99 (t, J = 8.73 Hz, 1 H) 8.38 (dd, J = 8.63, 3.89 Hz, 1 H) 8.53 (d, J = 5.48 Hz, 1 H) 9.26 (s, 1 H) |
| 142 | ¹H NMR, (400 MHz, <cd3od>) δ ppm 1.12 (d, J = 6.85 Hz, 3 H) 1.38 (d, J = 6.02 Hz, 6 H) 1.56-1.64 (m, 1 H) 1.65-1.73 (m, 1 H) 1.76-1.86 (m, 1 H) 1.92-2.01 (m, 2 H) 3.11 (s, 3 H) 3.13-3.22 (m, 1 H) 3.37-3.45 (m, 1 H) 3.47-3.64 (m, 2 H) 3.74 (s, 1 H) 4.06 (ddd, J = 10.69, 7.31, 3.72 Hz, 1 H) 4.27 (ddd, J = 10.45, 6.39, 3.94 Hz, 1 H) 4.72 (dt, J = 12.07, 6.02 Hz, 1 H) 6.78 (d, J = 10.17 Hz, 2 H) 7.74 (d, J = 5.72 Hz, 1 H) 7.99 (t, J = 8.71 Hz, 1 H) 8.37 (dd, J = 8.61, 3.91 Hz, 1 H) 8.55 (d, J = 5.62 Hz, 1 H) 9.13 (s, 1 H) |
| 143 | ¹H NMR, (400 MHz, <cd3od>) δ ppm 1.08 (d, J = 6.26 Hz, 3 H) 1.34-1.53 (m, 1 H) 1.60-1.75 (m, 1 H) 1.79-2.00 (m, 2 H) 2.17-2.29 (m, 1 H) 2.98 (s, 1 H) 3.09-3.24 (m, 2 H) 3.48-3.58 (m, 3 H) 3.91 (s, 3 H) 6.80 (d, J = 9.78 Hz, 2 H) 7.77 (s, 1 H) 8.00 (s, 1 H) 8.31-8.44 (m, 1 H) 8.47-8.60 (m, 1 H) 9.28 (s, 1 H) |
| 144 | ¹H NMR, (400 MHz, <cd3od>) δ ppm 1.13 (d, J = 7.04 Hz, 3 H) 1.51-1.72 (m, 2 H) 1.74-1.87 (m, 1 H) 1.89-1.98 (m, 2 H) 3.11 (s, 4 H) 3.35-3.43 (m, 1 H) 3.51-3.60 (m, 2 H) 3.66-3.74 (m, 1 H) 3.86-3.95 (m, 3 H) 4.00-4.11 (m, 1 H) 4.22-4.32 (m, 2 H) 6.75-6.87 (m, 2 H) 7.64-7.72 (m, 1 H) 7.93-8.03 (m, 1 H) 8.33-8.42 (m, 1 H) 8.48-8.57 (m, 1 H) 9.00-9.08 (m, 1 H) |
| 145 | ¹H NMR, (400 MHz, <cd3od>) δ ppm 1.03-1.11 (m, 3 H) 1.34-1.49 (m, 1 H) 1.63 (ddd, J = 12.42, 6.16, 3.33 Hz, 1 H) 1.81 (q, J = 12.13 Hz, 1 H) 1.92 (dd, J = 13.30, 2.74 Hz, 1 H) 2.14-2.27 (m, 1 H) 2.89-2.99 (m, 1 H) 3.05-3.19 (m, 2 H) 3.53 (s, 3 H) 7.10-7.18 (m, 3 H) 7.49-7.59 (m, 1 H) 7.70 (d, J = 5.48 Hz, 1 H) 8.47 (d, J = 5.48 Hz, 1 H) 9.35 (s, 1 H) |
| 146 | ¹H NMR (400 MHz, <dmso-$_{d6}$>) δ ppm 0.96 (d, J = 6.65 Hz, 3 H) 1.26 (d, J = 12.52 Hz, 1 H) 1.46 (br. s., 1 H) 1.54-1.80 (m, 3 H) 2.90 (br. s., 1 H) 3.07 (s, 3 H) 3.15-3.27 (m, 1 H) 3.38 (br. s., 1 H) 3.55 (br. s., 1 H) 3.64 (d, J = 5.48 Hz, 1 H) 3.87-3.91 (m, 1 H) 4.00 (d, J = 3.91 Hz, 1 H) 7.20-7.29 (m, 4 H) 7.30-7.44 (m, 2 H) 7.58 (s, 1 H) 7.95 (br. s., 2 H) 8.43 (d, J = 5.09 Hz, 1 H) 8.78 (s, 1 H) 10.12 (s, 1 H) |
| 147 | ¹H NMR, (400 MHz, <cd3od>) δ ppm 0.44 (d, J = 6.85 Hz, 3 H) 1.40 (dd, J = 6.02, 3.03 Hz, 6 H) 2.54 (ddd, J = 11.57, 4.62, 2.20 Hz, 1 H) 3.52-3.62 (m, 1 H) 3.63-3.72 (m, 1 H) 3.88 (dd, J = 11.64, 4.16 Hz, 1 H) 4.03-4.11 (m, 1 H) 4.14-4.23 (m, 1 H) 4.78 (dt, J = 12.06, 6.05 Hz, 1 H) 5.09 (t, J = 4.35 Hz, 1 H) 6.84 (d, J = 10.42 Hz, 2 H) 7.52 (d, J = 6.50 Hz, 1 H) 7.89 (d, J = 1.03 Hz, 1 H) 8.00 (t, J = 8.71 Hz, 1 H) 8.09 (d, J = 1.03 Hz, 1 H) 8.34-8.46 (m, 2 H) 9.18 (s, 1 H) |
| 148 | ¹H NMR, (400 MHz, <cd3od>) δ ppm 0.65 (d, J = 6.85 Hz, 3 H) 1.40 (dd, J = 6.02, 2.93 Hz, 6 H) 2.17-2.27 (m, 1 H) 2.83 (t, J = 12.98 Hz, 1 H) 3.22-3.29 (m, 1 H) 3.47-3.62 (m, 2 H) 3.64-3.73 (m, 4 H) 4.06-4.15 (m, 1 H) 4.76 (dt, J = 12.07, 6.02 Hz, 1 H) 6.83 (d, J = 10.51 Hz, 2 H) 7.25 (d, J = 9.68 Hz, 1 H) 7.51 (d, J = 6.60 Hz, 1 H) 8.01 (t, J = 8.66 Hz, 1 H) 8.37-8.44 (m, 2 H) 9.33 (s, 1 H) |
| 149 | ¹H NMR, (400 MHz, <cd3od>) δ ppm 0.94 (d, J = 6.75 Hz, 3 H) 1.38 (d, J = 6.02 Hz, 6 H) 1.43-1.57 (m, 1 H) 1.71 (d, J = 13.60 Hz, 1 H) 1.78-2.02 (m, 3 H) 3.10-3.21 (m, 1 H) 3.41 (dt, J = 12.41, 3.58 Hz, 1 H) 3.72 (s, 3 H) 4.08-4.16 (m, 1 H) 4.72 (dt, J = 12.09, 6.06 Hz, 1 H) 6.78 (d, J = 10.22 Hz, 2 H) 7.21 (d, J = 9.73 Hz, 1 H) 7.82 (d, J = 5.62 Hz, 1 H) 7.98 (t, J = 8.71 Hz, 1 H) 8.37 (dd, J = 8.61, 3.91 Hz, 1 H) 8.54 (d, J = 5.58 Hz, 1 H) 9.08 (s, 1 H) |
| 150 | ¹H NMR, (400 MHz, <cd3od>) δ ppm 0.91-1.01 (m, 3 H) 1.73-1.86 (m, 1 H) 1.90-2.01 (m, 1 H) 2.12-2.31 (m, 2 H) 2.34-2.46 (m, 1 H) 3.53-3.66 (m, 1 H) 3.77-3.88 (m, 1 H) 5.15-5.25 (m, 1 H) 6.03-6.13 (m, 1 H) 6.52-6.61 (m, 1 H) 7.10-7.24 (m, 2 H) 7.42-7.50 (m, 1 H) 7.53-7.66 (m, 1 H) 7.70-7.77 (m, 1 H) 7.77-7.85 (m, 1 H) 7.99-8.05 (m, 1 H) 8.36-8.43 (m, 1 H) 8.51-8.58 (m, 1 H) 8.76-8.82 (m, 1 H) |
| 151 | ¹H NMR (400 MHz, <dmso-$_{d6}$>) δ ppm −0.10-0.12 (m, 3 H) 1.64 (br. s., 2 H) 1.85-2.12 (m, 3 H) 3.43 (t, J = 11.15 Hz, 4 H) 3.52-3.73 (m, 5 H) 4.68 (br. s., 1 H) 7.07-7.26 (m, 3 H) 7.61 (s, 1 H) 7.85 (s, 3 H) 7.92-8.00 (m, 1 H) 8.05-8.18 (m, 2 H) 8.59 (br. s., 1 H) 10.16 (br. s., 1 H) |
| 152 | ¹H NMR, (400 MHz, <cd3od>) δ ppm 0.95 (d, J = 7.04 Hz, 3 H) 1.72-1.87 (m, 1 H) 1.96 (d, J = 14.09 Hz, 1 H) 2.11-2.46 (m, 3 H) 3.60 (br. s., 1 H) 3.84 (br. s., 1 H) 5.20 (d, J = 5.48 Hz, 1 H) 6.09 (t, J = 6.46 Hz, 1 H) 6.57 (d, J = 9.00 Hz, 1 H) 7.16 (t, J = 8.61 Hz, 2 H) 7.46 (d, J = 7.83 Hz, 1 H) 7.59 (quin, J = 7.43 Hz, 1 H) 7.74 (d, J = 7.04 Hz, 1 H) 7.86 (br. s., 1 H) 8.03 (t, J = 8.80 Hz, 1 H) 8.40 (dd, J = 8.41, 3.72 Hz, 1 H) 8.55 (d, J = 5.09 Hz, 1 H) 8.83 (d, J = 9.00 Hz, 1 H) |

TABLE 3-continued

| Ex # | ¹H-NMR data |
|---|---|
| 153 | ¹H NMR (400 MHz, <dmso-$_{d6}$>) δ ppm 0.96 (d, J = 6.65 Hz, 3 H) 1.25-1.40 (m, 1 H) 1.40-1.52 (m, 1 H) 1.56-1.76 (m, 3 H) 1.77-1.93 (m, 2 H) 2.11-2.36 (m, 2 H) 2.74-2.99 (m, 3 H) 3.24 (br. s., 1 H) 3.83-3.93 (m, 2 H) 7.24 (d, J = 5.09 Hz, 1 H) 7.36-7.50 (m, 2 H) 7.86 (br. s., 3 H) 8.18 (t, J = 9.00 Hz, 1 H) 8.30 (dd, J = 8.80, 4.11 Hz, 1 H) 8.45 (d, J = 5.09 Hz, 1 H) 8.56 (s, 1 H) 10.41 (s, 1 H) |
| 154 | ¹H NMR (400 MHz, <dmso-$_{d6}$>) δ ppm 0.52 (d, J = 6.65 Hz, 3 H) 1.64 (d, J = 13.30 Hz, 1 H) 1.79-2.02 (m, 2 H) 2.16-2.41 (m, 2 H) 3.20 (t, J = 12.13 Hz, 1 H) 3.81 (br. s., 1 H) 4.91 (t, J = 3.72 Hz, 1 H) 7.26 (t, J = 8.41 Hz, 2 H) 7.47-7.68 (m, 4 H) 7.80-7.87 (m, 1 H) 8.00 (br. s., 3 H) 8.13 (s, 1 H) 8.51 (d, J = 5.48 Hz, 1 H) 8.72 (s, 1 H) 9.60 (s, 1 H) |
| 155 | ¹H NMR (400 MHz, <dmso-$_{d6}$>) δ ppm 0.48 (d, J = 6.65 Hz, 3 H) 1.07-1.24 (m, 3 H) 1.60 (d, J = 13.30 Hz, 1 H) 1.78-1.97 (m, 2 H) 2.10-2.23 (m, 1H) 2.33 (q, J = 12.52 Hz, 1 H) 3.15 (t, J = 12.33 Hz, 1 H) 3.52 (q, J = 7.04 Hz, 2 H) 4.49-4.62 (m, 2 H) 4.88 (t, J = 3.72 Hz, 1 H) 7.27 (d, J = 8.61 Hz, 2H) 7.52 (d, J = 5.48 Hz, 1 H) 7.79-7.87 (m, 1 H) 8.00 (br. s., 3 H) 8.17 (t, J = 8.80 Hz, 1 H) 8.31 (dd, J = 8.61, 3.91 Hz, 1 H) 8.55 (d, J = 5.09 Hz, 1 H), 8.58 (s, 1 H) 10.52 (s, 1 H) |
| 156 | ¹H NMR (400 MHz, <dmso-$_{d6}$>) δ ppm 0.01 (d, J = 7.04 Hz, 3 H) 2.94-3.13 (m, 2 H) 3.21 (d, J = 10.56 Hz, 2 H) 3.31-3.44 (m, 1 H) 3.45-3.63 (m, 2H) 4.71 (t, J = 3.91 Hz, 1 H) 6.89 (t, J = 8.80 Hz, 2 H) 7.06 (d, J = 6.65 Hz, 1 H) 7.12-7.23 (m, 1 H) 7.31 (br. s., 2 H) 7.48 (s, 1 H) 7.80 (s, 2 H) 8.00 (d, J = 6.26 Hz, 1 H) 8.60 (s, 1 H) 9.04 (br. s., 1 H) |
| 157 | ¹H NMR (400 MHz, <dmso-$_{d6}$>) δ ppm 0.01 (d, J = 7.04 Hz, 3 H) 0.85-0.99 (m, 3 H) 2.01-2.15 (m, 1 H) 3.07-3.24 (m, 1 H) 3.30 (q, J = 7.04 Hz, 3H) 3.43 (d, J = 10.17 Hz, 2 H) 3.52-3.70 (m, 4 H) 4.26-4.40 (m, 2 H) 4.71 (br. s., 1 H) 6.95-7.09 (m, 2 H) 7.17 (d, J = 6.65 Hz, 1 H) 7.62 (s, 1 H), 7.88 (s, 1 H) 7.91-8.03 (m, 3 H) 8.07-8.20 (m, 2 H) 8.66 (s, 1 H) 10.17 (br. s., 1 H) |
| 158 | ¹H NMR, (400 MHz, <cd3od>) δ ppm 0.63 (d, J = 6.85 Hz, 3 H) 1.89 (dt, J = 11.38, 8.98 Hz, 1 H) 2.08-2.22 (m, 2 H) 2.40-2.53 (m, 2 H) 2.54-2.65 (m, 2 H) 2.78 (t, J = 12.76 Hz, 1 H) 3.08-3.27 (m, 2 H) 3.34-3.43 (m, 2 H) 3.46-3.59 (m, 2 H) 3.71 (s, 3 H) 4.02 (br. s., 1 H) 7.38-7.47 (m, 3 H) 8.06 (t, J = 8.68 Hz, 1 H) 8.39 (d, J = 6.46 Hz, 1 H) 8.46 (dd, J = 8.66, 3.96 Hz, 1 H) 9.39 (s, 1 H) |
| 159 | ¹H NMR, (400 MHz, <cd3od>) δ ppm 0.65 (d, J = 6.80 Hz, 3 H) 1.74-1.89 (m, 2 H) 2.06-2.25 (m, 3 H) 2.66 (s, 1 H) 2.76 (t, J = 12.18 Hz, 1 H) 3.12-3.22 (m, 1 H) 3.25-3.28 (m, 1 H) 3.36 (dd, J = 3.86, 2.20 Hz, 3 H) 3.45-3.58 (m, 4 H) 3.61-3.70 (m, 3 H) 3.72 (s, 3 H) 3.93-4.04 (m, 2 H) 4.04-4.10 (m, 1 H) 6.88-6.99 (m, 2 H) 7.42 (d, J = 6.31 Hz, 1 H) 8.03 (t, J = 8.68 Hz, 1 H) 8.33-8.47 (m, 2 H) 9.44 (s, 1 H) |
| 160 | ¹H NMR, (400 MHz, <cd3od>) δ ppm 9.16 (s, 1 H), 8.48 (dd, J = 8.6, 3.9 Hz, 1 H), 8.41 (d, J = 6.3 Hz, 1 H), 8.02-8.13 (m, 1 H), 7.93 (s, 1 H), 7.57 (d, J = 6.7 Hz, 1 H), 7.44 (d, J = 9.8 Hz, 2 H), 5.08 (t, J = 4.1 Hz, 1 H), 4.20-4.32 (m, 1 H), 4.06-4.16 (m, 1 H), 3.95-4.05 (m, 3 H), 3.87-3.95 (m, 2 H), 3.76-3.86 (m, 1 H), 3.56-3.69 (m, 1 H), 2.46-2.60 (m, 1 H), 2.16-2.32 (m, 2 H), 1.73 (d, J = 13.7 Hz, 2 H), 0.43 (d, J = 7.0 Hz, 3 H) |
| 161 | ¹H NMR, (400 MHz, <cd3od>) δ ppm 9.15 (s, 1 H), 8.46 (dd, J = 8.6, 3.9 Hz, 1 H), 8.41 (d, J = 6.7 Hz, 1 H), 8.12 (s, 1 H), 8.05 (t, J = 8.8 Hz, 1 H), 7.92 (s, 1 H), 7.58 (d, J = 7.0 Hz, 1 H), 7.11 (d, J = 9.8 Hz, 2 H), 5.08 (t, J = 4.3 Hz, 1 H), 4.19-4.31 (m, 1 H), 4.04-4.15 (m, 1 H), 3.99 (dd, J = 11.9, 4.1 Hz, 1 H), 3.80 (dd, J = 13.5, 4.1 Hz, 1 H), 3.60 (t, J = 12.9 Hz, 1 H), 2.45-2.60 (m, 4 H), 0.44 (d, J = 7.0 Hz, 3 H) |
| 162 | ¹H NMR, (400 MHz, <cd3od>) δ ppm 0.58 (d, J = 6.70 Hz, 3 H) 2.19 (br. s., 1 H) 2.79 (t, J = 13.01 Hz, 1 H) 3.20-3.28 (m, 1 H) 3.45 (d, J = 11.25 Hz, 1 H) 3.52-3.65 (m, 2 H) 3.71 (s, 3 H) 4.02 (br. s., 1 H) 4.43 (quin, J = 7.25 Hz, 1 H) 4.79 (t, J = 6.31 Hz, 1 H) 5.15-5.22 (m, 2 H) 7.39 (d, J = 9.63 Hz, 2 H) 7.48 (d, J = 6.46 Hz, 1 H) 8.07 (t, J = 8.71 Hz, 1 H) 8.40 (d, J = 6.26 Hz, 1 H) 8.47 (dd, J = 8.66, 3.86 Hz, 1 H) 9.39 (s, 1 H) |
| 163 | ¹H NMR, (400 MHz, <cd3od>) δ ppm 0.87-0.99 (m, 1 H) 1.14 (d, J = 6.70 Hz, 3 H) 1.26-1.38 (m, 1 H) 1.66 (d, J = 8.75 Hz, 2 H) 1.80 (br. s., 1 H) 1.89-1.98 (m, 2 H) 2.78-2.89 (m, 1 H) 3.12 (d, J = 11.74 Hz, 1 H) 3.68 (br. s., 1 H) 3.83 (br. s., 1 H) 3.88-3.97 (m, 1 H) 4.35-4.42 (m, 1 H) 4.75 (t, J = 6.26 Hz, 2 H) 5.15 (t, J = 7.29 Hz, 2 H) 7.31 (d, J = 9.54 Hz, 2 H) 7.56 (d, J = 4.99 Hz, 1 H) 8.02 (t, J = 8.80 Hz, 1 H) 8.40 (d, J = 5.33 Hz, 1 H) 8.50 (d, J = 5.04 Hz, 1 H) 8.82 (s, 1 H) |
| 164 | ¹H NMR, (400 MHz, <cd3od>) δ ppm 0.46 (d, J = 6.70 Hz, 3 H) 2.39 (d, J = 5.62 Hz, 1 H) 2.85 (t, J = 12.84 Hz, 1 H) 3.59 (br. s., 1 H) 3.80-3.90 (m, 1 H) 3.98-4.14 (m, 4 H) 4.25 (d, J = 12.03 Hz, 1 H) 5.08-5.17 (m, 1 H) 5.32 (d, J = 11.88 Hz, 1 H) 5.46 (br. s., 1 H) 6.88 (d, J = 9.05 Hz, 1 H) 7.55 (d, J = 6.70 Hz, 1 H) 7.69 (d, J = 10.12 Hz, 1 H) 8.10 (t, J = 8.61 Hz, 1 H) 8.33 (d, J = 6.46 Hz, 1 H) 8.39 (dd, J = 8.58, 3.45 Hz, 1 H) 8.97 (s, 1 H) 9.19 (s, 1 H) 9.55 (s, 1 H) |
| 165 | ¹H NMR, (400 MHz, <cd3od>) δ ppm 1.12 (d, J = 6.65 Hz, 3 H) 1.54-1.70 (m, 2 H) 1.72-1.84 (m, 1 H) 1.87-2.00 (m, 2 H) 2.71-2.90 (m, 2 H) 3.01-3.17 (m, 1 H) 3.64-3.71 (m, 1 H) 3.76-3.97 (m, 5 H) 6.74-6.83 (m, 2 H) 7.54-7.63 (m, 1 H) 7.92-8.02 (m, 1 H) 8.31-8.39 (m, 1 H) 8.46-8.52 (m, 1 H) 8.89-8.96 (m, 1 H) |
| 166 | ¹H NMR, (400 MHz, <cd3od>) δ ppm 1.02-1.18 (m, 3 H) 1.50-1.75 (m, 3 H) 1.87-2.03 (m, 2 H) 2.70-2.90 (m, 2 H) 3.02-3.18 (m, 1 H) 3.34-3.50 (m, 1 H) 3.66 (br. s., 1 H) 3.76-3.96 (m, 2 H) 7.08-7.18 (m, 3 H) 7.47-7.68 (m, 2 H) 8.46 (d, J = 5.48 Hz, 1 H) 9.20 (s, 1 H) |

TABLE 3-continued

| Ex # | ¹H-NMR data |
|---|---|
| 167 | ¹H NMR, (400 MHz, <cd3od>) δ ppm 0.94 (d, J = 6.70 Hz, 3 H) 1.24-1.36 (m, 1 H) 1.41-1.58 (m, 1 H) 1.62-1.99 (m, 5 H) 2.11 (br. s., 1 H) 2.37-2.62 (m, 4 H) 3.03-3.17 (m, 1 H) 3.73 (s, 3 H) 4.09 (br. s., 1 H) 7.17 (d, J = 9.10 Hz, 1 H) 7.36 (d, J = 9.54 Hz, 2 H) 7.68 (d, J = 5.33 Hz, 1 H) 8.02 (t, J = 8.68 Hz, 1 H) 8.40 (dd, J = 8.63, 3.74 Hz, 1 H) 8.49 (d, J = 5.28 Hz, 1 H) 8.91 (s, 1 H) |
| 168 | ¹H NMR, (400 MHz, <cd3od>) δ ppm 8.85 (s, 1 H), 8.58 (d, J = 5.48 Hz, 1 H), 8.38 (dd, J = 8.61, 3.52 Hz, 1 H), 8.07 (s, 1 H), 7.99 (t, J = 8.80 Hz, 1 H), 7.90 (s, 1 H), 7.82 (d, J = 5.09 Hz, 1 H), 6.84 (d, J = 10.17 Hz, 2 H), 4.98 (br. s., 1 H), 4.22 (br. s., 2 H), 3.89 (d, J = 12.52 Hz, 1 H), 3.78 (br. s., 2 H), 3.44 (s, 3 H), 2.64-2.74 (m, 2 H), 2.29 (br. s., 1 H), 2.02-2.18 (m, 2 H), 1.81 (d, J = 13.69 Hz, 1 H), 0.67 (d, J = 6.65 Hz, 3 H) |
| 169 | ¹H NMR, (400 MHz, <cd3od>) δ ppm 8.84 (s, 1 H), 8.65 (s, 1 H), 8.60 (d, J = 5.09 Hz, 1 H), 8.08 (s, 1 H), 7.90 (s, 1 H), 7.85 (d, J = 5.48 Hz, 1 H),7.63 (t, J = 7.83 Hz, 1 H), 7.25 (t, J = 8.80 Hz, 2 H), 5.00 (br. s., 1 H), 3.95 (d, J = 12.52 Hz, 1 H), 2.63-2.76 (m, 1 H), 2.38 (br. s., 1 H), 2.06-2.21 (m, 2 H), 1.84 (d, J = 12.91 Hz, 1 H), 0.70 (d, J = 6.65 Hz, 3 H) |
| 170 | ¹H NMR, (400 MHz, <cd3od>) δ ppm 0.94 (d, J = 6.60 Hz, 3 H) 1.50 (q, J = 13.17 Hz, 1 H) 1.65-1.84 (m, 4 H) 1.85-2.01 (m, 2 H) 2.09 (d, J = 11.59 Hz, 2 H) 3.04-3.18 (m, 2 H) 3.35-3.51 (m, 2 H) 3.64 (t, J = 9.24 Hz, 2 H) 3.73 (s, 3 H) 3.93-4.02 (m, 2 H) 4.09 (br. s., 1 H) 4.71 (br. s., 1 H) 6.86 (d, J = 10.37 Hz, 2 H) 7.18 (d, J = 10.07 Hz, 1 H) 7.70 (d, J = 5.43 Hz, 1 H) 7.99 (t, J = 8.61 Hz, 1 H) 8.36 (dd, J = 8.73, 3.94 Hz, 1 H) 8.50 (d, J = 5.33 Hz, 1 H) 8.93 (s, 1 H) |
| 171 | ¹H NMR, (400 MHz, <cd3od>) δ ppm 0.67 (d, J = 6.70 Hz, 3 H) 1.68-1.87 (m, 3 H) 2.00-2.20 (m, 4 H) 2.30 (br. s., 1 H) 2.63-2.77 (m, 1 H) 3.63 (t, J = 8.95 Hz, 2 H) 3.84-4.03 (m, 3 H) 4.66-4.76 (m, 1 H) 4.98 (br. s., 1 H) 6.86 (d, J = 10.17 Hz, 2 H) 7.82 (d, J = 5.18 Hz, 1 H) 7.89 (s, 1 H) 7.99 (t, J = 8.66 Hz, 1 H) 8.07 (s, 1 H) 8.37 (dd, J = 8.66, 3.86 Hz, 1 H) 8.58 (d, J = 5.28 Hz, 1 H) 8.80 (s, 1 H) |
| 172 | ¹H NMR, (400 MHz, <cd3od>) δ ppm 0.65 (d, J = 6.60 Hz, 3 H) 1.73-1.92 (m, 2 H) 2.00-2.17 (m, 3 H) 2.27 (br. s., 1 H) 2.37-2.60 (m, 4 H) 2.63-2.76 (m, 1 H) 3.86 (br. s., 1 H) 4.96 (br. s., 2 H) 7.35 (d, J = 9.63 Hz, 2 H) 7.78 (d, J = 5.28 Hz, 1 H) 7.89 (s, 1 H) 7.99-8.08 (m, 2 H) 8.37-8.43 (m, 1 H) 8.56 (d, J = 5.43 Hz, 1 H) 8.79 (s, 1 H) |
| 174 | ¹H NMR, (400 MHz, <cd3od>) δ ppm 0.50 (d, J = 7.04 Hz, 3 H) 1.84-1.96 (m, 1 H) 2.54-2.66 (m, 1 H) 3.04-3.15 (m, 1 H) 3.25-3.45 (m, 3 H) 3.61 (s, 3 H) 3.76-3.83 (m, 1 H) 7.01-7.16 (m, 3 H) 7.32-7.41 (m, 1 H) 7.46-7.58 (m, 1 H) 8.22-8.32 (m, 1 H) 9.33-9.42 (m, 1 H) |
| 175 | ¹H NMR, (400 MHz, <cd3od>) δ ppm 0.87 (d, J = 6.65 Hz, 3 H) 1.39-1.53 (m, 1 H) 1.62-1.99 (m, 4 H) 3.04-3.16 (m, 1 H) 3.32-3.37 (m, 1 H) 3.70 (s, 3 H) 4.03-4.11 (m, 1 H) 7.08-7.21 (m, 4 H) 7.49-7.60 (m, 1 H) 7.80 (d, J = 5.48 Hz, 1 H) 8.48 (m, 1 H) 9.29 (s, 1 H) |
| 176 | ¹H NMR, (400 MHz, <cd3od>) δ ppm 0.52 (d, J = 6.65 Hz, 3 H) 1.65-1.75 (m, 1 H) 1.90-2.16 (m, 3 H) 2.59-2.73 (m, 1 H) 3.26-3.35 (m, 1 H) 3.71-3.81 (m, 1 H) 4.91-4.97 (m, 1 H) 7.02-7.13 (m, 3 H) 7.40-7.51 (m, 1 H) 7.79 (s, 2 H) 8.00 (s, 1 H) 8.45-8.52 (m, 1 H) 9.12 (s, 1 H) |
| 177 | ¹H NMR, (400 MHz, <cd3od>) δ ppm 9.46 (s, 1 H), 8.48 (dd, J = 8.6, 3.9 Hz, 1 H), 8.42 (d, J = 6.3 Hz, 1 H), 8.08 (t, J = 8.8 Hz, 1 H), 7.39-7.53 (m, 3 H), 3.86-4.09 (m, 5 H), 3.72 (s, 3 H), 3.57 (dd, J = 8.4, 3.7 Hz, 2 H), 3.37-3.47 (m, 1 H), 3.19-3.28 (m, 1 H), 2.77 (t, J = 12.9 Hz, 1 H), 2.10-2.36 (m, 3 H), 1.64-1.86 (m, 2 H), 0.56 (d, J = 6.7 Hz, 3 H) |
| 178 | ¹H NMR, (400 MHz, <cd3od>) δ ppm 8.99 (s, 1 H), 8.54 (d, J = 5.5 Hz, 1 H), 8.42 (dd, J = 9.0, 3.9 Hz, 1 H), 8.04 (t, J = 8.8 Hz, 1 H), 7.75 (d, J = 5.5 Hz, 1 H), 7.39 (d, J = 9.8 Hz, 2 H), 7.19 (d, J = 9.8 Hz, 1 H), 4.12 (d, J = 9.0 Hz, 1 H), 3.84-4.04 (m, 4 H), 3.74 (s, 3 H), 3.39 (d, J = 3.5 Hz, 1 H), 3.14 (t, J = 12.1 Hz, 1 H), 2.12-2.28 (m, 2 H), 1.86-2.03 (m, 2 H), 1.64-1.85 (m, 4 H), 1.51 (q, J = 12.8 Hz, 1 H), 0.94 (d, J = 6.7 Hz, 3 H) |
| 179 | ¹H NMR, (400 MHz, <cd3od>) δ ppm 8.81 (s, 1 H), 8.60 (d, J = 5.5 Hz, 1 H), 8.42 (dd, J = 8.6, 3.9 Hz, 1 H), 8.08 (s, 1 H), 8.04 (t, J = 8.6 Hz, 1 H), 7.91 (s, 1 H), 7.84 (d, J = 5.5 Hz, 1 H), 7.38 (d, J = 9.8 Hz, 2 H), 5.00 (t, J = 3.9 Hz, 1 H), 3.81-4.04 (m, 4 H), 3.37 (br. s., 1 H), 2.64-2.80 (m, 1 H), 2.26-2.39 (m, 1 H), 2.02-2.25 (m, 4 H), 1.82 (d, J = 13.3 Hz, 1 H), 1.68 (d, J = 13.3 Hz, 2 H), 0.67 (d, J = 6.7 Hz, 3 H) |
| 180 | ¹H NMR, (400 MHz, <cd3od>) δ ppm 9.03 (s, 1 H), 8.55 (d, J = 5.5 Hz, 1 H), 8.41 (dd, J = 8.6, 3.9 Hz, 1 H), 8.02 (t, J = 8.6 Hz, 1 H), 7.80 (d, J = 5.9 Hz, 1 H), 7.20 (d, J = 9.8 Hz, 1 H), 7.07 (d, J = 9.4 Hz, 2 H), 4.12 (d, J = 9.4 Hz, 1 H), 3.74 (s, 3 H), 3.36-3.47 (m, 1 H), 3.09-3.23 (m, 1 H), 2.49 (s, 3 H), 1.65-2.04 (m, 4 H), 1.52 (q, J = 13.2 Hz, 1 H), 0.95 (d, J = 7.0 Hz, 3 H) |
| 181 | ¹H NMR, (400 MHz, <cd3od>) δ ppm 0.68 (d, J = 6.70 Hz, 3 H) 1.76-1.88 (m, 1 H) 2.02-2.20 (m, 2 H) 2.23-2.38 (m, 1 H) 2.49 (s, 3 H) 2.64-2.80 (m, 1 H) 3.35-3.39 (m, 1 H) 3.90 (dt, J = 12.72, 4.43 Hz, 1 H) 4.97-5.03 (m, 1 H) 7.07 (d, J = 9.44 Hz, 2 H) 7.84 (d, J = 5.48 Hz, 1 H) 7.91 (d, J = 0.98 Hz, 1 H) 8.02 (t, J = 8.71 Hz, 1 H) 8.09 (d, J = 1.03 Hz, 1 H) 8.41 (dd, J = 8.61, 3.96 Hz, 1 H) 8.60 (d, J = 5.48 Hz, 1 H) 8.84 (s, 1 H) |

TABLE 3-continued

| Ex # | ¹H-NMR data |
|---|---|
| 182 | ¹H NMR, (400 MHz, <cd3od>) δ ppm 0.94 (d, J = 6.75 Hz, 3 H) 1.51 (q, J = 12.78 Hz, 1 H) 1.71 (d, J = 13.64 Hz, 1 H) 1.80 (q, J = 12.41 Hz, 1 H) 1.88-2.02 (m, 2 H) 3.10-3.20 (m, 1 H) 3.41 (dt, J = 12.47, 3.55 Hz, 1 H) 3.74 (s, 3 H) 4.08-4.14 (m, 1 H) 4.36-4.45 (m, 1 H) 4.77 (td, J = 6.28, 1.47 Hz, 2 H) 5.16 (dd, J = 8.22, 6.21 Hz, 2 H) 7.20 (d, J = 9.73 Hz, 1 H) 7.33 (d, J = 9.10 Hz, 2 H) 7.78 (d, J = 5.58 Hz, 1 H) 8.04 (t, J = 8.71 Hz, 1 H) 8.42 (dd, J = 8.68, 3.94 Hz, 1 H) 8.55 (d, J = 5.53 Hz, 1 H) 8.98 (s, 1 H) |
| 183 | ¹H NMR, (400 MHz, <cd3od>) δ ppm 1.13 (d, J = 6.85 Hz, 3 H) 1.53-1.85 (m, 5 H) 1.85-2.00 (m, 2 H) 2.00-2.15 (m, 2 H) 2.70-2.94 (m, 2 H) 3.03-3.16 (m, 2 H) 3.56-3.70 (m, 3 H) 3.75-3.86 (m, 1 H) 3.87-4.05 (m, 3 H) 4.70 (dt, J = 8.03, 4.22 Hz, 1 H) 6.84 (d, J = 10.12 Hz, 2 H) 7.57 (d, J = 5.48 Hz, 1 H) 7.97 (t, J = 8.71 Hz, 1 H) 8.35 (dd, J = 8.63, 3.94 Hz, 1 H) 8.49 (d, J = 5.48 Hz, 1 H) 8.86 (s, 1 H) |
| 184 | ¹H NMR, (400 MHz, <cd3od>) δ ppm 1.13 (d, J = 6.85 Hz, 3 H) 1.58-1.73 (m, 2 H) 1.73-2.02 (m, 4 H) 2.05-2.23 (m, 1 H) 2.33-2.63 (m, 4 H) 2.72-2.92 (m, 2 H) 3.02-3.18 (m, 1 H) 3.69 (s, 1 H) 3.82 (dt, J = 9.06, 5.42 Hz, 1 H) 3.94 (td, J = 8.63, 5.09 Hz, 1 H) 7.36 (d, J = 9.49 Hz, 2 H) 7.59 (d, J = 5.48 Hz, 1 H) 8.03 (t, J = 8.71 Hz, 1 H) 8.40 (dd, J = 8.63, 3.94 Hz, 1 H) 8.51 (d, J = 5.43 Hz, 1 H) 8.92 (s, 1 H) |
| 185 | ¹H NMR, (400 MHz, <cd3od>) δ ppm 0.69 (d, J = 6.75 Hz, 3 H) 1.84 (d, J = 13.69 Hz, 1 H) 1.90-2.10 (m, 1 H) 2.16 (d, J = 12.47 Hz, 1 H) 2.32 (br. s., 1 H) 2.50-2.72 (m, 1 H) 3.94 (dt, J = 12.89, 4.56 Hz, 1 H) 5.04 (t, J = 4.16 Hz, 1 H) 7.22 (t, J = 8.29 Hz, 2 H) 7.58-7.70 (m, 1 H) 7.75 (d, J = 5.43 Hz, 1 H) 8.04 (t, J = 8.71 Hz, 1 H) 8.42 (dd, J = 8.66, 3.96 Hz, 1 H) 8.57 (d, J = 5.38 Hz, 1 H) 8.75 (s, 1 H) 8.81 (s, 1 H) |
| 186 | ¹H NMR, (400 MHz, <cd3od>) δ ppm 0.67 (d, J = 6.70 Hz, 3 H) 0.76-0.91 (m, 2 H) 0.98-1.08 (m, 2 H) 1.72-1.84 (m, 1 H) 1.96-2.17 (m, 3 H) 2.17-2.36 (m, 1 H) 2.58-2.78 (m, 1 H) 3.84 (dt, J = 12.67, 4.45 Hz, 1 H) 7.22 (t, J = 8.27 Hz, 2 H) 7.64 (tt, J = 8.49, 6.47 Hz, 1 H) 7.77 (s, 1 H) 7.82 (d, J = 5.58 Hz, 1 H) 8.04 (t, J = 8.73 Hz, 1 H) 8.42 (dd, J = 8.66, 3.96 Hz, 1 H) 8.59 (d, J = 5.38 Hz, 1 H) 8.86 (s, 1 H) |
| 187 | ¹H NMR, (400 MHz, <cd3od>) δ ppm 0.69 (d, J = 6.65 Hz, 3 H) 1.80 (d, J = 13.30 Hz, 1 H) 2.00-2.14 (m, 2 H) 2.17 (s, 3 H) 2.20-2.36 (m, 1 H) 2.60-2.80 (m, 1 H) 3.87 (dt, J = 12.63, 4.32 Hz, 1 H) 4.91 (d, J = 6.36 Hz, 1 H) 5.19 (s, 1 H) 5.75 (s, 1 H) 7.22 (t, J = 8.29 Hz, 2 H) 7.63 (tt, J = 8.48, 6.49 Hz, 1 H) 7.84 (br. s., 1 H) 8.03 (t, J = 8.71 Hz, 1 H) 8.09 (d, J = 1.86 Hz, 1 H) 8.41 (dd, J = 8.66, 3.91 Hz, 1 H) 8.54-8.63 (m, 1 H) 8.76-8.91 (m, 1 H) |
| 188 | ¹H NMR, (400 MHz, <cd3od>) δ ppm 0.66 (d, J = 6.75 Hz, 3 H) 1.63 (s, 6 H) 1.71-1.82 (m, 1 H) 1.90-2.18 (m, 2 H) 2.24 (d, J = 12.57 Hz, 1 H) 2.61-2.79 (m, 1 H) 3.85 (dt, J = 12.64, 4.34 Hz, 1 H) 7.21 (t, J = 8.29 Hz, 2 H) 7.57-7.70 (m, 1 H) 7.81 (d, J = 5.48 Hz, 1 H) 7.87 (s, 1 H) 8.02 (t, J = 8.71 Hz, 1 H) 8.41 (dd, J = 8.63, 3.99 Hz, 1 H) 8.57 (d, J = 5.58 Hz, 1 H) 8.82 (s, 1 H) |
| 189 | ¹H NMR, (400 MHz, <cd3od>) δ ppm 0.97 (s, 3 H) 1.45-1.60 (m, 2 H) 1.60-1.71 (m, 1 H) 1.80-1.90 (m, 1 H) 1.91-2.03 (m, 1 H) 2.97-3.11 (m, 1 H) 3.26-3.31 (m, 1 H) 3.60-3.67 (m, 1 H) 4.08-4.17 (m, 1 H) 4.35-4.45 (m, 1 H) 7.06-7.17 (m, 2 H) 7.48-7.65 (m, 2 H) 7.90-7.98 (m, 1 H) 8.28-8.36 (m, 1 H) 8.41-8.47 (m, 1 H) 8.91-8.97 (m, 1 H) |
| 190 | ¹H NMR, (400 MHz, <cd3od>) δ ppm 1.02-1.10 (m, 3 H) 1.52-1.67 (m, 2 H) 1.68-1.80 (m, 1 H) 1.88-1.96 (m, 1 H) 1.97-2.10 (m, 1 H) 3.04-3.16 (m, 1 H) 3.35-3.41 (m, 1 H) 3.67-3.73 (m, 1 H) 4.16-4.25 (m, 1 H) 4.43-4.52 (m, 1 H) 7.14-7.24 (m, 2 H) 7.56-7.69 (m, 2 H) 7.97-8.05 (m, 1 H) 8.36-8.43 (m, 1 H) 8.47-8.55 (m, 1 H) 8.94-9.00 (m, 1 H) |
| 191 | ¹H NMR, (400 MHz, <cd3od>) δ ppm 0.88-0.97 (m, 3 H) 1.42-1.55 (m, 1 H) 1.63-1.80 (m, 2 H) 1.85-1.98 (m, 2 H) 3.03-3.16 (m, 1 H) 3.36-3.41 (m, 1 H) 3.66-3.74 (m, 3 H) 3.85-3.92 (m, 3 H) 4.04-4.12 (m, 1 H) 6.78 (s, 1 H) 7.64-7.72 (m, 1 H) 7.92-8.01 (m, 1 H) 8.31-8.39 (m, 1 H) 8.45-8.51 (m, 1 H) 8.86-8.94 (m, 1 H) |
| 192 | ¹H NMR, (400 MHz, <cd3od>) δ ppm 0.64 (d, J = 6.65 Hz, 3 H) 1.73-1.85 (m, 1 H) 2.00-2.16 (m, 2 H) 2.21-2.34 (m, 1 H) 2.61-2.76 (m, 1 H) 3.34-3.41 (m, 1 H) 3.88 (s, 4 H) 4.95-5.02 (m, 1 H) 6.74-6.84 (m, 2 H) 7.79-7.85 (m, 1 H) 7.85-7.91 (m, 1 H) 7.93-8.01 (m, 1 H) 8.02-8.09 (m, 1 H) 8.31-8.40 (m, 1 H) 8.53-8.61 (m, 1 H) 8.81-8.89 (m, 1 H) |
| 193 | ¹H NMR, (400 MHz, <cd3od>) δ ppm 0.43 (d, J = 6.65 Hz, 3 H) 2.44-2.58 (m, 1 H) 3.57-3.67 (m, 1 H) 3.76-3.84 (m, 1 H) 3.93 (s, 3 H) 3.97-4.13 (m, 2 H) 4.19-4.29 (m, 1 H) 5.06-5.12 (m, 1 H) 6.79-6.89 (m, 2 H) 7.52-7.60 (m, 1 H) 7.84-7.91 (m, 1 H) 7.95-8.04 (m, 1 H) 8.07-8.14 (m, 1 H) 8.34-8.44 (m, 2 H) 9.07-9.13 (m, 1 H) |
| 194 | ¹H NMR, (400 MHz, <cd3od>) δ ppm −0.02-0.04 (m, 3 H) 1.94-2.07 (m, 1 H) 3.01-3.11 (m, 2 H) 3.16-3.24 (m, 1 H) 3.35-3.44 (m, 1 H) 3.50-3.59 (m, 1 H) 3.72-3.82 (m, 1 H) 6.78 (s, 1 H) 7.12-7.29 (m, 2 H) 7.49-7.52 (m, 1 H) 7.70-7.74 (m, 1 H) 7.97-8.04 (m, 1 H) 8.92-8.97 (m, 1 H) |
| 198 | ¹H NMR (400 MHz, <dmso-$d_6$>) δ ppm 0.59 (d, J = 6.65 Hz, 3 H) 1.16 (dd, J = 8.41, 6.85 Hz, 6 H) 2.06 (d, J = 3.91 Hz, 1 H) 3.07-3.33 (m, 5 H) 3.56 (s, 3 H) 3.86 (d, J = 9.78 Hz, 1 H) 4.18 (dq, J = 13.60, 6.68 Hz, 1 H) 7.19 (br. s., 1 H) 7.28-7.52 (m, 4 H) 7.78 (dd, J = 8.61, 1.96 Hz, 1 H) 7.86-8.06 (m, 4 H) 8.28-8.52 (m, 3 H) 9.16 (s, 1 H) 10.24 (s, 1 H) |

TABLE 3-continued

| Ex # | ¹H-NMR data |
|---|---|
| 199 | ¹H NMR (400 MHz, <dmso-$d_6$>) δ ppm 0.45 (d, J = 7.04 Hz, 3 H) 1.74-2.02 (m, 3 H) 2.07-2.41 (m, 2 H) 2.84-2.99 (m, 1 H) 3.08-3.22 (m, 1 H) 3.30 (d, J = 14.48 Hz, 2 H) 3.48 (d, J = 9.39 Hz, 1 H) 3.56 (s, 3 H) 3.69 (t, J = 11.15 Hz, 2 H) 3.79-4.00 (m, 3 H) 7.28 (d, J = 6.26 Hz, 1 H) 7.36 (d, J = 10.17 Hz, 1 H) 7.47 (d, J = 9.39 Hz, 2 H) 8.03 (br. s., 3 H) 8.23 (t, J = 8.80 Hz, 1 H) 8.29-8.46 (m, 2 H) 9.00 (br. s., 1 H) 10.36 (s, 1 H) |
| 200 | ¹H NMR (400 MHz, <dmso-$d_6$>) δ ppm 0.75 (d, J = 6.65 Hz, 3 H) 1.06-1.21 (m, 6 H) 1.42 (d, J = 12.91 Hz, 1 H) 1.51-1.71 (m, 2 H) 1.77 (d, J = 12.13 Hz, 2 H) 2.99 (br. s., 1 H) 3.32 (br. s., 1 H) 3.52-3.68 (m, 3 H) 3.85-3.99 (m, 1 H) 4.09 (dq, J = 13.79, 6.75 Hz, 1 H) 7.31-7.44 (m, 3 H) 7.69-7.85 (m, 5 H) 7.88 (ddd, J = 8.31, 4.60, 2.35 Hz, 1 H) 8.32 (d, J = 7.43 Hz, 1 H) 8.40 (dd, J = 7.83, 1.96 Hz, 1 H) 8.49 (d, J = 5.09 Hz, 1 H) 8.88 (s, 1 H) 10.36 (s, 1 H) |
| 201 | ¹H NMR (400 MHz, <dmso-$d_6$>) δ ppm 0.76 (d, J = 6.65 Hz, 3 H) 1.29-1.44 (m, 1 H) 1.44-1.80 (m, 4 H) 1.80-1.95 (m, 2 H) 2.18 (td, J = 13.21, 5.28 Hz, 1 H) 2.28 (td, J = 13.01, 5.67 Hz, 1 H) 2.79-2.93 (m, 1 H) 3.20 (br. s., 1 H) 3.53-3.63 (m, 3 H) 3.68 (t, J = 11.35 Hz, 2 H) 3.79-3.98 (m, 4 H) 7.33-7.53 (m, 3 H) 7.67-7.90 (m, 4 H) 8.11-8.23 (m, 1 H) 8.25-8.35 (m, 1 H) 8.48 (d, J = 5.48 Hz, 1 H) 8.54-8.63 (m, 1 H) 10.37-10.47 (m, 1 H) |
| 202 | ¹H NMR (400 MHz, <cdcl$_3$>) δ ppm 0.87 (br. s., 3 H) 1.27 (t, J = 6.65 Hz, 3 H) 1.45-1.68 (m, 2 H) 1.80 (br. s., 1 H) 2.05 (br. s., 1 H) 2.24 (br. s., 1 H) 2.99 (br. s., 1 H) 3.41-3.68 (m, 6 H) 4.23 (br. s., 1 H) 4.51-4.66 (m, 2 H) 6.79-7.19 (m, 3 H) 7.70-8.11 (m, 2 H) 8.20-8.64 (m, 3 H) 9.40-9.64 (m, 1 H) 10.17-10.40 (m, 1 H) |
| 203 | ¹H NMR (400 MHz, <cdcl$_3$>) δ ppm 0.42-0.71 (m, 3 H) 1.28 (br. s., 3 H) 2.06 (br. s., 1 H) 2.88 (br. s., 1 H) 3.25 (br. s., 1 H) 3.47-3.83 (m, 8 H) 4.10 (br. s., 1 H) 4.62 (br. s., 2 H) 6.83-7.06 (m, 1 H) 7.18 (br. s., 2 H) 7.48 (br. s., 1 H) 7.75 (br. s., 1 H) 8.34 (br. s., 2 H) 9.45-9.68 (m, 1 H) 10.05 (br. s., 1 H) |

Pim1, Pim2, Pim3 AlphaScreen Assays

Pim 1, Pim 2 & Pim 3 AlphaScreen assays using high ATP (11-125X ATP Km) were used to determine the biochemical activity of the inhibitors. The activity of Pim 1, Pim 2, & Pim 3 is measured using a homogeneous bead based system quantifying the amount of phosphorylated peptide substrate resulting from kinase-catalyzed phosphoryl transfer to a peptide substrate. Compounds to be tested are dissolved in 100% DMSO and directly distributed to a white 384-well plate at 0.25 μl per well. To start the reaction, 5 μl of 100 nM Bad peptide (Biotin-AGAGRSRHSSYPAGT-OH (SEQ ID NO:1)) and ATP (concentrations described below) in assay buffer (50 mM Hepes, pH=7.5, 5 mM MgCl$_2$, 0.05% BSA, 0.01% Tween-20, 1 mM DTT) is added to each well. This is followed by the addition of 5 μl/well of Pim 1, Pim 2 or Pim 3 kinase in assay buffer (concentrations described below). Final assay concentrations (described below) are in 2.5% DMSO. The reactions are performed for ~2 hours, then stopped by the addition of 10 μl of 0.75 μg/ml anti-phospho Ser/Thr antibody (Cell Signaling), 10 μg/ml Protein A AlphaScreen beads (Perkin Elmer), and 10 μg/ml streptavidin coated AlphaScreen beads in stop/detection buffer (50 mM EDTA, 95 mM Tris, pH=7.5, 0.01% Tween-20). The stopped reactions are incubated overnight in the dark. The phosphorylated peptide is detected via an oxygen anion initiated chemiluminescence/fluorescence cascade using the Envision plate reader (Perkin Elmer).

AlphaScreen Assay Conditions

| Enzyme source | Enzyme conc. (nM) | b-BAD peptide conc. (nM) | ATP conc. (uM) | ATP Km (app) (uM) |
|---|---|---|---|---|
| Pim 1 (INV) | 0.0025 | 50 | 2800 | 246 |
| Pim 2 (INV) | 0.01 | 50 | 500 | 4 |
| Pim 3 (NVS) | 0.005 | 50 | 2500 | 50 |

Compounds of the foregoing examples were tested by the Pim 1, Pim 2 & Pim 3 AlphaScreen assays and found to exhibit an IC$_{50}$ values as shown in Table 4 below. IC$_{50}$, the half maximal inhibitory concentration, represents the concentration of test compound that is required for 50% inhibition of its target in vitro.

Cell Proliferation Assay

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2x compounds were added to the cells in 96 well plates and incubated at 37° C. for 3 days.

After 3 days plates were equilibrated to room temperature and equal volume of CellTiter-Glow Reagent (Promega) was added to the culture wells. The plates were agitated briefly and luminescent signal was measured with luminometer. The percent inhibition of the signal seen in cells treated with DMSO alone vs. cells treated with control compound was calculated and used to determine EC$_{50}$ values (i.e., the concentration of a test compound that is required to obtain 50% of the maximum effect in the cells) for tested compounds, as shown in Table 4.

Using the procedures of the Pim1, Pim2, Pim3 AlphaScreen Assays the IC$_{50}$ concentrations of compounds of the previous examples were determined as shown in the Table 4.

Using the procedures of Cell Proliferation Assay, the EC$_{50}$ concentrations of compounds of the examples were determined in KMS 11 cells as shown in Table 4.

TABLE 4

| Ex # | Pim1 IC50 μM | Pim2 IC50 μM | Pim3 IC50 μM | KMS11 EC50 μM |
|---|---|---|---|---|
| 1 | 0.00006 | 0.00253 | 0.00252 | 0.094 |
| 2 | 0.00036 | 0.03007 | 0.01572 | 1.008 |
| 3 | 0.00014 | 0.04942 | 0.03053 | 1.130 |

TABLE 4-continued

| Ex # | Pim1 IC50 μM | Pim2 IC50 μM | Pim3 IC50 μM | KMS11 EC50 μM |
|---|---|---|---|---|
| 4 | 0.00006 | 0.00428 | 0.00154 | 0.148 |
| 5 | 0.00003 | 0.00124 | 0.00064 | 0.033 |
| 6 | 0.00024 | 0.00681 | 0.01100 | 3.090 |
| 7 | 0.00004 | 0.00139 | 0.00086 | 0.040 |
| 8 | 0.00035 | 0.02050 | 0.01423 | 0.499 |
| 9 | 0.00040 | 0.05937 | 0.01778 | 0.670 |
| 10 | 0.00057 | 0.03407 | 0.02088 | 1.833 |
| 11 | 0.00038 | 0.03331 | 0.01956 | 4.179 |
| 12 | 0.00021 | 0.01607 | 0.01572 | 0.716 |
| 13 | 0.00009 | 0.00482 | 0.00509 | 0.507 |
| 14 | 0.00004 | 0.00172 | 0.00102 | 0.045 |
| 15 | 0.00007 | 0.00356 | 0.00207 | 0.146 |
| 16 | 0.17209 | 21.7 | 8.3 | >10 |
| 17 | 0.00256 | 0.38852 | 0.15521 | 8.260 |
| 18 | 0.00005 | 0.00086 | 0.00099 | 0.267 |
| 19 | 0.00017 | 0.00259 | 0.00321 | 0.287 |
| 20 | 0.00014 | 0.00668 | 0.00678 | 0.476 |
| 21 | 0.00005 | 0.00766 | 0.00092 | 0.756 |
| 22 | 0.00037 | 0.01388 | 0.01165 | 0.530 |
| 23 | 0.02746 | 1.4 | 1.0 | >10 |
| 24 | 0.06819 | 2.7 | 1.7 | >10 |
| 25 | 0.00063 | 0.02504 | 0.01580 | 2.867 |
| 26 | 0.14276 | 7.1 | 4.8 | >10 |
| 27 | 0.00212 | 0.04198 | 0.05333 | 1.751 |
| 28 | 0.00680 | 0.23750 | 0.15437 | 4.874 |
| 29 | 0.00020 | 0.00944 | 0.00888 | 0.768 |
| 30 | 0.00072 | 0.07280 | 0.04426 | 9.686 |
| 31 | 0.00021 | 0.01045 | 0.01240 | 0.633 |
| 32 | 0.00297 | 0.10611 | 0.06386 | 7.958 |
| 33 | 0.00002 | 0.00068 | 0.00061 | 0.072 |
| 34 | 0.00076 | 0.04724 | 0.03991 | 3.753 |
| 35 | 0.00014 | 0.00794 | 0.00524 | 0.365 |
| 36 | 0.00059 | 0.02943 | 0.02876 | 0.979 |
| 37 | 0.00009 | 0.00300 | 0.00503 | 0.178 |
| 38 | 0.00056 | 0.04551 | 0.04371 | 5.949 |
| 39 | 0.00039 | 0.03092 | 0.02182 | 2.989 |
| 40 | 0.00017 | 0.01241 | 0.00875 | 0.964 |
| 41 | | 0.02032 | | 5.980 |
| 42 | 0.00004 | 0.00196 | 0.00100 | 0.063 |
| 43 | 0.00586 | 0.32741 | 0.11823 | 4.577 |
| 44 | 0.00338 | 0.28911 | 0.22295 | >10 |
| 45 | 0.64280 | >25 | >25 | >10 |
| 46 | 0.00020 | 0.02139 | 0.00304 | 0.348 |
| 47 | 0.17919 | 15.8 | 2.7 | >10 |
| 48 | 0.01063 | 0.42676 | 0.41111 | 9.416 |
| 49 | 0.00003 | 0.00120 | 0.00116 | 0.031 |
| 50 | 0.00024 | 0.01707 | 0.00535 | 0.470 |
| 51 | 0.00177 | 0.06911 | 0.03579 | 0.970 |
| 52 | 0.00850 | 0.72623 | 0.59094 | 4.386 |
| 53 | 0.00013 | 0.01432 | 0.01054 | 0.363 |
| 54 | 0.00009 | 0.00468 | 0.00174 | 0.891 |
| 55 | 0.00013 | 0.01118 | 0.00629 | 0.553 |
| 56 | 0.00002 | 0.00151 | 0.00062 | 0.036 |
| 57 | 0.00017 | 0.00647 | 0.00571 | 0.462 |
| 58 | 0.00002 | 0.00151 | 0.00049 | 0.168 |
| 59 | 0.01678 | 0.86628 | 0.58283 | 7.309 |
| 60 | 0.00022 | 0.01356 | 0.01080 | 0.202 |
| 61 | 0.00003 | 0.00107 | 0.00049 | 0.041 |
| 62 | 0.00003 | 0.00290 | 0.00128 | 0.106 |
| 63 | 0.00630 | 0.36441 | 0.09475 | 4.486 |
| 64 | 0.00001 | 0.00100 | 0.00022 | 0.044 |
| 65 | 0.04056 | 2.8 | 1.1 | >10 |
| 66 | 0.00003 | 0.00118 | 0.00073 | 0.224 |
| 67 | 0.00148 | 0.07360 | 0.07771 | 3.205 |
| 68 | 0.00028 | 0.01196 | 0.01485 | 0.847 |
| 69 | 0.00004 | 0.00117 | 0.00040 | 0.114 |
| 70 | 0.00075 | 0.01070 | 0.00819 | 0.144 |
| 71 | 0.00004 | 0.00170 | 0.00054 | 0.156 |
| 72 | 0.00003 | 0.00083 | 0.00043 | 0.065 |
| 73 | 0.00002 | 0.00137 | 0.00091 | 0.069 |
| 74 | 0.04346 | 2.48310 | 1.50872 | 7.843 |
| 75 | 0.00008 | 0.00337 | 0.00308 | 0.147 |
| 76 | 0.13046 | 6.6 | 4.3 | >10 |
| 77 | 0.00004 | 0.00144 | 0.00162 | 0.080 |
| 78 | 0.02538 | 1.1 | 1.0 | >10 |
| 79 | 0.00028 | 0.00257 | 0.00536 | 0.132 |
| 80 | 0.00003 | 0.00082 | 0.00079 | 0.050 |
| 81 | 0.00004 | 0.00089 | 0.00074 | 0.036 |
| 82 | 0.00003 | 0.00062 | 0.00032 | 0.048 |
| 83 | 0.00001 | 0.00063 | 0.00064 | 0.037 |
| 84 | 0.00133 | 0.06413 | 0.04181 | 3.201 |
| 85 | 0.00003 | 0.00113 | 0.00096 | 0.057 |
| 86 | 0.00308 | 0.09956 | 0.06764 | 5.155 |
| 87 | 0.00003 | 0.00074 | 0.00068 | 0.166 |
| 88 | 0.00003 | 0.00237 | 0.00124 | 0.093 |
| 89 | 0.01317 | 1.47124 | 0.58270 | 3.990 |
| 90 | 0.03105 | 1.9 | 1.0 | >10 |
| 91 | 0.00005 | 0.00226 | 0.00264 | 0.128 |
| 92 | 0.00010 | 0.00471 | 0.00369 | 0.175 |
| 93 | 0.00004 | 0.00368 | 0.00188 | 0.154 |
| 94 | 0.00003 | 0.00235 | 0.00279 | 0.356 |
| 95 | 0.00002 | 0.00138 | 0.00143 | 0.289 |
| 96 | 0.00004 | 0.00242 | 0.00507 | 0.186 |
| 97 | 0.00004 | 0.00133 | 0.00220 | 0.051 |
| 98 | 0.00004 | 0.00172 | 0.00158 | 0.074 |
| 99 | 0.00001 | 0.00108 | 0.00125 | 0.051 |
| 100 | 0.00006 | 0.00330 | 0.00373 | 0.165 |
| 101 | 0.00002 | 0.00301 | 0.00145 | 0.212 |
| 102 | 0.00003 | 0.00218 | 0.00210 | 0.454 |
| 103 | 0.00212 | 0.13033 | 0.10610 | 3.451 |
| 104 | 0.00535 | 0.13520 | 0.19792 | >10 |
| 105 | 0.00006 | 0.00374 | 0.00161 | 0.117 |
| 106 | 0.00031 | 0.02440 | 0.01673 | 0.792 |
| 107 | 0.00005 | 0.00769 | 0.00542 | 0.364 |
| 108 | 0.00008 | 0.00234 | 0.00581 | 0.155 |
| 109 | 0.00040 | 0.00161 | 0.01117 | 0.616 |
| 110 | 0.00009 | 0.01038 | 0.01791 | 0.825 |
| 111 | 0.00008 | 0.00074 | 0.00141 | 0.169 |
| 112 | 0.00008 | 0.00737 | 0.00415 | 0.258 |
| 113 | 0.00250 | 0.12003 | 0.11490 | 1.826 |
| 114 | | | 0.00188 | 0.053 |
| 115 | 0.00007 | 0.00248 | 0.00144 | 0.315 |
| 116 | 0.00012 | 0.00578 | 0.01210 | 0.323 |
| 117 | 0.00003 | 0.00153 | 0.00310 | 0.026 |
| 118 | 0.00002 | 0.00124 | 0.00174 | 2.455 |
| 119 | 0.00007 | 0.00907 | 0.00525 | 0.316 |
| 120 | 0.00140 | 0.14659 | 0.06752 | 6.060 |
| 121 | 0.00005 | 0.00593 | 0.01043 | 0.625 |
| 122 | 0.00005 | 0.00385 | 0.00384 | 0.321 |
| 123 | 0.00003 | 0.00153 | 0.00153 | 0.054 |
| 124 | 0.00005 | 0.00403 | 0.00202 | 0.040 |
| 125 | 0.00004 | 0.00179 | 0.00239 | 0.046 |
| 126 | 0.00070 | 0.00256 | 0.00778 | 0.267 |
| 127 | 0.00005 | 0.00198 | 0.00451 | 0.076 |
| 128 | 0.00024 | 0.00121 | 0.00411 | 2.099 |
| 129 | 0.00005 | 0.00246 | 0.00544 | 0.107 |
| 130 | 0.00003 | 0.00254 | 0.00170 | 0.109 |
| 131 | 0.00005 | 0.00255 | 0.00149 | 0.135 |
| 132 | 0.00004 | 0.00145 | 0.00108 | 0.016 |
| 133 | 0.00057 | 0.02866 | 0.01050 | 2.304 |
| 134 | 0.00054 | 0.02207 | 0.01019 | 0.468 |
| 135 | 0.00002 | 0.00078 | 0.00026 | 0.193 |
| 136 | 0.00004 | 0.00147 | 0.00249 | 0.038 |
| 137 | 0.00002 | 0.00103 | 0.00093 | 0.027 |
| 138 | 0.00003 | 0.00122 | 0.00258 | 0.020 |
| 139 | 0.00002 | 0.00124 | 0.00155 | 0.083 |
| 140 | 0.00002 | 0.00269 | 0.00134 | 0.100 |
| 141 | 0.00002 | 0.00117 | 0.00124 | 0.047 |
| 142 | 0.00002 | 0.00079 | 0.00087 | 0.078 |
| 143 | 0.00005 | 0.00302 | 0.00217 | 0.118 |
| 144 | 0.00002 | 0.00186 | 0.00123 | 0.056 |
| 145 | 0.00004 | 0.00090 | 0.00089 | 0.057 |
| 146 | 0.00002 | 0.00047 | 0.00039 | 0.018 |
| 147 | 0.00003 | 0.00169 | 0.00103 | 0.089 |
| 148 | 0.00002 | 0.00079 | 0.00055 | 0.091 |
| 149 | 0.00008 | 0.00888 | 0.00797 | 0.231 |
| 150 | 0.38044 | >25 | >25 | >10 |
| 151 | 0.00004 | 0.00204 | 0.00218 | 0.113 |
| 152 | 0.05163 | 6.8 | 4.6 | >10 |
| 153 | 0.00001 | 0.00074 | 0.00145 | 0.026 |
| 154 | 0.00005 | 0.00104 | 0.00074 | 0.257 |
| 155 | 0.00006 | 0.00220 | 0.00481 | 0.114 |
| 156 | 0.00004 | 0.00077 | 0.00080 | 0.178 |
| 157 | 0.00004 | 0.00120 | 0.00150 | 0.057 |

TABLE 4-continued

| Ex # | Pim1 IC50 μM | Pim2 IC50 μM | Pim3 IC50 μM | KMS11 EC50 μM |
|---|---|---|---|---|
| 158 | 0.00004 | 0.00081 | 0.00132 | 0.040 |
| 159 | 0.00002 | 0.00109 | 0.00075 | 0.046 |
| 160 | 0.00005 | 0.00190 | 0.00222 | 0.082 |
| 161 | 0.00002 | 0.00087 | 0.00076 | 0.068 |
| 162 |  | 0.00168 |  | 0.059 |
| 163 |  | 0.00183 |  | 0.053 |
| 164 |  | 0.27024 |  | >10 |
| 165 | 0.00002 | 0.00113 | 0.00095 | 0.066 |
| 166 | 0.00002 | 0.00040 | 0.00036 | 0.015 |
| 167 | 0.00018 | 0.00607 | 0.01257 | 0.240 |
| 168 | 0.00004 | 0.00531 | 0.00195 | 0.099 |
| 169 | 0.00079 | 0.06566 | 0.02227 | 2.363 |
| 170 | 0.00012 | 0.01384 | 0.00986 | 0.352 |
| 171 | 0.00002 | 0.01018 | 0.00251 | 0.398 |
| 172 | 0.00004 | 0.00169 | 0.00272 | 0.086 |
| 173 | 0.00005 | 0.00267 | 0.00132 | 0.136 |
| 174 | 0.00002 | 0.00065 | 0.00041 | 0.014 |
| 175 | 0.00009 | 0.00215 | 0.00252 | 0.091 |
| 176 | 0.00002 | 0.00077 | 0.00084 | 0.056 |
| 177 | 0.00004 | 0.00189 | 0.00296 | 0.069 |
| 178 | 0.00016 | 0.01494 | 0.02525 | 2.190 |
| 179 | 0.00003 | 0.00319 | 0.00516 | 0.266 |
| 180 | 0.00013 | 0.00747 | 0.00668 | 0.206 |
| 181 | 0.00003 | 0.00210 | 0.00175 | 0.108 |
| 182 | 0.00030 | 0.03743 | 0.02985 | 1.045 |
| 183 | 0.00001 | 0.00308 | 0.00075 | 0.058 |
| 184 | 0.00002 | 0.00204 | 0.00090 | 0.032 |
| 185 |  | 0.01333 |  | 0.417 |
| 186 | 0.00005 | 0.00405 | 0.00287 | 0.291 |
| 187 | 0.00004 | 0.00279 | 0.00203 | 0.163 |
| 188 |  | 0.00527 |  | 0.403 |
| 189 | 0.03192 | 4.4 | 1.3 | >10 |
| 190 | 0.00087 | 0.04726 | 0.04313 | >10 |
| 191 | 0.00019 | 0.02718 | 0.00971 | 0.747 |
| 192 | 0.00004 | 0.00442 | 0.00210 | 0.194 |
| 193 | 0.00003 | 0.00179 | 0.00062 | 0.092 |
| 194 | 0.00005 | 0.00154 | 0.00117 | 0.039 |
| 195 | 0.00010 | 0.01374 | 0.01423 | 0.528 |
| 196 | 0.00031 | 0.00260 | 0.00690 | 0.969 |
| 197 | 0.00007 | 0.00515 | 0.00209 | 0.400 |
| 198 | 0.00028 | 0.00218 | 0.00305 | 0.265 |
| 199 | 0.00005 | 0.00281 | 0.00356 | 0.098 |
| 200 | 0.00170 | 0.00519 | 0.01829 | 2.415 |
| 201 | 0.00017 | 0.02347 | 0.02474 | 0.424 |
| 202 | 0.00038 | 0.01614 | 0.01967 | 0.358 |
| 203 | 0.00005 | 0.00167 | 0.00152 | 0.059 |

Compound structures in the tables marked as "Chiral" were prepared and tested in optically active form, having the absolute stereochemistry as shown; other compounds were prepared and tested in racemic form, and the depicted structure represents the relative stereochemistry at each chiral center.

The invention claimed is:
1. A compound of Formula (A)

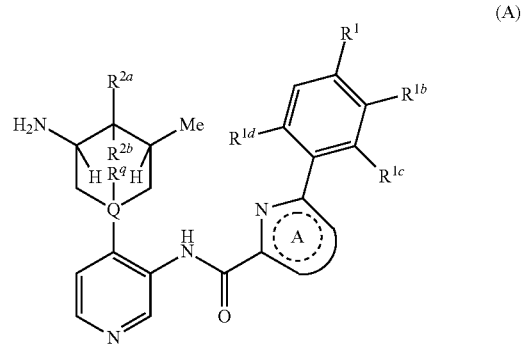

(A)

wherein:
groups attached to the ring containing Q that are depicted inside the ring are all syn to each other, and all groups attached to that ring that are depicted outside the ring are syn to one another;

Q is C or N;

$R^q$ is H when Q is C, and Rd is absent when Q is N;

$R^1$ is selected from H, $C_{1-4}$ alkyl, $C_{3-6}$ cycloalkyl, $C_{4-6}$ heterocyclyl, —$(CR'_2)_{1-3}$—OR' and —OR',
where each R' is independently H or $C_{1-4}$ alkyl,
and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;

$R^{1b}$, $R^{1c}$, and $R^{1d}$ are each independently selected from H, halo, OR', R', —$(CH_2)_{1-2}$OR', and $CONR'_2$;

one of $R^{2a}$ and $R^{2b}$ is H,
and the other of $R^{2a}$ and $R^{2b}$ is selected from CN, azido, amino, —OR, —$O(CH_2)_{1-3}$OR, —NRC(O)R, —NRC(O)OR, —$NHSO_2R$, —$SO_2R$, —$OSO_2R$, —SR, —S(O)R, —OP(O)$R_2$, and 1-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;

where each R is independently $C_{5-6}$ heteroaryl or $C_{1-4}$ alkyl optionally substituted with up to three groups selected from cyano, halo, hydroxy, carboxy, $C_{1-4}$ alkylsulfonyl, and $C_{1-4}$ alkoxy;

or $R^{2a}$ and $R^{2b}$ taken together may form a dialkyl ketal or 5-6 membered cyclic ketal, =O or =N—OR", where R" is H or $C_{1-4}$ alkyl;

ring A is selected from pyridinyl, pyrimidinyl, and pyrazinyl, each having N positioned as shown in Formula (I); and Ring A is optionally substituted with 1 or 2 groups selected from halo, CN, $NH_2$, hydroxy, $C_{1-4}$ alkyl, $C_{1-4}$ haloalkyl, $C_{1-4}$ alkoxy, and $C_{1-4}$ haloalkoxy;

or a pharmaceutically acceptable salt thereof.

2. The compound of claim 1, wherein $R^{2a}$ is —OMe, —$SO_2$Me, —NHCOOMe, or —O($CH_2)_2$—X, wherein X is —OMe, COOH, CN or —$SO_2$Me, or $R^{2a}$ is 1-triazolyl (e.g., 1,2,3-triazolyl) or 1-pyridonyl that is optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, and $C_{1-4}$ alkoxy, or —$SO_2$Me.

3. The compound of claim 2, wherein $R^1$ is selected from 2-hydroxy-2-propyl, methoxymethyl, ethoxymethyl, methoxy, ethoxy, isopropoxy, cyclopropyl, cyclobutyl, 1-hydroxycyclobutyl, cyclopentyl, tetrahydropyranyl, 4-F, 4-hydroxy-4-tetrahydropyranyl, 4-tetrahydropyranyloxy, and 4-tetrahydropyranyl.

4. The compound of claim 1, wherein $R^{2b}$ is OMe.

5. The compound of claim 1, which is a compound of Formula (I):

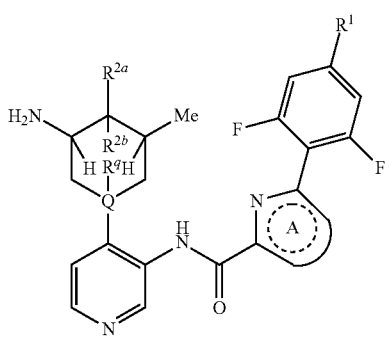

(I)

wherein:

groups attached to the ring containing Q that are depicted inside the ring are all syn to each other, and all groups attached to that ring that are depicted outside the ring are syn to one another;

Q is C or N;

$R^q$ is H when Q is C, and $R^q$ is absent when Q is N;

$R^1$ is selected from H, $C_{1-4}$ alkyl, $C_{3-6}$ cycloalkyl, $C_{4-6}$ heterocyclyl, —($CR'_2)_{1-3}$—OR' and —OR', where each R' is independently H or $C_{1-4}$ alkyl, and each alkyl, cycloalkyl and heterocyclyl is optionally substituted with up to two groups selected from halo, CN, $NH_2$, hydroxy, oxo, $C_{1-4}$ haloalkyl, $C_{1-4}$ alkoxy, and $C_{1-4}$ haloalkoxy;

one of $R^{2a}$ and $R^{2b}$ is H, and the other of $R^{2a}$ and $R^{2b}$ is selected from CN, azido, amino, —OR, —O($CH_2)_{1-3}$OR, —NRC(O)R, —NRC(O)OR, —NHSO$_2$R, —SO$_2$R, —OSO$_2$R, —SR, —S(O)R, —OP(O)$R_2$, and N-pyridonyl or 1-triazolyl optionally substituted with up to two groups selected from halo, $C_{1-4}$ alkyl, hydroxy-substituted $C_{1-4}$ alkyl, $C_{2-4}$ alkenyl, $C_{3-6}$ cycloalkyl, $C_{1-4}$ alkoxy, and $C_{5-6}$ heteroaryl;

where each R is independently $C_{5-6}$ heteroaryl or $C_{1-4}$ alkyl optionally substituted with up to three groups selected from cyano, halo, hydroxy, carboxy, $C_{1-4}$alkylsulfonyl, and $C_{1-4}$ alkoxy;

or $R^{2a}$ and $R^{2b}$ taken together may form a dialkyl ketal or 5-6 membered cyclic ketal, =O or =N—OR", where R" is H or $C_{1-4}$ alkyl;

Ring A is selected from pyridinyl, pyrimidinyl, and pyrazinyl, each having N positioned as shown in Formula (I); and Ring A is optionally substituted with 1 or 2 groups selected from halo, CN, $NH_2$, hydroxy, $C_{1-4}$ alkyl, $C_{1-4}$ haloalkyl, $C_{1-4}$ alkoxy, and $C_{1-4}$ haloalkoxy;

or a pharmaceutically acceptable salt thereof.

6. The compound of claim 5, wherein $R^{2a}$ is H.

7. The compound of claim 5, wherein $R^{2a}$ is selected from: —NHCOOMe, —O($CH_2)_2$—CN, —O($CH_2)_2$—$SO_2$Me, —OMe and —$SO_2$Me.

8. The compound of claim 5, wherein $R^{2b}$ is —OMe.

9. The compound of claim 5, wherein $R^{2a}$ and $R^{2b}$ taken together form =O or =N—OR", where R" is H or $C_{1-4}$ alkyl.

10. The compound of claim 5, wherein $R^1$ is selected from the group consisting of: H, methyl, ethyl, isopropyl, 2-hydroxy-2-propyl, methoxymethyl, ethoxymethyl, methoxy, ethoxy, isopropoxy, cyclopropyl, cyclobutyl, 1-hydroxycyclobutyl, cyclopentyl, tetrahydrofuranyl, 4-fluoro-4-tetrahydrofuranyl, tetrahydrothiopyran, and 4-tetrahydrothiopyran-1,1-dioxide; $R^{2a}$ is selected from the group consisting of: —OR, —OCH$_2$CH$_2$OR, —OCH$_2$CH$_2$CN, —OCH$_2$CH$_2$COOH, —OCH$_2$CH$_2$SO$_2$R, —CN, —NHC(O)OR, —NHC(O)R, $N_3$, $NH_2$, F, —NHSO$_2$R, —SO$_2$R, —SR, —S(O)R, unsubstituted triazole, and triazole substituted with Me, ethyl, cyclopropyl, hydroxymethyl, $C_{2-4}$ alkenyl, or thienyl; $R^{2b}$ is selected from the group consisting of: —OR, —OCH$_2$CH$_2$OR, —OCH$_2$CH$_2$CN, —OCH$_2$CH$_2$COOH, —OCH$_2$CH$_2$SO$_2$R, —CN, —NHC(O)OR, —NHC(O)R, $N_3$, $NH_2$, F, —NHSO$_2$R, —SO$_2$R, —SR, —S(O)R, unsubstituted triazole, and triazole substituted with Me, ethyl, cyclopropyl, hydroxymethyl, $C_{2-4}$ alkenyl, or thienyl; and wherein each R is methyl, ethyl or isopropyl.

11. The compound of claim 5, wherein $R^{2a}$ is selected from the group consisting of: —$SO_2$Me, —OCH$_2$CH$_2$CN, 1,2,4-triazol-1-yl, —OCH$_2$CH$_2$COOH, —OCH$_2$CH$_2$SO$_2$R, —CN and —NHC(O)OMe; or wherein $R^{2b}$ is —OMe, —CN, —OCH$_2$CH$_2$CN, 1,2,4-triazol-1-yl, —OCH$_2$CH$_2$COOH, —OCH$_2$CH$_2$SO$_2$R, —CN and —NHC(O)OMe.

12. The compound of claim 5, wherein Q is C.

13. The compound of claim 5, wherein Q is N.

14. The compound of claim 5, which is an optically active compound of Formula IIa:

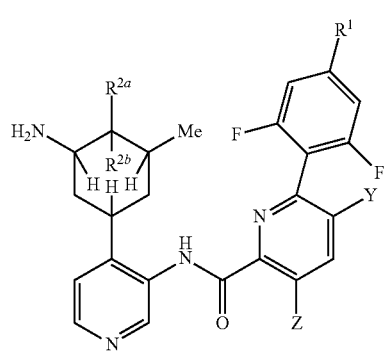

IIa wherein Y is H or F, and Z is H or $NH_2$.

15. A compound selected from the group consisting of: N-(4-((1R,3R,4S,5S)-3-amino-5-methyl-4-(1H-1,2,3-triazol-1-yl)cyclohexyl)pyridin-3-yl)-6-(2,6-difluorophenyl)-5-fluoropicolinamide, N-(4-((1R,3R,4S,5S)-3-amino-4-(2-methoxyacetamido)-5-methylcyclohexyl)pyridin-3-yl)-6-(2, 6-difluorophenyl)-5-fluoropicolinamide, N-(4-((1R,3R,4S, 5S)-3-amino-4-isobutyramido-5-methylcyclohexyl)pyridin-3-yl)-6-(2,6-difluorophenyl)-5-fluoropicolinamide, N-(4-((3R,4S,5S)-3-amino-5-methyl-4-(4-(thiophen-3-yl)-1H-1, 2,3-triazol-1-yl)piperidin-1-yl)pyridin-3-yl)-6-(2,6-difluorophenyl)-5-fluoropicolinamide, N-(4-((3R,4S,5S)-3-amino-5-methyl-4-(1H-1,2,3-triazol-1-yl)piperidin-1-yl) pyridin-3-yl)-6-(2,6-difluorophenyl)-5-fluoropicolinamide, N-(4-((1R,3R,5S,Z)-3-amino-4-(hydroxyimino)-5-methyl-cyclohexyl)pyridin-3-yl)-6-(2,6-difluorophenyl)-5-fluoropicolinamide, N-(4-((3R,4S,5S)-3-amino-5-methyl-4-(4-methyl-1H-1,2,3-triazol-1-yl)piperidin-1-yl)pyridin-3-yl)-6-(2, 6-difluorophenyl)-5-fluoropicolinamide, ethyl (1S,2R,4R, 6S)-2-amino-4-(3-(6-(2,6-difluorophenyl)-5-fluoropicolinamido)pyridin-4-yl)-6-methylcyclohexylcarbamate, isopropyl (1S,2R,4R,6S)-2-amino-4-(3-(6-(2,6-difluorophenyl)-5-fluoropicolinamido)pyridin-4-yl)-6-methylcyclohexylcarbamate, N-(4-((1R,3R, 4S,5S)-3-amino-5-methyl-4-propionamidocyclohexyl) pyridin-3-yl)-6-(2,6-difluorophenyl)-5-fluoropicolinamide, N-(4-((1R,3R,5S)-3-amino-5-methyl-4-oxocyclohexyl)pyridin-3-yl)-6-(2,6-difluorophenyl)-5-fluoropicolinamide, N-(4-((1R,3R,5S,E)-3-amino-4-(methoxyimino)-5-methyl-cyclohexyl)pyridin-3-yl)-6-(2,6-difluorophenyl)-5-fluoropicolinamide, N-(4-((1R,3R,5S,Z)-3-amino-4-(methoxy-imino)-5-methylcyclohexyl)pyridin-3-yl)-6-(2,6-difluorophenyl)-5-fluoropicolinamide, N-(4-((3R,4S,5S)-3-amino-4-(4-(methoxymethyl)-1H-1,2,3-triazol-1-yl)-5-methylpiperidin-1-yl)pyridin-3-yl)-6-(2,6-difluorophenyl)-5-fluoropicolinamide, N-(4-((1R,3R,4S,5S)-3-amino-4-(2-hydroxyethylsulfonyl)-5-methylcyclohexyl)pyridin-3-yl)-6-(2,6-difluorophenyl)-5-fluoropicolinamide, N-(4-((1S,3S, 4S,5R)-3-amino-5-methyl-4-(methylsulfonamido) cyclohexyl)pyridin-3-yl)-6-(2,6-difluorophenyl)-5-fluoropicolinamide, N-(4-((1R,3R,4R,5S)-3-amino-5-methyl-4-(methylsulfonamido)cyclohexyl)pyridin-3-yl)-6-(2,6-difluorophenyl)-5-fluoropicolinamide, N-(4-((3R,4S, 5S)-3,4-diamino-5-methylpiperidin-1-yl)pyridin-3-yl)-6-(2, 6-difluorophenyl)-5-fluoropicolinamide, N-(4-((3R,4S,5S)-3-amino-5-methyl-4-(methylsulfonamido)piperidin-1-yl) pyridin-3-yl)-6-(2,6-difluorophenyl)-5-fluoropicolinamide, N-(4-((1R,3R,4S,5S)-3-amino-4-((2-methoxyethyl)sulfo-nyl)-5-methylcyclohexyl)pyridin-3-yl)-6-(2,6-difluorophe-nyl)-5-fluoropicolinamide, N-(4-((3R,4S,5S)-4-acetamido-3-amino-5-methylpiperidin-1-yl)pyridin-3-yl)-6-(2,6-difluorophenyl)-5-fluoropicolinamide, methyl (1S,2R,4R, 6S)-2-amino-4-(3-(6-(2,6-difluorophenyl)-5-fluoropicolinamido)pyridin-4-yl)-6-methylcyclohexylcarbamate, methyl (1R,2S,4S,6R)-2-amino-4-(3-(6-(2,6-difluorophenyl)-5-fluoropicolinamido) pyridin-4-yl)-6-methylcyclohexylcarbamate, N-(4-((1S,3S, 4R,5R)-4-acetamido-3-amino-5-methylcyclohexyl)pyridin-3-yl)-6-(2,6-difluorophenyl)-5-fluoropicolinamide, N-(4-((1R,3R,4S,5S)-4-acetamido-3-amino-5-methylcyclohexyl) pyridin-3-yl)-6-(2,6-difluorophenyl)-5-fluoropicolinamide, N-(4-((1S,3S,4R,5R)-3-amino-5-methyl-4-(methylsulfona-mido)cyclohexyl)pyridin-3-yl)-6-(2,6-difluorophenyl)-5-fluoropicolinamide, N-(4-((1R,3R,4S,5S)-3-amino-5-me-thyl-4-(methylsulfonamido)cyclohexyl)pyridin-3-yl)-6-(2, 6-difluorophenyl)-5-fluoropicolinamide, N-(4-((1S,3S,4R, 5R)-3-amino-4-azido-5-methylcyclohexyl)pyridin-3-yl)-6-(2,6-difluorophenyl)-5-fluoropicolinamide, N-(4-((1R,3R, 4S,5S)-3-amino-4-azido-5-methylcyclohexyl)pyridin-3-yl)-6-(2,6-difluorophenyl)-5-fluoropicolinamide, N-(4-((1R,3R, 4R,5S)-4-acetamido-3-amino-5-methylcyclohexyl)pyridin-3-yl)-6-(2,6-difluorophenyl)-5-fluoropicolinamide, N-(4-((1R,3R,4S,5S)-3-amino-5-methyl-4-((R)-methylsulfinyl cyclohexyl)pyridin-3-yl)-6-(2,6-difluorophenyl)-5-fluoropicolinamide, N-(4-((1R,3R,4R,5S)-3-amino-5-methyl-4-((S)-methylsulfinyl)cyclohexyl)pyridin-3-yl)-6-(2,6-difluorophenyl)-5-fluoropicolinamide, N-(4-((1R,3R, 4S,5S)-3-amino-5-methyl-4-(methylthio)cyclohexyl) pyridin-3-yl)-6-(2,6-difluorophenyl)-5-fluoropicolinamide, N-(4-((1R,3R,4R,5S)-3-amino-5-methyl-4-(methylsulfonyl) cyclohexyl)pyridin-3-yl)-6-(2,6-difluorophenyl)-5-fluoropicolinamide, N-(4-((1R,3R,4R,5S)-3-amino-5-methyl-4-(methylthio)cyclohexyl)pyridin-3-yl)-6-(2,6-difluorophenyl)-5-fluoropicolinamide, N-(4-((1R,3R,4S, 5S)-3-amino-5-methyl-4-((R)-methylsulfinyl)cyclohexyl) pyridin-3-yl)-6-(2,6-difluorophenyl)-5-fluoropicolinamide, N-(4-((1R,3R,4S,5S)-3-amino-5-methyl-4-(methylsulfonyl) cyclohexyl)pyridin-3-yl)-6-(2,6-difluorophenyl)-5-fluoropicolinamide, (1R,2R,4R,6S)-2-amino-4-(3-(6-(2,6-difluo-rophenyl)-5-fluoropicolinamido)pyridin-4-yl)-6-methylcyclohexyl dimethylphosphinate, (1S,2R,4R,6S)-2-amino-4-(3-(6-(2,6-difluorophenyl)-5-fluoropicolinamido) pyridin-4-yl)-6-methylcyclohexyl dimethylphosphinate, (1S,2R,4R,6S)-2-amino-4-(3-(6-(2,6-difluorophenyl)-5-fluoropicolinamido)pyridin-4-yl)-6-methylcyclohexyl meth-anesulfonate, (1R,2R,4R,6S)-2-amino-4-(3-(6-(2,6-difluo-rophenyl)-5-fluoropicolinamido)pyridin-4-yl)-6-methylcyclohexyl methanesulfonate, N-(4-((6R,8R,10S)-6-amino-10-methyl-1,4-dioxaspiro[4.5]decan-8-yl)pyridin-3-yl)-6-(2,6-difluorophenyl)-5-fluoropicolinamide, N-(4-((6S, 8S,10R)-6-amino-10-methyl-1,4-dioxaspiro[4.5]decan-8-yl)pyridin-3-yl)-6-(2,6-difluorophenyl)-5-fluoropicolinamide, 3-((1R,2R,4R,6S)-2-amino-4-(3-(6-(2, 6-difluorophenyl)-5-fluoropicolinamido)pyridin-4-yl)-6-methylcyclohexyloxy)propanoic acid, 3-((1S,2S,4S,6R)-2-amino-4-(3-(6-(2,6-difluorophenyl)-5-fluoropicolinamido) pyridin-4-yl)-6-methylcyclohexyloxy)propanoic acid, N-(4-((1S,3S,4R,5R)-3-amino-5-methyl-4-(1H-1,2,4-triazol-1-yl)cyclohexyl)pyridin-3-yl)-6-(2,6-difluorophenyl)-5-fluoropicolinamide, N-(4-((1R,3R,4S,5S)-3-amino-5-methyl-4-(1H-1,2,4-triazol-1-yl)cyclohexyl)pyridin-3-yl)-6-(2,6-difluorophenyl)-5-fluoropicolinamide, N-(4-((1R,3R, 4S,5S)-3-amino-4-methoxy-5-methylcyclohexyl)pyridin-3-yl)-2-(2,6-difluorophenyl)pyrimidine-4-carboxamide, methyl (1R,2S,4S,6R)-2-amino-4-(3-(6-(2,6-difluoro-4-me-thylphenyl)-5-fluoropicolinamido)pyridin-4-yl)-6-methyl-cyclohexyl(methyl)carbamate, methyl (1S,2R,4R,6S)-2-amino-4-(3-(6-(2,6-difluoro-4-methylphenyl)-5-fluoropicolinamido)pyridin-4-yl)-6-methylcyclohexyl (methyl)carbamate, N-(4-((3S,4S,5R)-3-amino-4-cyano-5-methylpiperidin-1-yl)pyridin-3-yl)-6-(2,6-difluoro-4-methylphenyl)-5-fluoropicolinamide, N-(4-((3R,4S,5S)-3-amino-5-methyl-4-(1H-1,2,4-triazol-1-yl)piperidin-1-yl) pyridin-3-yl)-6-(2,6-difluorophenyl)-5-fluoropicolinamide, N-(4-((3S,4S,5R)-3-amino-4-cyano-5-methylpiperidin-1-yl)pyridin-3-yl)-6-(2,6-difluorophenyl)-5-fluoropicolinamide, methyl (3R,4S,5S)-3-amino-1-(3-(6-(2,6-difluoro-4-methylphenyl)-5-fluoropicolinamido)pyridin-4-yl)-5-methylpiperidin-4-yl(methyl)carbamate, methyl (1R,2S,4S, 6R)-2-amino-4-(3-(6-(2,6-difluorophenyl)-5-fluoropicolinamido)pyridin-4-yl)-6-methylcyclohexyl (methyl)carbamate, methyl (1S,2R,4R,6S)-2-amino-4-(3-(6-(2,6-difluorophenyl)-5-fluoropicolinamido)pyridin-4-yl)-6-methylcyclohexyl(methyl)carbamate, methyl (3R,4S,5S)-3-amino-1-(3-(6-(2,6-difluorophenyl)-5-fluoropicolinamido) pyridin-4-yl)-5-methylpiperidin-4-yl(methyl)carbamate, N-(4-((1R,3R,4R,5S)-3-amino-4-methoxy-5-methylcyclo-hexyl)pyridin-3-yl)-6-(2,6-difluoro-4-methylphenyl)-5-fluoropicolinamide, N-(4-((3R,4S,5S)-3-amino-5-methyl-4-(N-methylacetamido)piperidin-1-yl)pyridin-3-yl)-6-(2,6- difluorophenyl)-5-fluoropicolinamide, N-(4-((3R,4S,5S)-3-amino-4-(hydroxymethyl)-1H-1,2,3-triazol-1-yl)-5-methylpiperidin-1-yl)pyridin-3-yl)-6-(2,6-difluorophenyl)-5-fluoropicolinamide, N-(4-((1S,3S,4R,5R)-3-amino-4-cyano-5-methylcyclohexyl)pyridin-3-yl)-6-(2,6-difluorophenyl)-5-fluoropicolinamide, N-(4-((1R,3R,4S,5S)-3-amino-4-cyano-5-methylcyclohexyl)pyridin-3-yl)-6-(2,6-difluorophenyl)-5-fluoropicolinamide, 5-amino-N-(4-((1R,3R,4R,5S)-3-amino-4-methoxy-5-methylcyclohexyl)pyridin-3-yl)-2-(2,6-difluorophenyl)pyrimidine-4-carboxamide, N-(4-((1R,3R,4S,5S)-3-amino-5-methyl-4-(2-(methylsulfonyl)ethoxy)cyclohexyl)pyridin-3-yl)-6-(2,6-difluoro-4-methylphenyl)-5-fluoropicolinamide, N-(4-((1S,3S,4R,5R)-3-amino-5-methyl-4-(2-(methylsulfonyl)ethoxy)cyclohexyl)pyridin-3-yl)-6-(2,6-difluoro-4-methylphenyl)-5-fluoropicolinamide, N-(4-((1R,3R,4R,5S)-3-amino-4-methoxy-5-methylcyclohexyl)pyridin-3-yl)-6-(2,6-difluorophenyl)-5-fluoropicolinamide, N-(4-((1S,3S,4S,5R)-3-amino-4-methoxy-5-methylcyclohexyl)pyridin-3-yl)-6-(2,6-difluorophenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluorophenyl)-5-fluoropicolinamide, N-(4-((1S,3S,4R,5R)-3-amino-5-methyl-4-(2-(methylsulfonyl)ethoxy)cyclohexyl)pyridin-3-yl)-6-(2,6-difluorophenyl)-5-fluoropicolinamide, 5-amino-N-(4-((1R,3R,4S,5S)-3-amino-4-methoxy-5-methylcyclohexyl)pyridin-3-yl)-2-(2,6-difluorophenyl)pyrimidine-4-carboxamide, methyl ((3R,4S,5S)-3-amino-1-(3-(6-(2,6-difluoro-4-methylphenyl)-5-fluoropicolinamido)pyridin-4-yl)-5-methylpiperidin-4-yl)carbamate, methyl ((3R,4S,5S)-3-amino-1-(3-(6-(2,6-difluorophenyl)-5-fluoropicolinamido)pyridin-4-yl)-5-methylpiperidin-4-yl)carbamate, N-(4-((1R,3R,4S,5S)-3-amino-4-(2-cyanoethoxy)-5-methylcyclohexyl)pyridin-3-yl)-6-(2,6-difluoro-4-methylphenyl)-5-fluoropicolinamide, N-(4-((1S,3S,4R,5R)-3-amino-4-(2-cyanoethoxy)-5-methylcyclohexyl)pyridin-3-yl)-6-(2,6-difluoro-4-methylphenyl)-5-fluoropicolinamide, N-(4-((1R,3R,4S,5S)-3-amino-4-(2-cyanoethoxy)-5-methylcyclohexyl)pyridin-3-yl)-6-(2,6-difluorophenyl)-5-fluoropicolinamide, N-(4-((1S,3S,4R,5R)-3-amino-4-(2-cyanoethoxy)-5-methylcyclohexyl)pyridin-3-yl)-6-(2,6-difluorophenyl)-5-fluoropicolinamide, N-(4-((3R,4S,5S)-3-amino-4-azido-5-methylpiperidin-1-yl)pyridin-3-yl)-6-(2,6-difluorophenyl)-5-fluoropicolinamide, N-(4-((1R,3R,4S,5S)-3-amino-4-ethoxy-5-methylcyclohexyl)pyridin-3-yl)-6-(2,6-difluorophenyl)-5-fluoropicolinamide, N-(4-((1S,3S,4R,5R)-3-amino-4-ethoxy-5-methylcyclohexyl)pyridin-3-yl)-6-(2,6-difluoro-4-methylphenyl)-5-fluoropicolinamide, N-(4-((1S,3S,4R,5R)-3-amino-4-ethoxy-5-methylcyclohexyl)pyridin-3-yl)-6-(2,6-difluorophenyl)-5-fluoropicolinamide, N-(4-((1R,3R,4S,5S)-3-amino-4-ethoxy-5-methylcyclohexyl)pyridin-3-yl)-6-(2,6-difluoro-4-methylphenyl)-5-fluoropicolinamide, N-(4-((1R,3R,4S,5S)-3-amino-4-methoxy-5-methylcyclohexyl)pyridin-3-yl)-6-(2,6-difluorophenyl)-5-fluoropicolinamide, N-(4-((1R,3R,4S,5S)-3-amino-4-methoxy-5-methylcyclohexyl)pyridin-3-yl)-6-(2,6-difluoro-4-(2-methoxyethoxy)phenyl)-5-fluoropicolinamide, N-(4-((1R,3R,4S,5S)-3-amino-4-methoxy-5-methylcyclohexyl)pyridin-3-yl)-6-(4-(1,1-dioxidotetrahydro-2H-thiopyran-4-yl)-2,6-difluorophenyl)-5-fluoropicolinamide, N-(4-((1R,3R,4S,5S)-3-amino-4-methoxy-5-methylcyclohexyl)pyridin-3-yl)-6-(2,6-difluoro-4-isopropylphenyl)-5-fluoropicolinamide, N-(4-((1R,3R,4S,5S)-3-amino-4-methoxy-5-methylcyclohexyl)pyridin-3-yl)-6-(2,6-difluoro-4-(4-fluorotetrahydro-2H-pyran-4-yl)phenyl)-5-fluoropicolinamide, N-(4-((1R,3R,4S,5S)-3-amino-4-methoxy-5-methylcyclohexyl)pyridin-3-yl)-6-(2,6-difluoro-4-(2-hydroxypropan-2-yl)phenyl)-5-fluoropicolinamide, N-(4-((1R,3R,4S,5S)-3-amino-4-methoxy-5-methylcyclohexyl)pyridin-3-yl)-6-(2,6-difluoro-4-(1-hydroxycyclobutyl)phenyl)-5-fluoropicolinamide, N-(4-((1R,3R,4S,5S)-3-amino-4-methoxy-5-methylcyclohexyl)pyridin-3-yl)-6-(2,6-difluoro-4-(tetrahydro-2H-pyran-4-yl)phenyl)-5-fluoropicolinamide, N-(4-((1R,3R,4S,5S)-3-amino-4-methoxy-5-methylcyclohexyl)pyridin-3-yl)-6-(4-(ethoxymethyl)-2,6-difluorophenyl)-5-fluoropicolinamide, N-(4-((1R,3R,4S,5S)-3-amino-4-methoxy-5-methylcyclohexyl)pyridin-3-yl)-6-(2,6-difluoro-4-isopropoxyphenyl)-5-fluoropicolinamide, N-(4-((1R,3R,4S,5S)-3-amino-4-methoxy-5-methylcyclohexyl)pyridin-3-yl)-6-(2,6-difluoro-4-methylphenyl)-5-fluoropicolinamide, N-(4-((1S,3S,4R,5R)-3-amino-4-methoxy-5-methylcyclohexyl)pyridin-3-yl)-6-(2,6-difluoro-4-methylphenyl)-5-fluoropicolinamide, N-(4-((1R,3R,4S,5S)-3-amino-5-methyl-4-methylsulfonyl)cyclohexyl)pyridin-3-yl)-2-(2,6-difluorophenyl)pyrimidine-4-carboxamide, methyl ((3R,4S,5S)-3-amino-1-(3-(6-(2,6-difluoro-4-(2-methoxyethoxy)phenyl)-5-fluoropicolinamido)pyridin-4-yl)-5-methylpiperidin-4-yl)carbamate, methyl ((1S,2R,4R,6S)-2-amino-4-(3-(6-(2,6-difluoro-4-(2-methoxyethoxy)phenyl)-5-fluoropicolinamido)pyridin-4-yl)-6-methylcyclohexyl)carbamate, N-(4-((1R,3R,4S,5S)-3-amino-5-methyl-4-(methylsulfonyl)cyclohexyl)pyridin-3-yl)-6-(2,6-difluoro-4-((tetrahydro-2H-pyran-4-yl)oxy)phenyl)-5-fluoropicolinamide, N-(4-((1R,3R,4S,5S)-3-amino-5-methyl-4-(methylsulfonyl)cyclohexyl)pyridin-3-yl)-6-(2,6-difluoro-4-(1-hydroxycyclobutyl)phenyl)-5-fluoropicolinamide, 3-amino-N-(4-((1R,3R,4S,5S)-3-amino-5-methyl-4-(methylsulfonyl)cyclohexyl)pyridin-3-yl)-6-(2-fluoro-5-(isopropylcarbamoyl)phenyl)picolinamide, N-(4-((1R,3R,4S,5S)-3-amino-5-methyl-4-(methylsulfonyl)cyclohexyl)pyridin-3-yl)-6-(2,6-difluoro-4-(4-fluorotetrahydro-2H-pyran-4-yl)phenyl)-5-fluoropicolinamide, 3-amino-N-(4-((1R,3R,4S,5S)-3-amino-4-(2-cyanoethoxy)-5-methylcyclohexyl)pyridin-3-yl)-6-(2-fluoro-5-(isopropylcarbamoyl)phenyl)picolinamide, N-(4-((1R,3R,4S,5S)-3-amino-5-methyl-4-(methylsulfonyl)cyclohexyl)pyridin-3-yl)-6-(2,6-difluoro-4-methoxyphenyl)-5-fluoropicolinamide, N-(4-((1S,3S,4R,5R)-3-amino-5-methyl-4-(pyridin-2-yloxy)cyclohexyl)pyridin-3-yl)-6-(2,6-difluorophenyl)-5-fluoropicolinamide, 3-amino-N-(4-((1R,3R,4S,5S)-3-amino-5-methyl-4-(methylsulfonyl)cyclohexyl)pyridin-3-yl)-6-(2,6-difluorophenyl)-5-fluoropicolinamide, N-(4-((1R,3R,4S,5S)-3-amino-5-methyl-4-(methylsulfonyl)cyclohexyl)pyridin-3-yl)-6-(4-(ethoxymethyl)-2,6-difluorophenyl)-5-fluoropicolinamide, N-(4-((1R,3R,4R,5S)-3-amino-4-methoxy-5-methylcyclohexyl)pyridin-3-yl)-6-(2,6-difluoro-4-(4-hydroxytetrahydro-2H-pyran-4-yl)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-(4-hydroxytetrahydro-2H-pyran-4-yl)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-(4-hydroxytetrahydro-2H-pyran-4-yl)phenyl)-5-fluoropicolinamide, N-(4-((1R,3R,4S,5S)-3-amino-5-methyl-4-(methylsulfonyl)cyclohexyl)pyridin-3-yl)-6-(2,6-difluoro-4-methylphenyl)-5-fluoropicolinamide, N-(4-((1R,3R,4S,5S)-3-amino-5-methyl-4-(pyridin-2-yloxy)cyclohexyl)pyridin-3-yl)-6-(2,6-difluorophenyl)-5-fluoropicolinamide, N-(4-((1R,3R,4R,5S)-3-amino-4-methoxy-5-methylcyclohexyl)pyridin-3-yl)-6-(2,6-difluoro-4-(2-methoxyethoxy)phenyl)-5-fluoropicolinamide, N-(4-((1R,3R,4S,5S)-3-amino-5-methyl-4-(2-(methylsulfonyl)ethoxy)

cyclohexyl)pyridin-3-yl)-6-(4-(ethoxymethyl)-2,6-difluorophenyl)-5-fluoropicolinamide, 3-amino-N-(4-((1R,3R,4R,5S)-3-amino-4-methoxy-5-methylcyclohexyl)pyridin-3-yl)-6-(2-fluoro-5-(isopropylcarbamoyl)phenyl)picolinamide, N-(4-((1R,3R,4R,5S)-3-amino-4-methoxy-5-methylcyclohexyl)pyridin-3-yl)-6-(2,6-difluoro-4-(4-fluorotetrahydro-2H-pyran-4-yl)phenyl)-5-fluoropicolinamide, 3-amino-N-(4-((1R,3R,4S,5S)-3-amino-5-methyl-4-(2-(methylsulfonyl)ethoxy)cyclohexyl)pyridin-3-yl)-6-(2-fluoro-5-(isopropylcarbamoyl)phenyl)picolinamide, N-(4-((1R,3R,4S,5S)-3-amino-5-methyl-4-(2-(methylsulfonyl)ethoxy)cyclohexyl)pyridin-3-yl)-6-(2,6-difluoro-4-(4-fluorotetrahydro-2H-pyran-4-yl)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-(2-methoxyethoxy)phenyl)-5-fluoropicolinamide, N-(4-((3R,4S,5S)-3-amino-5-methyl-4-(1H-1,2,3-triazol-1-yl)piperidin-1-yl)pyridin-3-yl)-6-(2,6-difluoro-4-(2-methoxyethoxy)phenyl)-5-fluoropicolinamide, N-(4-((1R,3R,4R,5S)-3-amino-4-methoxy-5-methylcyclohexyl)pyridin-3-yl)-6-(4-(ethoxymethyl)-2,6-difluorophenyl)-5-fluoropicolinamide, N-(4-((1R,3R,4R,5S)-3-amino-4-methoxy-5-methylcyclohexyl)pyridin-3-yl)-6-(2,6-difluoro-4-((tetrahydro-2H-pyran-4-yl)oxy)phenyl)-5-fluoropicolinamide, N-(4-((1R,3R,4R,5S)-3-amino-4-methoxy-5-methylcyclohexyl)pyridin-3-yl)-6-(2,6-difluoro-4-(1-hydroxycyclobutyl)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-(1-hydroxycyclobutyl)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-((tetrahydro-2H-pyran-4-yl)oxy)phenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-isopropoxyphenyl)-5-fluoropicolinamide, N-(4-((1R,3R,4R,5S)-3-amino-4-methoxy-5-methylcyclohexyl)pyridin-3-yl)-6-(2,6-difluoro-4-isopropoxyphenyl)-5-fluoropicolinamide, N-(4-((1R,3R,4R,5S)-3-amino-4-methoxy-5-methylcyclohexyl)pyridin-3-yl)-6-(2,6-difluoro-4-methoxyphenyl)-5-fluoropicolinamide, N-(4-((1R,3R,4S,5S)-3-amino-5-methyl-4-(2-(methylsulfonyl)ethoxy)cyclohexyl)pyridin-3-yl)-6-(2,6-difluoro-4-methoxyphenyl)-5-fluoropicolinamide, 3-amino-N-(4-((1R,3R,4R,5S)-3-amino-4-methoxy-5-methylcyclohexyl)pyridin-3-yl)-6-(2,6-difluorophenyl)-5-fluoropicolinamide, 3-amino-N-(4-((1R,3R,4S,5S)-3-amino-5-methyl-4-(2-(methylsulfonyl)ethoxy)cyclohexyl)pyridin-3-yl)-6-(2,6-difluorophenyl)-5-fluoropicolinamide, N-(4-((3R,4S,5S)-3-amino-5-methyl-4-(1H-1,2,3-triazol-1-yl)piperidin-1-yl)pyridin-3-yl)-6-(2,6-difluoro-4-isopropoxyphenyl)-5-fluoropicolinamide, methyl (3R,4S,5S)-3-amino-1-(3-(6-(2,6-difluoro-4-isopropoxyphenyl)-5-fluoropicolinamido)pyridin-4-yl)-5-methylpiperidin-4-ylcarbamate, methyl (1S,2R,4R,6S)-2-amino-4-(3-(6-(2,6-difluoro-4-isopropoxyphenyl)-5-fluoropicolinamido)pyridin-4-yl)-6-methylcyclohexylcarbamate, N-(4-((1S,3S,4R,5R)-3-amino-5-methyl-4-(2-oxopyridin-1(2H)-yl)cyclohexyl)pyridin-3-yl)-6-(2,6-difluorophenyl)-5-fluoropicolinamide, N-(4-((3R,4S,5S)-3-amino-5-methyl-4-(1H-1,2,3-triazol-1-yl)piperidin-1-yl)pyridin-3-yl)-6-(2,6-difluoro-4-(4-fluorotetrahydro-2H-pyran-4-yl)phenyl)-5-fluoropicolinamide, N-(4-((1R,3R,4S,5S)-3-amino-5-methyl-4-(2-oxopyridin-1(2H)-yl)cyclohexyl)pyridin-3-yl)-6-(2,6-difluorophenyl)-5-fluoropicolinamide, N-(4-((1R,3R,4S,5S)-3-amino-4-(2-cyanoethoxy)-5-methylcyclohexyl)pyridin-3-yl)-6-(2,6-difluoro-4-(4-fluorotetrahydro-2H-pyran-4-yl)phenyl)-5-fluoropicolinamide, N-(4-((1S,3R,4S,5S)-3-amino-5-methyl-4-(1H-1,2,3-triazol-1-Y1)cyclohexyl)pyridin-3-yl)-6-(4-(ethoxymethyl)-2,6-difluorophenyl)-5-fluoropicolinamide, N-(4-((3R,4S,5S)-3-amino-5-methyl-4-(1H-1,2,3-triazol-1-yl)piperidin-1-yl)pyridin-3-yl)-6-(4-(ethoxymethyl)-2,6-difluorophenyl)-5-fluoropicolinamide, methyl (3R,4S,5S)-3-amino-1-(3-(6-(2,6-difluoro-4-(1-hydroxycyclobutyl)phenyl)-5-fluoropicolinamido)pyridin-4-yl)-5-methylpiperidin-4-ylcarbamate, methyl (3R,4S,5S)-3-amino-1-(3-(6-(2,6-difluoro-4-tetrahydro-2H-pyran-4-yloxy)phenyl)-5-fluoropicolinamido)pyridin-4-yl)-5-methylpiperidin-4-ylcarbamate, N-(4-((3R,4S,5S)-3-amino-5-methyl-4-(1H-1,2,3-triazol-1-yl)piperidin-1-4Pyridin-3-yl)-6-(2,6-difluoro-4-(4-hydroxytetrahydro-2H-pyran-4-yl)phenyl)-5-fluoropicolinamide, N-(4-((3R,4S,5S)-3-amino-5-methyl-4-(1H-1,2,3-triazol-1-yl)piperidin-1-4Pyridin-3-yl)-6-(2,6-difluoro-4-methylphenyl)-5-fluoropicolinamide, methyl (3R,4S,5S)-3-amino-1-(3-(6-(2,6-difluoro-4-(oxetan-3-yl)phenyl)-5-fluoropicolinamido)pyridin-4-yl)-5-methylpiperidin-4-ylcarbamate, N-(4-((1R,3R,4S,5S)-3-amino-4-(2-cyanoethoxy)-5-methylcyclohexyl)pyridin-3-yl)-6-(2,6-difluoro-4-(oxetan-3-yl)phenyl)-5-fluoropicolinamide, N-(4-((3R,4S,5S)-3-amino-5-methyl-4-(1H-1,2,3-triazol-1-yl)piperidin-1-yl)pyridin-3-yl)-6-(2,6-difluoro-4-(oxetan-3-yl)phenyl)-5-fluoropicolinamide, N-(4-((1R,3R,4S,5S)-3-amino-4-(2-cyanoethoxy)-5-methylcyclohexyl)pyridin-3-yl)-6-(2,6-difluoro-4-methoxyphenyl)-5-fluoropicolinamide, 3-amino-N-(4-((1R,3R,4S,5S)-3-amino-4-(2-cyanoethoxy)-5-methylcyclohexyl)pyridin-3-yl)-6-(2,6-difluorophenyl)-5-fluoropicolinamide, methyl 1S,2R,4R,6S)-2-amino-4-(3-(6-(2,6-difluoro-4-(1-hydroxycyclobutyl)phenyl)-5-fluoropicolinamido)pyridin-4-yl)-6-methylcyclohexylcarbamate, N-(4-((1R,3R,4S,5A)-3-amino-5-methyl-4-(1H-1,2,3-triazol-1-yl)cyclohexyl)pyridin-3-yl)-6-(2,6-difluoro-4-(2-methoxyethoxyl)phenyl)-5-fluoropicolinamide, methyl (1S,2R,4R,6S)-2-amino-4-(3-(6-(2,6-difluoro-4-(tetrahydro-2H-pyran-4-yloxy)phenyl)-5-fluoropicolinamido)pyridin-4-yl)-6-methylcyclohexylcarbamate, N-(4-((1R,3R,4S,5S)-3-amino-5-methyl-4-(1H-1,2,3-triazol-1-yl)cyclohexyl)pyridin-3-yl)-6-(2,6-difluoro-4-(tetrahydro-2H-pyran-4-yloxy)phenyl)-5-fluoropicolinamide, N-(4-((1R,3R,4S,5S)-3-amino-5-methyl-4-(1H-1,2,3-triazol-1-yl)cyclohexyl)pyridin-3-yl)-6-(2,6-difluoro-4-(1-hydroxycyclobutyl)phenyl)-5-fluoropicolinamide, methyl ((3R,4S,5S)-3-amino-1-(3-(6-(2,6-difluoro-4-methoxyphenyl)-5-fluoropicolinamido)pyridin-4-yl)-5-methylpiperidin-4-yl)carbamate, methyl ((3R,4A,5S)-3-amino-1-(3-(3-amino-6-(2,6-difluorophenyl)-5-fluoropicolinamido)pyridin-4-yl)-5-methylpiperidin-4-yl)carbamate, methyl (1S,2R,4R,6S)-2-amino-4-(3-(3-amino-6-(2,6-difluorophenyl)-5-fluoropicolinamido)pyridin-4-yl)-6-methylcyclohexylcarbamate, 3-amino-N-(4-((1R,3R,4S,5S)-3-amino-5-methyl-4-(1H-1,2,3-triazol-1-yl)cyclohexyl)pyridin-3-yl)-6-(2,6-difluorophenyl)-5-fluoropicolinamide, methyl (3R,4S,5S)-3-amino-1-(3-(6-(2,6-difluoro-4-(4-hydroxytetrahydro-2H-pyran-4-yl)phenyl)-5-fluoropicolinamido)pyridin-4-yl)-5-methylpiperidin-4-ylcarbamate, methyl (1S,2R,4R,6S)-2-amino-4-(3-(6-(2,6-difluoro-4-(4-hydroxytetrahydro-2H-pyran-4-yl)phenyl)-5-fluoropicolinamido)pyridin-4-yl)-6-methylcyclohexylcarbamate, N-(4-((1R,3R,4S,5S)-3-amino-5-methyl-4-(1H-1,2,3-triazol-1-yl)cyclohexyl)pyridin-3-yl)-6-(2,6-difluoro-4-(4-hydroxytetrahydro-2H-pyran-4-yl)phenyl)-5-fluoropicolinamide, methyl (1S,2R,4R,6S)-2-amino-4-(3-(6-(2,6-difluoro-4-methylphenyl)-5-fluoropicolinamido)

pyridin-4-yl)-6-methylcyclohexylcarbamate, N-(4-((1R,3R,4S,5S)-3-amino-5-methyl-4-(1H-1,2,3-triazol-1-yl)cyclohexyl)pyridin-3-yl)-6-(2,6-difluoro-4-methylphenyl)-5-fluoropicolinamide, methyl (1S,2R,4R,6S)-2-amino-4-(3-(6-(2,6-difluoro-4-(oxetan-3-yl)phenyl)-5-fluoropicolinamido)pyridin-4-yl)-6-methylcyclohexylcarbamate, N-(4-((1R,3R,4S,5S)-3-amino-4-(2-cyanoethoxy)-5-methylcyclohexyl)pyridin-3-yl)-6-(2,6-difluoro-4-((tetrahydro-2H-pyran-4-yl)oxy)phenyl)-5-fluoropicolinamide, N-(4-((1R,3R,4S,5S)-3-amino-4-(2-cyanoethoxy)-5-methylcyclohexyl)pyridin-3-yl)-6-(2,6-difluoro-4-(1-hydroxycyclobutyl)phenyl)-5-fluoropicolinamide, N-(4-((1R,3R,4S,5S)-3-amino-4-(4-cyano-1H-1,2,3-triazol-1-yl)-5-methylcyclohexyl)pyridin-3-yl)-6-(2,6-difluorophenyl)-5-fluoropicolinamide, N-(4-((1R,3R,4S,5S)-3-amino-4-(4-cyclopropyl-1H-1,2,3-triazol-1-yl)-5-methylcyclohexyl)pyridin-3-yl)-6-(2,6-difluorophenyl)-5-fluoropicolinamide, N-(4-((1R,3R,4S,5S)-3-amino-5-methyl-4-(4-(prop-1-en-2-yl)-1H-1,2,3-triazol-1-yl)cyclohexyl)pyridin-3-yl)-6-(2,6-difluorophenyl)-5-fluoropicolinamide, N-(4-((1R,3R,4S,5S)-3-amino-4-(4-(2-hydroxypropan-2-yl)-1H-1,2,3-triazol-1-yl)-5-methylcyclohexyl)pyridin-3-yl)-6-(2,6-difluorophenyl)-5-fluoropicolinamide, 2-((1R,2S,4S,6R)-2-amino-4-(3-(6-(2,6-difluorophenyl)-5-fluoropicolinamido)pyridin-4-yl)-6-methylcyclohexyloxy)acetic acid, 2-((1S,2R,4R,6S)-2-amino-4-(3-(6-(2,6-difluorophenyl)-5-fluoropicolinamido)pyridin-4-yl)-6-methylcyclohexyloxy)acetic acid, methyl (1S,2R,4R,6S)-2-amino-4-(3-(6-(2,6-difluoro-4-methoxyphenyl)-5-fluoropicolinamido)pyridin-4-yl)-6-methylcyclohexylcarbamate, N-(4-((1R,3R,4S,5S)-3-amino-5-methyl-4-(1H-1,2,3-triazol-1-yl)cyclohexyl)pyridin-3-yl)-6-(2,6-difluoro-4-methoxyphenyl)-5-fluoropicolinamide, N-(4-((3R,4S,5S)-3-amino-5-methyl-4-(1H-1,2,3-triazol-1-yl)piperidin-1-yl)pyridin-3-yl)-6-(2,6-difluoro-4-methoxyphenyl)-5-fluoropicolinamide, 3-amino-N-(4-((3R,4S,5S)-3-amino-5-methyl-4-(1H-1,2,3-triazol-1-yl)piperidin-1-yl)pyridin-3-yl)-6-(2,6-difluorophenyl)-5-fluoropicolinamide, N-(4-((1R,3R,4S,5S)-3-amino-5-methyl-4-(1H-1,2,3-triazol-1-yl)cyclohexyl)pyridin-3-yl)-6-(2,6-difluoro-4-(4-fluorotetrahydro-2H-pyran-4-yl)phenyl)-5-fluoropicolinamide, 3-amino-N-(4-((1R,3R,4S,5S)-3-amino-5-methyl-4-(1H-1,2,3-triazol-1-yl)cyclohexyl)pyridin-3-yl)-6-(2-fluoro-5-(isopropylcarbamoyl)phenyl)picolinamide, 3-amino-N-(4-((3R,4S,5S)-3-amino-5-methyl-4-(1H-1,2,3-triazol-1-yl)piperidin-1-yl)pyridin-3-yl)-6-(2-fluoro-5-(isopropylcarbamoyl)phenyl)picolinamide, methyl (3R,4S,5S)-3-amino-1-(3-(3-amino-6-(2-fluoro-5-(isopropylcarbamoyl)phenyl)picolinamido)pyridin-4-yl)-5-methylpiperidin-4-ylcarbamate, methyl (3R,4S,5S)-3-amino-1-(3-(6-(2,6-difluoro-4-(4-fluorotetrahydro-2H-pyran-4-yl)phenyl)-5-fluoropicolinamido)pyridin-4-yl)-5-methylpiperidin-4-ylcarbamate, methyl (1S,2R,4R,6S)-2-amino-4-(3-(3-amino-6-(2-fluoro-5-(isopropylcarbamoyl)phenyl)picolinamido)pyridin-4-yl)-6-methylcyclohexylcarbamate, methyl 1S,2R,4R,6S)-2-amino-4-(3-(6-(2,6-difluoro-4-(4-fluorotetrahydro-2H-pyran-4-yl)phenyl)-5-fluoropicolinamido)pyridin-4-yl)-6-methylcyclohexylcarbamate, methyl (1S,2R,4R,6S)-2-amino-4-(3-(6-(4-(ethoxymethyl)-2,6-difluorophenyl)-5-fluoropicolinamido)pyridin-4-yl)-6-methylcyclohexylcarbamate, methyl (3R,4S,5S)-3-amino-1-(3-(6-(4-(ethoxymethyl)-2,6-difluorophenyl)-5-fluoropicolinamido)pyridin-4-yl)-5-methylpiperidin-4-ylcarbamate and the pharmaceutically acceptable salts thereof.

16. A pharmaceutical composition comprising a compound of claim 15, admixed with at least one pharmaceutically acceptable excipient.

17. A method of treating a cancer selected from: carcinoma of the lungs, pancreas, thyroid, ovaries, bladder, breast, prostate or colon, melanoma, myeloid leukemia, multiple myeloma, erythro leukemia, villous colon adenoma and osteosarcoma or an autoimmune disorder selected from: Crohn's disease, inflammatory bowel disease, rheumatoid arthritis and chronic inflammatory disease, comprising the step of: administering to a subject in need thereof a therapeutically effective amount of a compound according to claim 15, or a pharmaceutically acceptable salt thereof.

18. A compound selected from methyl (1R,2S,4S,6R)-2-amino-4-(3-(5-amino-2-(2,6-difluorophenyl)thiazole-4-carboxamido)pyridin-4-yl)-6-methylcyclohexyl(methyl)carbamate, methyl (1S,2R,4R,6S)-2-amino-4-(3-(5-amino-2-(2,6-difluorophenyl)thiazole-4-carboxamido)pyridin-4-yl)-6-methylcyclohexyl(methyl)carbamate, N-(4-((1R,3R,4S,5S)-3-amino-4-methoxy-5-methylcyclohexyl)pyridin-3-yl)-2-(2,6-difluorophenyl)thiazole-4-carboxamide, 5-amino-N-(4-((3S,4S,5R)-3-amino-4-cyano-5-methylpiperidin-1-yl)pyridin-3-yl)-2-(2,6-difluorophenyl)thiazole-4-carboxamide, 5-amino-N-(4-((1S,3S,4R,5R)-3-amino-4-(2-cyanoethoxy)-5-methylcyclohexyl)pyridin-3-yl)-2-(2,6-difluorophenyl)thiazole-4-carboxamide, 5-amino-N-(4-((1R,3R,4S,5S)-3-amino-4-(2-cyanoethoxy)-5-methylcyclohexyl)pyridin-3-yl)-2-(2,6-difluorophenyl)thiazole-4-carboxamide, 5-amino-N-(4-((1R,3R,4R,5S)-3-amino-4-methoxy-5-methylcyclohexyl)pyridin-3-yl)-2-(2,6-difluorophenyl)thiazole-4-carboxamide, 5-amino-N-(4-((1R,3R,4S,5S)-3-amino-4-ethoxy-5-methylcyclohexyl)pyridin-3-yl)-2-(2,6-difluorophenyl)thiazole-4-carboxamide, methyl ((3R,4S,5S)-3-amino-1-(2-(5-amino-2-(2,6-difluorophenyl)thiazole-4-carboxamido)phenyl)-5-methylpiperidin-4-yl)carbamate, 5-amino-N-(4-((1R,3R,4S,5S)-3-amino-4-methoxy-5-methylcyclohexyl)pyridin-3-yl)-2-(2,6-difluorophenyl)thiazole-4-carboxamide, 5-amino-N-(4-((1R,3R,4S,5S)-3-amino-5-methyl-4-(methylsulfonyl)cyclohexyl)pyridin-3-yl)-2-(2,6-difluorophenyl)thiazole-4-carboxamide, N-(4-((1R,3R,4S,5S)-3-amino-5-methyl-4-(methylsulfonyl)cyclohexyl)pyridin-3-yl)-2-(2,6-difluorophenyl)thiazole-4-carboxamide, N-(4-((3R,4S,5S)-3-amino-5-methyl-4-(1H-1,2,3-triazol-1-yl)piperidin-1-yl)pyridin-3-yl)-2-(2,6-difluorophenyl)thiazole-4-carboxamide, N-(4-((1R,3R,4S,5S)-3-amino-5-methyl-4-(2-(methylsulfonyl)ethoxy)cyclohexyl)pyridin-3-yl)-2-(2,6-difluorophenyl)thiazole-4-carboxamide, N-(4-((1R,3R,4R,5S)-3-amino-4-methoxy-5-methylcyclohexyl)pyridin-3-yl)-2-(2,6-difluorophenyl)thiazole-4-carboxamide, 5-amino-N-(4-((1R,3R,4S,5S)-3-amino-5-methyl-4-(2-(methylsulfonyl)ethoxy)cyclohexyl)pyridin-3-yl)-2-(2,6-difluorophenyl)thiazole-4-carboxamide, 5-amino-N-(4-((1R,3R,4S,5S)-3-amino-5-methyl-4-(1H-1,2,3-triazol-1-yl)cyclohexyl)pyridin-3-yl)-2-(2,6-difluorophenyl)thiazole-4-carboxamide, 5-amino-N-(4-((3R,4S,5S)-3-amino-5-methyl-4-(1H-1,2,3-triazol-1-yl)piperidin-1-yl)pyridin-3-yl)-2-(2,6-difluorophenyl)thiazole-4-carboxamide, N-(4-((1R,3R,4S,5S)-3-amino-5-methyl-4-(1H-1,2,3-triazol-1-yl)cyclohexyl)pyridin-3-yl)-2-(2,6-difluorophenyl)thiazole-4-carboxamide and a pharmaceutically acceptable salt thereof.

19. A pharmaceutical composition comprising a compound of claim 18, admixed with at least one pharmaceutically acceptable excipient.

20. A method of treating a cancer selected from: carcinoma of the lungs, pancreas, thyroid, ovaries, bladder, breast, prostate or colon, melanoma, myeloid leukemia, multiple myeloma, erythro leukemia, villous colon adenoma and osteosarcoma or an autoimmune disorder selected from: Crohn's disease, inflammatory bowel disease, rheumatoid arthritis and chronic inflammatory disease, comprising the step of: administering to a subject in need thereof a therapeutically effective amount of a compound according to claim 18, or a pharmaceutically acceptable salt thereof.

* * * * *